US006402037B1

(12) United States Patent
Prasad et al.

(10) Patent No.: US 6,402,037 B1
(45) Date of Patent: Jun. 11, 2002

(54) TWO-PHOTON UPCONVERTING DYES AND APPLICATIONS

(75) Inventors: Paras N. Prasad, Williamsville; Jayant D. Bhawalker, Tonawanda; Ping Chin Cheng, Williamsville, all of NY (US); Shan Jen Pan, Amherst, NY (US)

(73) Assignee: The Research Foundation of State University of New York, Amherst, NY (US)

( * ) Notice: Subject to any disclaimer, the term of this patent is extended or adjusted under 35 U.S.C. 154(b) by 0 days.

(21) Appl. No.: 09/441,720

(22) Filed: Nov. 16, 1999

Related U.S. Application Data

(62) Division of application No. 09/265,625, filed on Mar. 10, 1999, which is a division of application No. 08/712,143, filed on Sep. 5, 1996, now Pat. No. 5,912,257.
(60) Provisional application No. 60/003,296, filed on Sep. 6, 1995, provisional application No. 60/005,924, filed on Oct. 27, 1995, provisional application No. 60/010,330, filed on Dec. 15, 1995, and provisional application No. 60/025,798, filed on Aug. 27, 1996.

(51) Int. Cl.[7] ............................................. G06K 19/00

(52) U.S. Cl. ...................................... 235/487; 235/454

(58) Field of Search .............................. 235/494, 487, 235/454; 369/100; 514/356; 546/239; 250/338.1; 252/542; 264/1.33; 430/338, 343; 574/356, 709; 568/34

(56) References Cited

U.S. PATENT DOCUMENTS

| | | |
|---|---|---|
| 3,636,473 A | 1/1972 | Young |
| 3,833,863 A | 9/1974 | Webster et al. |
| 4,288,861 A | 9/1981 | Swainson et al. |
| 4,987,021 A | 1/1991 | Kanno et al. |
| 5,034,613 A | 7/1991 | Denk et al. |
| 5,064,952 A | 11/1991 | Chang et al. |
| 5,196,383 A | 3/1993 | Ito et al. |
| 5,198,460 A | 3/1993 | Pandey et al. |
| 5,214,036 A | 5/1993 | Allison et al. |
| 5,222,092 A | 6/1993 | Hench et al. |
| 5,239,549 A | 8/1993 | Tajima et al. |
| 5,253,198 A | 10/1993 | Birge et al. |
| 5,254,638 A | 10/1993 | Novak et al. |
| 5,268,862 A | 12/1993 | Rentzepis |
| 5,289,407 A | 2/1994 | Strickler et al. |
| 5,314,905 A | 5/1994 | Pandey et al. |
| 5,325,324 A | 6/1994 | Rentzepis et al. |
| 5,354,858 A | 10/1994 | Morgan et al. |
| 5,380,510 A | 1/1995 | Matsui et al. |
| 5,412,043 A | 5/1995 | Novak et al. |
| 5,420,081 A | 5/1995 | Mattes et al. |
| 5,439,570 A | 8/1995 | Sessler et al. |
| 5,568,460 A * | 10/1996 | Saikan et al. ............... 369/100 |
| 5,829,448 A | 11/1998 | Fisher et al. |
| 5,832,931 A | 11/1998 | Wachter et al. |
| 5,912,257 A * | 6/1999 | Prasad et al. ............... 514/356 |

FOREIGN PATENT DOCUMENTS

| | | |
|---|---|---|
| JP | 1-106022 | 4/1989 |
| WO | WO 94/07142 | 3/1994 |

OTHER PUBLICATIONS

*Chemical Abstracts* 111 (23): 501 (1989), abstract No. 221816h of Jpn. Kokai Tokkyo Koho JP, 1,106,022 to Kurihara et al.

WPI Acc No: 89–162520/22 Abstract of JP 116022.

Denk et al., "Two–Photon Laser Scanning Fluorescence Microscopy," *Science,* 2:73–76 (1990).

*Chemical Abstracts* 120 (24): 815 (1994), abstract No. 310566e of Ashwell et al., "A Two–Legged Spacer Molecule for Alternate Layer LB Film Deposition with Optically Nonlinear Dyes", *Mater Res. Soc. Symp. Proc.* 247: 728–92 (1992).

Mukherjee, "Two–Photon Pumped Unconverted Lasing in Dye Doped Polymer Waveguides," *Appl. Phys. Lett.,* 62:3423–3425 (1993).

Tutt et al., "A Review of Optical Limiting Mechanisms and Devices Using Organics, Fullerenes, Semiconductors and Other Materials," *Prog. Quant. Electr.,* 17:299–338 (1993).

Chemical Abstracts 121 (14): 93 (1994), abstract No. 159364k of Moon et al., "Synthesis, Characterization and Properties of NLO Dye–Containing Polyurethane", *Mol Cryst. Liq. Cryst. Sci. Technol., Sect.* A 247: 91–7 (1994).
He et al., "Dye Film Leaky Waveguide Laser," *Optics Communications,* 111:82–85 (1994).
Tsien, "Fluorescence Imaging Creates a Window on the Cell," *Chemical and Engineering News,* 34–44 (Jul. 18, 1994).
Chemical Abstracts 123: 955 (1995), abstract No. 241083t of Zhao et al. , "Newly Synthesized Dyes and Their Polymer/Glass Composites for One–and Two–Photon Pumped Solid–State Cavity Lasing", *Chem. Mater.* 7: 1979–83 (1995).
Gvishi et al., "Probing the Microenvironment of Polymer–Impregnated Composite Glass Using Solvatochromic Dye," *Chem. Mater.,* 7:1703–1708 (1995).
He et al., "Optical Limiting Effect in a Two–Photon Absorption Dye Doped Solid Matrix," *Appl. Phys. Lett.,* 67:2433–2435 (1995).
He et al., "Two–Photon Absorption Based Optical Limiting and Stabilization in Organic Molecule–Doped Solid Materials," *Optics Communications,* 117:133–136 (1995).
He et al., "Two–Photon–Pumped Cavity Lasing in a Dye–Solution–Filled Hollow–Fiber System," *Optics Letters,* 20:2393–2395 (1995).
Nogués, et al., "Sol–Gel Methods Can Yield Complex, Economical Optics," *Laser Focus World,* 90–93 (Dec. 1995).
Zhao et al., "Newly Synthesized Dyes and Their Polymer/Glass Composites for One–and Two–Photon Pumped Solid–State Cavity Lasing," *Chemistry of Materials,* 7:1979–1983 (1995).
Bhawalkar et al., "Efficient, Two–Photon Pumped Green Upconverted Cavity Lasing in a New Dye," *Optics Communications,* 124: 33–37 (1996).
Bhawalkar et al., "Two–Photon Laser Scanning Fluorescence Microscopy–From a Fluorophore and Specimen Perspective," *Bioimaging,* 4:168–178 (1996).
Bhawalkar et al., "Three–Dimensional Laser Scanning Two–Photon Fluorescence Confocal Microscopy of Polymer Materials Using a New, Efficient Upconverting Fluorophore," *Scanning,* 18:562–566 (1996).
He et al., "Properties of Two–Photon Pumped Cavity Lasing in Novel Dye Doped Solid Matrices," *IEEE Journal of Quantum Electronics,* 32: 749–755 (1996).
He et al., "Two–Photon Pumped Cavity Lasing in Novel Dye Doped Bulk Matrix Rods," *Appl. Phys. Lett.,* 67:3703–3705 (1996).
He et al., "Upconversion Dye–Doped Polymer Fiber Laser," *Appl. Phys. Lett.,* 68: 3549–3551 (1996).
Ashwell et al., "A Two–Legged Spacer Molecule for Alternate Layer LB Film Deposition with Optically Nonlinear Dyes", *Mater. Res. Soc. Symp. Proc.,* 247:782–92 (1992).
Moon et al., "Synthesis and Characterization and Properties of NLO Dye–Containing Polyurethane", *Mol Cryst. Liq. Cryst. Sci., Technol., Sect A,* 247:91–7 (1994).

\* cited by examiner

*Primary Examiner*—Karl D. Frech
(74) *Attorney, Agent, or Firm*—Nixon Peabody LLP

(57) ABSTRACT

The present invention is directed to styryl dyes having the formula:

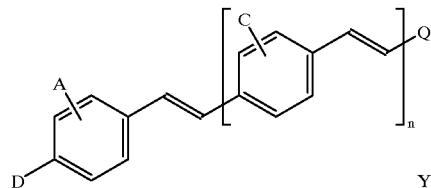

wherein
  D is an electron donating group;
  Q is an electron acceptor selected from the group consisting of electron acceptors having the formulae:

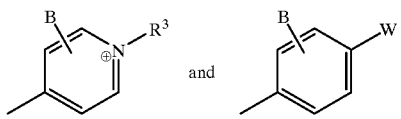

W is an electron accepting group,
  $R^3$ is selected from the group consisting of substituted or unsubstituted alkyl or substituted or unsubstituted aryl moieties, n is an integer from 0 to 4,
  A, B, and C are substituents of their rings and are each independently selected from the group consisting of alkyl, alkoxy, hydroxyalkyl, sulfoalkyl, carboxyalkyl, and hydrogen, and
  Y is a counterion The present invention discloses media and methods for recording data. A three-dimensional matrix including a plurality of dye molecules, such a styryl dye molecule of the present invention, is provided. A first volume element in the matrix is exposed to actinic radiation for a duration and at an intensity effective to alter detectably a fraction between 0.3 and 0.7 of the dye molecules contained therein. The detectably altered dye molecules are substantially uniformly dispersed in the first volume element. The data storage methods and media of the present invention have approximately $10^{12}$ volume elements per square centimeter, and each of the volume elements can store a single bit, digital information of approximately 8 bits, or analog information. The data storage methods and media of the present invention are particularly useful for storing or archiving a series of two-dimensional black and white or color images, such as frames of a movie. Methods for reading data stored in the data storage media of the present invention using confocal microscopy are also disclosed.

31 Claims, 34 Drawing Sheets

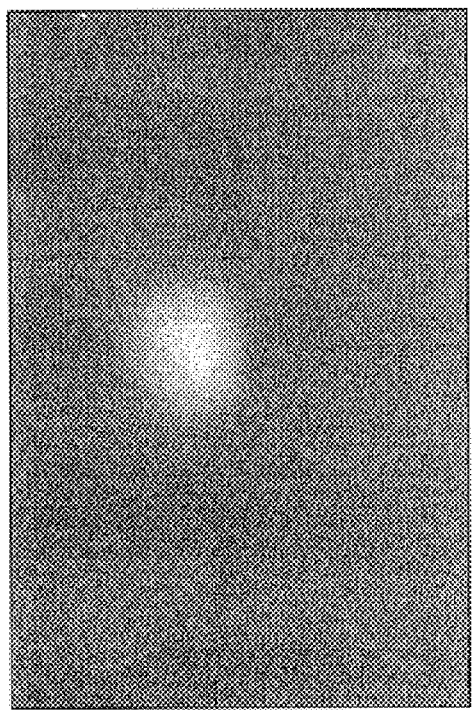 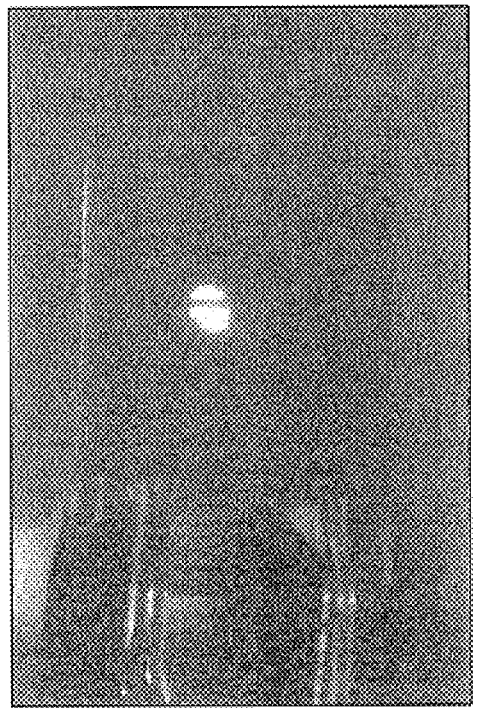
*FIG. 5A*  *FIG. 5B*

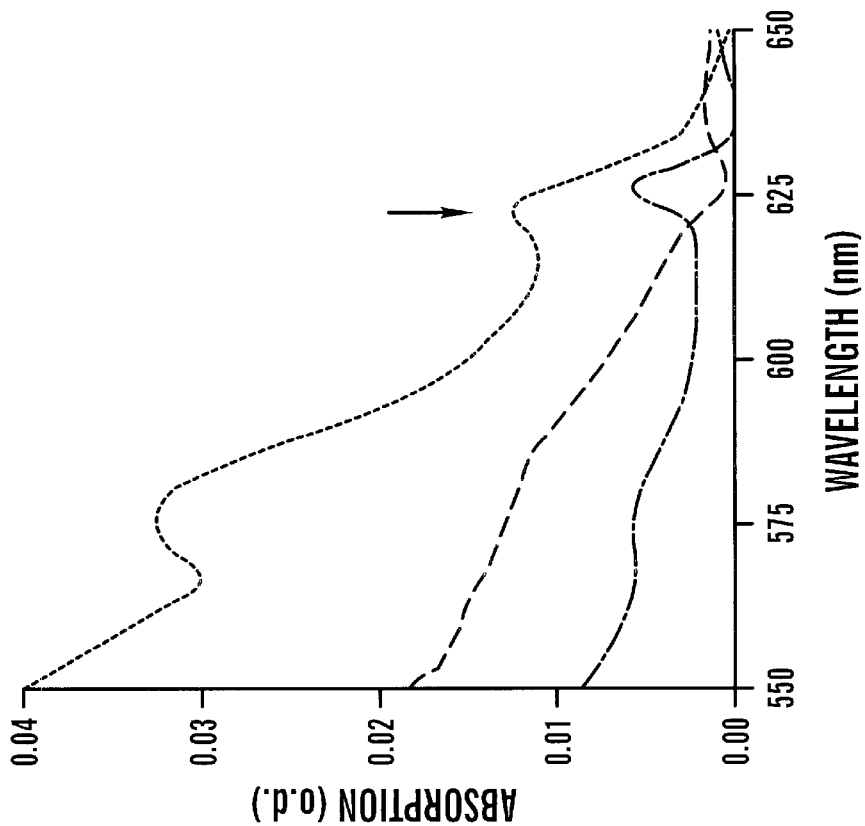
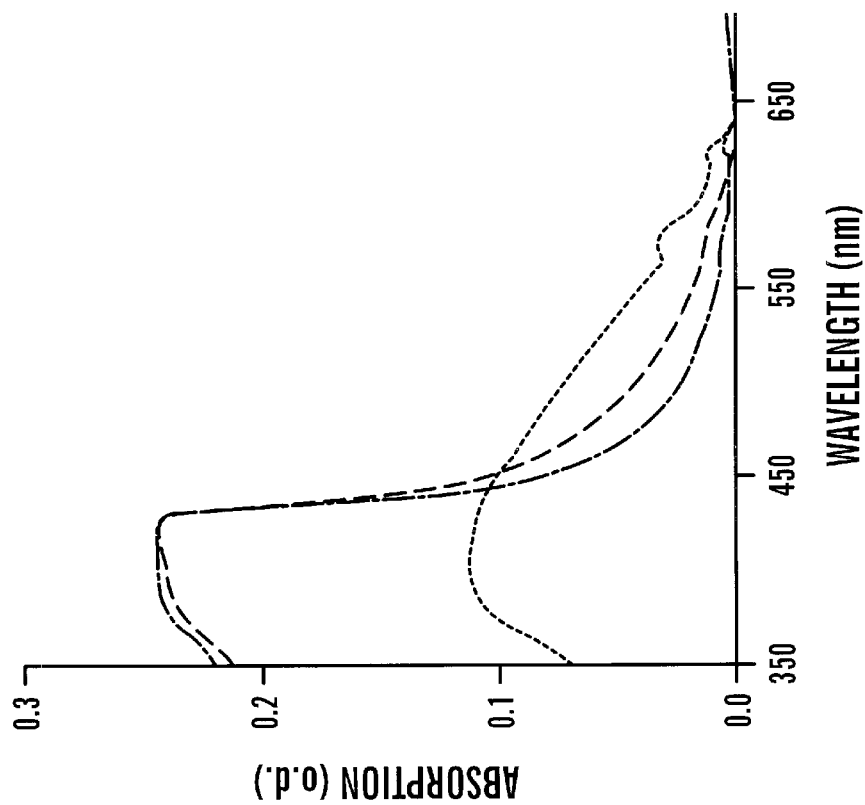
FIG. 20B
FIG. 20A

TWO-PHOTON UPCONVERTING DYES AND APPLICATIONS

This application is a division of U.S. patent application Ser. No. 09/265,625, filed Mar. 10, 1999, entitled "Two-Photon Upconverting Dyes and Applications," which is a division of 08/712,143, filed Sep. 5, 1996, now U.S. Pat. No. 5,912,257, issued Jun. 15, 1999, which claims the benefit of U.S. Provisional Patent Application Ser. No. 60/003,296, filed Sep. 6, 1995; U.S. Provisional Patent Application Ser. No. 60/005,924, filed Oct. 27, 1995; U.S. Provisional Patent Application Ser. No. 60/010,330, filed Dec. 15, 1995; and U.S. Provisional Patent Application Ser. No. 60/025,798, filed Aug. 27, 1996. All of these applications are incorporated herein by this reference.

This invention was made through the support of the Air Force Office of Scientific Research (Grant No. F49620-91-0053); the Air Force Office of Scientific Research and the Polymer Branch of the Air Force Wright Laboratory (Grant Nos. F49620-93-C0017 and F33615-94-C-5803); and the U.S. Air Force Office of Scientific Research/BMDO (Grant No. F49620-94-10335). The Federal Government may retain certain rights in the invention.

FIELD OF THE INVENTION

The present invention relates to styryl dyes and compositions and to methods for using these dyes and compositions; to porous glass-polymer composites and to methods for using these composites; to methods and compositions for generating singlet oxygen and for killing cells and viruses; and to methods and media for storing and reading data generally and, more particularly, for reading and storing data in three dimensions.

BACKGROUND OF THE INVENTION

Frequency Upconversion

Frequency upconversion lasing is an important area of research and has become more interesting and promising in recent years. Compared to other coherent frequency upconversion techniques, such as optical harmonic generation or sum frequency mixing based on second- or third-order nonlinear optical processes, the major advantages of upconversion lasing techniques are: i) elimination of phase-matching requirements, ii) feasibility of using semiconductor lasers as pump sources, and iii) capability of adopting waveguide and fiber configurations. To date, two major technical approaches have been used to achieve frequency upconversion lasing: one is based on direct two-photon (or multi-photon) excitation of a gain medium (two-photon pumped); the other is based on sequential stepwise multi-photon excitation (stepwise multi-photon pumped).

The earliest reported two-photon pumped ("TPP") lasing was observed in PbTe crystal at 15° K. by Patel et al. *Phys. Rev. Lett.* 16:971–974 (1966). The pump wavelength was 10.6 μm, and the lasing wavelength was about 6.5 μm. Since then, TPP lasing action has also been observed in a number of other semiconductor crystals (Yoshida et al., *Japan. S. Appl. Phys.* 14:1987–1993 (1975); Gribkovskii et al., *Sov. J. Quantum Electron.* 9:1305–1307 (1979); Gao et al., *Proc. SPIE-Int. Soc. Opt. Eng.* 322:37–43 (1982); and Yang et al., *Appl. Phys. Lett.* 62:1071–1073 (1993)), but low operating temperature (about 10 to 260° K.) requirements limited their usefulness. A few reference papers report room temperature TPP lasing in metal vapor or gas systems (Bloom et al., *Appl. Phys. Lett.* 24:427–428 (1974); Willenberg et al., *Appl. Phys. Lett.* 37:133–135 (1980); and Goldston et al., *Laser Focus World*, 27:27–29 (1991)). In addition, room-temperature upconversion lasing has been successfully achieved in rare-earth-ion doped crystals (Silversmith et al., *Appl. Phys. Lett.* 51:1977–1979 (1987); MacFarlane et al., *Appl. Phys. Lett.* 52:1300–1302 (1988); Pollack et al., *Appl. Phys. Lett.* 54:869–871 (1989); Nguyen et al., *Appl. Opt.* 28:3553–3555 (1989); and McFarlane *Appl. Phys. Lett.* 54:2301–2302 (1989)), inorganic glasses (Bennett et al,. *Ceram. Trans.* 28:321–321 (1992) and Mita et al., *Appl. Phys. Lett.* 62:802–804 (1993)), and optical fibers (Hanna et al., *Opt. Commun.* 78:187–194 (1990) and Niccacio et al., *IEEE J. Quantum Electron.* QE-30:2634–2638 (1994)). These systems essentially involve sequential multiple photon absorption with single photon absorption to intermediate metastable states.

By contrast, there were more reported experimental results of TPP lasing behavior in organic dye solutions using commercial dyes, such as Rhodamine 6G, Rhodamine B, dimethyl POPOP ("DMP"), and 1,3,1',3'-tetramethyl-2,2'-dioxopyrimide-6,6'-carbocyanine hydrogen sulfate ("PYC"). (Rapp et al., *Phys. Lett.* 8:529–531 (1971); Topp et al., *Phys. Rev.* A3:358–364 (1971); Rubinov et al., *Appl. Phys. Lett.* 27:358–360 (1975); Prokhorenko et al., *Sov. S. Quantum Electron.* 11:139–141(1981); Qiu et al., *Appl. Phys.* B48:115–124 (1989); Zaporozhchenko et al., *Sov. J. Quantum Electron.* 19:1179–1181 (1989); and Swok et al., *Op. Lett.* 17:1435–1437 (1992)). However, commercial applications, especially those in recording, printing, display, communication, and the like, require, compact, lightweight, inexpensive, minimal maintenance lasers. In this respect, liquid dye lasers suffer a number of drawbacks, including the toxicity of the solvents used to dissolve the dye, concern over solvent evaporation, flow fluctuations in the dye solution, and difficulty of use in terms of size and maintenance. Moreover, most two-photon absorption ("TPA") induced stimulated emissions in dye solutions are cavityless lasing or superradiation (directional ASE). Recently, TPP upconversion stimulated emission was reported by Mukherjee, *Appl. Phys. Lett.* 62, 3423–3425 (1993) in a 4-dicyanomethylene-2-methyl-6-p-dimethylaminostyryl-4H-pyran ("DCM") doped poly(methyl methacrylate) ("PMMA") channel waveguide configuration.

However, DCM, like most commercial and other known dyes, has a TPA cross-section of from approximately $1 \times 10^{-50}$ cm$^4$-sec to approximately $1 \times 10^{-48}$ cm$^4$-sec, which is insufficient to achieve practical conversion efficiencies. In addition, solid state dye lasers have low damage resistance, which has been attributed to either polymer photodegradation or conversion of the dye to a non-emissive species. In view of the deficiencies in present day solid state dye lasers, dyes having greater TPA cross-sections and solid dye laser systems more resistant to photodegradation are desirable.

Optical Limiting

Optical limiting effects and devices are becoming increasingly important in the areas of nonlinear optics and optoelectronics. In particular, these materials are used in protective eyewear against intense infrared laser radiation exposure, in windows for sensitive detectors, and as stabilizers for laser beams used in optical communications and data processing by reducing beam intensity fluctuation. For optical power limiting applications, the material must have a low absorption of light at low intensity and must show a decrease of transmissivity at high intensities so that, at sufficiently high intensities, transmitted intensity levels off. There are several different mechanisms, such as reverse saturable absorption ("RSA"), two-photon absorption ("TPA"), nonlinear refraction (including all types of beam-induced refractive index changes), and optically induced scattering, which could lead to optical limiting behavior (Tutt et al., *Prog. Quant. Electr.* 17:299 (1993)). A number of research studies of optical limiting effects, related to TPA processes in semiconductor materials, have been reported (Walker et al., *Appl. Phys. Lett.* 48:683 (1986); Chang et al., *J. Appl.Phys.* 71:1349 (1992); Van Stryland et al., *Opt. Eng.* 24:613 (1985); and Hutchings et al., *J. Opt. Soc. Am.* B9:2065 (1992)). However, the two-photon absorption cross section of these materials is quite weak, which limits their applicability in many optical power-limiting situations. The search for new materials having larger TPA cross-sections and stronger optical power-limiting properties in the infrared continues.

Infrared Beam Detection

Since infrared light is not visible to the human eye, focusing, aligning, and adjusting the shape of infrared beams, particularly infrared laser beams, requires the use of a device which permits the user to visualize the beam. Conventional, commercially available infrared detection and indication cards, manufactured by Kodak and Kentek, respectively, typically employ a material which operates on thermal release effect principles, becoming visible when exposed to infrared radiation. Because of the nature of the visible effect, i.e. a color change in the surface layer of the card, the card is opaque and must be viewed from the side from which it is exposed. This is frequently inconvenient and makes beam alignment difficult, if not impossible. Furthermore, the commercially available detection sheets exhibit saturation at intensities lower than those used in most infrared laser applications. Consequently, these cards are of little value in assessing the intensity or intensity profile of the beam to which they are exposed. Moreover these detection cards have undesirably short lifetimes, especially when used to detect intense infrared laser beams, and degrade non-uniformly and unpredictably, making their use unreliable. The nature of the thermal mechanism by which these cards operate results in diffusion of the visible image, especially at the beam's perimeter. Since beam focus is often assessed and adjusted based on the sharpness of the image created, distortion of the visual image by the detection material is highly undesirable.

Recently, a new infrared detection card, consisting of an inorganic crystal powder dispersed in a plastic substrate cast into a film, has become available. The crystal powder produces visible light by second harmonic generation when exposed to infrared radiation and, consequently, may be observed from either side of the card. Nevertheless, the material is easily saturated, and cannot be used to assess beam intensity or intensity profile due to the scattering or diffusional nature of the dispersed powder. In addition, the low conversion efficiency of non-phase-matched second harmonic generation necessitates the use of large amounts of the crystal to achieve a reasonably visible image. This, when coupled with the high cost of the crystal, makes these infrared detection cards prohibitively expensive for most applications.

For these and other reasons, a needs remain for a transparent infrared detection card which produces an easily discernible image at reasonable cost and for one whose response is not saturated at intensities commonly encountered.

Lasing Media

Lasers (an acronym for light amplification by stimulated emission radiation) are light amplifying devices which produce high intensity pulses of monochromatic light concentrated in a well collimated beam commonly called a laser beam. The laser beam has found wide application in photography, communications, industrial measuring instruments, and the like.

Various materials have been used as lasing media. For example, it is known that stimulated emission can be produced in various organic solutions. The first such solutions were of dyes, as reported by Sorokin et al, *IBM Journal*, 2:130 (March 1967) ("Sorokin"), and, since then, devices which have been used to produce such stimulated radiation have commonly been known as "dye lasers". Some materials which fluoresce or scintillate outside the visible spectrum also have been used. A compilation of materials which have served as the active material in dye lasers is provided in Sorokin, in Kagan et al., *Laser Focus*, 26 (September 1968) ("Kagan"), and in Hecht, *The Laser Guidebook*, New York:McGraw Hill, pp. 263–295 (1992) ("Hecht").

U.S. patents which describe dye lasers include U.S. Pat. No. 3,541,470 to Lankard et al.; U.S. Pat. No. 3,679,995 to Sorokin; U.S. Pat. No. 3,684,979 to Myer et al.; U.S. Pat. No. 3,818,371 to Herz et al.; U.S. Pat. No. 4,397,023 to Newman et al.; U.S. Pat. No. 4,603,422 to Fletcher; and references cited therein.

The characteristics of traditional dye lasers which make them attractive are the possibilities of wide spectral range and tunability at low cost. The laser can be operated anywhere in the visible or into the ultraviolet or infrared ranges simply by employing a solution which emits electromagnetic radiation at the desired spectral wavelength.

Traditional dye lasers have not achieved their full potential because of various disadvantages. These include: (1) difficulty in pumping a number of useful materials because of low quantum efficiency or high excited state losses due to singlet-triplet transitions or due to triplet absorptions; (2) low conversion efficiencies, high coupling energy losses, and low repetition rates resulting from thermal effects induced during pumping; and (3) dye circulation problems and other limitations posed by thermal effects.

Several attempts have been made in the prior art to overcome these deficiencies by incorporating a traditional laser dye solution into a solid matrix. For example, Pacheco et al., "A Solid-State Flash-lamp-Pumped Dye Laser Employing Polymer Hosts," *Proceedings of the International Conference on Lasers '87* (1987) ("Pacheco") incorporated a laser dye solution into polymer hosts, such as polymethylmethacrylate, polycarbonate, and polystyrene. Polymer hosts, however, are not ideal for dye laser applications because they possess low photostability and low thermal stability.

Avnir, "The Nature of the Silica Cage as Reflected by Spectral Changes and Enhanced Photostability of Trapped Rhodamine 6G," *J. Phys. Chem.*, 88:5956–5959 (1984) ("Avnir") discloses the incorporation of Rhodamine 6G dye into a sol-gel derived silica matrix by adding the Rhodamine 6G dye to a silica sol prior to gelation. When a dopant compound is mixed into a sol before gelation, however, gradients are inevitably formed in the final product due to the migration of the dopant to the surface of the product during the subsequent aging and drying stages. Reaction byproducts are thus trapped within the matrix. Further, dye lasers prepared according to this method cannot be subjected to high temperature stabilization treatments without risking decomposition of the incorporated dye.

U.S. Pat. No. 4,878,224 to Kuder et al. ("Kuder") incorporated a solution of a laser dye and, a solvent into the pores of a porous glass matrix and then sealed the glass matrix to prevent migration of any of the solution components out of the pores. Dye lasers prepared according to this method, however, may be inefficient because solvent selection is highly critical. Not only must the solvent be compatible with the laser dye while in solution, but it must also possess photostability and thermal stability during lasing. Further, it is the solvent taken in combination with the laser dye, rather than the dye alone, which must provide adequate lasing effects.

U.S. Pat. No. 5,222,092 to Hench et al. ("Hench") describes a dye laser comprising a highly porous, consolidated silica sol-gel monolith having incorporated therein a laser dye. The laser dye is introduced into the pores of the matrix in a solvent and the solvent is then removed, thus depositing the dye as an adsorbed layer on the inner surfaces of the pores of the silica sol-gel matrix. Hench further describes sealing the surface of the dye-containing monolith with a polymer by contacting the monolith with an organic polymer solution to prevent migration of the dye out of the pores and to prevent contamination of the pores. However, the material disclosed in Hench possesses voids which contain air which can quench the lasing process. Further, the difference in refractive index between the air and silica sol-gel matrix can result in internal reflections which reduce laser output.

Another approach is based on the methods described in Pope et al., *J. Mater. Res.*, 4:1018 (1989). It involves infusion of a monomer containing the desired lasing dye into a porous sol-gel matrix and then polymerization of the monomer in situ to produce a matrix containing dye dispersed in polymer in the pores of the matrix. The methods are described in Reisfeld et al., *SPIE Proc.* 1182:230 (1989) ("Reisfeld"); Gvishi et al., *SPIE Proc.* 1972:390 (1993) ("Gvishi"); Shamrakov et al., *Chem. Phys. Lett.* 213:47 (1993) ("Shamrakov"); He et al., *Opt. Comm.* 111:82 (1994) ("He"); Dunn, "Sol-gel Encapsulated molecules: Optical Probes and Optical Properties," in Klein, ed., *Sol-Gel Optics: Processing and Applications*, Kluwer Academic Publishers, Chapter 14 (1993) ("Dunn"); Lo et al., Appl. Phys. B, 56:385 (1993) ("Lo"); and Canva et al., *SPIE Proc.*, 2288:298 (1994) ("Canva"). However, these composites are limited in that the method for their preparation requires that the dye be sufficiently soluble in monomer to produce a material with a dye concentration effective to permit lasing. This limitation is particularly problematic in situations where the lasing proceeds via a two photon absorption mechanism which frequently requires high dye concentrations.

Another deficiency in all of the aforementioned attempts to produce dye-doped matrices for use in lasing applications relates to the desirability of incorporating more than one dye to increase the range of wavelengths at which the laser can emit. Incorporating more than one dye in the solid polymer matrix described in Pacheco, in the sol gel described in Avnir, in the solutions described in Kuder, in the adsorbed layer described in Hench, and in the polymers described in Reisfeld, Gvishi, Shamrakov, He, Dunn, Lo, and Canva inevitably leads to quenching of one of the dyes by the other.

Attempts to incorporate optically-active materials into photostable optically transparent media for use as building blocks for photonic devices has not been limited to lasing dyes. The photonic properties of fullerenes have been a subject of extensive investigation in recent years. Their nonlinear optical properties and optical power limiting behavior have drawn much of the attention (Kafafi et al., *SPIE Proceedings on "Fullerenes and Photonics"* 2284:134 (1994); Justus et al., *Opt. Lett.* 18:1603 (1993); and Tutt et al., *Nature* 356:225 (1992)). In addition, luminescence from $C_{60}$ solutions at room temperature has recently been reported in Kim, *J. Am. Chem. Soc.* 114:4429 (1992). The past studies have mostly used fullerenes in solution and in a pure solid film form, although fullerene doped polymers have been described in Kost et al., *Opt. Lett* 18:334 (1993) and Prasad et al., *SPIE Proceedings on "Fullerenes and Photonics"* 2284:148 (1994). However, because of their limited solubility, fullerenes cannot be doped in high concentrations. Furthermore, devices which require a long interaction length (such as optical power limiters) need a high optical quality bulk form. Sol-gel processes offer the ability to prepare high optical quality bulks with a long interaction length. However, due to the limited solubility of fullerenes in solvents used for sol-gel processing, past approaches used fullerene suspensions to prepare films, xerogels (Bentivegna et al., *Appl. Phys. Lett.* 62:1721 (1993)), and sonogels (McBranch et al, *SPIE Proceedings on "Fullerenes and Photonics"* 2284:15 (1994)). Because the fullerenes are in suspension in the matrix in which they are dispersed, the optical transparency of the composites are compromised, and the long interaction lengths required are not attained.

To overcome the above-described limitations, as well as for other reasons, a need remains for photostable, optically-transparent media which incorporate photoactive materials.

Photodynamic Therapy

A promising new modality for controlling and treating tumors is photodynamic therapy ("PDT"). This technique uses a photosensitizer, which localizes at or near the tumor site and, when irradiated in the presence of oxygen, serves to produce cytotoxic materials, such as singlet oxygen ($O_2(^1\Delta_g)$) from benign precursors (e.g. ($O_2(^3\Sigma_g-)$). Diamagnetic porphyrins and their derivatives are the photosensitizers of choice for PDT. It has been known for decades that porphyrins, such as hematoporphyrin, localize selectively in rapidly growing tissues including sarcomas and carcinomas. Hematoporphyrin derivative ("HPD") is an incompletely characterized mixture of monomeric and oligomeric porphyrins. The oligomeric species, which are believed to have the best tumor-localizing ability, are marketed under the trade name PHOTOFRI II and are currently undergoing phase III clinical trials for obstructed endobronchial tumors and superficial bladder tumors. The mechanism of action is thought to be the photoproduction of singlet oxygen ($O_2$ ($^1\Delta_g$)), although involvement of superoxide anion or hydroxyl and/or porphyrin-based radicals cannot be entirely ruled out Promising as HPD is, it and other available photosensitizers (such as the phthalocyanihes and naphthophthalocyanines) suffer from serious disadvantages.

While porphyrin derivatives have high triplet yields and long triplet lifetimes (which allows them to transfer excitation energy efficiently to triplet oxygen), their absorption in the Q-band region parallels that of heme-containing tissues, typically having absorption bands at about 520 nm to about 620 nm. This generally limits the penetration of exciting radiation to depths of 2 to 5 mm. The biologic response is, on average, 2–3 times deeper than the lights direct penetration depth. As a result, the greatest attainable depth of PDT induced cellular changes is up to 15 mm, but, in most cases, it is less then a half this value. Since most of the incident energy used in photo-treatment is dispersed or attenuated by the patients' tissues before reaching the center of a deep-seated tumor, little of the light is available for singlet oxygen production and therapy at the tumor site.

This has limited the use of PDT to the treatment of tumors at or near the skin surface, such as those involved in bladder carcinomas, skin malignancies, and brain tumors. Clinically, PDT has found clinical use in the treatment of superficial and early tumors of the head and neck, often saving patients from additional surgery. PDT also appears promising as an adjuvant inoperative treatment of recurrent head and neck carcinomas. However, recent statistics from the National Cancer Institute estimate that pancreatic cancer is now the fourth most common cause of cancer death in the United States. One of the factors contributing to the lethality of pancreatic cancer is that the pancreas is deep-seated in the body and is not readily accessible for treatment by PDT.

Attempts to increase the effectiveness of PDT at greater depths by increasing the intensity of the light used to excite the photosensitizers have failed, largely because of the damage that such high intensity light inflicts on heme-containing tissues. On the other hand, attempts to increase the PDT effect by increasing the concentration of porphyrin photosensitizer have been thwarted by the inability of the body to metabolize the photosensitizer rapidly. Significant amounts of the sensitizing porphyrin thus remain in the patient's body, typically localized in the skin, long after photodynamic tumor treatment has ended, which makes patients photosensitive for weeks following treatment and requires that they stay out of bright light, especially sunlight, for that period. Increasing the dosage of photosensitizer only exacerbates this photosensitivity.

Most efforts to increase the effectiveness of photodynamic treatment of deep-seated or large tumors have focused on developing sensitizers which absorb in the spectral region where living tissues are relatively transparent (i.e. 700–1100 nm).

For example, some phthalocyanines and naphthophthalocyanines absorb in a spectral range in which there is less absorption by heme-containing biological materials. However, they have significantly lower triplet yields, they tend to be quite insoluble in polar protic solvents, and they are difficult to functionalize.

Other compounds, such as porphyrin derivatives having extended $\pi$ networks, purpurins, verdins, chlorophyl-like species, benzoporphyrins, and sulfonated phthalocyanines and napthophthalocyanines have also been tested. Of these, only the napthophthalocyanines absorb efficiently in the desirable >700 nm spectral region. However, these naptho-phthalocyanines are difficult to prepare in a chemically pure, water soluble form and have only minimal absorption in regions outside of the regions where heme-containing biological materials absorb.

A third generation of sensitizers, having absorption at longer (650 nm or greater) wavelengths, such as those based on the texaphrin macrocycle described in U.S. Pat. No. 5,439,570 to Sessler et al., have permitted a 30% increase in treatment depths. However, even these sensitizers fail to absorb at wavelengths sufficiently long to permit penetration of the exciting radiation to the depths at which many deep-seated tumors lie.

The photodynamic generation of singlet oxygen has also been exploited in a number of other areas, such as, blood purification. Blood purification has become increasingly important in view of the concern with blood's role in the transmission of acquired immunodeficiency syndrome ("AIDS"). AIDS, first reported in 1981 as occurring among male homosexuals, is a fatal human disease which has now reached pandemic proportions. At present, sexual relations and needle-sharing are the dominant mechanisms for the spread of AIDS. However, cases where infection is transmitted by transfused blood have not been uncommon. Since testing of blood supplies has begun, the number of AIDS infections due to blood transfusions has dropped considerably. However, an absolutely fail-proof means must be developed to insure that all stored blood samples are free of the AIDS virus (and, ideally, other blood-borne pathogens).

Serologic tests for HIV-1 are insufficient to detect all infected blood samples, particularly those derived from donors who have contracted the disease but who have not yet produced detectable antibodies.

Since testing procedures cannot, at present, insure that blood is free of the HIV virus, blood purification is an attractive alternative. Any blood purification procedure used to remove AIDS virus or other blood-borne pathogens should operate without introducing undesirable toxins, damaging normal blood components, or inducing the formation of harmful metabolites. This precludes the use of common antiviral systems, such as those based on heating, UV irradiation, or purely chemical means. A promising approach is the photodynamic one alluded to above. Research at the Baylor Research Foundation have shown that HPD and PHOTOFRIN™, in far lower dosages than are required for tumor treatment, act as efficient photosensitizers for the photo-deactivation of cell-free HIV-1, herpes simplex virus ("HSV"), hepatitis, and other enveloped viruses. The success of this procedure derives from the fact that these photosensitizers localize selectively at or near the morphologically characteristic and physiologically essential viral membrane ("envelope") and catalyze the formation of singlet oxygen upon photoirradiation. The singlet oxygen destroys the essential membrane envelope, killing the virus and eliminating infectivity. Photodynamic blood purification procedures, therefore, rely on the use of photosensitizers which localize selectively at viral membranes, just as more classic tumor treatments require photosensiiizers that are absorbed or retained preferentially at tumor sites. Simple enveloped DNA viruses like HSV-1 are good models for testing putative photosensitizers for potential use in killing the far more hazardous HIV-1 retrovirus. This correspondence holds only as far as freely circulating (as opposed to intracellular) viruses are concerned. Complete prophylactic removal of HIV-1 from blood products will require the destructive removal of the virus from within monocytes and T lymphocytes.

The above-described photodynamic blood purification methods suffer from several drawbacks. One of these relates to the porphyrin sensitizer having absorption which is substantially at the same wavelengths as the heme group in hemoglobin, an important constituent in blood. As a result, a portion of the light used to irradiate the photosensitizer is absorbed by the heme. This has two consequences. First, it limits the intensity of the radiation that can be used because the energy absorbed by the heme is dissipated via thermal pathways resulting in localized heating of the hemoglobin protein. At increased intensities, the hemoglobin molecule cannot dissipate the heat to its surroundings fast enough to prevent its thermal denaturation. Second, the absorption of the irradiating light by the heme attenuates the depth to which the light will penetrate. This necessitates that the blood be irradiated in thin vessels or with agitation. Thin vessels have high surface areas which tends to damage the delicate red blood cells. Agitation of blood is often devastating to red blood cells and requires expensive equipment and, even then, cannot be achieved without some loss.

A need, therefore, remains for new photodynamic blood treatment methods and photodynamic therapy protocols.

Data Storage

The need for data storage and processing has been increasing at a high rate. In response to this need, significant advances in memory design have been made. Two major considerations which impact the desirability and utility of various memory devices are cost per bit of information stored and access time. For example, conventional magnetic tape storage costs $10^{-5}$ ¢/bit and has an access time of 100 seconds. Disk, drum, and core storage have considerably faster access times (300 msec, 10 msec, and 1 μsec, respectively) and considerably higher costs (0.05, 0.01, and 2 ¢/bit, respectively). Semiconductor storage devices offer yet faster access times (100 nsec) but at still higher cost (20 ¢/bit).

Optical data storage systems have access times of 10 nsec and costs which range from $10^{-4}$ to $10^{-3}$ ¢/bit. Conventional two-dimensional optical data storage can register information at about $10^8$ bits per square centimeter using visible or infrared wavelengths at the diffraction limit. In view of the increasing need for still less expensive data storage systems with still faster access times, and recognizing that cost and access time is governed in large measure by the density of the stored data, efforts have focused on increasing data storage density.

It has been proposed that by writing and reading data in a three-dimensional format, data storage densities of greater that $10^{12}$ bits per cubic centimeter could be achieved. U.S. Pat. Nos. 4,466,080 and 4,471,470 to Swainson et al. (collectively "Swainson"), for example, disclose the use of two intersecting beams of radiation which are matched to selected optical properties of an active medium to form and to detect inhomogeneities. In such a system, a stack of two-dimensional planar bit arrays effectively multiplies data density by the number of planes in the third dimension. In media which are linearly photoactive, the primary difficulty with such a scheme is cross-talk between planes. However, writing with three-dimensional resolution in thick media can be accomplished by using media which are non-linearly photoactive.

Consider, for example, a focused Gaussian beam well below the saturating intensity, incident on a physically thick but optically thin absorbing sample. In the case where the optically active medium is linear, the same amount of energy is absorbed in each plane perpendicular to the axis of the incident beam, irrespective of the distance from the focal plane, because the net flux passing through each plane is approximately the same. Since the photoactivity is of a linear photoactive medium is proportional to absorption, planes above and below the particular plane being addressed are strongly contaminated. Where the photoactive media is quadratically dependent on intensity, however, net excitation per plane falls off with the inverse of the square of the distance from the plane being addressed. Therefore, information can be written in the plane being addressed without significantly contaminating adjacent planes, if the planes are sufficiently spaced.

Several approaches to three-dimensional optical data storage have been investigated. These include: holographic recording on photorefractive media (Poch, *Introduction to Photorefractive Nonlinear Optics*, New York:John Wiley and Sons (1993) and Gunter et al., eds., *Topics in Applied Physics*, Vols. 61 & 62 *Photorefractive Materials and Their Applications I* and *II*, Berlin:Springer-Verlag, (1989 (Vol. 61) and 1990 (Vol 62))); hole burning (Moerner, ed., *Persistent Spectral Hole Burning: Science and Applications* Berlin:Springer (1987)), and photon echo (Kim et al., *Opt. Lett.*, 14:423–424 (1989)).

U.S. Pat. No. 5,289,407 to Stickler et al. employs confocal microscopy to write information in a three-dimensional two-photon active liquid acrylate ester blend photopolymer as submicron volume elements of altered index of refraction. Each element is either written (characterized by a changed index of refraction) or unwritten (characterized by an unchanged index of refraction). The pattern of inhomogeneities in the three-dimensional photopolymer are then detected by differential interference contrast or confocal microscopy. The writing speed is slow (on the order of 10 ms), although significant improvement is said to be possible. A more fundamental disadvantage to the method, however, is the need to use a light in the blue region of the visible spectrum to read the stored data Most polymers have reduced transparency in the blue region, and, consequently, the use a blue read light limits the depth at which data can be read.

Two-photon based data storage in polymer systems have also been described in Parthenopoulos et al., "Three-dimensional Optical Storage Memory,"*Science*, 245:843–845 (1989); Parthenopoulos et al., "Two-photon Volume Information Storage in Doped Polymer Systems," *J. Appl. Phys.*, 68:5814–5818 (1990); Dvornikov et al., Accessing 3D memory Information by Means of Nonlinear Absorption," *Opt. Comm.*, 119:341–346 (1995); U.S. Pat. No. 5,268,862 to Rentzepis; and U.S. Pat. No. 5,325,324 to Rentzepis et al. In these systems, two beams (532 nm and 1064 nm) were made to intersect in the bulk of the polymer sample containing a spirobenzopyran dispersed therein. At the point of intersection, the spirobenzopyran undergoes two-photon absorption and transformation to a form which fluoresces when excited by two 1064 nm photons. Each data point could assume one of two states (exposed or unexposed), and, in this manner, data was stored as an three-dimensional array of binary information. The lifetime of the transformed state of the sprirobenzopyran was on the order of minutes at room temperature and on the order of days in dry ice. These lifetimes, though suitable for some applications, do not meet the lifetime requirements of many data storage applications.

For these and other reasons, the need exists for data storage media having the capacity to store information at higher densities.

SUMMARY OF THE INVENTION

The present invention relates to a composition which includes a matrix material and a styryl compound dispersed therein. The styryl compound has the formula:

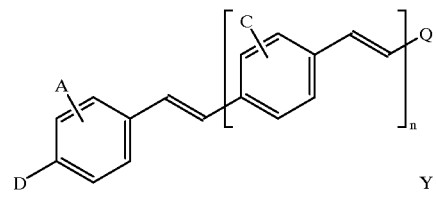

wherein
D is an electron donating group;
Q is an electron acceptor selected from the group consisting of electron acceptors having the formulae:

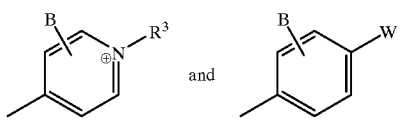

W is an electron accepting group,
R³ is selected from the group consisting of substituted or unsubstituted alkyl or substituted or unsubstituted aryl moieties,
n is an integer from 0 to 4, A, B, and C are substituents of their rings and are each independently selected from the group consisting of alkyl, alkoxy, hydroxyallyl, sulfoalkyl, carboxyallyl, and hydrogen, and Y is a counterion.

The present invention also provides a method of detecting infrared radiation. The method comprises placing a styryl compound having the above formula at a location potentially exposed to the infrared radiation and evaluating whether the styryl compound has been exposed to the infrared radiation at the location.

Another aspect of the present invention pertains to a method for reducing intensity of infrared radiation. The method comprises providing a styryl compound having the above formula and passing infrared radiation through the compound.

The present invention also relates to a method for converting infrared radiation to visible radiation. The method includes providing a styryl compound having the above formula and exposing the compound to infrared radiation.

The present invention further relates to a styryl compound having the formula:

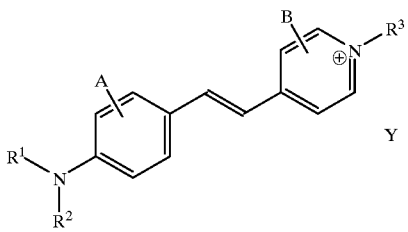

wherein $R^1$, $R^2$, and $R^3$ are the same or different and are selected from the group consisting of substituted or unsubstituted alkyl or substituted or unsubstituted aryl moieties, A and B are substituents of their rings and are each independently selected from the group consisting of alkyl, alkoxy, hydroxyalkyl, sulfoalkyl, carboxyalkyl, and hydrogen, and Y is a counterion.

The styryl compounds and compositions of the present invention have much greater two-photon absorption cross-sections, much stronger upconversion fluorescence emission, and increased stability compared to the organic dyes of the prior art. Moreover, they are inexpensive to make and are readily incorporated into matricies. These and other properties of these compounds make them well-suited for use in two-photon pumped cavity lasing, two-photon pumped up-conversion lasing, optical power limiting, optical power stabilization, optical signal reshaping, and infrared beam detection and indication.

In another aspect, the present invention also relates to a composite comprising a glass having pores. The pores have a pore surface, on which is coated a coating material. The composite further comprises a polymeric material in the pores.

The invention also relates to a process for producing an optically responsive composite. The process comprises providing a glass having pores, which pores have a pore surface coated with an optically responsive coating. A monomeric material is infused into the pores and permitted to polymerize to produce a polymeric material.

The composites of the present invention are of high optical quality and can be large-sized monolithic bulk forms useful in various photonic functions such as lasing, optical power limiting, and non-linear optical response. Because the pores of the glass contain a polymer whose refractive index is closer to the refractive index of the glass than is the refractive index of air, the composites of the present invention exhibit enhanced optical properties. Furthermore, the polymer-filled pores of the composites of the present invention provide a convenient way to prevent migration of the coated material out of the composite as well as to inhibit contamination of the composite with materials which reduce their damage threshold or shorten their lifespan.

The composites are particularly useful to form multiphasic nanostructured composites wherein the phase separation can be on the nanometer scale. By dispersing a second optically responsive material in the polymeric material, a composite having two phases, an interfacial phase comprising the coated material on the pore surface and a polymer phase comprising the dispersed material in the polymer, can be produced. In contrast to composites containing two optically responsive materials mixed in a single phase, the multiphasic nanostructured composites of the present invention retain the optical response characteristic of each material. In terms of applying the present invention to tunable lasers by using two laser dyes which reside in different phases, reduced energy transfer between the dyes results in a composite having a broad tunability range of lasing. Similarly, by using two optical power limiters, each localized in a separate phase of the composite of the present invention, a composite having optical limiting properties over an expanded wavelength and power range can be constructed.

The present invention, in yet another aspect thereof, relates to a method for producing singlet oxygen. A composition which includes a photosensitizer having absorption at a wavelength from about 380 nm to about 760 nm and a dye capable of converting photons having energies of from about 660 to about 1300 nm to photons having energies of from about 380 to about 760 nm is formed. The composition is exposed to light having a wavelength of from about 660 nm to about 1300 nm in the presence of oxygen to produce singlet oxygen.

The present invention also relates to a method of killing cells or viruses. An effective amount of a photosensitizer having absorption at a wavelength from about 380 nm to about 760 nm is provided proximate to the cells or viruses. An effective amount of a dye capable of converting photons having energies of from about 660 to about 1300 nm to photons having an energies of from about 380 to about 760 nm is also provided proximate to the cells or viruses. The dye is then exposed to light having a wavelength of from about 660 to about 1300 nm in the presence of oxygen under conditions effective to produce a cytotoxic effect on the cells or viruses.

In another aspect, the present is directed to a composition which includes a photosensitizer and a dye. The photosensitizer has absorption at a wavelength from about 380 nm to about 760 nm, and the dye is capable of converting photons having energies of from about 660 nm to about 1300 nm to photons having an energies of from about 380 to about 760 nm. The composition, when exposed to light having a wavelength from about 660 nm to about 1300 nm, produces singlet oxygen.

The methods and compositions of the present invention produce singlet oxygen in masses which are substantially opaque to 380–760 nm light or in situations where a material absorbing 380–760 nm light attenuates the penetration of the 380–760 nm light. These methods and compositions are especially useful when light-induced singlet oxygen generation is desired in biological materials, such as in photodynamic therapy or blood purification protocols.

In yet another aspect, the present invention relates to a method for recording data. A three-dimensional matrix, including a plurality of dye molecules, is provided. A first volume element in the three-dimensional matrix is exposed to actinic radiation for a duration and at an intensity effective to alter detectably a fraction between 0.3 and 0.7 of the dye molecules contained therein. The detectably altered dye molecules are substantially uniformly dispersed in the first volume element.

The present invention also relates to another method for recording data. The method includes providing a three-dimensional matrix including a plurality of dye molecules having the formula:

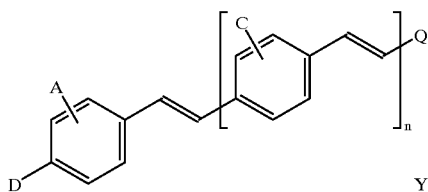

wherein D, Q, W, $R^3$, n, A, B, C, and Y are defined as above. The method further includes exposing a first volume element in the three-dimensional matrix to actinic radiation under conditions effective to alter detectably all or a fraction of the dye molecules contained in the first volume element.

In another aspect, the present is directed to a data storage medium. The data storage medium includes a three-dimensional matrix, including a first volume element, and a plurality of dye molecules. A fraction between about 0.3 and about 0.7 of the dye molecules contained in the first volume element are detectably altered, and the detectably altered dye molecules are substantially uniformly dispersed through the first volume element.

The present invention is also directed to a data storage medium which includes a three-dimensional matrix and a plurality of dye molecules substantially uniformly dispersed in the three-dimensional matrix. The dye molecules have the formula:

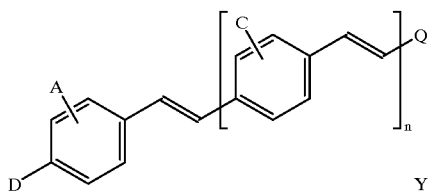

wherein D, Q, W, $R^3$, n, A, B, C, and Y are defined as above.

The data storage methods and media of the present invention have approximately $10^{12}$ volume elements per square centimeter. Each of the volume elements can store a single bit, digital information of approximately 8 bits, or analog information. Because of its ability to store analog data, such as grayscale value or color density values, the methods and media of the present invention are particularly useful for storing or archiving a series of two-dimensional black and white or color images, such as frames of a movie.

BRIEF DESCRIPTION OF THE DRAWINGS

FIG. 1 demonstrates the effects of a saturable absorption medium, a linear medium, and an optical limiting medium on incident (input) radiation.

FIG. 2 are schematics illustrating the use of the compounds of the present invention in optical limiting applications.

FIGS. 5A and 5B, respectively, are scanned images of a cross-linked polyurethane polymer sheet containing dye1 and a commercial infrared detector sheet manufactured by Kodak, each exposed to a Nd-YAG laser beam.

FIG. 12A represents the pulse waveform of the Nd-YAG laser beam used to pump the 7 mm-long, dye1-doped poly(hydroxyethyl methacrylate) ("poly(BEMA)") rod used in Example 15. FIGS. 12B, 12C, and 12D represent the two-photon pumped, ~600 nm cavity lasing pulse waveforms at pump energy levels of 0.88 mJ, 0.93 mJ, and 1.5 mJ, respectively.

FIG. 20A is an absorption spectrum of BBTDOT-doped composite glass (dashed line), $C_{60}$-doped composite glass (dotted line), and BBTDOT+$C_{60}$-doped composite glass (dash-dotted line). FIG. 20B is a magnified spectrum of the red region of FIG. 20A. The arrow indicates the 0→0 transition centered at 622 nm.

FIG. 22 depicts the normalized transmitted intensity as a function of the incident intensity for the three composite glasses at 532 (empty circles) and 800 nm (filled circles). The dotted line represents the linearity of the system used for measurement.

DETAILED DESCRIPTION OF THE INVENTION

Styryl Compounds and Compositions

Figure 1A:
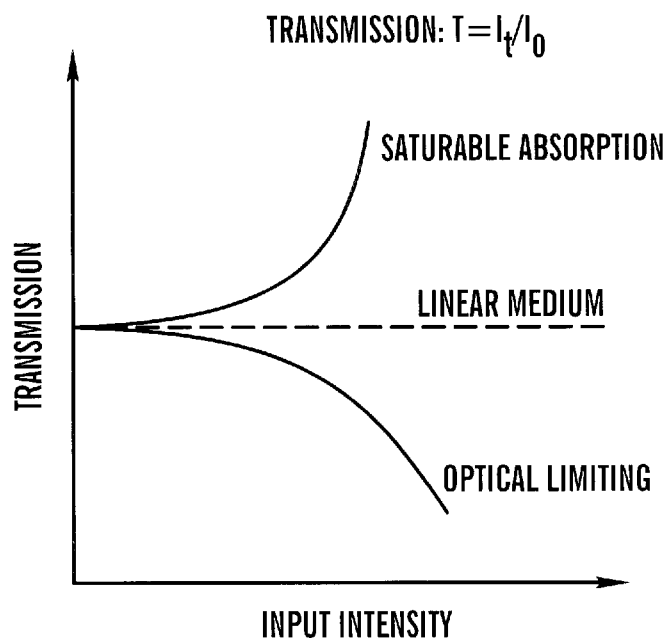
FIG. 1A is a plot of transmission, T ($T=T_t/I_o$), as a function of input intensity. $I_o$.

The present invention relates to dyes and dye compositions and to methods for using these dyes and dye compositions in two-photon pumped cavity lasing, in infrared beam detection, and in optical limiting. One aspect of the present invention relates to a compound having the formula:

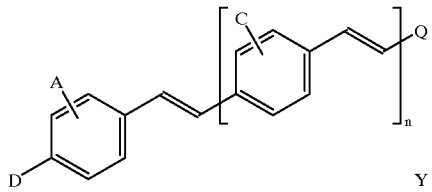

D is an electron donating group. Suitable electron donating groups include unsubstituted amines having the formula —$NH_2$, monosubstituted amines having the formula —$NHR^1$, disubstituted amines having the formula —$NR^1R^2$, alcohols having the formula —OH, ethers having the formula —$OR^1$, or amides having the formula —NHC(O)$R^1$. Preferably, the electron donating group is a disubstituted amine.

Q is an electron acceptor selected from the group consisting of electron acceptors having the formulae:

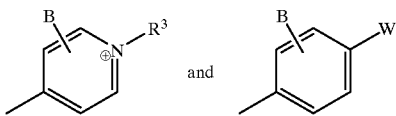

and

W is an electron accepting group. Suitable electron accepting groups include, for example, —$NO_2$, —CN, —C(CN)=C(CN)$_2$, substituted or unsubstituted alkyl sulfates or substituted or unsubstituted aryl sulfates having the formula —$SO_2R^3$ (e.g. methyl sulfate, ethyl sulfate, phenyl sulfate, and tolyl sulfate), ketones having the formula —C(O)$R^3$, carboxylic acids having the formula —COOH, carboxylic acid esters having the formula —COO$R^3$, or carboxylic acid salts having the formula —COOM, where M is a cation. Suitable cations include ammonium ions and metal ions, such as alkali metal ions (e.g. $Li^+$, $Na^+$, and $K^+$), alkaline earth metal ions (e.g. $Mg^{2+}$ and $Ca^{2+}$), and transition metal ions. Preferably, W is a sulfate having the formula —$SO_2R^3$.

$R^1$, $R^2$, and $R^3$ are substituted or unsubstituted alkyl groups, preferably of from 1 to 8 carbon atoms (e.g., methyl, ethyl, propyl, and the like), or substituted or unsubstituted aryl groups, preferably of from 6 to 20 carbon atoms (e.g., phenyl, tolyl). $R^1$, $R^2$, and $R^3$ may each be substituted with any of a number of known substituents, such as sulfo, carboxy, cyano, halogen (e.g., fluoro, chloro), hydroxy, alkenyl (e.g., allyl, 2-carboxy-allyl), alkoxy (e.g., methoxy, ethoxy), aryl (e.g., phenyl, p-sulfophenyl), aryloxy (e.g., phenyloxy), carboxylate (e.g., methoxycarbonyl, ethoxycarbonyl), acyloxy (e.g., acetyloxy), acyl (e.g., acetyl, propionyl), and others known to those skilled in the art. Each of $R^1$, $R^2$, and $R^3$ can be the same or different and the combination is selected primarily with consideration given to the substitution's effect on the solubility of the dye, although other factors, such as availability of starting materials and synthetic ease, may enter into the selection. Solubility is generally increased with alkyl groups bearing polar or ionizable substituents, such as hydroxyalkyl, sulfoalkyl, and carboxyalkyl, having from 1 to 8 carbon atoms.

n is an integer from 0 to 4, and, preferably, n is 0.

A, B, and C are substituents of their rings and are each independently selected from the group consisting of alkyl, alkoxy, hydroxyalkyl, sulfoalkyl, carboxyalkyl, preferably having from 1 to 8 carbon atoms, and hydrogen. Preferably, each of A, B, and C are hydrogen.

Y is a counterion necessary to balance the charge of the compound. The counterion may be ionically complexed to the molecule or it may be part of the dye molecule itself to form an intramolecular salt. Such counterions are well-known in the art. For example, when Y is an anion (e.g., when D is —$NR^1R^2$, Q is —($C_5H_4N$)—$R^3$, and $R^1$, $R^2$, and $R^3$ are unsubstituted alkyl), examples of Y include tetraphenylborate, chloride, bromide, iodide, p-toluene sulfonate, methane sulfonate, methyl sulfate, ethyl sulfate, perchlorate, $BF_4^-$, $PF_6^-$; and the like. When Y is a cation (e.g., when D is —$NR^1R^2$, Q is —($C_5H_4N$)—$R^3$, and two or more of $R^1$, $R^2$, and $R^3$ are sulfoalkyl or carboxyalkyl), examples of Y include sodium, potassium, triethylammonium, and the like. It is to be understood that where A, B, C, W, and D are non-ionic, no counterion, Y, need be present.

One preferred compound of the present invention has the formula:

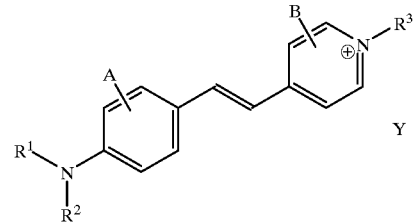

where $R^1$, $R^2$, and $R^3$, A, and B are defined as above. Because of their enhanced solubility, compounds having this formula where $R^1$ and $R^3$ are selected from the group consisting of hydroxyalkyl, sulfoalkyl, and carboxyalkyl and where $R^2$ is unsubstituted alkyl are particularly preferred. Another preferred compound has the formula:

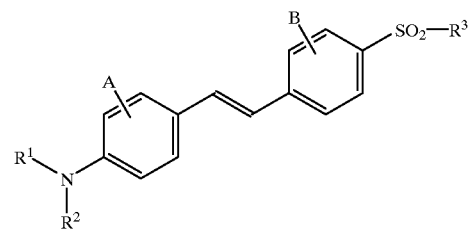

where $R^1$, $R^2$, and $R^3$, A, and B are defined as above. Because of their enhanced solubility, compounds having these formulae where $R^1$ and $R^3$ are selected from the group consisting of hydroxyalkyl, sulfoalkyl, and carboxyalkyl and where $R^2$ is unsubstituted alkyl are more preferred. Of these, the most preferred compounds are those where $R^1$ is hydroxyethyl, $R^2$ is C1 to C4 unsubstituted alkyl, and $R^3$ is C2 to C8 hydroxyalkyl.

Illustrative examples of compounds of the present invention are as follows:

trans-4-[p-(N,N-dimethylamino)styryl]phenyl methyl sulfate;

trans-4-[p-(N,N-dimethylamino)styryl]phenyl ethyl sulfate;

trans-4-[p-(N,N-dimethylamino)styryl]phenyl 2-hydroxyethyl sulfate;

trans-4-[p-(N,N-dimethylamino)styryl]phenyl 3-hydroxypropyl sulfate;

trans-4-[p-(N,N-dimethylamino)styryl]phenyl 4-hydroxybutyl sulfate;

trans-4-[p-(N,N-dimethylamino)styryl]phenyl 6-hydroxyhexyl sulfate;

trans-4-[p-(N-methyl-N-ethylamino)styryl]phenyl methyl sulfate;

trans-4-[p-(N-methyl-N-ethylamino)styryl]phenyl ethyl sulfate;

trans-4-[p-(N-methyl-N-ethylamino)styryl]phenyl 2-hydroxyethyl sulfate;

trans-4-[p-(N-methyl-N-ethylamino)styrylphenyl 3-hydroxypropyl sulfate;

trans-4-[p-(N,N-methyl-N-ethylamino)styryl]phenyl 4-hydroxybutyl sulfate;

trans-4-[p-(N-methyl-N-ethylamino)styryl]phenyl 6-hydroxyhexyl sulfate;

trans-4-[p-(N,N-diethylamino)styryl)phenyl methyl] sulfate;
trans-4-[p-(N,N-diethylamino)styryl]phenyl ethyl sulfate;
trans-4-[p-(N,N-diethylamino)styryl]phenyl 2-hydroxyethyl sulfate;
trans-4-[p-(N,N-diethylamino)styryl]phenyl 3-hydroxypropyl sulfate;
trans-4-[p-(N,N-diethylamino)styryl]phenyl 4-hydroxybutyl sulfate;
trans-4-(p-(N,N-diethylamino)styryl]phenyl 6-hydroxyhexyl sulfate;
trans-4-[p-(N-methyl-N-(2-hydroxyethyl)amino)styryl] phenyl methyl sulfate;
trans-4-[p-(N-methyl-N-(2-hydroxyethyl)amino)styryl] phenyl ethyl sulfate;
trans-4-[p-(N-methyl-N-(2-hydroxyethyl)amino)styryl] phenyl 2-hydroxyethyl sulfate;
trans-4-[p-(N-methyl-N-(2-hydroxyethyl)amino)styryl] phenyl 3-hydroxypropyl sulfate;
trans-4-[p-(N-methyl-N-(2-hydroxyethyl)amino)styryl] phenyl 4-hydroxybutyl sulfate;
trans-4-[p-(N-methyl-N-(2-hydroxyethyl)amino)styryl] phenyl 6-hydroxyhexyl sulfate,
trans-4-[p-(N-ethyl-N-(2-hydroxyethyl))amino)styryl] phenyl methyl sulfate;
trans-4-[p-(N-ethyl-N-(2-hydroxyethyl)amino)styryl] phenyl ethyl sulfate;
trans-4-[p-(N-ethyl-N-(2-hydroxyethyl)amino)styryl] phenyl 2-hydroxyethyl sulfate;
trans-4-[p-(N-ethyl-N-(2-hydroxyethyl)amino)styryl] phenyl 3-hydroxypropyl sulfate;
trans-4-[p-(N-ethyl-N-(2-hydroxyethyl)amino)styryl] phenyl 4-hydroxybutyl sulfate;
trans-4-[p-(N-ethyl-N-(2-hydroxyethyl)amino)styryl] phenyl 6-hydroxyhexyl sulfate;
trans-4-[p-(N,N-di-(2-hydroxyethyl)amino)styryl]phenyl methyl sulfate;
trans-4-[p-(N,N-di-(2-hydroxyethyl)amino)styryl]phenyl ethyl sulfate;
trans-4-[p-(N,N-di-(2-hydroxyethyl)amino)styryl]phenyl 2-hydroxyethyl sulfate;
trans-4-[p-(N,N-di-(2-hydroxyethyl)amino)styryl]phenyl 3-hydroxypropyl sulfate;
trans-4-[p-(N,N-di-(2-hydroxyethyl)amino)styryl]phenyl 4-hydroxybutyl sulfate;
trans-4-[p-(N,N-di-(2-hydroxyethyl)amino)styryl]phenyl 6-hydroxyhexyl sulfate;
trans-4-[p-(N,N dimethylamino)styryl]-N-methylpyridinium tetraphenylborate;
trans-4-[p-(N,N-dimethylamino)styryl]-N-ethylpyridinium tetraphenylborate;
trans-4-[p-(N-methyl-N-ethylamino)styryl]-N-methylpyridinium tetraphenylborate;
trans-4-[p-(N-methyl-N-ethylamino)styryl]-N-ethylpyridinium tetraphenylborate;
trans-4-[p-(N,N-diethylamino)styryl]-N-methylpyridinium tetraphenylborate;
trans-4-[p-(N,N-diethylamino)styryl]-N-ethylpyridinium tetraphenylborate;
trans-4-[p-(N,N-dimethylamino)styryl]-N-(2-hydroxyethyl)pyridinium tetraphenylborate;
trans-4-[p-(N-methyl-N-(2-hydroxyethyl)amino)styryl]-N-methylpyridinium tetraphenylborate;
trans-4-[p-(N-methyl-N-(2-hydroxyethyl)amino)styryl]-N-(2-hydroxyethyl)pyridinium tetraphenylborate;
trans-4-[p-(N,N-diethylamino)styryl]-N-(2-hydroxyethyl)pyridinium tetraphenylborate;
trans-4-[p-(N-ethyl-N-(2-hydroxyethyl)amino)styryl]-N-ethylpyridinium tetraphenylborate;
trans-4-[p-(N-ethyl-N-(2-hydroxyethyl)amino)styryl]-N-(2-hydroxyethyl)pyridinium tetraphenylborate;
trans-4-[p-(N,N-di-(2-hydroxyethyl)amino)styryl]-N-(2-hydroxyethyl)pyridinium tetraphenylborate;
trans-4-[p-(N-methyl-N-ethylamino)styryl]-N-(2-hydroxyethyl)pyridinium tetraphenylborate;
trans-4-[p-(N-methyl-N-(2-hydroxyethyl)amino)styryl]-N-ethylpyridinium tetraphenylborate;
trans-4-[p-(N-ethyl-N-(2-hydroxyethyl)amino)styryl]-N-methylpyridinium tetraphenylborate;
trans-4-[p-(N,N-di-(2-hydroxyethyl)amino)styryl]-N-ethylpyridinium tetraphenylborate;
trans-4-[p-(N,N-di-(2-hydroxyethyl)amino)styryl]-N-methylpyridinium tetraphenylborate;
trans-4-[p-N,N-dimethylamino)styryl-N-methylpyridinium iodide;
trans-4-[p-(N,N-dimethylamino)styryl]-N-ethylpyridinium iodide;
trans-4-[p-(N-methyl-N-ethylamino)styryl]-N-methylpyridinium iodide;
trans-4-[p-(N-methyl-N-ethylamino)styryl]-N-ethylpyridinium iodide;
trans-4-[p-(N,N-diethylamino)styryl]-N-methylpyridinium iodide;
trans-4-[p-(N,N-diethylamino)styryl]-N-ethylpyridinium iodide;
trans-4-[p-(N,N-dimethylamino)styryl]-N-(2-hydroxyethyl)pyridinium iodide;
trans-4-[p-(N-methyl-N-(2-hydroxyethyl)amino)styryl]-N-methylpyridinium iodide;
trans-4-[p-(N-methyl-N-(2-hydroxyethyl)amino)styryl]-N-(2-hydroxyethyl)pyridinium iodide;
trans-4-[p-(N,N-di-(2-hydroxyethyl)amino)styryl]-N-(2-hydroxyethyl)pyridinium iodide;
trans-4-[p-(N,N-diethylamino)styryl]-N-(2-hydroxyethyl)pyridinium iodide;
trans-4-[p-(N-ethyl-N-(2-hydroxyethyl)amino)styryl]-N-ethylpyridinium iodide;
trans-4-[p-(N-ethyl-N-(2-hydroxyethyl)amino)styryl]-N-(2-hydroxyethyl)pyridinium iodide;
trans-4-[p-(N-methyl-N-ethylamino)styryl]-N-(2-hydroxyethyl)pyridinium iodide;
trans-4-[p-(N-methyl-N-(2-hydroxyethyl)amino)styryl]-N-ethylpyridinium iodide;
trans-4-[p-(N-ethyl-N-(2-hydroxyethyl)amino)styryl]-N-methylpyridinium iodide;
trans-4-[p-(N,N-di-(2-hydroxyethyl)amino)styryl]-N-ethylpyridinium iodide;
trans-4-[p-(N,N-di-(2-hydroxyethyl)amino)styryl]-N-methylpyridinium iodide;
trans-4-[p-N-methyl-N-sulfobutylamino)styryl]-N-methylpyridine;
trans-4-[p-(N-methyl-N-sulfobutylamino)styryl]-N-sulfobutylpyridine;

trans-4-p-(N,N-diethylamino)styryl]-N-sulfobutylpyridine;

trans-4-[p-N-ethyl-N-sulfobutylamino)styryl]-N-ethylpyridine;

trans-4-[p-(N-ethyl-N-sulfobutylamino)styryl]-N-sulfobutylpyridine;

trans-4-[p-(N-methyl-N-ethylamino)styryl]-N-sulfobutylpyridine;

trans-4-[p-(N-methyl-N-sulfobutylamino)styryl-N-ethylpyridine;

trans-4-[p-(N-ethyl-N-sulfobutylamino)styryl]-N-methylpyridine;

trans-4-[p-(N-methyl-N-sulfobutylamino)styryl]-N-(2-hydroxyethyl)pyridine;

trans-4-[p-N-methyl-N-(2-hydroxyethyl)amino)styryl]-N-sulfobutylpyridine;

trans-4-[p-(N-ethyl-N-sulfobutylamino)styryl]-N-(2-hydroxyethyl)pyridine;

trans-4-[p-(N-ethyl-N-(2-hydroxyethyl)amino)styryl]-N-sulfobutylpyridine; and trans-4-[p-(N,N-di-(2-hydroxyethyl)amino)styryl]-N-sulfobutylpyridine.

Particularly preferred are compounds having the formulae:

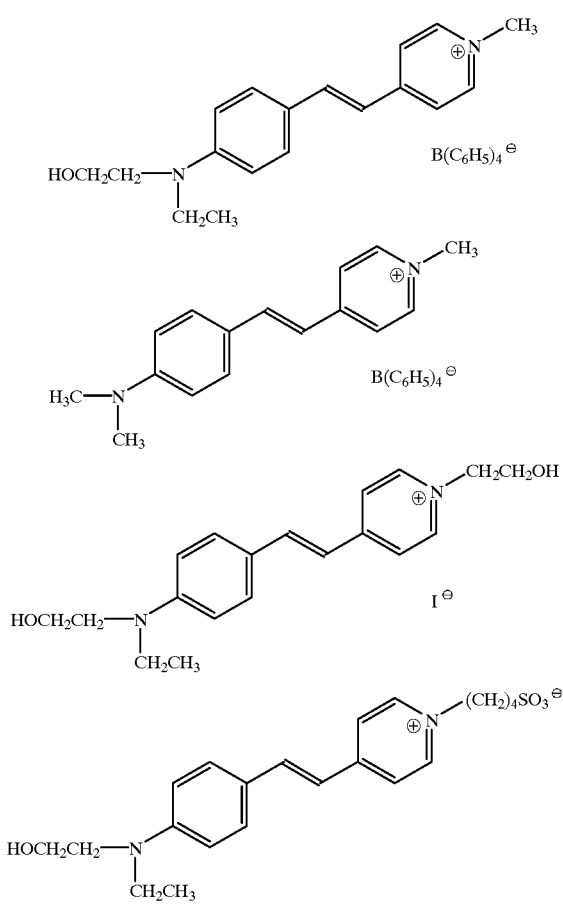

and

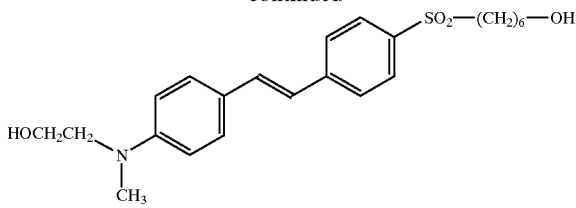

Where n is 0, styryl compounds of the present invention can be synthesized by providing an appropriate methyl-substituted derivative having the formula:

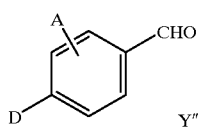

wherein

Q is as defined above and

Y' represents a counterion as necessary to balance the charge of the methyl-substituted derivative and reacting this methyl substituted derivative with an appropriate benzaldehyde derivative having the formula:

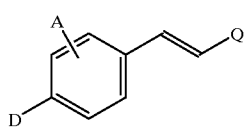

wherein

D and A are as defined above and

Y" represents a counterion as necessary to balance the charge of the N,N-disubstituted-p-aminobenzaldehyde under conditions effective to form a styryl compound having the formula:

$$\underset{D}{\overset{A}{\diagdown}}\diagup\diagdown Q$$

Typically, equimolar amounts of the two reactants are dissolved in an organic solvent and heated, preferably at the reflux temperature of the solvent, for ½ to 72 hours, preferably for 16 hours. Suitable solvents include alcohol solvents, such as methanol, ethanol, isopropanol, and n-butanol; ketone solvents, such as acetone, methyl ethyl ketone, and cyclopentanone; ester-containing solvents, such as ethyl acetate and isopropyl acetate; ether solvents, such as tetrahydrofuran, diglyme, and dioxane; chlorinated hydrocarbons, such as methylene chloride, chloroform, and carbon tetrachloride; pyridine; and dimethylformamide. Preferably, a solvent is chosen in which both reactants are substantially soluble and, ideally, the styryl compound is substantially insoluble. Ethanol is particularly preferred. Addition of a catalytic amount of a base, preferably a catalytic amount of a weak Lewis base, such as piperidine, triethylamine, pyridine, or triethanolamine, to the reaction mixture is advantageous.

After heating, the styryl compound of the present invention can be separated by inducing precipitation by, for example, chilling the reaction mixture or by adding a cosolvent, miscible with the reaction solvent but in which the compound is insoluble or less soluble. Suitable solvents include lower alkanes, such as pentane, hexane, or petroleum ether, or ether solvents, such as diethyl ether. Alternatively, if the compound contains ionizable substituents, such as carboxyalkyl moieties, the compound can be effectively separated by addition of an acid, preferably a strong mineral acid, such as hydrochloric acid. Where the styryl compound produced is charged positively, such as when Q is —($C_5H_4N$)—$R^3$, D is —$NR^1R^2$, and none of $R^1$, $R^2$, $R^3$, A, and B are ionizable, the compound may also be separated by adding a molar excess of anion, either, as a solid, or preferably as a concentrated solution. Suitable anions include chloride, bromide, iodide, $BF_4^-$, $PF_6^-$, tetraarylborate, such as tetraphenylborate, sulfonate, alkyl sulfate, such as methyl sulfate and ethyl sulfate, and perchlorate. The anion can be delivered as a solid or as a concentrated solution in a solvent miscible with the reaction solvent, and is delivered as a salt thereof. Preferably, the salt cation is readily solvated by the reaction solvent so as to promote the solubility of the salt therein. Consequently, early alkali metal ions, such as sodium and potassium, and quaternary ammonium ions are preferred. Precipitation by anion addition is most effectively achieved using solid sodium tetraphenylborate.

Subsequent to isolation, the compounds of the present invention can optionally be purified by recrystallization, solvent extraction using, for example, a Soxhlet extraction apparatus, chromatography, such as HPLC or conventional column chromatography, or other conventional purification methods. In addition, subsequent to isolation, the ions associated with the styryl compound can be exchanged, for example, from iodide to tetraphenylborate, by dissolving the styryl compound in a suitable solvent, preferably in a minimal amount of hot solvent, adding a molar excess of the desired anion in the form of a concentrated solution or solid of an appropriate salt, and then inducing precipitation, for example, by cooling the solution or by adding a miscible solvent in which the compound is insoluble. Alternatively, the ions can be changed by passing a solution of the compound through an appropriate ion exchanger.

Where the methyl-substituted derivative is a N-substituted-4-methylpyridine derivative, many suitable methyl-substituted derivatives are commercially available. Preparation of many others are well known in the art and are described in Tramontini, *Synthesis* 1973: 703–775, which is hereby incorporated by reference. Typically, these reactants are prepared from 4-methylpyridine by reaction with an appropriate alkyl or substituted alkyl halide, $BF_4^-$, or $PF_6^-$ under conditions effective to form the N-substituted-4-methyl pyridine derivative having the formula:

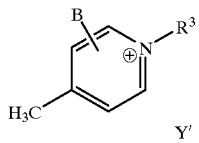

Suitable alkyl halides include, for example, methyl iodide, methyl bromide, ethyl iodide, ethyl bromide, propyl iodide, propyl bromide, 2-hydroxyethyl iodide, and 2-hydroxyethyl bromide. Where $R^3$ is an sulfoalkyl, such as sulfoethyl, sulfopropyl or sulfobutyl, the N-sulfoalkyl-4-methylpyridinium inner salt is preferably provided by reaction of the 4-methylpyridine with an appropriate alkanesultone, such as propansultone or butansultone. The reaction is typically conducted in a suitable solvent at from room temperature to the boiling point of the solvent, depending on the nature of the halide or sultone, and for from ½ hour to 7 days. Typically, heating the reaction reduces the time required. Suitable solvents for this reaction include aromatic hydrocarbons, such as benzene, toluene, and xylenes, chlorinated alkanes, such as chloroform, methylene chloride, carbon tetrachloride, and tetrachloroethylene, alkane solvents, such as pentane, hexanes, and petroleum ether, ether solvents, such as diethyl ether, tetrahydrofuran, diglyme, and dioxane, and alcohol solvents such as methanol, ethanol, isopropanol, and butanol. Alternatively, the reaction can be conducted neat, without solvent, in excess halide or sultone. Preferably, toluene is employed as the reaction solvent. The reaction product typically crystallizes upon cooling to room temperature, or precipitation may be induced by cooling further in ice or by addition of a non-polar solvent. The pyridine derivative thus formed is separated and purified by standard methods.

Where the methyl-substituted derivative is a toluene derivative substituted in the 4-position with an electron acceptor and has the formula

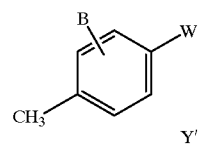

many suitable methyl-substituted derivatives are commercially available. Alternatively, appropriately substituted derivative can be prepared by conventional methods for synthesizing 4-substituted toluenes. For example, 4-sulfonyl toluene derivatives having the formula

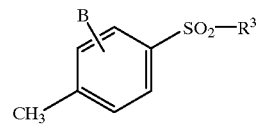

can be prepared by oxidation of a corresponding tolyl thioether having the formula

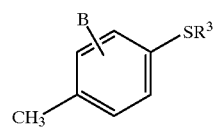

with, for example, hydrogen peroxide at 50 to 90° C., preferably 70° C., for 4 to 24 hours, preferably 10 hours. 4-carboxytoluene derivatives can be prepared from 4-methylbenzaldehyde by oxidation. 4-cyanotoluene derivatives can be prepared from 4-halotoluenes by nucleophilic substitution with, for example, a cyanide salt.

Benzaldehyde derivatives suitable for use as starting materials can be obtained commercially or prepared by techniques well known to those skilled in the art. Where D is —$NR^1R^2$, the N,N-disubstituted benzaldehyde derivatives can be prepared by the methods described in Zhao et al., *Chem. Mater.*, 7:1237–1242 (1995), which is hereby incorporated by reference. Briefly, the N,N-disubstituted-p-aminobenzaldehyde can be prepared by reaction of a 4-halobenzaldehyde, such as 4-fluorobenzaldehyde with an appropriate disubstituted amine in the presence of a base, such as potassium carbonate or sodium carbonate, under conditions effective to form the N,N-disubstituted-p-aminobenzaldehyde. Appropriate disubstituted amines include dimethylamine, diethylamine, methyl ethyl amine, methyl hydroxyethyl amine, ethyl hydroxyethyl amine, methyl sulfopropyl amine, ethyl sulfopropyl amine, methyl sulfobutyl amine, and ethyl sulfobutyl amine. Typically, a 10% to 1000% excess of amine is employed. Preferably, the amine-benzaldehyde molar ratio is ~3. The base is typically used in a 10% to 50% molar excess based on the amount of benzaldehyde. In addition, use of a catalytic amount of a quaternary ammonium salt, such as tricaprylyl methylammonium chloride, is advantageous. Suitable reaction solvents include aromatic hydrocarbons, such as benzene, toluene, and xylenes, chlorinated alkanes, such as chloroform, methylene chloride, carbon tetrachloride, and tetrachloroethylene, alkane solvents, such as pentane, hexanes, and petroleum ether, ether solvents, such as diethyl ether, tetrahydrofuran, diglyme, and dioxane, and alcohol solvents such as methanol, ethanol, isopropanol, and butanol, dimethylformamide, and dimethylsulfoxide ("DMSO"). The reaction is conducted at from about room temperature to about 150° C., preferably from 90° C. to 110° C. for 8 hours to 96 hours. Separation and purification of the resulting N,N-disubstituted-p-aminobenzaldehyde can be effected by conventional methods.

Where n is greater than 0, the compounds of the present invention can be prepared by reaction of a compound having the formula

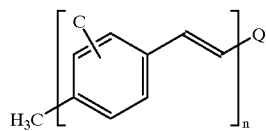

with an appropriate benzaldehyde derivative under conditions described above for the synthesis of styryl compounds where n is 0. The starting material

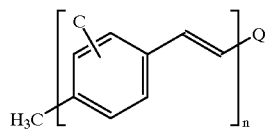

can be prepared by reaction of 4-methylbenzaldehyde with an appropriate methyl substituted derivative having the formula:

This produces the starting material with n=1. By reacting the n=1 starting material with another equivalent of 4-methylbenzaldehyde, starting material where n is 2 is produced. Further repetitions of this reaction can be used to prepare starting materials where n is 3 or 4. Each of these reactions is preferably conducted in an alcohol solvent, preferably ethanol, for 24 hours, at the reflux temperature of the solvent, and in the presence of a base catalyst, such as potassium carbonate.

The present invention further relates to a composition comprising a matrix material and a compound having the formula:

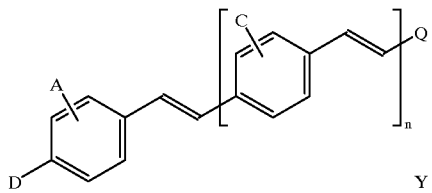

wherein
D is an electron donating group;
Q is an electron acceptor selected from the group consisting of electron acceptors having the formulae:

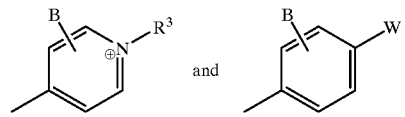

W is an electron accepting group,
$R^3$ is selected from the group consisting of substituted or unsubstituted alkyl or substituted or unsubstituted aryl moieties,
n is an integer from 0 to 4,
A, B, and C are substituents of their rings and are each independently selected from the group consisting of alkyl, alkoxy, hydroxyalkyl, sulfoalkyl, carboxyalkyl, and hydrogen, and
Y is a counterion
dispersed in the matrix. When Y is an anion, such as when A and B are hydrogen, D is —$NR^1R^2$, Q is —$(C_5H_4N)$—$R^3$, and $R^1$, $R^2$, and $R^3$ are unsubstituted alkyl or hydroxyalkyl, Y is preferably tetra-substituted borate, such as tetramethylborate, tetrapropylborate, tetratolylborate, diphenyldimethylborate, diphenylditolylborate, or, more preferably, tetraphenylborate. The solubility of the styryl compound in the matrix may be modified by altering the nature of $R^1$, $R^2$, and $R^3$. Generally, the greater the polarity of the groups and the greater the number of polar groups, the more soluble the dye in the matrix. In many applications suitable solubility is achieved where A and B are hydrogen, and where $R^1$, $R^2$, and $R^3$ are selected from the group consisting of unsubstituted alkyl hydroxyalkyl, sulfoalkyl, and carboxyalkyl. Where n is 0, D is —$NR^1R^2$, and Q is —$(C_5H_4N)R^3$, preferred compounds are those where A and B are hydrogen, $R^2$ is unsubstituted alkyl, and $R^1$ and $R^3$ are selected from the group consisting of hydroxyalkyl, sulfoalkyl, and carboxyalkyl.

The matrix material can be any material which is capable of dispersing the styryl compound. For example, the matrix can be a liquid in which the compound is either suspended, so as to form stable solid dispersion, such as a colloid, or dissolved. Suitable dispersing liquids include alcohol solvents, such as methanol, ethanol, isopropanol, and n-butanol; ketone solvents, such as acetone, methyl ethyl ketone, and cyclopentanone; ester-containing solvents, such as ethyl acetate and isopropyl acetate; ether solvents, such as tetrahydrofuran, diglyme, and dioxane; chlorinated hydrocarbons, such as methylene chloride, chloroform, and carbon tetrachloride; acetonitrile; pyridine; dimethylformamide; and dimethylsulfoxide.

Alternatively, the compounds of the present invention can be incorporated into various polymeric matrix materials to produce compositions which are useful in two-photon pumped cavity lasing, in infrared beam detection, and in optical limiting. That is to say, the styryl compounds, set forth above, may be incorporated into such materials as acrylic and methacrylic polymers, styrene polymers, vinyl halide polymers, cyanoethylated cellulosic materials, aminoplastic resins, polyester resins, cellulose acetate polymers such as cellulose acetate butyrate, etc., nitro cellulose, cellulose propionate, and cured epoxy-type polymers. Examples of polymeric matrix materials which may be used with the styryl compounds of the present invention include: polymers, i.e., homopolymers and copolymers, of polyol (allyl carbonate) monomers, polymers, i.e., homopolymers and copolymers, of polyfunctional acrylate monomers, polyacrylates, poly(alkylacrylates), such as poly(methyl methacrylate), cellulose acetate, cellulose triacetate, cellulose acetate propionate, cellulose acetate butyrate, poly (vinyl acetate), poly(vinyl alcohol), poly(vinyl chloride), poly(vinylidene chloride), polyurethanes, polycarbonates, poly(ethylene terephthalate), polystyrene, copoly(styrene-methyl methacrylate) copoly(styrene-acrylonitrile), poly (vinyl butyral) and polymers, i.e., homopolymers and copolymers, of diallylidene pentaerytlritol, particularly copolymers with polyol (allyl carbonate) monomers, e.g., diethylene glycol bis(allyl carbonate), and acrylate monomers.

Blends of the aforesaid transparent polymers are also suitable as matrix materials. Preferably, the matrix material is an optically clear polymerized organic material prepared from a polycarbonate resin, such as the carbonate-linked resin derived from bisphenol A and phosgene, which is sold under the trademark LEXAN; a poly(methyl methacrylate), such as the material sold under the trademark PLEXIGLAS; poly(2-hydroxyethyl methacrylate); and polymerizates of urethanes and epoxy materials. The resultant compositions of matter may be formed into such articles as discs, plates, films, rods, and the like, by any known molding, casting, spray drying etc. technique.

The various esters of acrylic acid and methacrylic acid which may be used to form the polymers comprising the major constituent of the compositions of the present invention are those having the formula:

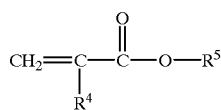

wherein $R^4$ is hydrogen or a methyl radical and $R^5$ is an allyl radical having from 1 to 6. carbon atoms, inclusive. Compounds, which are represented by the above formula and, consequently, which may be used in the present invention include methyl acrylate, ethyl acrylate, n-propyl acrylate, isopropyl acrylate, n-butyl acrylate, isobutyl acrylate, t-butyl acrylate, amyl acrylate, hexyl acrylate, methyl methacrylate, ethyl methacrylate, n-propyl methacrylate, isopropyl methacrylate, n-butyl methacrylate, isobutyl methacrylate, t-butyl methacrylate, amyl methacrylate, hexyl methacrylate, 2-hydroxyethyl methacrylate, and the like.

The acrylic and methacrylic acid esters may be polymerized alone or in combination with other ethylenically unsaturated monomers in amounts such that the final polymer has a preponderance of the acrylic or methacrylic acid ester therein, i.e., at least 51%, by weight, based on the total weight of the monomers. Comonomers useful for this purpose are set forth hereinbelow.

The styrene monomers, which may also be employed to produce the compositions of the present invention, are those having the formula

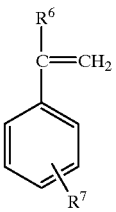

wherein $R^6$ is hydrogen or a lower alkyl radical having 1 to 4 carbon atoms, inclusive, and $R^7$ is hydrogen, a lower alkyl radical having 1 to 4 carbon atoms, inclusive, or a halogen radical. Suitable monomers represented by the above formula include styrene, methyl styrene, ethyl styrene, propyl styrene, butyl styrene, chloro styrene, bromo styrene, fluoro styrene, iodo styrene, α-butyl styrene, α-methyl methylstyrene, α-methyl ethylstyrene, α-butyl ethylstyrene, α-ethyl chlorostyrene, α-propyl iodostyrene, and the like.

These styrene monomers may also be polymerized alone or in combination with other ethylenically unsaturated monomers.

The vinyl halide monomers which may be used to produce the compositions of the present invention are well known in the art and generally vinyl chloride is the most practical for reasons of availability and cost. However, vinyl fluoride has become more important in recent years and its use is also contemplated herein. These vinyl halide polymers may be used as pure homopolymers, however. inasmuch as commercially available polymeric vinyl halide resins generally are produced containing minor amounts, i.e., up to about 2.0% of copolymeric material, resins of this sort are also applicable herein. Commercially available poly (vinyl chloride) also, for example, may contain about 1.0% or less of other constituents such as vinyl acetate, in copolymeric form. These polymers are also useful herein. These vinyl halides may additionally be employed with varying amounts of comonomers, generally in amounts as indicated above in regard to the esters of acrylic and methacrylic acids.

Examples of applicable comonomeric compounds which may be copolymerized with the acrylates, styrenes and vinyl halides set forth above in amounts less than about 50%, by weight, based on the total weight of the monomers, include the unsaturated alcohol esters, more particularly the allyl, methallyl, crotyl, 1-chloroallyl, 2-chloroallyl, cinnamyl, vinyl, methvinyl, 1-phenylallyl, butenyl, etc., esters of saturated and unsaturated aliphatic and aromatic monobasic and polybasic acids such, for instance, as acetic, propionic, butyric, valeric, caproic, crotonic, oxalic, malonic, succinic, glutaric, adipic, pimelic, suberic, azelaic, sebacic, citraconic, mesaconic, itaconic, acetylene dicarboxylic aconitic, benzoic, phenylacetic, phthalic, terephthalic, benzoylphthalic, etc., acids; the saturated monohydric alcohol esters, e.g., the methyl, ethyl, propyl, isopropyl, butyl, sec.-butyl, amyl, etc.; esters of ethylenically unsaturated aliphatic monobasic and polybasic acids, illustrative examples of which appear above, vinyl cyclic compounds (including monovinyl aromatic hydrocarbons), e.g., styrene, o-, m-, and p-chlorostyrenes, -bromostyrenes, -fluorostyrenes, -methylstyrenes, -ethylstyrenes, -cyanostyrenes, the various polysubstituted styrenes such, for example, as the various ditri-, and tetra-chlorostyrenes, -bromostyrenes, -fluorostyrenes -methylstyrenes, -ethylstyrenes, -cyanostyrenes, etc., vinyl naphthalene, vinyl-cyclohexane, vinyl furane, vinyl pyridine, vinyl dibenzofuran, divinyl benzene, trivinyl benzene, allyl benzene, diallyl benzene, N-vinyl carbazole, the various allyl cyanostyrenes, the various alpha-substituted styrenes and alpha-substituted ring-substituted styrenes, e.g., alpha -methyl styrene, alpha -methyl-para -methyl styrene, etc.; unsaturated ethers, e.g., ethyl vinyl ether, diallyl ether, ethyl methallyl ether, etc.; unsaturated amides, for instance, N-allyl -caprolactam, acrylamide, and N-substituted acrylamides, e.g., N-methyl acrylamide, N-allyl acrylamide, N-methyl acrylamide, N-phenyl acrylamide, etc.; unsaturated ketones, e.g., methyl vinyl ketone, methyl allyl ketone, etc.; methylene malonic esters, e.g., methylene methyl malonate, etc.; ethylene; unsaturated polyhydric alcohol (e.g., butenediol, etc.) esters of saturated and unsaturated, aliphatic and aromatic, monobasic and polybasic acids.

Other examples of monomers that can be copolymerized are the vinyl halides, more particularly, vinyl fluoride, vinyl chloride, vinyl bromide, and vinyl iodide, and the various vinylidene compounds, including the vinylidene halides, e.g. vinylidene chloride, vinylidene bromide, vinylidene fluoride, and vinylidene iodide, other comonomers being added if needed in order to improve the compatibility and copolymerization characteristics of the mixed monomers.

More specific examples of allyl compounds, that can be copolymerized are allyl alcohol, methallyl alcohol, diallyl carbonate, allyl lactate, allyl alphahydroxyisobutyrate, allyl trichlorosilane, diallyl methylgluconate, diallyl tartronate, diallyl tartrate, diallyl mesaconate, the diallyl ester of muconic acid, diallyl chorophthalate, diallyl dichlorosilane, the diallyl ester of endomethylene tetrahydrophthalic anhydride, triallyl tricarballylate, triallyl cyanurate, triallyl citrate, triallyl phosphate, tetrallyl silane, tetrallyl silicate, hexallyl disiloxane, etc. Other examples of allyl compounds that may be employed are given, for example, in U.S. Pat. No. 2,510,503, which is hereby incorporated by reference.

Among the monomers which are suitable for use in carrying out the present invention are, for example, compounds such as acrylonitrile, and other compounds, e.g., the various substituted acrylonitriles (e.g., methacrylonitrile, ethacrylonitrile, phenylacrylonitrile, etc.), the various N-substituted acrylamides and alkacrylamides, for instance, N-dialkyl acrylamides and methacrylamides, e.g., N-dialkyl acrylamides and methacrylamides, e.g., N-dimethyl, -diethyl, -dipropyl, -dibutyl, etc., acrylamides and methacrylamides and the like.

The cyanoethylated cellulosic materials employed in the formation of the compositions of the present invention may be prepared from the cellulose of wood pulp or wood fiber after removal of the lignin and the like therefrom. Additionally, α-cellulose flock, regenerated cellulose fibers such as viscose, cotton linters, and natural cellulose materials such as cotton, jute, ramie, and linen may be used in such forms as fibers, yarns, fabrics, raw stock, batting and the like. Additionally, the cellulosic material may be non-fibrous, e.g., in the form of felted or webbed materials. The fibrous forms of the cellulose may be employed in woven or knitted condition. It is also within the scope of the present invention to employ methyl cellulose, ethyl cellulose, and the like as the starting material.

The cyanoethylation of the cellulosic materials may be carried out by reacting the natural or regenerated cellulosic material with acrylonitrile in various ways. The physical properties of the resultant products will vary with the nature of the cellulosic material, its molecular weight, the method of treatment and the like. However, said properties are affected most noticeably by the extent to which the cellulosic material has been cyanoethylated.

The cyanoethylation of the cellulosic material is usually defined in one of two ways, i.e., either by its nitrogen content, expressed in weight percent of nitrogen, or by a decimal fraction representing the number of cyanoethyl groups introduced per anhydroglucose unit. This decimal fraction is usually referred to as the "degree of substitution." Complete cyanoethylation of cellulose generally corresponds to a nitrogen content of about 13.1% or slightly above, and a degree of substitution of about 3. A nitrogen content of at least 10% and a corresponding degree of substitution of about 2.3 is generally present in the most commonly available materials.

At low degrees of substitution, that is, a degree of substitution up to about 2, cyanoethylation does not greatly alter the solubility or the physical appearance of the cellulose, i.e., the fibrous characteristics thereof are generally retained. However, as the degree of substitution increased progressively above 2, the fibrous characteristics of the cellulose gradually diminish and resemblances of the product to a thermoplastic resin, become increasingly apparent. Additionally, the product develops a solubility in certain organic solvents which the cellulosic material did not have.

As mentioned above, substantially any cellulosic material can be utilized in the production of the compositions of the present invention. Cellulose, and some chemically related compounds, are structurally polymers of anhydroglucose, and different polymers are generally classified in terms of the number of anhydroglucose units in a molecule. Chemically, an anhydroglucose unit is a trihydric alcohol, one hydroxyl group being a primary hydroxyl and the other two being secondary. Celluloses are predominately 1 to 4 unit polymers, the number of polymerized units usually being referred to as the degree of polymerization.

As with any other polymer, each cellulosic polymer is a mixture of polymers of different molecular weight and it is the average degree of polymerization which determines the classification of the ultimate product. The celluloses used in the present invention generally have a degree of polymerization of at least about 2000, although those celluloses having degrees of polymerization below 2000 are also useful herein. The viscose rayons for example, have a degree of polymerization of from about 250 to 350. Natural cotton has a degree of polymerization of about 850 to 1000 and many wood pulp derivatives have a degree of polymerization in excess of 1000. All these celluloses however, may be used in the practice of the present invention.

The cyanoethylation procedures used to form the starting composition of the present invention do not form part of the instant invention and any known procedure for achieving this result may be employed. One such method is shown, for example, in U.S. Pat. No. 2,332,049, which is hereby incorporated by reference. Additional procedures are shown in U.S. Pat. Nos. 2,375,847, 2,840,446, 2,786,736, 2,860, 946, and 2,812,999, which are all hereby incorporated by reference. In general, the procedure for preparing the cyanoethylated celluloses involves reacting a cellulosic material with acrylonitrile in the presence of an alkali and precipitating and washing the resultant cyanoethylated produce. Generally, the amount of acrylonitrile which is used is 10–20 times the amount of cellulosic material being treated. The particular alkali employed is not critical and such materials as potassium hydroxide and sodium hydroxide may be used. A good general procedure is to employ about 2.5 to about 7.0 weight percent of alkali, based on the weight of the cellulosic material.

The aminoplast resins employed in the practice of the present invention are synthetic resins prepared by the condensation reaction of an amino (including imino) or amido (including imido) compound with an aldehyde. Resinous condensates of this type, as well as methods for their preparation, have been shown innumerable times in the prior art, and adequate disclosures of them may be found in, for example, U.S. Pat. Nos. 2,197,357, 2,310,004, 2,328,592 and 2,260,239, which are hereby incorporated by reference.

Melamine is a suitable aminotriazine reactant for preparing the heat-curable or potentially heat-curable partially polymerized aminotriazine-aldehyde resinous reaction products which are used in the practice of the present invention, but other aminotriazines, e.g., mono- di-, and tri-substituted melamines, such as the mono-, di- and trimethylmelamines, and the like, guanamines, such as formoguanamine, acetoguanamine, benzoguanamine, and the like, as well as mixtures of aminotriazines, may be utilized as reactants. Similarly, formaldehyde, typically in aqueous solution, is a common aldehyde reactant, but other aldehydes, e.g., acetaldehyde propionaldehyde, butyraldehyde, benzaldehyde, and the like, or compounds engendering aldehydes, e.g., paraformaldehyde, hexamethylenetetramine, and the like, may also be employed. The properties desired in the finished product and economic considerations are among the elements which will determine the choice of the particular aminotriazine and aldehyde employed.

The mole ratio of aldehyde to aminotriazine in such resinous reaction products is not critical, and may be within the order of from about 1.5:1 to about 4:1, respectively, depending on the nature of the starting materials and the characteristics desired in the final product, but it is preferred that the mol ratio be within the order of from about 2:1 to about 3:1, respectively.

Conventional reaction conditions are observed in preparing the aminotriazine-aldehyde resins, i.e., the aldehyde and the aminotriazine may be heat-reacted at temperatures ranging from about 40° C. to reflux temperature, i.e. about 100° C., for periods of time ranging from about 30 to 120 minutes, at a pH ranging from about 7.0 to 10, preferably in an aqueous medium. Any substance yielding acidic or alkaline aqueous solutions may be used to regulate the pH, for example, alkaline materials such as alkali metal or alkaline earth metal oxides, e.g., sodium, potassium or calcium hydroxide or sodium or potassium carbonate; mono-, di-, or tri-alkylamines, e.g., triethylamine or triethanolamine; alkylene polyamines or polyakylene polyamines, eg., 3,3'-iminobispropylamine, and the like.

Other amido or imido compounds having at least two aldehyde-reactable hydrogen atoms attached to amidogen nitrogen atoms may also be used in preparing the aminoplast resins used in the present invention. For example, urea and those of its derivatives which have beer, commonly used in the preparation of aminoplast resinous compositions, such as for example the alkylureas, e.g., mono- and dimethylurea, halourea and the like may be used.

The properties of the thermosetting aminoplast resins can be further modified, if desired, by incorporating various other substances into the aminotriazine-aldehyde resin. Included among such substances are plasticizers such as the α-alkyl-D-glucosides, e.g., α-methyl-D-glucoside, disclosed in U.S. Pat. No. 2,773,848 to Lindenfelser, which is hereby incorporated by reference, methylol derivatives corresponding to the general formula:

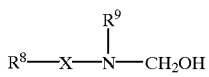

wherein $R^8$ represents an alkyl, aryl, or aralkyl group, $R^9$ represents a hydrogen atom or an alkyl, alkylol, aryl or acyl group, and X represents,

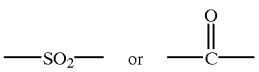

e.g., N-methylol p-toluenesulfonamide (which may be formed in situ by the addition of p-toluenesulfonamide to an amidogen-formaldehyde reaction mixture) and the like, or combinations of these glucosides and methylol derivatives, e.g., a mixture of α-methyl-D-glucoside and p-toluenesulfonamide, as disclosed in U.S. Pat. No. 2,773,788 to Magrane et al, which is hereby incorporated by reference.

The aminoplast resinous molding materials may be prepared by first impregnating a fibrous filler, such as chopped α-cellulose, with an aminoplast resin, in syrup form, drying the impregnated material to a low volatile content, usually in the order of about 10% or less, converting the dried material to a fine, fluffy powder while blending it with various commonly employed additives, such as curing catalysts, pigments, mold lubricants, and the like, and finally densifying and granulating the powdered molding composition, thus converting it to a form especially suited for commercial molding techniques and to which the styryl compounds may be added.

The polyester resins employed in the practice of the present invention may be either thermoplastic or thermosetting. They are all relatively well known in the art and are prepared by reacting polycarboxylic acids, or their anhydrides with polyhydric alcohols. The thermosetting polyesters are prepared using a procedure wherein at least one of the rective components contains (α,β-ethylenic unsaturation. By following this procedure, resinous, essentially linear esterification or condensation products containing a plurality of ethylenically unsaturated linkages distributed along the backbones of their polymer chains are produced.

The use of α,β-ethylenically unsaturated polycarboxylic acids provides a convenient method of introducing ethylenic unsaturation into the polyester resins. It is preferred to employ α,β-ethylenically unsaturated dicarboxylic acids, such as maleic, fumaric, citraconic, γ,γ-dimethylcitraconic, mesaconic, itaconic, α-methylitaconic, γ-methylitaconic, teraconic, and the like, as well as mixtures thereof, but minor amounts of αβ-ethylenically unsaturated polycarboxylic acids containing three or more carboxyl groups, such as aconitic acid and the like, together with the particular α,β-ethylenically unsaturated dicarboxylic acid or acids chosen, may also be used.

Whenever available, the anhydrides of any of the aforementioned α,β-ethylenically unsaturated polycarboxylic acids may be substituted for said acids in whole or in part.

Any of the large class of polyhydric alcohols ordinarily used in preparing reactive polyester resins may be employed in the practice of the present invention. While dihydric alcohols, and especially saturated aliphatic diols, are commonly-used co-reactants in the preparation of the polyester resins, it is not mandatory that all of the polyol used be of this type, in that small amounts, e.g., usually up to about 10% of the total equivalents of hydroxyl groups present in the esterification mixture, of polyols having more than two hydroxyl groups may also be employed. Among the dihydric alcohols which may be employed are saturated aliphatic diols such as ethylene glycol, propylene glycol, butylene glycol, diethylene glycol, dipropylene glycol, triethylene glycol, tetraethylene glycol, butanediol-1,2, butanediol-1,3, butanediol-1,4, pentanediol-1,2, pentanediol-1,3, pentanediol-1,4, pentanediol-1,5, hexanediol-1,2, hexanediol-1,3, hexanediol-1,4, hexanediol-1,5, hexanediol-1,6, neopentyl glycol and the like, as well as mixtures thereof. Among the polyols having more than two hydroxyl groups which may be employed in minor amounts, together with the above-mentioned diols, are saturated aliphatic polyols such as glycerol, trimethylol ethane, trimethylol propane, pentaerythritol, dipentaerythritol, arabitol, xylitol, dulcitol, adonitol, sorbitol, mannitol, and the like, as well as mixtures thereof.

In forming the thermoplastic polyester resins useful herein, the above alcohols are reacted with non-polymerizable polycarboxylic acids, i.e., acids which are saturated or which contain only benzenoid unsaturation, such as oxalic, malonic, succinic, glutaric, adipic, pimelic, suberic, azelaic, sebacic, malic, tartaric, tricarballylic, citric, phthalic, isophthalic, terephthalic, cyclohexanedicarboxylic, endomethylenetrahydrophthalic, and the like, as well as mixtures thereof.

These saturated acids may be used alone to form thermoplastic resins or in combination with the above-mentioned unsaturated acids in the formation of thermosetting resins in order to impart many beneficial properties thereto. For example, nonpolymerizable polycarboxylic acids having only two carboxyl groups, and no other reactive substituents, may be employed to impart a desirable degree of flexibility which may not be achieved by the use of the $\alpha,\beta$-ethylenically unsaturated polycarboxylic acids alone. Where such nonpolymerizable polycarboxylic acids are employed, the amount thereof should constitute at least about 20% but not more than about 80% of the total equivalents of carboxyl groups present in the esterification mixture. Preferably, such nonpolymerizable polycarboxylic acids may be employed in amounts ranging from about 25% to about 75% of the total equivalents of carboxyl groups present in the esterification mixture.

Halogenated unsaturated polycarboxylic acids may also be employed in the preparation of the thermosetting polyester resins of the present invention for purposes of imparting various desirable properties thereto as mentioned above in regard to the saturated acids. Examples of halogenated acids which may be used include monochloro- and monobromomaleic, monochloro- and monobromofumaric, monochloro- and monobromomalonic, dichloro- and dibromomalonic, monochloro- and monobromosuccinic, $\alpha,\beta$-dichloro- and dibromosuceinic, hexachloroendomethylene-tetrahydrophthalic, and the like, as well as mixtures thereof Whenever available, the anhydrides of any of these halogenated acids may also be substituted therefore in whole or in part.

Among the halogenated polyols that may be employed are 2,2'-chloromethylpropanediol-1,3, adducts of hexachlorocyclopentadiene with unsaturated polyols, such as butenediols, pentenediols, and the like, and adducts of hexachlorocyclopentadiene with polyols having three or more hydroxyl groups, one of which is etherified with an unsaturated alcohol reactive with hexachlorocyclopentadiene. Among the latter are compounds such as 3-[1,4,5,6,7,7-hexachlorobicyclo-(2.2.1)-5-hepten-2-yloxyl]-1,2-propanediol, which is the adduct of hexachlorocyclopentadiene with vinyl glycerol ether, 3-[1,4,5,6,7,7-hexachlorobicyclo-(2.2.1)-5-hepten-2-yl]-methoxy-1,2-propanediol, which is the adduct of hexachlorocyclopentadiene with allyl glycerol ether, adducts of hexachlorocyclopentadiene with vinyl and allyl ethers of pentaerythritol, and the like. Mixtures of these halogenated polyols may also be employed, if desired.

The esterification mixtures, from which both the thermoplastic and the thermosetting polyester resins employed in the practice of the present invention are prepared, are generally formulated so as to contain at least a stoichiometric balance between carbonyl and hydroxyl groups. Thus, where a diol and a dicarboxylic acid are employed, they are usually reacted on at least a mol to mol basis. In common commercial practice, a small excess of polyol, usually in the range of from about 5% to about 15% excess, is employed. This is done primarily for economic reasons, i.e., to insure a rapid rate of esterification.

Both types of polyester resins used in the practice of the present invention are formed in the manner customarily observed in the art. Thus, the particular polycarboxylic acid or acids and polyol or polyols employed are reacted at elevated temperatures and atmospheric pressure. Since resinifying reactants of this type are prone to develop undesirable color when in contact with air at elevated temperatures, it is generally considered good practice to conduct the esterification reaction in an inert atmosphere, such as can be obtained by bubbling an inert gas, e.g., carbon dioxide, nitrogen, and the like, through the esterification mixture. The reaction temperature is not critical, thus the reaction will preferably be carried out at a temperature which usually will be just below the boiling point of the most volatile component of the reaction mixture, generally the polyol.

The esterification mixture should be sufficiently reacted so as to ultimately produce a polyester resin having an acid number not appreciably more in about 75. It is preferred to employ polyester resins having acid numbers ranging from about 30 to about 50.

Further details pertaining to the preparation of polyester resins of the types employed in the practice of the present invention are disclosed in U.S. Pat. No. 2,255,313 to Ellis and in U.S. Pat. Nos. 2,443,735 to 2,443,741, inclusive, to Kropa, and these patents are hereby incorporated into the present application by reference.

The thermosetting polyester resins of the present invention, in combination with the styryl compounds, may be cross-linked by the addition of a suitable cross-linking agent.

The polyester resins are cross-linked by admixing them with a monomer compound containing the polymerizable $CH_2$=C<group to give a composition that may be cured to a stable thermoset condition. One may use about 10 parts by weight of the monomeric material to about 90 parts by weight of the polyester resin up to about 60 parts of the monomeric material to about 40 parts of the polyester resin. The preferred embodiment, however, is to use from about 25 parts of the monomeric material to about 35 parts of the monomeric material with about 75 parts to about 65 parts, respectively, of the polyester resin.

The monomeric material containing the polymerizable $CH_2$=<group which may be used in the practice of the present invention, has a boiling point of at least 60° C. Among the polymerizable monomeric materials that will find use in our invention are those such as styrene, sidechain alkyl and halo substituted styrenes such as alpha methylstyrene, alpha chlorostyrene, alpha ethylstyrene and the like or alkyl and halo ring-substituted styrenes such as ortho, meta and paraalkyl styrenes such as o-methylstyrene, p-ethylstyrene, meta-propylstyrene, 2,4-dimethylstyrene, 2,5-diethylstyrene, bromostyrene, chlorostyrene, dichlorostyrene, and the like. Still further, one can make use of the allyl compounds such as dialyl phthalate, tetrachlorodiallyl phthalate, allyl alcohol, methallyl alcohol, allyl acetate, allyl methacrylate, diallyl carbonate, allyl lactate, allyl alphahydroxyisobutyrate, allyl trichlorosilane, allyl acrylate, diallyl malonate, diallyl oxalate, allyl gluconate, allyl methylgluconate, diallyl adipate, diallyl sebacate, diallyl citraconate, the diallyl ester of muconic acid, diallyl itaconate, diallyl chlorophthalate, diallyl dichlorosilane, the diallyl ester of endomethylene tetrahydrophthalic anhydride, the diallyl ester of tetrachloroendomethylenetetrahydrophthalic anhydride, triallyl citrate, triallyl phosphate trimethallyl phosphate, tetrallyl silane, tetrallyl silicate, hexallyl disiloxane and the like. These monomeric materials may be used either singly or in combination with one another.

When the thermosetting polyester resin is combined with the cross-linking monomeric material, it is desirable to incorporate therein a polymerization inhibitor in order to prevent premature gelation of the resinous composition, particularly if it is expected that said composition will be subjected to prolonged periods of storage or if it is expected that it will be subjected to temperatures significantly higher than room temperature. With the polymerization inhibitor, the resinous composition will remain stable at room temperature for months without noticeable deterioration. Amongst the polymerization inhibitors may be used are any of those which are conventially known and used in the art such as hydroquinone, benzaldehyde, ascorbic acid, isoascorbic acid, resorcinol, tannin, symmetrical di-(beta-naphthyl)-p-phenylene diamine, phenolic resins, sulfur compounds and the like. The concentration of the inhibitor is preferably and as a general rule less than 1% by weight is usually sufficient. However, with the preferred inhibitors, e.g., polyhydric phenols and aromatic amines, one may make use of such small amounts of 0.01% to 0.1%, by weight.

The thermosetting polyester resins can readily be solidified without benefit of catalyst by the application of heat or by the application of heat and pressure. However, in such an operation without benefit of a catalytic agent the time element makes it desirable to incorporate into the composition conventional polymerization catalysts such as the organic superoxides, the alcoholic and acidic peroxides. Among the preferred catalysts are: the acidic peroxides, e.g., benzoyl peroxide, phthalic peroxide, succinic peroxide and benzoyl acetic peroxide; fatty oil acid peroxides, e.g., coconut oil acid peroxides, lauric peroxide, stearic peroxide and oleic peroxide; alcohol peroxides, e.g., tertiary-butyl hydroperoxide, usually called tertiarylbutyl peroxide and terpene oxides, e.g., ascaridole. Still other polymerization catalysts might be used in some instances, e.g., soluble cobalt salts (particularly the linoleate and naphthenate), p-toluene sulfonic acid, aluminum chloride, stannic chloride and boron trifluoride and azobisisobutyronitrile.

The above polymer matrix materials are usually transparent, but may be translucent or, in some applications, opaque to visible light. Preferably, the polymer does not linearly absorb or only weakly absorbs infrared radiation in the region from 750 to 1200 nm. The polymer matrix material is selected based on the application to which the composition is to be put. For instance, as detailed below, where the application requires a film, such as for infrared detection, the polymer is preferably a film-forming polymer, such as the polyurethane coating material EPOXYLITE #9653-2 (Epoxylite Corp., Irvine Calif.). On the other hand, where a three-dimensional material is preferred, such as for use in optical limiting or in two-photon pumped cavity lasing, casting polymers, such as poly(HEMA) or EPO-TEX301 (Epoxy Technology, Inc., Billerica, Mass.) are preferred.

Another class of suitable matrix materials are sol-gel glasses, preferably those having bulk glass densities of from about 0.5 to about 1 g/cm$^3$ and refractive indices of from 1.4 to 1.5. A styryl compound of the present invention and a polymerizable monomer, preferably poly(hydroxyethyl methacrylate), are impregnated into the bulk glass. The monomer is then polymerized by heating, by irradiation, or by the passage of time at room temperature. Optionally, the monomer may contain polymerization initiators, such as 2,2'-azobisisobutyronitrile ("AIBN"), preferably in a initiator to monomer mole ratio of from 0.25 to 2%. The styryl compound and monomer may be introduced simultaneously or sequentially. Simultaneous impregnation is preferred but requires that the styryl compound be soluble in the monomer. Furthermore, the monomer must have a surface tension which permits penetration of the monomer into the sol gel bulk glass. In the latter regard, for many glasses, alkyl methacrylate is preferred to hydroxyalkyl methacrylates. However, many compounds of the present invention are only marginally soluble in alkyl methacrylates. In this situation, an alternative impregnation method is preferred. First, the styryl compound, dissolved in a suitable solvent, such as a ketone solvent, is contacted, by immersing, spraying, dripping, brushing, and the like, with the bulk sol gel glass. The solvent is removed, and the dye-doped glass is then contacted with a monomer solution, optionally containing a polymerization initiator, for ½ to 72 hours, at from room temperature to about 80° C., to impregnate the glass with the monomer. Polymerization of the monomer, such as by heating, by irradiating, or by passage of time at near-room temperatures from 25° C. to 50° C., preferably in a sealed container in the absence of oxygen, completes formation of the sol gel composition.

Alternatively, the procedures used to impregnate the sol gel with the styryl compound and polymer can be used to introduce the compound and polymer into a Vycor glass having pore size from about 20 Å to about 100 Å, preferably from about 35 to about 50 Å. Vycor glasses suitable for use in the compositions of the present invention are commercially available, for example, from Corning Glass Inc., Corning, N.Y.

As indicated above, the compositions of the present invention can be in the form of fiber. Alternatively, the compositions can be formed into a free standing film, preferably having a thickness of from about 0.001 to about 1 mm. The composition can also be coated as a film on a substrate, such as paper, a polymer film, a metal sheet, or glass. Preferably, the composition forms a film from about 0.01 to about 0.05 mm thick on the substrate.

The composition can also be in the form of a three dimensional article, preferably having two parallel faces, such as a rod. The faces can be polished by conventional methods, such as by manual grinding using a diamond grinding wheel, by abrading the surface using abrasives, such as silicon carbide paper, preferably with increasing grit ranging from 60 to 2000 and preferably using a lubricant, such as water, or by polishing on cloths with 10 to 0.1 $\mu$m grade diamond paste, preferably using an automated grinding and polishing machine, such as the METASERV™ 2000 (Buehler VK Ltd., Coventry, England), or by combinations thereof. Polishing is best effected by sequentially performing the above steps.

Using the aforementioned methods, compositions containing from about 0.001 to about 0.1 M of styryl compound are achieved. In general, it is preferred that the styryl compound be as concentrated as possible without forming aggregates. Aggregate formation is minimized and compound concentration is maximized when the styryl compound's concentration in the matrix material is from about 0.0015 to about 0.01 M.

The styryl compounds and compositions of the present invention have strong two-photon absorption with a cross section that is significantly greater than commercial dyes, such as Rhodamine, DCM, and DMP. The compounds also exhibit intense emission having a wavelength from about 300 to about 680 nm when excited by infrared laser radiation. These properties make the styryl compounds and compositions useful active materials in a variety of applications, such as infrared beam detection, two-photon induced optical power limiting, and two-photon pumped lasing.

One aspect of the present invention relates to a method of detecting infrared radiation. The method includes placing the styryl compounds of the present invention at a location potentially exposed to the infrared radiation and evaluating whether the styryl compound has been exposed to the infrared radiation at the location. The dye is preferably dispersed in a matrix material, as described above with reference to the compositions of the present invention, preferably in a concentration of from about 0.001 M to about 0.1 M, more preferably from about 0.0015 M to about 0.01 M. Where the matrix material is a polymer, polyurethanes, polyesters, polyalkyacrylic acids or esters, epoxies, polyimides, polyamides, polyureas, phenal-formaldehyde polymers, urea-formaldehyde polymers, melamine-formaldehyde polymers, and mixtures thereof are particularly preferred, because of their superior resistance to thermal and photo-induced degradation. Although the detecting method of the present invention can be practiced with compositions having any geometric form, compositions in the form of a film, either free-standing or coated on a substrate, such as plastic, glass, paper, and the like, are preferred. Where a substrate is employed, it is preferably transparent to visible light, so that the composition coated thereon can be viewed from either side. The styryl compound-containing film, whether free standing or coated, can be laminated to protect the composition from abrasion. Of course, the laminating layers must be substantially transparent to the infared radiation being detected and to the visible light being emitted. Optionally, the laminating layers may include ultraviolet absorbers to inhibit photodegradation of the polymeric matrix material.

The detection method of the present invention can also be practiced using dye dispersed in a glass, such as a sol gel glass or Vycor glass, as described above.

Alternatively, the dye of the present invention can be dispersed in a solution, contained by a vessel having walls transparent to the infrared radiation detected and the visible radiation emitted. Preferably, the vessel is formed from two closely-spaced, parallel sheets of material inert to the solvent matrix, sealed at the edges, thereby containing the dye dispersed in the solvent matrix.

The method of the present invention can be used to detect any type of high intensity infrared radiation in the range from 700 to 1300 nm, including coherent, incoherent, polarized, pulsed laser, continuous laser, and diffuse infrared radiation Because of the high intensities associated with pulsed laser radiation, the methods of the present invention are particularly well-suited for detecting radiation from these sources. In particular, the infrared detector is envisaged as an aid in aligning infrared laser beams, such as those produced by, for example, Ti-sapphire, Ruby, Alexandrite, Helium-Neon, GaAlAs and InGaAs diode, Nd-YLF, Nd-glass, and Nd-YAG lasers. Whether the dye has been exposed to infrared is evaluated by detecting the visible light emitted therefrom, for example, by visually observing the compound. Typically, the intensity of the emitted radiation is visible to the unaided human eye under ambient lighting conditions when the infrared intensity is greater than 1 $MW/cm^2$. Infrared intensities less than 1 $MW/cm^2$ can be seen by darkening the room in which observation is made or by viewing the emission through a filter which cuts all but the region of the visible spectrum in which emission occurs. Alternatively, exposure of the dye to infrared radiation can be evaluated by detecting visible emission by any conventional analytical method, such as, for example, by using a spectrophotometer or a photomultiplier. In this manner; intensities of infrared radiation much too weak to produce intensities visible to the eye can be detected.

In another aspect of the present invention, there is provided a method for detecting the cross-sectional shape of an infrared laser bear. The method comprises detecting infrared radiation as discussed above at various locations potentially exposed to an infrared laser beam. The infrared radiation intensity detected at the various locations is then correlated to the cross-sectional shape of the infrared laser beam. One method of practicing this embodiment of the invention is to place the infrared detector in the beam path, to adjust the position of the infrared detector until the entire beam cross-section impacts the infrared detector, and to determine visually the shape of the emitted light. The shape of the emitted light correlates substantially to the cross-sectional shape of the laser beam. Alternatively, the infrared detector can be divided into arbitrarily sized pixels, and each pixel evaluated, such as electro-optically, for emission of visible light. The geometric configuration of the boundary between those pixels exposed and those pixels not exposed indicates the cross-sectional shape of the beam.

A feature of the compounds and compositions of the present invention is that they increase emission intensity as the intensity of infrared exposing radiation increases over the infrared intensity range from 0 to about 200 $MW/cm^2$. Because of the two-photon absorption process, the emission follows a square law. This is in contrast to the infrared detection materials presently on the market, which exhibit saturation at infrared intensities of less than 1 $MW/cm^2$. Accordingly, the present invention provides a method for detecting the cross-sectional intensity profile of an infrared laser beam. The method comprises detecting infrared radiation intensity using the method provided therefor by the present invention at various locations potentially exposed to an infrared laser beam and then correlating the infrared radiation intensity detected at the various locations to the cross-sectional intensity profile of the infrared laser beam. As in the previous detection methods, the infrared intensity is preferably detected visually by evaluating the intensity of emitted visible light. Since, for infrared intensities less than 200 $MW/cm^2$, the intensity of emitted visible light increases as the square of the infrared intensity increases, the visible intensity profile corresponds directly with the infrared intensity profile of the infrared beam. Alternatively, the intensity of emission from each arbitrarily small pixel can be evaluated, for example, photoelectrically using a photomultiplier. This method of detecting the cross-sectional intensity profile of a laser beam permits adjustment of optics to maximize focus of the beam at a particular point or to find the focal plane of the optical system. Further, the method permits evaluation of beam homogenization and attenuation efforts.

Many infrared laser beams fluctuate in intensity with time. The detection method of the present invention can also be used to detect the temporal profile of infrared beam intensity. The method includes detecting infrared radiation as discussed above at a location potentially exposed to an infrared laser beam at various times. The infrared radiation intensity detected at the location is then correlated with the temporal intensity profile of the infrared laser beam.

As mentioned above, and as evident from the foregoing discussion, it is envisioned that the detection method of the present invention will find use in evaluating the characteristics of infrared laser beams. However, the detection method of the invention is not limited thereto and can also be used to detect the presence of unwanted potentially harmful stray reflections from infrared laser beams.

The present invention further relates to a method for reducing intensity of infrared radiation. The method includes providing a styryl compound of the instant invention and passing infrared radiation through the styryl compound. In this manner, the styryl compound reduces intensity of the infrared radiation. The styryl compound is preferably dispersed in a matrix material, as described above with respect to the compositions of the present invention. The matrix material can be a polymer such as a polyurethane, a polyester, a polyalkyacrylic acid or ester, or mixtures thereof; a glass, such as a sol gel glass or Vycor glass; or a liquid. The styryl compound can be present in the matrix material in any concentration depending on the degree of intensity reduction desired and the thickness of (i.e. path length of the radiation through) the matrix material. Useful reductions in intensity at practical matrix thicknesses are effected when the compound is present in the matrix material in a concentration of from about 0.001M to about 0.1M, more preferably from about 0.0015M to about 0.01M. To reach a higher efficiency, the compound is preferably present in as great a concentration as possible, consistent with avoiding aggregate formation. Although the matrix may be of any geometrical form, it is preferred that the matrix have two parallel faces such as in a cylindrical rod or a film. The matrix material is chosen based on its infrared transparency and its capacity to be readily shaped into the desired form. Film forming polymers are preferred in cases where a film is desired, and casting polymers are preferred in cases where a rod form is required.

Figure 1B:
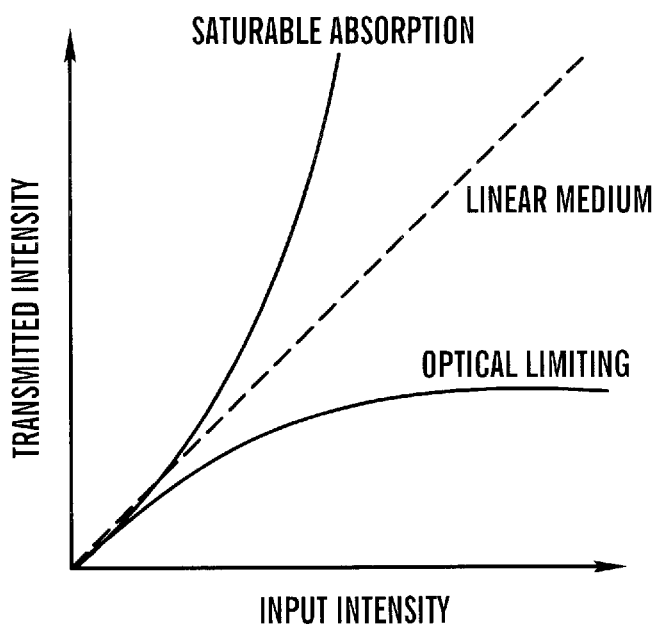
FIG. 1B, is a plot of transmitted intensity, $I_t$, as a function of input intensity, $I_o$, for each of the three media.
Figure 2A:
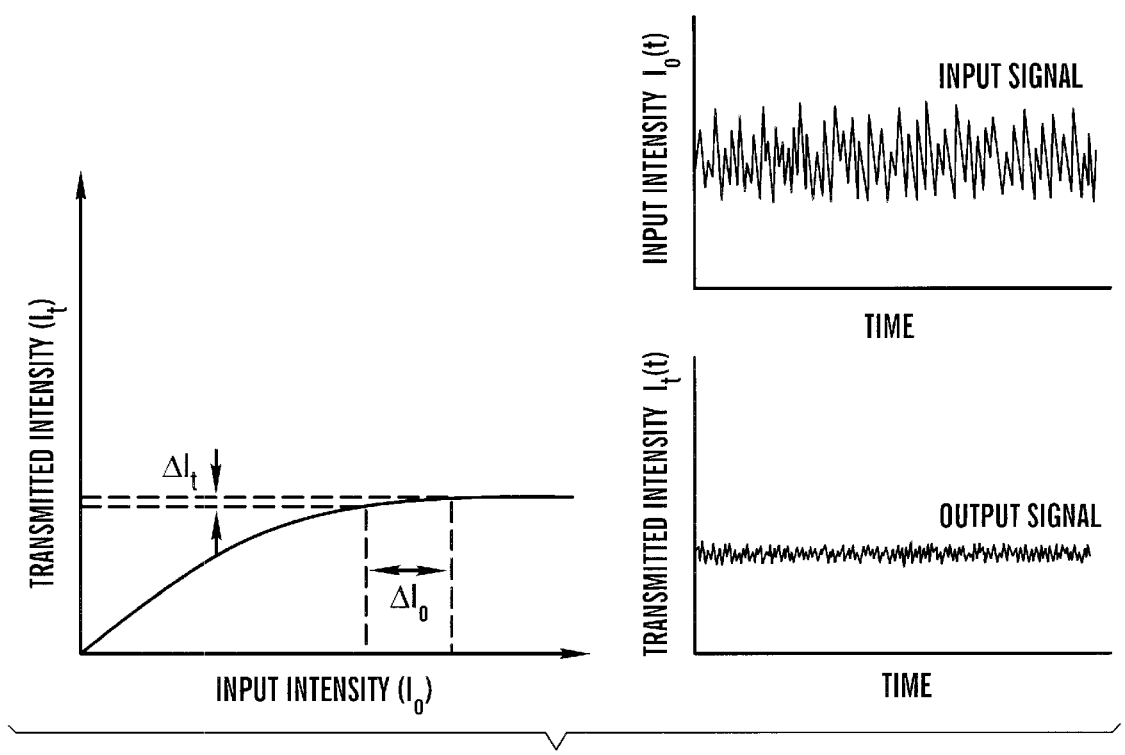
FIG. 2A displays the transmitted intensity as a function of the input intensity through a typical composition of the present invention. At higher input levels, a larger input intensity variation, $\Delta I_o$, results in a smaller output intensity variation, $\Delta I_t$, due to the intrinsic two-photon absorption exhibited by the compounds of the present invention.
Figure 2B:
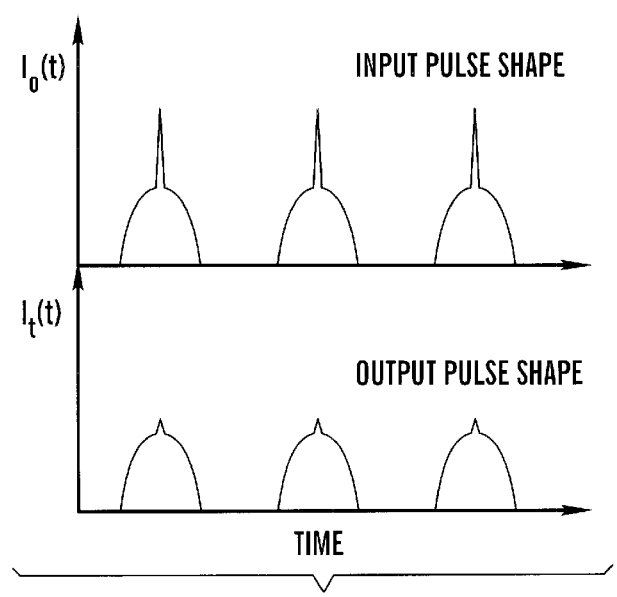
FIG. 2B shows a plot of $I_o$ as a function of time, t, of an input pulse and a plot of $I_t$ as a function of time, of the typical resulting pulse transmitted by the compound of the present invention.

As noted above, the strong two-photon absorption properties of the compounds and compositions of the present invention increase with increasing intensity of incident infrared radiation. Consequently, as depicted in FIGS. 1A and 1B, in the limit of low intensity incident infrared radiation, conversion via the TPA mechanism to a visible emission is low, and the transmitted infrared intensity increases linearly with increasing incident infrared intensity. At higher incident infrared intensities, conversion of infrared radiation to a visible emission is high and the transmitted infrared intensity approaches a saturated maximum. Thus, as shown in FIG. 1A and 1B, the optical limiting effect does not simply reduce infrared intensity, which can be done by using an optical attenuator or filter. Instead, the styryl compounds and compositions of the present invention reduce the transmitted intensity of higher input intensity infrared radition more than lower input intensity infrared radition. Consequently, method of reducing infrared radiation of the present invention is particularly well suited for automatically controlling the transmitted intensity of infrared radiation at a stable level, as indicated in FIG. 2A, and for reshaping a transmitted infrared intensity profile, as indicated in FIG. 2B. This phenomenon has been described in detail with respect to another dye in He et al., "Two Photon Absorption Based Optical Limiting and Stabilization in Organic Molecule-Doped Solid Materials," *Optics Communications*, 117:133–136 (1995), which is hereby incorporated by reference.

Without wishing to be limited by the theory which follows, it is believed that the TPA induced reduction in transmissivity can be expressed as $$I(L)=I_o/(1+I_o L\beta)$$

where I(L) is the transmitted incident intensity; L is the thickness of the matrix material; $I_o$ is the incident infrared intensity; and p is the TPA coefficient of the sample medium and is a linear function of the concentration of the styryl compound in the matrix. As one of ordinary skill in the art will recognize, the maximum transmitted intensity can be adjusted as desired by varying the thickness of matrix material or the concentration of the styryl compound in the matrix material or both.

The above-described method can be used to reduce intensity of infrared radiation having wavelengths corresponding to the two-photon absorption of the compounds of the present invention or, more specifically, wavelengths from about 700 nm to about 1300 nm. The method is particularly useful in reducing the intensity of infrared radiation produced by a Nd-YAG laser.

Reducing infrared intensity by the above method can be advantageously employed to protect sensitive infrared detectors, such as those containing a photoelectronic materials, such as photomultipliers or a infrared-sensitive photodiodes, from damage caused by intense infrared radiation, particularly, because the method reduces high intensity incident radiation to a greater degree than lower intensity incident radiation. The intensity of the infrared radiation incident on the sensitive infrared detector is reduced simply by placing a styryl compound of the present invention, preferably dispersed in a matrix material, between the infrared detector and the source of infrared radiation. The compound can be placed external to the detector, such as by mounting the compound in an appropriate holder in the infrared light path in front of the infrared detector. The invention also provides a device for detecting infrared radiation comprising an infrared detector and a window comprising a compound of the present invention positioned at a location where incident infrared radiation passes through the window prior to entering the detector. Where the compound is dispersed in a polymeric matrix material or a glass matrix material, the window can be cast from the matrix material, or the matrix material can be coated on a pre-existing window of the device. Alternatively, the window can be a cell suitable for containing a liquid and filled with a styryl compound dispersed in an appropriate solvent.

The method of reducing infrared radiation of the present invention can also be employed to protect the eyes of those potentially exposed to intense infrared radiation. To this end, the present invention, in a further aspect thereof, provides eyewear having a lenses containing the compounds of the present invention. Eyewear, as used herein, includes glasses, such as safety glasses and prescription glasses, safety goggles, and face shields. The lenses of the eyewear can be made of any material substantially transparent to at least a portion of the visible spectrum, such as glass or a polymer, such as those described in U.S. Pat. No. 5,147,585 to Blum, which is hereby incorporated by reference. The lens can contain the compound as an integral part of the lens, dispersed therein at the time of its manufacture, or the lens can be coated with a matrix material having the compound dispersed therein, such as with a composition described above. Methods for coating lenses with polymeric materials are detailed in, for example, U.S. Pat. No. 4,758,448 to Sandvig et al. and U.S. Pat. No: 5,147,585 to Blum, which are hereby incorporated by reference.

In another aspect of the present invention, a method for converting infrared radiation to visible light is provided. The method includes providing a styryl compound of the present invention and exposing the compound to infrared radiation. In this manner, the compound converts the infrared radiation to visible radiation, such as visible red radiation. Preferably, the compound is dispersed in a matrix material as described above, such as a polymer, a glass, or a liquid. Suitable glasses include sol gel glasses and Vycor glasses. Suitable polymers include polyesters, polyurethanes, polyalkyacrylic acids or esters, epoxies, polyimides, polyamides, phenalformaldehyde polymers, urea-formaldehyde polymers, melamine-formaldehyde polymers, and mixtures thereof. Suitable dispersing liquids include alcohol solvents, such as methanol, ethanol, isopropanol, and n-butanol; ketone solvents, such as acetone, methyl ethyl ketone, and cyclopentanone; ester-containing solvents, such as ethyl acetate and isopropyl acetate; ether solvents, such as tetrahydrofuran, diglyme, and dioxane; chlorinated hydrocarbons, such as methylene chloride, chloroform, and carbon tetrachloride; acetonitrile; pyridine; dimethylformamide; and dimethylsulfoxide. Where the compound is dispersed in a glass or polymer matrix material, the material can be of any suitable geometric form. One suitable form is a three-dimensional solid having at least two parallel sides, such as a cylindrical rod, separated by a distance of from 2 to 20 mm. Other suitable forms are an optical fiber and an optical waveguide. The compound can be dispersed in the aforementioned matrix materials in any suitable concentration, preferably from about 0.001M to about 0.1M, more preferably from about 0.0015M to about 0.01M.

The above described method can be used to convert infrared radiation having wavelengths corresponding to the two-photon absorption spectra of the compounds of the present invention, or, more specifically, from about 700 to about 1300 nm; to radiation having wavelengths from about 350 to about 680 nm. The method is particularly useful for converting infrared radiation produced by a Nd-YAG laser although other infrared sources, such as, for example, Ti-sapphire, ruby, Alexandrite, semiconductor diode, Nd-YLF, and Nd-glass lasers, can be converted. The emitted radiation can be coherent (laser) radiation or it can be incoherent (non-laser) radiation, such as when the compounds or compositions of the present invention absorb two-photons and fluoresce. With regard to the production of fluorescent radiation, the compounds and compositions of the present invention, can be used as fluorophores in two-photon based microscopy and two-photon based imaging as described in Tsien, "Fluoroscence Imaging Creates a Window on the Cell," *Chem. Eng. News*, pp. 34–44 (Jul. 18, 1994) and Denk et al., "Two-Photon Laser Scanning Microscopy," *Science*, 2:73–76 (1990), which are hereby incorporated by reference.

A laser is also provided by the present invention. The laser comprises a source capable of producing infrared radiation, and a styryl compound of the present invention. The compound is positioned at a location where infrared radiation from the source exposes the compound. The compound converts the infrared radiation to visible radiation. Construction details of the laser, including appropriate pump sources and cavity optics, are the same as those used in conventional (solution) dye lasers, such as those described in Hecht, which is hereby incorporated by reference. The infrared laser source is preferably a Q-switched pulsed Nd-YAG laser having a pulse width of from 1 ns to 100 ns, a spectral width of less than 10 cm$^{-1}$, an angular divergence of from 0.5 mrad to about 2.5 mrad, and a repetition rate of from 0.1 Hz to about 1 kHz. To achieve cavity lasing, two parallel plane reflective surfaces, such as dielectric-coated mirrors, can be employed. The pump beam can be coupled into the cavity by any of the conventional methods, such as by focused normal incidence.

The two-photon pumped lasing mechanism, by which the above laser is believed to operate, has several advantages. Most dyes dissociate easily when pumped by ultraviolet or visible light but are more resistant to infrared pumping. Therefore, the life of the laser dye is extended by the two-photon pumping mechanism. Additionally, in two-photon pumped lasing, absorption of the pump beam by the medium is very small. As a result, the bulk of the medium can be used rather than only the surface layer, as is the case in conventional one-photon lasing. Consequently, the gain length can be made very large, for example, by using waveguides or optical fibers doped with the compounds of the present invention. As a result, highly efficient lasing can be achieved.

Multiphasic Composite Glasses

Figure 19:
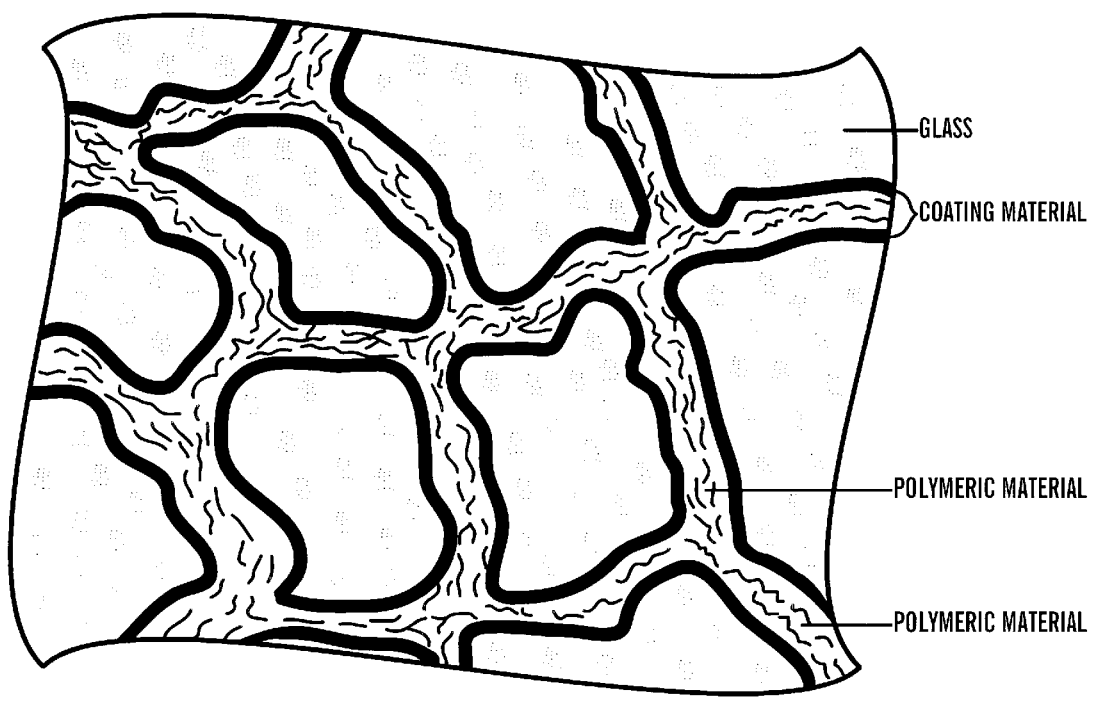
FIG. 19 is a simplified schematic representation of the composite of the present invention.

The present invention also relates to porous glass-polymer composites and to methods for using these composites. One aspect of the present invention relates to a composite comprising a glass having pores, a coating material on the surface of the pores, and a polymeric material in the pores. The composite is schematically shown in FIG. 19.

The porous glass, which, in part, forms the composite of the present invention, can be any porous three dimensional network of interconnecting, covalently bonded oxides, such as oxides of silicon, germanium, aluminum, titanium, boron, zironium, and mixtures thereof.

Porous glasses can be divided into two distinct categories, consolidated and unconsolidated. Unconsolidated glasses are composed of discrete particles, and porosity in these glasses is dependent upon particle size and type of packing. A consolidated media is one in which the solid structure forms a continual and generally permanent network resulting from sintering, deposition from solution, polymeric growth, or selective dissolution, to name a few methods. Type VI silica is a consolidated porous media and has virtually total interconnectivity.

The porous glass is preferably a Type VI gel-silica, more preferably a Type VIA gel-silica, wherein at least 80% of the pores of the highly porous, consolidated silica sol-gel monolith are interconnected, more preferably wherein at least 98% of the pores are interconnected.

The porous glass according to the present invention possesses an average pore diameter which can vary widely depending on the desired mechanical strength, which tends to decrease as the pore diameter increases. However, the average pore diameter typically ranges from about 10 Å to about 500 Å, preferably from about 20 Å to about 100 Å, and even more preferably from about 40 Å to about 50 Å. The total pore volume of the porous glass can be from about 20 to about 80%, preferably from about 60 to about 70% of the total volume of the porous glass.

The density of the porous glass may be from about 1.3 g/cc to about 1.7 g/cc, and preferably is from about 1.4 g/cc to about 1.5 g/cc. The specific surface area of the monolith may be from about 10 m$^2$/g to about 1000 m$^2$/g, preferably from about 200 m$^2$/g to about 1000 m$^2$/g, and more preferably from about 800 m$^2$/g to about 900 m$^2$/g.

The porous glass useful in the composites of the present invention is preferably transparent for wavelengths of from about 160 nm to about 4.5 microns at about room temperature and preferably maintains this range of wavelengths at temperatures greater than about 50° C., more preferably at temperatures greater than about 100° C., even more preferably at temperatures greater than about 400° C., and most preferably at temperatures greater than about 1,000° C. The highly porous, consolidated silica sol-gel monolith is also preferably transparent for wavelengths of from about 160 nm to about 300 nm and most preferably for wavelengths of about 160 nm to about 235 nm, at about room temperature. As used here and throughput this specification, the term "transparent" or "transparency" means a percent transmittance of 50% or greater.

In addition to glasses containing only an oxide of a single element, it may be desirable in certain circumstances to use porous glasses having additional materials incorporated therein to achieve certain desired effects.

One example of such an additional material is the oxides of alkalies, alkali earths, and other metals, such as $Na_2O$, $CaO$, $TiO_2$, $ZrO_2$, $Al_2O_3$, which are frequently used to modify the physical properties of the glass. Other additional materials include rare earth metal ions, present, for example, as their chloride, nitrate, acetate, or sulfate salts, which are conventionally employed to produce lasing glasses. These rare-earth metal ions include, for example, lanthanide ions, such as $Er^{3+}$, $yb^{3+}$, $Ho^{3+}$, $Tm^{3+}$, and $Nd^{3+}$, and actinide ions. Details relating to rare-earth doped glasses and methods for uniformly incorporating these metals into glasses are described in U.S. Pat. No. 5,196,383 to Ito et al., which is hereby incorporated by reference.

In still other situations it may be desirable that the glass include certain organic materials, such as fullerenes, which have been shown to have optical limiting properties Methods for incorporating such materials into sol-gel glasses are detailed in, for example, U.S. Pat. No. 5,420,081 to Mattes et al. and Dai et al., "Preparation of $C_{60}$-doped Solid Silica Gel via Sol-Gel Process," *J. Am. Ceram. Soc.* 79:2865 (1992), which are hereby incorporated by reference.

Other glasses suitable for use in the present invention include a Vycor glass having pore size from about 20 Å to about 100 Å, preferably from about 35 Å to about 50 Å. Vycor glasses suitable for use in the composites of the present invention are commercially available, for example, from Corning Glass, Inc., Corning, N.Y.

Other suitable glasses include those prepared by the two-step hydrolysis sol-gel process described in Gvishi et al. *Ph.D. Thesis*, Jerusalem Israel: The Hebrew University of Jerusalem (1993), which is hereby incorporated by reference.

The surface of the pores of the glass are coated with a coating material which can occupy between about 1 to 100 percent of the surface area of the pores. The coating material can be an optically responsive material, such as a laser dye, an optical power limiter, or an optically responsive coating material having a non-linear optical response.

Laser dyes useful for coating the surface of the pores include many organic compounds which exhibit lasing activity, such as those compiled in Maeda, *Laser Dyes*, Orlando, Florida: Academic Press (1984), Sorokin, Kagan, and Hecht, which are hereby incorporated by reference. Particularly useful laser dyes include cyanine, xanthrenetriarylmethane, acridine, azine, chlorophyl, polyphenylene, condensed aromatic ring, coumarin, oxazole, phthalimide, pteridine, stilbene, and styrene dyes. Many known laser dyes and their optical properties are described in Brackmann, *LAMBDACHROME*™ Laser Des Gottingen, Germany: Lambda Physik Gmbll (1994), which is hereby incorporated by reference.

Useful laser dyes include those dyes capable of undergoing one-photon excitation as well as those capable of two photon excitation. Suitable laser dyes in the latter category include styryl dyes of the present invention, such as trans-4-[p-(N-ethyl-N-hydroxyethylamino)styryl]-N-methylpyridinium tetraphenyborate, trans-4-[p-(N,N-dimethylamino)styryl]-N-methylpyridinium tetraphenyborate, trans-4-[p--ethyl-N-hydroxyethylamino) styryl]-N-hydroxyethylpyridinium iodide, trans-4-[p-(N-ethyl-N-hydroxyethylamino)styryl]-N-butansulfonpyridinum, and 4-[N-(2-(hydroxyethyl)-N-methyl)aminophenyl]-(6-hydroxyhexylsulfonyl)stilbene.

The laser dye component of the composite of the present invention can be present in the composite at any concentration capable of exhibiting a lasing effect. Typical concentrations are from about $10^{-7}$ to about $10^{-1}$ moles per liter of the glass in which the laser dye is incorporated. Preferred dye concentrations are from about $10^{-6}$ to about $10^{-2}$ moles per liter of glass.

As indicated above, the coating material can alternatively be an optical power limiter. Suitable optical power limiters include those described in Tutt et al., *Prog. Quant. Elect.*, 17:299 (1993), which is hereby incorporated by reference. One particularly useful optical power limiter is bisbenzothiazole 3,4-didecyloxy thiophene ("BBTDOT") the synthesis and optical properties of which are respectively described in Zhao et al., *Chem Mater.* 2:670 (1990), and in He et al., *Optics Lett.* 20:437 (1995), which are hereby incorporated by reference. Another class of suitable optical power limiters are the fullerenes, particularly $C_{60}$ and $C_{70}$, many of which are commercially available or which can be prepared by the methods described in Hanmmond et al., *Fullerenes: Synthesis, Properties, and Chemistry*, Washington, D.C.: American Chemical Society (1992), which is hereby incorporated by reference.

The optically responsive coating material can also be a material having a non-linear optical response. Such materials typically have third-order susceptabilities ("$\chi^{(3)}$") greater than $10^{-9}$ esu. Such materials include macrocycles, polydiacetylenes (preferably polymerized in the pores), and other conjugated structures, such as phthalocyanines.

The coating material can be a single compound or a plurality of compounds (such as two or more laser dyes, two or more optical power limiters, one or more laser dyes and one or more amplifiers, and the like. Alternatively, the coating material can comprise an optically responsive material and other materials, such as polymers. Where the coating material is a plurality of compounds, the compounds can be mixed in a single layer on the surface of the pores, or they can be deposited in discrete or semi-discrete layers on the pore surface. Where a plurality of compounds are used and the compounds are such that one compound will quench the excited state of one of the other compounds, it is particularly preferred that they form discrete layers on the pore surface with a barrier layer, such as a polymeric layer, between the discrete layers.

The pores contain a polymeric material, which, preferably, fills from 10 to 100 percent of the remaining pore volume (that is, the volume of the pores not occupied by the coating material). Preferably the pores are filled by the polymer.

Suitable polymeric materials include those described above in connection with compositions comprising a matrix material and a styryl dye. Preferred polymers have an index of refraction close to that of the glass in which the pores are formed. For example, where the-glass is a silica glass, the preferred polymeric material is poly (methyl methacrylate).

The present invention also relates to a composite wherein a dispersed material is optionally dispersed in the polymeric material which is contained in the pores of the glass. The optional dispersed material can be an optically responsive material, such as a laser dye, an optical power limiter, or a nonlinear optically responsive material, examples of and selection criteria for which include those discussed above for coating materials. Several additional considerations in selecting the dispersed material should be noted. First, the dispersed material should be chemically inert to and miscible with the polymer, and, as noted below, preferably miscible with the monomer from which the polymer forms. Second, when using a dispersed material, it is advantageous that the composite coating material and dispersed material be selected so that coating material's solubility in suitable solvents and the dispersed material's solubility in the polymeric material be maximized. For example, a composite having a poly(methyl methacrylate) ("PMMA") polymeric material, a trans-4-[p-(N-ethyl-N-hydroxyethylamino) styryl]-N-hydroxyethylpyridinium iodide laser dye, and a Rhodamine 6G laser dye would advantageously have the trans-4-[p-(N-ethyl-N-hydroxyethylamino)styryl]-N-hydroxyethylpyridinium iodide dye coating the pore surface and the Rhodamine 6G dye dispersed in the polymer because the insolubility of trans-4-[p-(N-ethyl-N-hydroxyethylamino)styryl]-N-hydroxyethylpyridinium iodide in PMMA and, more importantly, its insolubility in methyl methacrylate monomer would make preparation of an PMMA-containing trans-4-[p-(N-ethyl-N-hydroxyethylamino)styryl]-N-hydroxyethylpyridinium iodide composite difficult.

Although it is generally preferred that the optional dispersed material form a solution in the polymer, the dispersed material may be in the form of microaggregates or crystals. Where the dispersed material is insoluble in the polymer but soluble in the monomer, aggregation can be minimized by rapid polymerization of the monomer, such as by the use of light, heat, and polymerization initiators.

The composite of the present invention is particularly advantageous where each of the dispersed and coating materials is a dye and where one of the dyes would quench the other's excited state if both dyes were dispersed in a single phase, such as in a solution. Where two such dyes are employed, maximum composite life is achieved when the coating material is insoluble in the polymeric material and in the monomeric material so that migration of the coating dye from the coating phase into the polymer phase, where quenching could occur, is minimized.

The composite of the present invention is produced by providing a glass having pores, the surface of which pores are coated with a coating material, as detailed above. A monomeric material is infused into the pores of the glass thus provided, and the monomeric material is permitted to polymerize.

The monomer is selected based on its size relative to the size of the pores to ensure that the monomer can penetrate the pores of the glass. Furthermore, the monomer must have a surface tension which permits penetration of the monomer into the glass pores. In this regard, for many glasses, allyl methacrylates are preferred to hydroxyalkyl allylates. Another factor influencing monomer selection relates to the refractive index of the polymer formed upon polymerization, the importance of which is discussed above.

Prior to the aforementioned polymerization step, a dispersed material can be infused into the pores. This can be done, for example, by exposing the porous glass containing monomer to the dispersed material for a time effective for the dispersed material to diffuse into the monomer. However, this time is generally extremely long, and, consequently, it is preferred that the infusion of the dispersed material be effected simultaneously with the infusion of the monomeric material. This can be achieved by infusing a composition comprising the monomeric material and the dispersed material into the pores. Optionally, the monomer may contain polymerization initiators, such as 2,2'-azobisisobutyronitrile ("AIBN") or a peroxide (e.g., benzoyl peroxide), preferably in an initiator to monomer ratio of from 0.25 to 5%, more preferably from 0.5 to 2%. Alternatively or additionally, polymerization may be accelerated by the application of heat or light, or polymerization may be effected by permitting the passage of time at near room temperatures (i.e. from 25° C. to 40° C.). Irrespective of how the polymerization reaction is initiated or sustained, it is preferably conducted in a sealed container and in the absence of oxygen.

The porous glass having a pore surface coated with a coating material can be advantageously provided by providing a glass having pores and coating the coating material on the surface of the pores. In a preferred method for coating the pores with the coating material, the porous glass is contacted with a composition containing a solvent and a coating material under conditions effective to infuse the solvent and the coating material into the pores of the glass, and then removing the solvent. Contacting may be achieved by any suitable means, such as by spraying, brushing, or dripping the solution onto the glass or, preferably, by immersing the glass into the solution. The term "solvent" refers to a medium which is fluid at ambient temperatures and capable of dissolving a sufficient amount of the coating material (e.g., a laser dye) to exhibit the desired activity (e.g., lasing activity).

The coating material component of the solution which is incorporated into the porous glass when preparing the composite of the present invention is preferably employed in a concentration of from about $10^{-4}$ to about $10^{-2}$ molar, more preferably in a concentration of about $10^{-3}$ to about $10^{-2}$ molar of the coating material in the solution. In cases where the coating material is minimally soluble in the solvent, such as $C_{60}$ in toluene, it is preferred that a saturated solution be employed.

The solvent component of the solution may be a single solvent or a mixture of solvents. Suitable organic solvents include, but are not limited to, aliphatic, alicyclic, and aromatic media such as n-octane, cyclohexane, methylene chloride, trichloroethylene, carbon tetrachloride, dibutyl ether, dioxane, tetrahydrofuran, dimethylformamide, ethanol, butanol, acetone, diethylketone, acetonitrile, benzene, chlorobenzene, toluene, xylene, mesitylene, and the like. Water or a mixture of water with a miscible organic solvent also can be utilized when the aqueous media is compatible with the coating material.

The step wherein the solvent is removed to form a substantially solvent free porous glass having its pore surface coated with coating material can vary widely but is typically carried out at a temperature of from about 0° C. to about 300° C., preferably from about 10° C. to about 200° C., and most preferably from about 20° C. to about 100° C. The duration of this solvent removal step may last from about 1 hours to about 48 hours, and can be reduced when conducted under vacuum. The optimal temperature for solvent removal depends on the thermal stability of the coating material and glass and the boiling point of the solvent.

The substantially solvent free coated porous glass obtained after the solvent removal is typically characterized by having molecules of the coating material physically adsorbed on the inner surfaces of the pores of the glass. In a preferred embodiment, the molecules of the coating material are present in a solid state, such as a crystalline solid state, with no significant amount of solvent being present.

Alternatively, in certain instances, coating the surface of the pores can be effected by exposing the surface of the pores of the glass to the coating material in gaseous form, such as under high vacuum, and permitting the gaseous coating material to condense on the pore surfaces, such as by removing the vacuum.

Porous glasses suitable for the preparing the composites of the present invention can be obtained a number of ways. For example, the porous glass can be a Vycor glass (having pore size from about 20 Å to about 100 Å, preferably from about 35 Å to about 50 Å) obtained commercially from Corning Glass, Inc., Corning N.Y.

Alternatively, suitable porous glasses can be prepared by sol gel processes which comprise:

(a) hydrolyzing and polycondensing one or more alkoxide precursors to form a sol comprising a plurality of particles suspended in a liquid;

(b) cross-liking the particles to form a gel;

(c) aging the gel to form an aged gel;

(d) removing the liquid from the aged gel to form a dried, aged gel; and (e) stabilizing the dried, aged gel to produce the porous glass.

Suitable alkoxide precusers include tetraalkoxy silanes, such as tetramethoxysilane and tetraethoxysilane, and those described in Brinker et al., Sol-gel *Science*, San Diego, Calif.: Academic Press (1990), which is hereby incorporated by reference.

Preferably, either $HNO_3$ or a combination of $HNO_3$ and H is used as catalyst for the hydrolysis reaction. More preferably, $HNO_3$ or a combination of $HNO_3$ and HF is first added to deionized $H_2O$, and then one or more selected alkoxide precursors is mixed into this acid solution. The molar ratio of water to the alkoxide precursor is preferably kept at about 16.

The time and temperature of the stabilization step (e) above are both important in producing a highly porous, consolidated porous glass with well defined characteristics, such as a uniform pore size, a known pore surface area, and a known total pore volume. Changes in these process parameters will influence the physical characteristics of the sol-gel, such as pore size, pore surface area, and pore volume, within a very wide range. An important feature of the sol-gel process is that, with sufficient control of the kinetics and ultrastructure, it is possible to produce optically transparent pure silica components which have substantial quantities of interconnected pores of size smaller than will scatter visible light and, with some grades of gel-silica, even ultraviolet light. This optically transparent porous silica is termed a Type VI silica.

The process schedule for highly porous, consolidated silica sol-gel glasses is more fully described in U.S. Pat. No. 5,222,092 to Henchet al., Hench et al., "Gel-Silica Optics," *SPIE Proc.* 878:76 (1988), Hench et al., "The Sol-Gel Process," *Chem. Rev.* 90:33 (1990), and Nogues et al., "Fast, Radiation-hard Scintillating Detector: A Potential Application for Sol-Gel Glass," *J. Amer. Ceram. Soc.* 17:1159 (1988), which are hereby incorporated by reference.

The porous glasses used to form the composites of the present invention, can be processed over a wide range of stabilization temperatures. Throughout this range of stabilization temperatures, the highly porous, consolidated silica sol-gel monolith is transparent through the visible and at least a part of the ultraviolet spectrum because the pores of the monolith have a very small average radius, for example, as small as 10 Å, and thus do not scatter light. The pore dimensions, specific surface area, and total pore volume of these gel-silicas are commonly determined by the use of quantitative $N_2$ adsorption-desorption isotherms.

The step wherein the liquid is removed to form a dried, aged gel, step (d) above, can vary widely but is preferably carried out a temperature of from about 150° C. to about 180° C. The step wherein the dried, aged gel is stabilized, step (e) above, is typically cared out at a stabilization temperature of from about 180° C. to about 1,100° C., preferably from about 200° C. to about 950° C., and more preferably at a stabilization temperature of from about 450° C. to about 550° C. The duration of stabilization step (e) can vary greatly but typically lasts from about 10 to about 200 hours. Preferably, the stabilization step (e) lasts about 20 hours. A summary of the physical and ultrastructural characteristics of glasses produced by sol gel processes and the effects of stabilization temperature and duration on pore size and consolidation are detailed in U.S. Pat. No. 5,222,092 to Hench et al., which is hereby incorporated by reference.

The surface finish ranges define the size of any surface deformities, which cannot be smaller than the underlying pore size of the monolith. The surface finish is also directly related to the transmission capabilities of the monolith and thus its suitability for use in optical applications.

The composites take on the form of the porous glass from which they are made. The glass can be cast in the form of fiber to form a fiber composite. Alternatively, the glass can be cast into a free standing film, preferably having a thickness of from about 0.001 to about 1 mm. The glass can also be coated as a film on a substrate, such as paper, a polymer film, a metal sheet, or glass. Preferably, the glass forms a film from about 0.01 to about 0.05 mm thick on the substrate.

The glass, and the resulting composite, can also be in the form of a three dimensional article, preferably having two parallel faces, such as a rod. The faces can be polished by conventional methods, such as by manual grinding using a diamond grinding wheel, by abrading the surface using abrasives, such as silicon carbide paper, preferably with increasing grit ranging from 60 to 2000 and preferably using a lubricant, such as water, or by polishing on cloths with 10 to 0.1 $\mu$ grade diamond paste, preferably using an automated grinding and polishing machine, such as the METASERV™ 2000 (Buehler VK Ltd., Coventry, England), or by combinations thereof. Polishing is best effected by sequentially performing the above steps.

In an especially preferred embodiment of the invention, the sol is cast into a mold, such as a cuvette, and gelled within the mold under conditions which produce the desired net shape and the desired net surface.

The composites of the present invention are of high optical quality and are useful in various photonic functions such as lasing, optical power limiting, and non-linear optical response.

The composites are particularly useful to form multiphasic nanostructured composites wherein the phase separation can be on the nanometer scale. By dispersing a second optically responsive material in the polymeric material, a composite having two phases, an interfacial phase comprising the coated material on the pore surface and a polymer phase comprising the dispersed material in the polymer, can be produced. In contrast to composites containing two optically responsive materials mixed in a single phase, the multiphasic nanostructured composites of the present invention retain the optical response characteristic of each material. In terms of applying the present invention to tunable lasers by using two laser dyes which reside in different phases, reduced energy transfer between the dyes results in a composite having a broad tunability range of lasing. Similarly, by using two optical power limiters, each localized in a separate phase of the composite of the present invention, a composite having optical limiting properties over an expanded range can be constructed.

Accordingly, the present invention further relates to a method for reducing the intensity of radiation. The method comprises providing a composite of the present invention comprising an optically responsive coating material which is an optical power limiter and passing radiation through the composite. In this manner, the composite reduces the intensity of the radiation. In a preferred embodiment, the polymer of the composite contains a second optical power limiter dispersed therein. Preferably, the optical power limiter (or, in the case where a second optical power limiter is dispersed in the polymer, one of the two optical power limiters) has an absorption, more preferably an absorption maximum, corresponding to the wavelength of the radiation. Suitable optical power limiters include dyes which are capable of undergoing two-photon absorption processes. As noted above, optical power limiters have absorptivities which increase with increasing intensity of the incident radiation. At low incident intensities, conversion via the two-photon absorption ("TPA") process is low, and the transmitted intensity increases with increasing incident intensity. At higher incident intensities, conversion of the incident radiation is high and the transmitted intensity approaches a saturated maximum. Thus, the composite of the present invention does not simply reduce intensity, which can be done by using an optical attenuator or filter. Rather, the composite of the present invention reduces the transmitted intensity of higher incident radiation more than lower incident radiation. Consequently, the method of reducing intensity of radiation of the present invention is particularly well suited for automatically controlling the transmitted intensity of incident radiation at a stable level and for reshaping a transmitted intensity profile. The phenomenon has been described in detail in He et al., "Two Photon Absorption Based Optical Limiting and Stabilization in Organic Molecule-Doped Solid Materials," *Optics Comm.*, 117:133–136 (1995), which is hereby incorporated by reference. As one skilled in the art will recognize, the maximum transmitted intensity can be adjusted by varying the thickness of the composite through which the radiation passes or the concentration of the optical power limiter(s) incorporated in the composite or both.

Reducing intensity by the above method can be advantageously employed to protect sensitive detectors, such as those containing a photoelectronic materials, such as photomultipliers or sensitive photodiodes, from damage caused by intense radiation, particularly, because the method reduces high intensity incident radiation to a greater degree than lower intensity incident radiation. The intensity of the radiation incident on the sensitive detector is reduced simply by placing the composite of the present invention containing an optical power limiter coated on its pore surface between the detector and the source of radiation. The optical power limiter is preferably active at the wavelength of the incident radiation. The composite can be placed external to the detector, such as by mounting the composite in an appropriate holder in the light path in front of the detector. The invention also provides a device for detecting radiation comprising a detector and a window comprising a composite of the present invention positioned at a location where incident radiation passes through the window prior to entering the detector. The composite used in this embodiment of the present invention can optionally contain a second optical power limiter dispersed in the polymer which is contained in the pores of the glass. In this case, at least one of the optical power limiters is preferably active at the wavelength of the incident radiation The method of reducing radiation of the present invention can also be employed to protect the eyes of those potentially exposed to intense radiation. To this end, the composites of the present invention can be used in the fabrication of eyewear, such as glasses (e.g., safety glasses and prescription glasses) safety goggles, and face shields. The lenses of the eyewear can also comprise other materials which are substantially transparent to at least a portion of the visible spectrun, such as glass or a polymer, such as those described in U.S. Pat. No. 5,147,585 to Blum, which is hereby incorporated by reference. The lens can contain the composite as an integral part of the lens, dispersed therein at the time of its manufacture, or the composite of the present invention can be cast as a film on a lens blank.

In another aspect of the present invention, a method for changing the wavelength of radiation is provided. The method includes providing a composite of the present invention containing a laser dye suitable for changing the wavelength of incident radiation and exposing the composite to radiation. In this manner, the composite changes the wavelength of the incident radiation. In a preferred embodiment, the composite contains a second laser dye dispersed in the polymeric material. By selection of a suitable pair of laser dyes, the method of the present invention can be practiced with a single composite for a range of incident radiation wavelengths broader than could be achieved with either laser dye alone. Suitable dyes for increasing the wavelength include laser dyes which undergo conventional one-photon processes.

Dyes which undergo two-photon processes, such as two-photon absorption are known to decrease the wavelength of incident radiation. Thus by using composites of the present invention comprising a dye which undergoes two photon processes, the composites can be used to decrease the wavelength of incident radiation. Again, by dispersing a second two-photon dye in the polymeric material, the range of wavelengths which can be decreased using a single composite can be advantageously increased. The method for decreasing the wavelength of radiation is particularly useful for converting laser radiation because the two photon processes require high intensity radiation (such as that available from lasers, particularly pulsed lasers) in order to operate efficiently.

In either the case of increasing or decreasing radiation wavelength, the emitted radiation can be coherent (laser) radiation or it can be incoherent (non-laser) radiation, such as when the composites of the present invention absorb photons and fluoresce. With regard t6 the production of fluorescent radiation, the composites of the present invention containing one or more two-photon dyes can be used as fluorophores in two-photon based microscopy and two-photon based imaging as described in Tsien, "Fluoroscence Imaging Creates a Window on the Cell," *Chem. Eng. News*, pp. 34–44 (Jul. 18, 1994) and Denk et al., "Two-Photon Laser Scanning Microscopy," *Science*, 2:73–76 (1990), which are hereby incorporated by reference. In this regard, the stability and chemical inertness of the composites of the present invention make them ideal for in vivo use.

A laser is also provided by the present invention. The laser comprises a source capable of producing radiation, and a composite of the present invention having, as a coating material, a laser dye. The laser dye can be a one-photon laser dye, or it can be a dye which is capable of two-photon lasing. The composite is positioned at a location where radiation from the source exposes the composite, and the composite converts the radiation from the source into laser radiation. Construction details of the laser, including appropriate pump sources and cavity optics, are the same as those used in conventional (solution) dye lasers, such as those described in Schaefer, ed., *Dye Lasers*, 2nd ed., Vol. 1: *Topics in Applied Physics*, New York:Springer Verlag (1977) and Hecht, which are hereby incorporated by reference. The source is preferably a Q-switched pulsed laser having a pulse width of from 1 ns to 100 ns, a spectral width of less than 10 $cm^{-1}$, an angular divergence of from 0.5 mrad to about 2.5 mrad, and a repetition rate of from 0.1 Hz to about 1 kHz. To achieve cavity lasing, two parallel plane reflective surfaces, such as dielectric-coated mirrors, can be employed. The pump beam can be coupled into the cavity by any of the conventional methods, such as by focused normal incidence. The composite can optionally further comprise a second laser dye which is dispersed in the polymeric material contained in the pores of the porous glass. In such an arrangement the optical properties of each laser dye is substantially unaffected by the presence of the other dye. By an appropriate choice of laser dye combination, such as a laser dye tunable in the blue and a laser dye tunable in the red, a single composite can provide tunability across the wavelength range of the two dyes. This wavelength range is broader than that available from either dye alone or from a monophasic mixture of the two dyes.

Two-Photon Photodynamic Therapy

The present invention also relates to a method of killing cells or viruses. An effective amount of a photosensitizer having absorption at a wavelength from about 380 nm to about 760 nm is provided proximate to the cells or viruses. An effective amount of a dye capable of converting photons having energies of from about 660 to about 1300 nm to photons having an energies of from about 380 to about 760 nm is also provided proximate to the cells or viruses. The dye is then exposed to light having a wavelength of from about 660 to about 1300 nm in the presence of oxygen under conditions effective to produce a cytotoxic effect on the cells or viruses.

As used herein, killing refers not only to the destruction of the cells or viruses but also to any effect on the cells or viruses which reduces their adverse impact on the mammal or, in the case where the cells or viruses are infectious, on other mammals. Thus killing also is meant to include, for example, reducing the ability of the cells or viruses to replicate, reducing their ability to produce toxic materials, and reducing their ability to infect other cells.

The photosensitizer of the present invention can be any molecule which is capable of absorbing light of about 380 to about 760 nm wavelength and which causes the destruction of cells or viruses. Suitable photosensitizers include those agents which are known to be useful in photodynamic therapy, such as those described in Fisher et al., *Lasers in Surgery and Medicine*, 17:2–31 (1995) ("Fisher"), which is hereby incorporated by reference, or in the photodynamic purification of blood. Alternatively, or additionally, the photosensitizers can be compounds which are capable of generating singlet oxygen when exposed to light having a wavelength in the range from about 660 to about 1300 nm in the presence of oxygen.

One group of suitable photosensitizers are porphyrins and porphyrin analogs, the structure, properties, and preparation of which have been extensively reviewed, such as in Dolphin ed., *The Porphyrins*, New York:Academic Press, Vols. I–VII (1978–1979) ("Dolphin"), which is hereby incorporated by reference. Porphyrins are highly π-conjugated macrocyclic tetradentate tetrapyrroles. Porphyrin analogs, as used herein, include multidentate, pyrrole-based, highly π-conjugated macrocycles.

Suitable photosensitizers include hematoporphyrin derivatives ("HPD"), which are formed by treating hematoporphyrin with a mixture of sulfuric and acetic acids as described, for example, in Kessel ed., *Porphyrin Photosensitization*, Plenum Press (1983), which is hereby incorporated by reference. The EPDs can also be size segregated aggregates, such as the ones described in U.S. Pat. No. 4,649,151 to Dougherty et al. ("Dougherty"), which is hereby incorporated by reference. Dihematoporphyrin ether ("DHE"), a purified form of these aggregates, described in Dougherty and marketed under the trademark PHOTOFRIN™ II, is particularly useful in the practice of the present invention.

Other examples of such porphyrin analogs include the chlorins, such as those described in Spikes, *J. Photochem. Photobiol. B:Biol.*, 6:259–274 (1990) and Pandey *Photochem. Photobiol.*, 53:65–72 (1991), which are hereby incorporated by reference; the pyropheophorbides, such as those described in U.S. Pat. No. 5,198,460 to Pandey et al., which is hereby incorporated by reference; and the expanded porphyrins, such as those derived from tripyrroledimethines, to which the trivial name texaphyrin has been assigned. Suitable texaphyrins are described in U.S. Pat. No. 5,439,570 to Sessler et al., which is hereby incorporated by reference. Yet other porphyrin analogs, suitable for use as photosensitizers in the practice of the present invention, include the so-called "green porphyrins". These molecules, which have absorbances in the red-orange range, are hydrobenzoporphyrins produced by Diels Alder reaction of acetylinic derivatives with protoporphyrin IX ring structures. Their structure, chemical and physical properties, and preparation is described, for example, in U.S. Pat. No. 5,214,036 to Allison et al., which is hereby incorporated by reference.

Another group of compounds suitable for use as photosensitizers in the practice of the present invention are the phthalocyanines and analogs of these phthalocyanines, the preparation and properties of which are described in Dolphin and in Rosenthal, *Photochem. Photobiol.*, 53:859–870 (1991) which are hereby incorporated by reference. One class of phthalocyanine analogs is the naphthophthalocyanines.

The photosensitizers can also be dyes belonging to the rhodamine or cyanine classes, particularly those which are described in Oseroff et al., *Proc. Natl. Acad. Sci. U.S.A.*, 83:9729 (1986), Gulliya et al., *J. L. Cell Biol. Int. Rep.*, 12:305 (1988), and Detty et al., *J. Am. Chem. Soc.*, 110:5920 (1988), which are hereby incorporated by reference. Furocoumarin, methoxsaten, and bergapten, and their derivatives, are yet other examples of photosensitizers suitable for use in the practice of the present invention. Their preparation and use in photosensitization are described in U.S. Pat. No. 4,727,027 to Wiesehahn et al., Parsons et al., *Photochem. Photobiol.*, 32:813 (1980), and Kornhauser et al., *Science*, 217:733 (1982), which are hereby incorporated by reference. Other useful photosensitizers include various chlorophyl derivatives derived from both bacteria and higher plants, such as those described in Beems et al., *Photochem.*

*Photobiol.*, 46:639 (1987), Cubeddu, et al., *Photochem. Photobiol.*, 46:633 (1987), Kessel et al., *Photochem. Photobiol.*, 40:403 (1984), and Kessel et al., *Cancer Res.*, 46:2248 (1986), which are hereby incorporated by reference; purpins and verdins, such as those described in Morgan et al., *Photochem. Photobiol.*,46:46 (1987), which is hereby incorporated by reference; and the benz-fused porphyrins described in Dolphin, 196*th American Chemical Society Meeting, Los Angeles, September*, 1988, Abstract no. 312 (1988) and Richter et al., *J. of Natl. Cancer Inst.*, 79:1327 (1987), which are also hereby incorporated by reference.

In some applications, such as where the photosensitizer is to be mixed with biological materials, it is desirable that the photosensitizer have appreciable solubility in polar solvents, especially water. In such cases it may be desirable that the photosensitizer have a side chain containing ionizable moieties, such as amines, carboxylic acids, and sulfoalkyl groups. In cases where it is desired that the photosensitizer accumulate in tumor tissues at higher concentrations than in normal tissue, side chains which increase the photosensitizer's lipophilicity, such as those containing long-chain aliphatic moieties, can be employed.

The dye which is used in the method of the present invention can be any compound capable of converting photons having energies of from about 660 to about 1300 nm to photons having an energies of from about 380 to about 760 nm. Suitable dyes include those which are organic. Preferably, the conversion is effected by a two-photon upconversion mechanism. Suitable upconverting dyes include Rhodamine B, dimethyl POPOP ("DMP"), 1,3,1', 3'-tetramehtyl-2,2'-dioxopyrimide-6,6'-carbocyanine hydrogen sulfate ("PYC"), 4-dicyanomethylene-2-methyl-6-p-dimethylaminostyryl-4H-pyran ("DCM"), and their analogs, as well as stilbene and coumarin dyes. More preferably, the upconverting dye has a two-photon absorption cross section of greater than about $1 \times 10^{-50}$ cm$^4$-sec. Upconverting dyes having two photon absorption cross sections of from about $5 \times 10^{-50}$ cm$^4$-sec to about $1 \times 10^{-45}$ cm$^4$-sec are most preferred.

Dyes suitable for use in the methods of the present invention include, but are not limited to, the above-described styryl dyes of the present invention. Styryl dyes are particularly preferred because they have a strong two-photon absorption with a cross section that is significantly greater than commercial dyes, such as Rhodamine, DCM, and DMP. The dyes also exhibit intense emission at a wavelength ranging from about 300 to about 680 nm when excited by laser radiation having a wavelength of from about 660 nm to about 1300 nm.

The dye or photosensitizer can be provided proximate to the cells or viruses by any suitable means. In cases where the method is carried out in vivo in a mammal, the dye or sensitizer is typically administered to the mammal, as described in detail below. Where the method is carried in vitro, the dye or sensitizer can simply be mixed with a sample of the cells or viruses to be killed, preferably in some fluid medium.

It is preferred that the dye or photosensitizer or both preferentially accumulate on the cells or viruses whose killing is desired. However, the present invention does not require that this be the case. For example, the photosensitizer can be designed to selectively accumulate on the cells or viruses to be killed and the dye can be substantially uniformly distributed throughout the mammal or throughout the mammal's circulatory system.

The dye or photosensitizer or both, having been provided proximate to the cells or viruses whose killing is desired, is then optionally allowed to accumulate on the cells or viruses. This is typically effected by waiting a period of time, typically from 15 minutes to several hours, prior to exposing the dye to light.

The dye is then exposed to light having wavelengths of from about 660 run to about 1300 nm. The specific wavelength of irradiating light is chosen so that it has appreciable intensity at a wavelength at which the dye absorbs, preferably at or near the absorption maximum of the dye. Suitable and preferred wavelengths for a particular dye can be readily determined from its absorption spectrum. For applications where killing is to be effected in the presence of biological materials, light having wavelengths at which biological materials have minimum absorption (i.e. from about 700 to about 1100 nm) is preferred.

The light can be polychromatic or monochromatic; preferably, it is laser light. A variety of laser sources emitting in the range from 660 to 1300 nm are available. Suitable sources will be apparent to the skilled practitioner and are summarized, for example, in Hecht, which is hereby incorporated by reference. One particularly useful laser source is a mode-locked Ti-sapphire laser, preferably operated at 790 to 800 nm and having pulse durations as short as possible (typically on the order of tens of femtoseconds). Another laser source well suited for irradiating the dye in the practice of the present invention is a Q-switched pulsed Nd-YAG laser having an output of 1060 =nm. Spectral widths of less than 10 cm$^{-1}$ are preferred. The angular divergence of the laser can be from about 0.5 mrad to about 2.5 mrad, depending on the distance of the laser from and the size of the area being irradiated. Repetition rates of from 0.1 Hz to about 1 kHz are suitable. The light dose used in the practice of the present invention is dependent on a variety of factors, including the size of the area to be irradiated, the depth of the cell to be killed, the nature of the material through which the light must pass to reach the area of the cell, the type of cell to be killed, and the efficiencies of the dye and photosensitizer. Typical radiant exposures are in the range from about 10 to about 1000 J/cm$^2$.

Laser radiation having as high frequency pulses with a pulse duration as short as possible, preferably ranging from several tens of femtoseconds to several nanoseconds, and having pulse peak powers of from about 10 to about 1000 MW, preferably several hundreds of megawatts, are preferred. High power pulsed lasers have the advantage of delivering considerable amounts of energy to the irradiated area with significantly reduced thermal side effects. This means that the light delivery rate can be increased without increasing the temperature of the material being irradiated, resulting in a reduction in the time required for treatment, and, in the case where thermally-sensitive biological materials are exposed, a reduction in the danger of unwanted destruction.

Laser light that is tightly focused on the area being irradiated is particularly preferred. It is well known in non-linear optics that two-photon induced processes exhibit the so-called "power threshold behavior", which means that the efficiency of the two-photon process scales with the square of the light's power. For this reason, high power densities are needed to trigger two-photon processes. This gives rise to yet another important clinical benefit. When the laser beam is tightly focused on the irradiated area to produce the light-induced two photon effect, no photochemical action will occur before or after the focal point of the irradiating laser beam. In other words, high spatial selectivity, which is extremely important, especially when employing the method in vivo, such as in the PDT treatment of brain cancers, is attainable using the methods of the present invention.

Because the method of the present invention uses light which is not appreciably absorbed by biological materials, the light penetrates much farther into tissue compared to conventional PDT. This is particularly true when the light has a wavelengths of 1060 nm (such as that from a Nd-YAG laser) or about 800 nm (such as that from a Ti-sapphire laser) where there is an excellent optical transparency window for tissue penetration.

Although the mechanism by which the method of the present invention works has not been established, it is believed that the dye, upon irradiation, absorbs energy and transfers it to the photosensitizer which then leads to the killing of the cell or virus. It is unclear whether the transfer of energy from the dye to the photosensitizer proceeds radiatively, non-radiatively, or otherwise. The mechanism by which the excited photosensitizer kills the cells or viruses is, likewise, unclear. However, by analogy to the widely-held view in conventional photodynamic therapy, it is believed that, upon excitation by the dye, the photosensitizer transfers energy to endogenous oxygen to convert it to singlet oxygen. This singlet oxygen is thought to be responsible for the cytotoxic effects. The practice of the present invention, however, is not dependent upon understanding the mechanism by which the method works, and, consequently, the invention is not intended to be limited to any particular mechanism.

The methods of the present invention can be used in many of the same applications in which conventional photodynamic techniques are employed. For example, the method of the present invention can be used in the treatment of biological products in vitro (such as blood for transfusion) for infectious agents, since the presence of a membrane in such agents promotes the accumulation of the photosensitizer. For example, blood plasma or blood which is to be used for transfusion or banked for future transfusion can be mixed with the dye and photosensitizer and then irradiated with light of appropriate wavelength in accordance with the method of the present invention to effect sterilization. In addition, biological products, such as Factor VIII, which are prepared from biological fluids can be irradiated in the presence of the dye and photosensitizer to destroy contaminants.

In addition to in vitro applications, the method of the present invention can be employed for the in vivo destruction of cells of a mammal, such as cells of abnormal or undesirable tissue. Like conventional PDT, the method is particularly useful for the killing of cells which replicate at an abnormally high rates, such as those of tumors. However, unlike conventional PDT methods, which are limited to shallow tumors, such as those of the head and neck, the methods of the present invention can also be used to treat deep-seated tumors, such as those in the pancreas. The method is also useful for the destruction of neoplastics, such as bronchial, cervical, esophageal, or colon cancers.

The method can also be used to dissolve plaques in blood (see, e.g., U.S. Pat. No. 4,512,762 to Spears and Fisher and the references cited therein, which are hereby incorporated by reference) and to treat topical conditions such as acne, athlete's foot, warts, papilloma, and psoriasis (see, e.g. Fisher and the references cited therein, which are hereby incorporated by reference).

In vivo uses, such as these, can be effected by administering to the mammal a therapeutically effective amount of the dye and a therapeutically effective amount of the photosensitizer. The dye and sensitizer can be coadministered or administered separately, by any conventional route, such as orally, parenterally, or topically. Examples of parenteral administration are intramuscular, intravenous, intraperitoneal, rectal, and subcutaneous administration.

The dye, photosensitizer, or both can be administered locally or systemically. Local administration can be effected, for example, by injection of the dye, photosensitizer, or both proximate to the target tissues, cells, or viruses In local treatment of superficial tumors or skin disorders, the dye, photosensitizer, or both are best topically administered using standard topical compositions involving lotions, suspension, or pastes. Systemic administration can be implemented by intravenous, subcutaneous, intramuscular, or even intraperitoneal injection; by implantation of a slow release or sustained release system; by suppository; or, if properly formulated, orally. Formulations for these modes of administration are well known in the art; exemplary formulations are described, for example, in Remmington's Pharmaceutical Sciences, Easton, Pa.:Mack Publishing Co. ("Remmington").

The dye, photosensitizer, or both can be administered in the form of a composition made up in a suitable form appropriate for the desired use; e.g., oral, parenteral, or topical administration. One such composition, to which the present invention is also directed, includes both the dye and the photosensitizer.

Suitable dosage forms for oral use include tablets, dispersible powders, granules, capsules, suspensions, syrups, and elixirs. Inert diluents and carriers for tablets include, for example, calcium carbonate, sodium carbonate, lactose, and talc. Tablets may also contain granulating and disintegrating agents such as starch and alginic acid, biriding agents such as starch, gelatin, and acacia, and lubricating agents such as magnesium stearate, stearic acid, and talc. Tablets may be uncoated or may be * coated by known techniques to delay disintegration and absorption. Inert diluents and carriers which may be used in capsules include, for example, calcium carbonate, calcium phosphate, and kaolin. Suspensions, syrups, and elixirs may contain conventional excipients, for example, methyl cellulose, tragacanth, sodium alginate; wetting agents, such as lecithin and polyoxyethylene stearate; and preservatives, e.g., ethyl-p-hydroxybenzoate.

Dosage forms suitable for parenteral administration include solutions, suspensions, dispersions, emulsions, and the like. They may also be manufactured in the form of sterile solid compositions which can be dissolved or suspended in sterile injectable medium immediately before use. They may contain suspending or dispersing agents known in the art and can be in a dry, lyophilized form or in the form of a liquid suspension. In many situations, the lyophilized form is preferred, because it can be stably stored for periods of up to several months without the danger of bleaching by prolonged exposure of the dye or photosensitizer to ambient light.

The dye, photosensitizer, or both also can be encapsulated in a liposome administered in the form of a liposomal capsule, as described in more detail below.

The diluent, carrier, and other ingredients used in the composition should be selected so that they do not interfere the ability of the dye to convert 660 to 1300 nm light to 380 to 760 nm light or the ability of the photosensitizer to kill cells or viruses.

It will be appreciated that the actual preferred amount of dye and photosensitizer used in the practice of the method of the present invention will vary according to the particular dye and photosensitizer combination, the particular composition formulated, the mode of application, and the particular situs, host and disease being treated. Many factors, such as body weight, sex, diet, time of administration, route of administration, rate of excretion, condition of the host, drug combinations, reaction sensitivities and severities, and severity of disease, will be taken into account by those skilled in the art. Administration can be carried out continuously or periodically within the maximum tolerated dose. For dyes and photosensitizers which are administered systemically and which are not specific to the target tissue, cell, or virus, dye dosages ranging from about 0.1 to about 50 and photosensitizer dosages ranging from about 0.1 to about 10 mg/kg of the mammal's body weight, are typical. For dyes and photosensitizers which are highly specific to target tissues, such as those which include a highly specific monoclonal immunoglobulin preparation or specific receptor ligand, considerably lower dosages may be used. Optimal application rates for a given set of conditions can be ascertained by those skilled in the art using conventional dosage administration tests in view of the above guidelines.

The dyes, photosensitizers, or both can be derivatized in order to provide a specific targeting mechanism. Commonly used target-specific components include monoclonal antibodies and ligands which bind to a cellular receptor.

The target-specific component can be, for example, an immunoglobulin or portion thereof or a ligand specific for a particular receptor. The immunoglobulin component can be any of a variety of materials. It may be derived from polyclonal or monoclonal antibody preparations and may contain whole antibodies or immunologically reactive fragments of these antibodies such as F(ab')$_2$, FAB, or FAB' fragments. Use of such immunologically reactive fragments as substitutes for whole antibodies is well known in the art. See, for example, Spiegelberg, in *Immunoassays in the Clinical Laboratory*, 3:1–23 (1978) ("Spiegelberg"), which is hereby incorporated by reference.

Polyclonal anti-sera are prepared in conventional ways by injecting a suitable mammal with antigen to which antibody is desired, assaying the antibody level in serum against the antigen, and preparing anti-sera when the titers are high. Monoclonal antibody preparations may also be prepared conventionally such as by the method of Koehler and Milstein using peripheral blood lymphocytes or spleen cells from immunized animals and immortalizing these cells either by viral infection, by fusion with myelomas, or by other conventional procedures, and screening for production of the desired antibodies by isolated colonies. Formation of the fragments from either monoclonal or polyclonal preparations is effected by conventional means as described by Spiegelberg, which is hereby incorporated by reference.

Particularly useful antibodies include the monoclonal antibody preparation CAMAL1 which can be prepared as described by Malcolm, et al., *Ex. Hematol.*, 12:539–547 (1984), which is hereby incorporated by reference; polyclonal or monoclonal preparations of anti-MI antibody as described by New et al., J. Immunol., 130:1473–1477 (1983), which is hereby incorporated by reference, and B16G antibody which is prepared as described by Maier et al., *J. Immunol.*, 131:1843 (1983) and Steel et al., *Cell Immunol.*, 90:303 (1984), which are hereby incorporated by reference.

The foregoing list of antibodies suitable for conjugation with the dye or photosensitizer is exemplary and certainly not limiting. Once the target tissue is known, antibody specific for this tissue may be prepared by conventional means. Therefore, the invention is applicable to effecting toxicity against any desired target.

The ligand specific for receptor refers to a moiety which binds a receptor at cell surfaces and, thus, possesses spatial and electronic geometries which are complementary to those of the receptor. It is well understood that a wide variety of cell types have specific receptors designed to bind hormones, growth factors, or neuro-transmitters. Examples of such ligands include the steroid hormones, such as progesterone, estrogens, androgens, and the adrenal cortical hormones; growth factors, such as epidermal growth factor, nerve growth factor, fibroblast growth factor, and so forth; other protein hormones, such as human growth hormone, parathyroid hormone, and so forth; and neurotransmitters, such as acetylcholine, serotonin, and dopamine. Any analog of these substances which succeeds in binding to the receptor is also included.

The conjugation of the target-cell specific component to the dye or photosensitizer used in the methods of the present invention can be effected by any convenient means. For proteins, such as Ig and certain receptor ligands, a direct bond between these moieties may be effected, for example, using a dehydrating agent such as a carbodiimide. A particularly preferred method of covalently binding the photosensitizers to the immunoglobulin moiety is treatment with 1-ethyl-3(3-dimethylamino propyl) carbodiimide ("EDCI") in the presence of a reaction medium consisting essentially of dimethyl sulfoxide ("DMSO"). This method is particularly effective where the photosensitizer is a porphyrin or a porphyrin analog. Other dehydrating agents, such as dicyclohexycarbodiimide or diethylcarbodiimide, could also be used as well as conventional aqueous and partially aqueous media.

As indicated above, the dye and photosensitizer can be provided proximate to the cell or virus together, as when they are coadministered to a mammal, or they can be provided separately. Where the dye and photosensitizer are provided together, the dye and photosensitizer can be administered in a composition, to which the present invention is also directed. The composition comprises a photosensitizer having an absorption at a wavelength from about 380 to about 760 nm and a dye which is capable of converting photons having energies from about 660 nm to about 1300 nm to photons having energies from 380 nm to about 760 nm.

Suitable dyes and photosensitizers include those which were discussed above as being appropriate for use in the methods of killing cells or viruses.

The dye and photosensitizer can be encapsulated in a liposome. The liposome can be formed of any suitable phospholipid, such as phosphatidyl inositol, phosphatidyl serine, phosphatidyl glycerol, phosphatic acid, diphosphatidyl glycerol, poly(ethylene glycol)-phosphatidyl ethanolamine, diiyristoylphosphatidyl glycerol, dioleoylphosphatidyl glycerol, dilauryloylphosphatidyl glycerol, dipaimitotylphosphatidyl glycerol, distearyloylphosphatidyl glycerol, dimyristoyl phosphatic acid, dipalmitoyl phosphatic acid, diimyristoyl phosphitadyl serine, dipalritoyl phosphatidyl serine, brain phosphatidyl serine, phosphatidyl choline, phosphatidyl ethanolamine, sphingomyeline, lecithin, lysolecithin, lysophatidylethanolamine, cerebrosides, dimnyristoylphosphatidyl choline, dipalnitotylphosphatidyl choline, distearyloylphosphatidyl choline, dielaidoylphosphatidyl choline, dioleoylphosphatidyl choline, dilauryloylphosphatidyl choline, 1-myristoyl-2-palmitoyl phosphatidyl choline, 1-pahnitoyl-2-myristoyl phosphatidyl choline, 1-paknitoyl-2-stearoyl phosphatidyl choline, 1-stearoyl-2-palmitoyl phosphatidyl choline, dimyristoyl phosphatidyl ethanolamine, dipalmitoyl phosphatidyl ethanolamine, brain sphingomyelin, dipalmitoyl sphingomyelin, distearoyl sphingomyelin, and mixtures thereof.

Liposomes are completely closed bilayer membranes containing an encapsulated aqueous phase. Liposomes may be any of a variety of multilamellar vesicles ("MLV") (onion-like structures characterized by concentric membrane bilayers each separated by an aqueous layer) or unilamellar vesicles (possessing a single membrane bilayer).

The following parameters of liposome preparations are functions of vesicle size and lipid concentration as follows: (1) Captured volume, defined as the volume enclosed by a given amount of lipid, is expressed as units of liters entrapped per mole of total lipid (l/mol) and (2) Encapsulation efficiency, defined as the fraction of the aqueous compartment sequestered by the bilayers, is expressed as a percentage. The captured volume depends upon the radius of the liposomes and the number of internal membrane bilayers which in turn is affected by the lipid composition of the vesicles and the ionic composition of the medium. The encapsulation efficiency is directly proportional to the lipid concentration; when more lipid is present, more solute can be sequestered within liposomes. (See Deamer et al., *Liposomes*, Ostro, ed., New York:Marcel Dekker, Inc., pp. 27–51 (1983), which is hereby incorporated by reference).

Methods for preparing liposomes containing dye and photosensitizer generally follow conventional liposome preparation methods, such as those reviewed by Szoka et al., *Am Rev. Biophys. Bioeng.* 9:467 (1980) ("Szoka et al.") which is hereby incorporated by reference.

In one preferred method, vesicle-forming lipids are taken up in a suitable organic solvent or solvent system, and dried (or lyophilized) in vacuo or under an inert 5 gas to a lipid film. The dye or photosensitizer or both are preferably included in the lipids forming the film. The concentration of dye or photosensitizer or both in the lipid solution may be included in molar excess of the final maximum concentration of drug in the liposomes, to yield maximum drug entrapment in the liposomes.

The aqueous medium used in hydrating the dried lipid or lipid/drug is a physiologically compatible medium, preferably apogee-free physiological saline or 5% dextrose in water, as used for parenteral fluid replacement. The solution is mixed with any additional solute components, such as a water-soluble iron chelator, and/or a soluble secondary compound, such as a peptide immunostimulator, at a desired solute concentration. The lipids are allowed to hydrate under rapid conditions (using agitation) or slow conditions (without agitation). The lipids hydrate to form a suspension of multilamellar vesicles whose size range is typically between about 0.5 microns to 10 microns or greater. In general, the size distribution of MLVs in the above procedure can be shifted toward smaller sizes by hydrating the lipid film more rapidly while shaking. The structure of the resulting membrane bilayer is such that the hydrophobic (non-polar) "tails" of the lipid orient toward the center of the bilayer, while the hydrophilic (i.e. polar) "heads" orient towards the aqueous phase.

In another method, dried vesicle-forming lipids and the dye, photosensitizer, or both, mixed in the appropriate amounts, are dissolved, with warming if necessary, in a water-miscible organic solvent or mixture of solvents. Examples of such solvents are ethanol, or ethanol and dimethylsulfoxide (DMSO) in varying ratios. The drug/lipid/solvent mixture then is added to a sufficient volume of aqueous receptor phase to cause spontaneous formation of liposomes. The aqueous receptor phase may be warmed if necessary to maintain all lipids in the melted state. The receptor phase may be stirred rapidly or agitated gently. The dye/photosensitizer/lipid/solvent mixture may be injected rapidly through a small orifice, or poured in directly. After incubation of several minutes to several hours, the organic solvents are removed, by reduced pressure, dialysis, or diafiltration, leaving a liposome suspension suitable for human administration.

In another method, dried vesicle-forming lipids, dye, and photosensitizer, mixed in the appropriate amounts, are dissolved, with warming if necessary, in a suitable organic solvent with a vapor pressure and freezing point sufficiently high to allow removal by freeze-drying (lyophilization). Examples of such solvents are tert-butanol and benzene. The dye/photosensitizer/lipid/solvent mixture then is frozen and placed under high vacuum. Examples of methods for freezing include "shell-freezing", in which the container containing the dye/photosensitizer/lipid/solvent mixture is swirled or spun to maximize contact of the liquid with the walls of the vessel, and the container is placed in a cooled substance such as liquid nitrogen or carbon dioxide ice mixed with a solvent such as an alcohol or acetone. The mixture thus is frozen rapidly without segregation of the constituents of the drug/lipid/solvent mixture. A fluffy, dry powder results from removal of the solvent by lyophilization. This dye/photosensitizer/lipid powder may be stored for extended periods under conditions that reduce chemical degradation of the constituents or the absorption of moisture. Examples of such conditions include sealed under an atmosphere of dry, inert gas (such as argon or nitrogen), and storage in the cold. In cases where the dye/photosensitizer/lipid is to be administered in vivo, reconstitution is performed by adding a physiologically compatible aqueous medium, preferably a pyrogen-free physiological saline or 5% dextrose in water, as used for parenteral fluid replacement. Reconstitution causes the spontaneous formation of liposomes, which may be refined in size by methods detailed below.

Alternatively, where the liposomes are prepared to contain encapsulated dye or photosensitizer or both, a liposome preparation method which yields high encapsulation efficiency may be preferred. For example, the reverse-phase evaporation method described by Szoka yields encapsulation efficiencies as high as about 50%. As a result, losses of the encapsulated compound (e.g., a peptide hormone) are minimized. The reverse-phase evaporation vesicles ("REV") produced by this method are predominantly oligolamellar and have heterogeneous sizes which are largely between about 0.3 and 20 microns and average 0.4 to 0.5 microns.

The liposome suspension may be sized to achieve a selective size distribution of vesicles. The sizing serves to eliminate larger liposomes and to produce a defined size range having optimal pharmacokinetic properties.

Several techniques are available for reducing the size and size heterogeneity of liposomes. Sonicating a liposome suspension either by bath or probe sonication produces a progressive size reduction down to small unilamellar vesicles less than about 0.025 microns in size. Homogenization is another method which relies on shearing energy to fragment large liposomes into smaller ones. In a typical homogenization procedure, MLVs are recirculated through a standard emulsion homogenizer or extruded at high shear forces through a small orifice until selected liposome sizes are observed. In both methods, the particle size distribution can be monitored by conventional laser-beam particle size discrimination.

Extrusion of liposomes through a small-pore polycarbonate membrane is an effective method for reducing liposome sizes down to a relatively well-defined size distribution, depending on the pore size of the membrane. Typically, the suspension is cycled through the membrane several times until the desired liposome size distribution is achieved. The liposomes may be extruded through successively smaller-pore membranes, to achieve a gradual reduction in liposome size.

Centrifugation and molecular sieve chromatography are other methods which are available for producing a liposome suspension with reduced particle sizes. These two methods both involve preferential removal of larger liposomes, rather than conversion of large particles to smaller ones. Liposome yields are correspondingly reduced.

Cholesterol and sterols may be incorporated into the liposomes of the present invention in order to alter the physical properties of the lipid bilayers. Multilamellar and unilamellar liposomes containing cholesterol can be prepared according to the procedures described above with respect to the preparation of liposomes from phospholipids. Suitable sterols for incorporation in the liposomes includes cholesterol, cholesterol derivatives, cholesteryl esters, vitamin D, phytosterols, steroid hormones, and mixtures thereof Useful cholesterol derivatives include cholesterol-phosphocholine, cholesterolpolyethylene glycol, and cholesterol-$SO_4$, while the phytosterols may be sitosterol, campesterol, and stigmasterol. It may also be possible to utilize the salt forms of organic acid derivatives of sterols, as described in U.S. Pat. No. 4,891,208 to Janoff et al., which is hereby incorporated by reference.

The composition of the present invention can be in a dry, lyophilized form or in the form of a liquid suspension. However, the lyophilized form is preferred, because it can be stably stored for periods of up to several months without bleaching or other photodegradation of the dye or photosensitizer. On the other hand, suspensions of the composition of the present invention in buffered, neutral pH saline are stable for periods of only hours up to months, depending upon the temperature, concentration of the dye and photosensitizer, phospholipid constituents, and the amount of ambient light to which the suspension is exposed.

The composition can also comprise a pharmaceutically acceptable excipient, such as water, saline, dextrose, glycerol and the like. In such a composition the dye and photosensitizer can be present in any concentration suitable for the composition's intended use. Where the composition is to be used in vivo, the dye and photosensitizer can be present in a concentration of from about 0.5 to about 350 mg/ml of excipient and from about 0.5 to about 150 mg/ml of excipient, respectively.

Typically, the dye and photosensitizer are present in the composition in a molar ratio of from about 500:1 and about 1:20.

The present invention also relates to a method for producing singlet oxygen. A composition which includes a photosensitizer having absorption at a wavelength from about 380 nm to about 760 nm and a dye capable of converting photons having energies of from about 660 to about 1300 nm to photons having energies of from about 380 to about 760 nm is formed. The composition is exposed to light having a wavelength of from about 660 to about 1300 nm in the presence of oxygen to produce singlet oxygen.

Suitable photosensitizers are compounds known in the art to be capable of generating singlet oxygen. These include, for example, the porphyrins, porphyrin analogs, phthalocyanines, and phthalocyanine analogs, examples of which were discussed above in connection with methods of killing cells or viruses. Examples of suitable dyes include those dyes which are useful in the above-described methods of killing cells and viruses. The molar ratio of dye to photosensitizer is generally selected to effect maximum singlet oxygen generation, although other factors, such as solubility and cost of the dye and photosensitizer, will also be taken into account. Suitable molar ratios of dye and photosensitizer are from about 500:1 to about 1:20. Similarly, the concentrations of the dye and the photosensitizer are chosen to effect maximum singlet oxygen generation, but other factors, such as cost and solubility of the dye and photosensitizer as well as the availability of oxygen in the composition to be converted to singlet oxygen and the use to which the composition is to be put, should also be considered. Dye and photosensitizer concentrations of from about 0.5 to about 350 mg/ml of composition and from about 0.5 to about 150 mg/ml of the composition, respectively, are typical.

The light to which the dye is exposed can be monochromatic or polychromatic and, preferably, has a non-zero intensity at a wavelength at which the dye absorbs, typically from about 660 to about 1300 nm. The light can be any high intensity radiation in the range from 660 to 1300 nm, including coherent, incoherent, polarized, pulsed laser, and diffuse radiation. Light sources capable of delivering this type of light include, for example, Nd-YAG lasers, Ti-sapphire lasers, as well as other lasers, such as those described in Hecht. Because of the high intensities generally needed to effect two-photon processes, it is preferred that the laser be a pulsed laser having a pulse duration as short as possible, preferably ranging between several tens of femtoseconds and several nanoseconds, and having pulse peak powers of several hundreds of megawatts.

The singlet oxygen generation method of the present invention can be used in any process in which singlet oxygen generation is necessary or desirable. For example, in accordance with the present understanding of the mechanism by which photodynamic therapy operates, the method of generating singlet oxygen can be used to kill undesirable cells or viruses. Alternatively, singlet oxygen, generated in accordance with the method of the present invention, can be used in a variety of organic syntheses. One well-known synthetic use of singlet oxygen is the addition of $O_2$ to 1,3-dienes, such as to form cyclic peroxide adducts. The cycloaddition reaction is applicable not only to 1,3-dienes but also to reactive aromatic nuclei, such as anthracenes, oxazines, farans, substituted thiophenes, purines, imidazoles, and oxygenated aromatic systems. (See, e.g., House, *Modern Synthetic Reactions*, 2nd ed., Menlo Park, Calif.:Benjamin/Cummings Publishing Co., pp. 337–351 (1972) ("House"), and the references described therein, which is hereby incorporated by reference.) Another well-known use of singlet oxygen is in the formation of allylic hydroperoxides from olefins possessing three or four alkyl substituents, as described, for example, in House and the references cited therein, which are hereby incorporated by reference. This conversion of substituted olefins to hydroperoxides and, after reduction, to allylic alcohols is of particular interest because, unlike oxidations with peroxide derivatives, singlet oxygen oxidation produces a product in which the oxygen is bonded to one, rather than both, of the carbon atoms of the original double bond.

The dye and photosensitizer used in the methods and compositions of the present invention can be covalently bonded to each other through any of the linkages which are commonly used to covalently bind two porphyrins or a small molecule to a protein.

One such covalently bonded dye porphyrin moiety has the formula: $PS\text{-}Z^1\text{-}G^1\text{-}Z^2\text{-}DY$, wherein PS is the photosensitizer and DY is the dye. $Z^1$ and $Z^2$ are the same or different and represent, a bridging group, such as an alkylene, an arylene, or an arylalkylene, suitable examples of which include methylene, 1,2-ethylene, 1,3-propylene, 1,4-butylene, 1,5-pentylene, 1,6-hexylene, 1,4-phenylene, 4,4'-biphenyl, and the like. $Z^1$ and $Z^2$ are attached, directly or indirectly and preferably covalently, to the photosensitizer and dye, respectively. Where the photosensitizer is a porphyrin, $Z^1$ is can be attached, directly or indirectly, to the porphyrin at any position, preferably at the meso carbon or one of the pyrrole's beta carbons. Where the dye is a styryl dye having the formula:

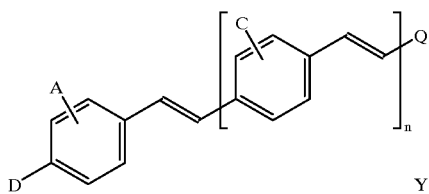

where D has the formula $-NHR^1$, $-NR^1R^2$, $-OR^1$, or $-NHC(O)R^1$, Q has the formulae:

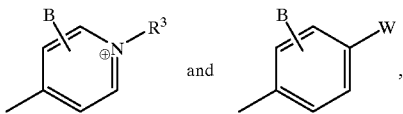

and

W has the formula $-SO_2R^3$, $C(O)R^3$, or $COOR^3$, and $R^1$, $R^2$, and $R^3$ are substituted or unsubstituted alkyl groups or substituted or unsubstituted aryl groups, $Z^2$ is preferably attached, directly or indirectly, to the dye through one (or more) of A, B, C, $R^1$, $R^2$, or $R^3$. G is a group which links $Z^1$ and $Z^2$ and can be, for example, an ester (—C(O)O—), an ether (—O—), a thioether (—S—), a disulfide (—S—S—), an amine (—NH—), an amide (C(O)NH—), and the like. Alternatively, G can be a nullity, so that the terminal carbon of $Z^1$ and the terminal carbon of $Z^2$ are bonded directly to each other, such as when the coupling is formed by an Ullmann reaction.

As the skilled practitioner will recognize, methods for covalently bonding the dye and the photosensitizer are analogous to those used in the covalent coupling of porphyrin molecules, except of course, that here one of the porphyrins is replaced with the dye. These coupling reactions are described in Dolphin and the references cited therein. The coupling reactions can also be effected by methods which are commonly employed to covalently bond porphyrins or other photosensitizers to proteins and other biological macromolecules.

Generally, the coupling reactions involve reacting a dye having the formula DY-$Z^2$-$G^2$ with a photosensitizer having the formula PS-$Z^1$-$G^3$, where $G^2$ and $G^3$ are moieties which, when reacted together, form $G^1$. For example, where $G^1$ is an ether, $G^2$ can be a halide (e.g. —Cl) and $G^3$ can have the formula —OM, where M is a metal ion, such as sodium ion. Alternatively, exploiting the well known reaction of an acid (or acid halide) with an alcohol to form an ester, the dye and photosensitizer can be coupled by reacting, for example, DY-$Z^2$-COCl with PS—$Z^1$—OH.

Three-Dimensional Data Storage

The present invention, in yet another aspect thereof, relates to a method for recording data. A three-dimensional matrix which contains a plurality of dye molecules is provided.

Preferably, the dye molecules are uniformly distributed in the matrix material. That is, the concentration of dye molecules in any arbitrarily selected volume element within the matrix is the same as the concentration of the dye molecules within the matrix taken as a whole. The dye molecules can be of any suitable concentration, but, preferably, the concentration of the dye molecules is as high as possible, limited, of course, by the ability of the matrix material to disperse uniformly the dye molecules therein without aggregation or other phenomenon which adversely impacts uniform distribution. Preferably, the concentration of the dye molecules in the matrix is from about 0.001 M to about 0.4 M and, more preferably, from about 0.01 M to about 0.05 M.

The matrix is preferably made of a material which substantially uniformly disperses the dye molecules. The material from which the matrix is made is also preferably transparent, more preferably substantially transparent, most preferably having a transmittance of greater than 75%, to the actinic radiation used to store the data and to the actinic radiation that will be used to read the data.

Suitable matrix materials for dispersing the dye molecules include polymers, such as those described above in connection with compositions comprising a matrix material and a styryl dye. Preferred polymers are poly(methyl methacrylate) and poly(2-hydroxyethyl methacrylate).

The above polymer matrix materials are usually transparent, but may be translucent or, in some applications, opaque to visible light. Preferably, the polymer does not linearly absorb or only weakly absorbs infrared radiation in the region from 750 to 1200 nm. The polymer matrix material is selected based on the absorbance spectrum (more accurately the two-photon absorbance spectrum), the solubility of the dye in the matrix material, cost, diffusion rate of the dye molecule through the matrix material, and the like.

Another class of suitable matrix materials are sol-gel glasses, preferably those having bulk glass densities of from about 0.5 to about 1 g/cm$^3$ and refractive indices of from 1.4 to 1.5. A styryl compound of the present invention and a polymerizable monomer, preferably poly(hydroxyethyl methacrylate), are impregnated into the bulk glass. The monomer is then polymerized by heating, by irradiation, or by the passage of time at room temperature. Optionally, the monomer may contain polymerization initiators, such as 2,2'-azobisisobutyronitrile ("AIBN"), preferably in a initiator to monomer mole ratio of from 0.25 to 2%. The styryl compound and monomer may be introduced simultaneously or sequentially. Simultaneous impregnation is preferred but requires that the styryl compound be soluble in the monomer. Furthermore, the monomer must have a surface tension which permits penetration of the monomer into the sol gel bulk glass. In the latter regard, for many glasses, alkyl methacrylate is preferred to hydroxyalkyl methacrylates. However, many compounds of the present invention are only marginally soluble in alkyl methacrylates. In this situation, an alternative impregnation method is preferred. First, the styryl compound, dissolved in a suitable solvent, such as a ketone solvent, is contacted, by immersing, spraying, dripping, brushing, and the like, with the bulk sol gel glass. The solvent is removed, and the dye-doped glass is then contacted with a monomer solution, optionally containing a polymerization initiator, for ½ to 72 hours, at from room temperature to about 80° C., to impregnate the glass with the monomer. Polymerization of the monomer, such as by heating, by irradiating, or by passage of time at near-room temperatures from 25° C. to 50° C., preferably in a sealed container in the absence of oxygen, completes formation of the sol gel composition.

Alternatively, the procedures used to impregnate the sol gel with the styryl compound and polymer can be used to introduce the compound and polymer into a Vycor glass having pore size from about 20 Å to about 100 Å, preferably from about to about 50 Å. Vycor glasses suitable for use in the compositions of the present invention are commercially available, for example, from Corning Glass Inc., Corning, N.Y.

The three-dimensional matrix having dye molecules dispersed therein preferably has two parallel faces. The faces can be polished by conventional methods, such as by manual grinding using a diamond grinding wheel, by abrading the surface using abrasives, such as silicon carbide paper, preferably with increasing grit ranging from 60 to 2000 and preferably using a lubricant, such as water, or by polishing on cloths with 10 to 0.1 μm grade diamond paste, preferably using an automated grinding and polishing machine, such as the METASERV™ 2000 (Buehler VK Ltd., Coventry, England), or by combinations thereof. Polishing is best effected by sequentially performing the above steps. Alternatively, the faces can be trimmed on an ultramicrotone with a glass knife.

Dye molecules suitable for the practice of the present invention include any dye which can be detectably altered by actinic radiation. Preferred dyes are those which are detectably alterable by two-photon processes. The two-photon processes can be, for example, photobleaching, wherein the dye molecule subsequent to being detectably altered lacks an optical response which the unaltered dye molecule had.

For example, the dye molecule can be a colored photochromic dye, such as a spirobenzopyran or a spirooxazine (including a spirobenzoxazine, and a spironaphthoxazine), which, upon exposure to actinic radiation, is converted via a two-photon upconversion process to a form which lacks this color. Other suitable photochromic dyes are those disclosed in Brown, ed., *Photochromism*, vol. 3 in Weissberger's *Techniques of Organic Chemistry*, New York:Wiley Interscience (1971), which is hereby incorporated by reference.

Alternatively, the dye molecule can be a fluorescer which, upon exposure to intense actinic radiation, undergoes a two-photon upconversion process, which destroys the dyes ability to fluoresce. Suitable two-photon upconverting dyes include Rhodamine B, dimethyl POPOP ("DMP"), 1,3,1', 3'-tetramehtyl-2,2'-dioxopyrimide-6,6'-carbocyanine hydrogen sulfate ("PYC"), 4-dicyanomethylene-2-methyl-6-p-dimethylaminostyryl-4H-pyran ("DCM"), and their analogs, as well as stilbene and coumarin dyes. More preferably, the upconverting dye has a two-photon absorption cross section of greater than about $1 \times 10^{-50}$ cm$^4$-sec. Upconverting dyes having two-photon absorption cross sections of from about $5 \times 10^{-50}$ cm$^4$-sec to about $1 \times 10^{-45}$ cm$^4$-sec are most preferred.

Dyes suitable for use in the methods of the present invention include styryl dyes, such as those of the present invention, described above. Preferably, the dye is (4-[N-(2-hydroxyethyl)-N-methyl)aminophenyl]-4'-(6'-hydroxyhexylsulfonyl)stilbene) ("APSS"). Styryl dyes are particularly preferred because they have a strong two-photon absorption with a cross section that is significantly greater than commercial dyes, such as Rhodamine, DCM, and DMP. The dyes also exhibit intense emission at a wavelength ranging from about 300 to about 680 nm when excited by laser radiation having a wavelength of from about 660 nm to about 1300 nm.

The three-dimensional matrix material includes a first volume element, which, according to the method of the present invention, is exposed to actinic radiation. The size of the volume element is not critical to the practice of the present invention, but small volume elements, such as those having a volume of from about 0.001 μm$^3$ to about 10 μm$^3$, preferably from about 0.01 μm$^3$ to about 1 μm$^3$, are preferred. Most preferably, the volume element is sized so as to be the smallest volume which can be uniquely addressed by the actinic radiation used. Where a focused laser beam having a Gaussian cross section is employed, uniquely addressing means that the volume outside of the volume element is exposed to an intensity no more than 10% of the intensity to which the volume element is exposed. The shape of the volume element is likewise not critical. Typically, a hexahedral shape or ellipsoidal shape is employed having dimensions on the order of tenths of microns, such as 0.5×0.5×0.8 microns.

In most cases the matrix will contain more than one volume element. These volume elements can be discrete (i.e. non-overlapping with one another), or they can be overlapping or they can be continuously overlapping. Preferably, each of the elements is sufficiently separated from other volume elements so that the exposing actinic radiation, when directed at one of the volume elements, does not expose other (particularly adjacent) volume elements to an intensity and for a duration effective to detectably alter the dye molecules contained in the other particularly adjacent) volume elements. Most preferably, the volume elements are separated by distances sufficient so that each volume element can be uniquely addressed by the actinic radiation.

As used herein, actinic radiation includes electromagnetic radiation, such as ultraviolet, visible, near infrared, infrared radiation, or combinations thereof. The actinic radiation can be monochromatic or polychromatic and, preferably, has a non-zero intensity at a wavelength at which the dye absorbs, preferably from about 660 to about 1300 nm. It can be coherent, incoherent, polarized, laser, pulsed laser, focused laser, or diffuse radiation. The actinic radiation is preferably high intensity radiation in the range from 660 to 1300 nm. Preferably, it is laser radiation in the form of a laser beam.

A variety of laser sources emitting in the range from 660 to 1300 nm are available. Suitable sources will be apparent to the skilled practitioner and are summarized, for example, in Hecht, which is hereby incorporated by reference. One particularly useful laser source is a mode-locked Ti-sapphire laser, preferably operated at 790 to 800 nm and having pulse durations as short as possible (typically on the order of tens of femtoseconds). Another laser source well suited for irradiating the dye in the practice of the present invention is a Q-switched pulsed Nd-YAG laser having an output of 1060 nm. Spectral widths of less than 10 cm$^{-1}$ are preferred. The angular divergence of the laser can be from about 0.5 mrad to about 2.5 mrad, depending on the distance of the laser from and the size of the volume element being irradiated. Repetition rates of from 0.1 Hz to about 500 MHz are suitable. Because of the high intensities generally needed to effect two-photon processes, it is preferred that the laser be a pulsed laser having a pulse duration as short as possible, preferably ranging between several tens of femtoseconds and several nanoseconds, and having pulse peak powers of several hundreds of megawatts.

As indicated above, optimization of the process of the present invention requires that the data be written in a third dimension, which requires that the actinic radiation selectively access volume elements in planes below those in the surface of the matrix and that these planes be as closely spaced as possible. This can be achieved by manipulating the actinic radiation prior to the radiation entering the matrix material.

One such manipulation involves focusing laser radiation provided in the form of a laser beam. Methods for focusing laser beams are well known to those in the art and are described in Hecht, which is hereby incorporated by reference. One focusing technique uses an confocal microscope, such as those described in U.S. Pat. No. 5,034,613 to Denk et al. ("Denk"), which is hereby incorporated by reference. By adjusting the microscope optics, the vertical location of the focal point in the matrix can be selected, and, in this manner, a volume element in the interior of the matrix can be selectively exposed.

Alternatively, the actinic radiation can be laser radiation provided in the form of two or more laser beams made to intersect at the volume element to be exposed. The two or more laser beams can intersect at right angles to each other (in the case where number of beams is two or three), or two or more of the two or more laser beams can intersect at an oblique angle. The two or more laser beams can be provided by a single laser, the beam from which is split by one or more beam splitters into a plurality of beams, each of which is then directed by conventional optics to intersect at the volume element to be exposed. Optics and methods suitable for producing two beams in this manner are described, for example, in Hecht, which is hereby incorporated by reference. Alternatively, the two or more laser beams can be provided by two or more lasers.

To store a multiplicity of data points, the data storage method of the peasant invention can be carried out for another volume element (e.g., a second volume element, a third volume element, and so on). This involves moving the laser beam relative to the matrix to another volume element and exposing the another volume element (e.g. the second volume element, the third volume element, and so on) to laser radiation for a duration and at intensity effective to alter detectably a fraction of the dye molecules contained in the another element.

In the case where the laser beam is a focused laser beam, such as with an confocal microscope, this can be effected by shifting the laser beam relative to the matrix in an X-Y plane within the matrix and shifting the focal point of the laser beam relative to the matrix material along a Z axis. As used in this context, the Z axis is coincident with the laser beam and the X-Y plane is orthogonal to the laser beam. Shifting the focal point relative to the matrix material can be achieved by moving the matrix material in a Z direction relative to the focusing optics or by adjusting the focusing optics so that the focal point moves relative to the matrix material or both.

In the case where the laser radiation is provided by two intersecting laser beams, moving the laser beam relative to the matrix material can be carried out by shifting one of the laser beams relative to the matrix in an X-Y plane, orthogonal to the first laser beam, within the matrix material and shifting the second laser beam relative to the matrix in a X-Z plane, orthogonal to the second laser beam so that the two laser beams intersect at the new volume element to be exposed. This can be done by moving the laser beams or by moving the matrix material or both. Since maintaining intersection of the laser beams is no small task, it is preferred that the laser beams remain spatially fixed and that the matrix material be moved. This is especially true in cases where more than two beams are employed or in cases where the two or more beams are not orthogonal to one another.

Although the method used to move the matrix relative to the laser beam is not critical to the practice of the present invention, to store data with temporal and spatial efficiency, it is desirable that the movement be accurate and that it be carried out quickly. As indicated above, this can be done by mechanically moving the matrix material in one or more of the three dimensions and scanning the beam in the remaining of the three dimensions. The method employed, depends, in part, on whether the data is to be stored serially (that is, whether temporally adjacent data storage operations are conducted in spatially adjacent volume elements) or randomly and on whether the data to be stored is spatially digital or analog.

A variety of methods for scanning the matrix are known to those skilled in the art, and any of these are suitable for practicing the present invention. For example, the matrix can be scanned using a stepper motor or a continuous motor connected to a mechanism for translating the rotational motion of the motor to linear motion. Such a translating mechanism can be, for example, a rack and pinion mechanism or to a screw mechanism. Matrix scanning can also be effected with a plurality of magnetic coils driven by a voltage source, preferably, a computer controlled voltage source. The matrix can also be scanned by applying a voltage to change the dimensions of a piezoelectric material which is in contact with the matrix or with a stage supporting the matrix. Scanning the matrix in two of the three dimensions can also be achieved using a rotating disk format, such as those employed in compact disk ("CD") systems and other conventional commercial data storage products.

Alternatively, the laser beam can be scanned optically by using scanning mirrors in the optical path of the laser beam. Further details regarding beam scanning are available, for example, in Denk, which is hereby incorporated by reference.

Irrespective of whether the X-Y scanning is effected optically or by stage scanning (i.e., by moving the matrix), in cases where the laser beam is focused, such as with a confocal microscope, the focal point can be scanned (in the Z direction). In the case where a confocal microscope is used, the focal position of the focal point relative to the matrix can be adjusted by rotating the focus control knob, such as with a stepper or continuous motor. Alternatively, the position of the focal point relative to the matrix can be controlled by moving the matrix in the Z direction, for example, with a stepper motor connected to a means for translating rotational motion to linear motion or with electromagnetic coils, as described above for controlling X-Y position.

Scanning can be effected in an analog manner or in a digital manner. In analog scanning the volume elements overlap in one of the three dimensions. This is generally effected by moving the matrix continuously in the one analog dimension, such as with a continuous motor or with a electromagnetic coil having a ramp voltage applied thereto. Alternatively, one of the scanning mirrors can be continuously moved to effect a continuous movement of the beam in one of the X or Y directions. Yet another alternative is to adjust the position of the focal point in a confocal microscopy set-up by rotating the focusing knob in a continuous fashion so as to provide analog data storage in the Z direction.

The data stored in each of the volume elements can be binary, digital, or analog. Independently of this, the data stored in each of the volume elements can be stored as binary, digital, or analog data. Interconversion of binary, digital, and analog data, such as by electrical or electronic manipulations, is well known in the art. Whether the data is stored in binary, digital, or analog form depends on the number of possible states which each of the volume elements can assume when it is exposed.

As indicated above, data is stored in each of the elements by exposing the volume element to actinic radiation for a duration and at an intensity effective to detectably alter a fraction of the dye molecules contained therein.

When a single intensity/duration combination is used to expose each of the exposed volume elements, the fraction of dye molecules detectably altered in each of the exposed volume elements is the same. Preferably, this fraction is greater than 0.6, more preferably, greater than 0.7, and, most preferably, greater than 0.8.

Conversely, the unwritten state is characterized by a fraction of detectably altered dye molecules, preferably, less than 0.4, more preferably, less than 0.3, and, most preferably, less than 0.2.

When each of the exposed volume elements is exposed to one of a finite number, N, greater than one of intensity/duration combinations, the fraction of dye molecules detectably altered in each of the exposed volume elements will have one of N+1 potential values. (Here, one is added to N to account for the unexposed volume element, in which the fraction of detectably altered molecules is not be detectably different than zero.)

For example, when the number of intensity/duration combinations employed is 3, the data storage medium can include, in addition to a first volume element, a second volume element and a third volume element, each of which contain a fraction of detectably altered dye molecules. The fraction of the dye molecules detectably altered in the second volume element is detectably different than the fraction of the dye molecules detectably altered in the first volume element, and the fraction of the dye molecules detectably altered in the third volume element is detectably different than the fractions of the dye molecules detectably altered in the first and second volume elements. Thus, each volume element in this data storage medium can be used, for example, to store hexadecimal data in hexadecimal form without converting the hexadecimal data to binary form. Alternatively, each volume element can be used to store 4 bits of binary data.

As yet another illustration of the data storage media of the present invention wherein data is stored in digital form, consider a data storage medium containing, in addition to the first volume element, 254 additional volume elements where the fraction of the dye molecules detectably altered in each of the 254 additional volume elements is detectably different than the fraction of the dye molecules detectably altered in each of the other 254 additional volume elements and in the first volume element. Each volume element of this data storage medium is thus able to store, for example, 8 bits of binary data or, alternatively, ASCII text without converting the ASCII text to binary form.

In principle, the value of N can depend on the number of dye molecules per volume element, the ability to selectively focus the actinic radiation on the volume element being exposed, the effect of perturbing the stored data by each reading cycle, the anticipated number or reading cycles, the diffusion rate of the dye molecules through the matrix, the time for which the data needs to be stored, and the tolerance for error. Data stored using intensity/duration combinations in excess of N is considered to be stored as analog data.

As indicated above, the fraction of dye molecules detectably altered in each volume element is depends on two factors: (1) the intensity of the exposing actinic radiation and (2) the duration of exposure. Generally, it is preferred to hold one of these factors constant and to adjust the other so that the fraction of dye molecules detectably altered correlates with the data to be stored. Intensity can be adjusted by, for example, passing the actinic radiation through an attenuator, such as a rotatable dichroic mirror. By changing the angle of the dichroic mirror with respect to the path of the actinic radiation, the intensity of the actinic radiation transmitted through the dichroic mirror can be modulated. The duration for which the actinic radiation exposes the volume element can be adjusted, for example, by placing a shutter in the path of the actinic radiation and controlling the length of time for which the shutter is open. In cases where the dye molecules are two-photon active and exposure is modulated temporally (such as with a shutter), the fraction of molecules detectably altered correlates linearly with exposure duration. Intensity modulation, on the other hand, gives rise to a quadratic dependence of fraction of molecules detectably altered on intensity.

The methods and data storage media of the present invention are particularly well-suited for the storage of two-dimensional images, such as pictures, photographs, charts and graphs, and the like. The two-dimensional image comprises a two-dimensional array of pixels. These pixels may be discrete (i.e. non-overlapping) in both directions, or, alternatively, they may be overlapping or continuous in one of the two dimensions and discrete in the other dimension.

Each pixel has a value associated with it. For example, in the case of the black-and-white image, the value associated with each pixel can be its gray level, determined, for example, by a densitometer. In the case where the image is a color image, the value associated with each pixel can be, for example, the density of one of the colors making up the color image. Typically, color images can be broken down into three primary colors and a gray level, and these can be determined using a densitometer with an appropriate color filter.

The two-dimensional array of pixels is mapped to a two-dimensional array of volume elements in the three-dimensional matrix. This is done by exposing a volume element in the two-dimensional array of volume elements to actinic radiation for a duration and at an intensity effective to alter a fraction of the dye molecules contained in the volume element which correlates to the value associated with the corresponding pixel. The value can be binary, as in the case of a line drawing or a half-tone picture. Alternatively, it can be digital, as in the case where the image is stored as a stepped gray scale, or it can be analog, as in the case where the image is stored as a continuous gray scale.

As indicated above, the image can be divided into discrete pixels, and these discrete pixels can be mapped to the data storage medium of the present invention as discrete volume elements. In this embodiment, the value of a pixel is sampled, such as with a densitometer, and the value is converted to an analog, digital, or binary signal. A volume element is selected to receive the data from the image, such as by moving the matrix or by moving the laser beam or beams delivering the actinic radiation. The volume element is then exposed for a duration and at an intensity controlled by the signal. For example, the signal can be fed to a motor which controls the angle of a dichroic mirror through which the, beam delivering the actinic radiation passes, and the angle of the mirror (and, thus, the intensity of the beam passing therethrough) can be adjusted to correlate to the signal. Alternatively, the signal can be used to control (through, for example, a solenoid) the time for which a shutter through which the actinic radiation passes is opened. After completion of the data recording operation for the first pixel, the value of the next, preferably adjacent, discrete pixel is sampled, and a second signal is generated. The matrix is moved relative to the actinic radiation optics to access a second volume element which is spatially disjoint from the first volume element, and the second volume element is exposed under the control of the signal from the second pixel. This process is repeated until every pixel making up the two-dimensional image is stored in the two-dimensional array of volume elements.

In the case where the pixels are overlapping in one of the dimensions, these overlapping pixels are mapped to the data storage medium of the present invention as overlapping volume elements. In this embodiment, the value of a pixel is sampled, converted to a signal, and used to control the exposure of a first volume element. The device used to sample pixel value is then shifted to a new pixel, which, in part, overlaps the pixel just sampled. The matrix is shifted relative to the actinic radiation optics to provide access to a second volume element which overlaps the first volume element to the extent that the second pixel overlaps the first pixel, and the second volume element is exposed under the control of the signal from the second pixel. By repeating the operation, the entire two-dimensional image is mapped to the two-dimensional array.

In the case where the pixels are continuous in one of the two dimensions of the image, the image can be scanned along the continuous dimension with a device for measuring the value being recorded, such as gray level or color density, to produce a continuous signal. The matrix is moved continuously (relative to the actinic radiation optics) at a rate corresponding to the rate of scanning of the image. For example, where the continuous dimension of the image being recorded is 20 mm, and the corresponding dimension of the matrix's two-dimensional array is 2 mm, the rate of scanning the matrix can be one-tenth the image scan rate. While moving the matrix continuously relative to the actinic radiation optics, the intensity the actinic radiation can be modulated by continuously adjusting the angle of a dichroic mirror in response to the continuous signal generated by the image scanning device. When scanning and exposing in the continuous dimension is complete, the image scanning device is shifted in the second dimension, the position of the matrix relative to the optics is shifted in the second dimension of the matrix's two-dimensional array, and the scanning and exposing operations are repeated. In this manner, the entire image can be raster scanned and recorded in the data storage medium of the present invention.

The method of the present invention can be used to map a second value of the same image to a second two-dimensional array of volume elements in the same matrix. The second value can be, for example, the color density of a second color. By repeating this operation, for a third color and for the gray level of the two-dimensional image, a full color image can be stored in the data storage medium of the present invention.

The method of the present invention can also be used to record a plurality of images in adjacent two-dimensional arrays of volume elements. The plurality of images can be, for example, the frames of a movie or other time-evolved scene or scenes. By reading the X-Y plane quickly, so that each two-dimensional image is reconstructed before the human brain can "see" it, and by scanning the Z dimension at a rate which corresponds to the rate at which the images were made (such as, in the case of a movie, at the frames per second rate), the movie or time-evolved scene or scenes can be replayed.

The data stored in, for example, the first volume element of the data storage medium of the present invention can be read by detecting the fraction of dye molecules contained in the first volume element that are detectably altered. Where the dye molecules are two-photon upconversion fluorescers, and where the detectably altered dye molecules are photobleached, the detecting can be carried out by exposing the first volume to actinic radiation. The actinic radiation is of an intensity and the exposing is conducted for a duration effective to induce the dye molecules in the first volume element to undergo a two-photon upconversion process and fluoresce. The dye molecules originally contained in the first volume which were detectably altered by photobleaching during the data storage process do not fluoresce. The fluorescence from the first element is detected and correlated with the fraction of dye molecules in the first volume element that are detectably altered.

Typically, the actinic radiation used for reading is the same as the actinic radiation used for storing. For example, where the actinic radiation used to store data at the first element is electromagnetic radiation of a particular wavelength, the actinic radiation used to read the data can be electromagnetic radiation of that same particular wavelength.

Figure 31:
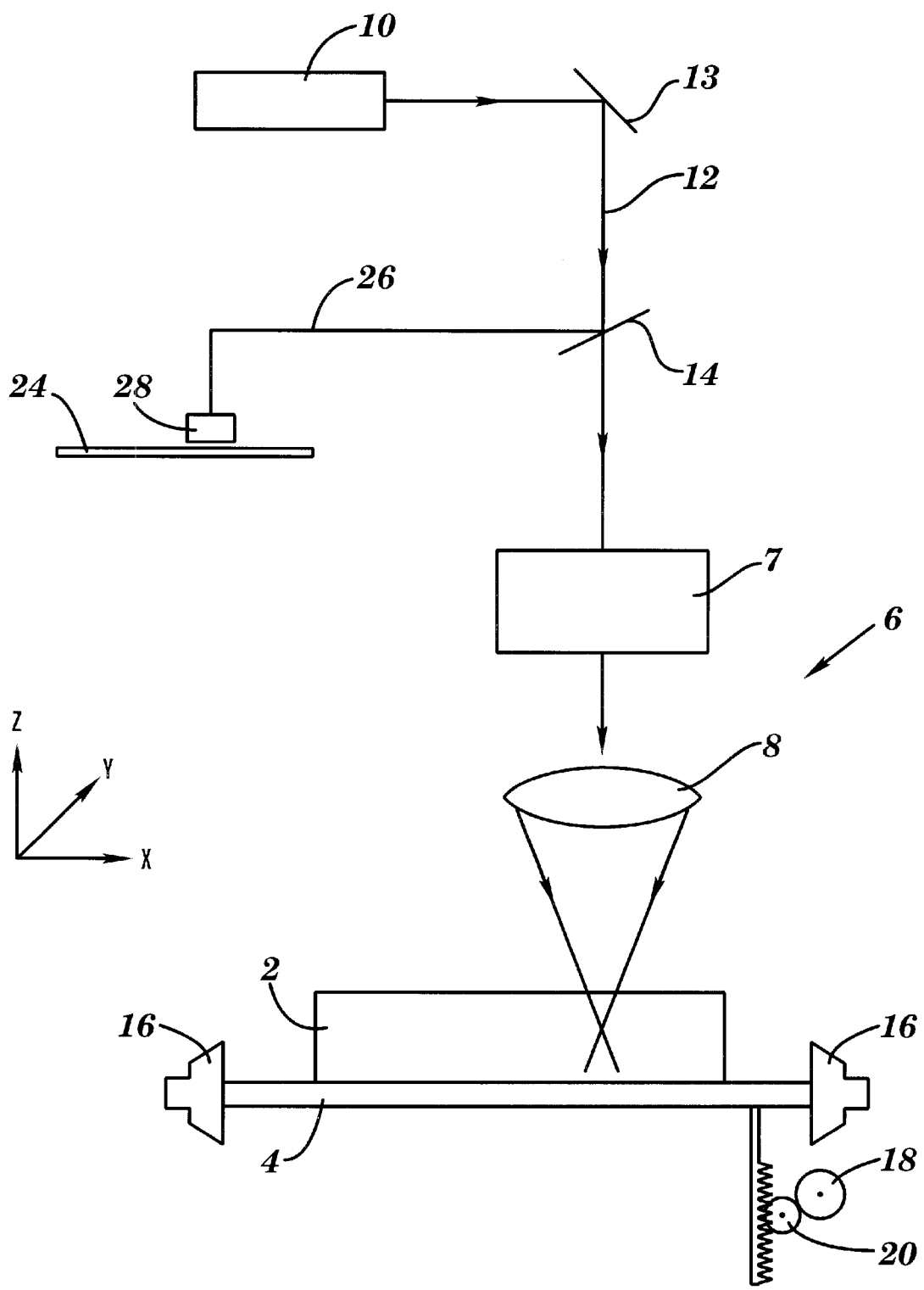
FIG. 31 is a schematic diagram illustrating a method according to the present invention for storing data.

A preferred embodiment of the data storage method of the present invention is depicted in FIG. 31. Matrix 2 is placed on stage 4 of an inverted microscope generally indicated at 6, and which may be a confocal microscope. Matrix 2 is exposed through high numerical aperture ("N.A.") objective lens 8, such as a Nikon planapo 6X (1.4 N.A.), with 90 fs pulses of, for example, 798 nm wavelength light from a Ti:Sapphire laser diagrammatically illustrated at 10. Laser beam 12 is supplied to microscope 6 by way of stationary mirror 13, rotatable dichroic mirror 14, and, optionally, beam scanning optics, diagrammatically illustrated at 7. Matrix 2, carried on stage 4, is translated in the X direction by magnetic coils 16 and in the Y direction (perpendicular to the plane of the paper) by a second set of magnetic coils (not shown). By adjusting the voltage applied to magnetic coils 16 and the magnetic coils not shown, stage 4 is translated in the X-Y plane and a two-dimensional array of volume elements in matrix 2 is defined (Alternatively, stage 4 can be kept spatially fixed in the X-Y plane, and beam 12 can be translated in the X-Y plane by beam scanning optics 7.) Stage 4 is moved in the Z direction by stepper motor focus controller 18 which is connected to focusing knob 20 of microscope 6. By moving stage 4 in the Z direction, laser beam 12 is made to focus at different X-Y planes. In this manner different two-dimensional planes of volume elements are defined, so that three-dimensional stacks of data can be written into matrix 2. The intensity of laser beam 12 is modulated by rotatable dichroic mirror 14. In the case where the data being stored is that of two-dimensional image 24, the position of rotatable dichroic mirror 14 can be controlled by signal 26 produced by densitometer 28 as it scans two-dimensional image 24.

The reading process can be carried out by exposing the entire matrix to actinic radiation and selectively detecting fluorescence only from the first volume element; by selectively exposing the first volume element and detecting fluorescence from the entire matrix; or by selectively exposing the first volume element and selectively detecting fluorescence only from the first volume element.

Selectively exposing the first volume element in the reading process can be effected by the same methods and devices discussed above in relation to selectively exposing particular volume elements for data storage purposes. In particular, a confocal microscope is preferably used to selectively expose the first volume element to the actinic radiation used to read the data stored in the first element. The confocal microscope can also be used to detect selectively fluorescence from the first volume element. Using a confocal microscope to detect the emitted fluorescence is particularly preferred because the adjustable confocal pin hole provided in the collection optics of the confocal microscope minimizes background fluorescence collected from dye molecules above and below the plane of focus. Thus, even though dye molecules above and below the first volume element may be inadvertently exposed to actinic radiation of sufficient intensity and for sufficient duration to cause them to undergo two-photon fluorescence, the confocal microscope limits fluorescence detection to the dye molecules in the first element.

Preferably, the actinic radiation is of an intensity and duration insufficient to detectably alter (e.g. photobleach) the dye molecules contained in the first element, so that the data stored therein remains unchanged after the reading process. By reading the stored data with actinic radiation of an intensity and duration insufficient to detectably alter the dye molecules, the data storage media of the present invention can be used as "write once, read many" ("WORM") data storage media Reading a plurality of data points stored in different volume elements of the data storage medium of the present invention requires that the actinic radiation used to read the data or the detection optics or both be moved to a second volume element. This can be done by moving the matrix, such as by using stepper or continuous motors or electromagnets, for example, as described above with respect to data storage. Alternatively, where the actinic radiation laser radiation is in the form of one or more laser beam(s), the volume element being read can be selected by adjusting the position of the laser beam(s) or, where a focused laser beam is employed, by adjusting the laser beam's focal point, for example, as described above with respect to data storage.

Figure 32:
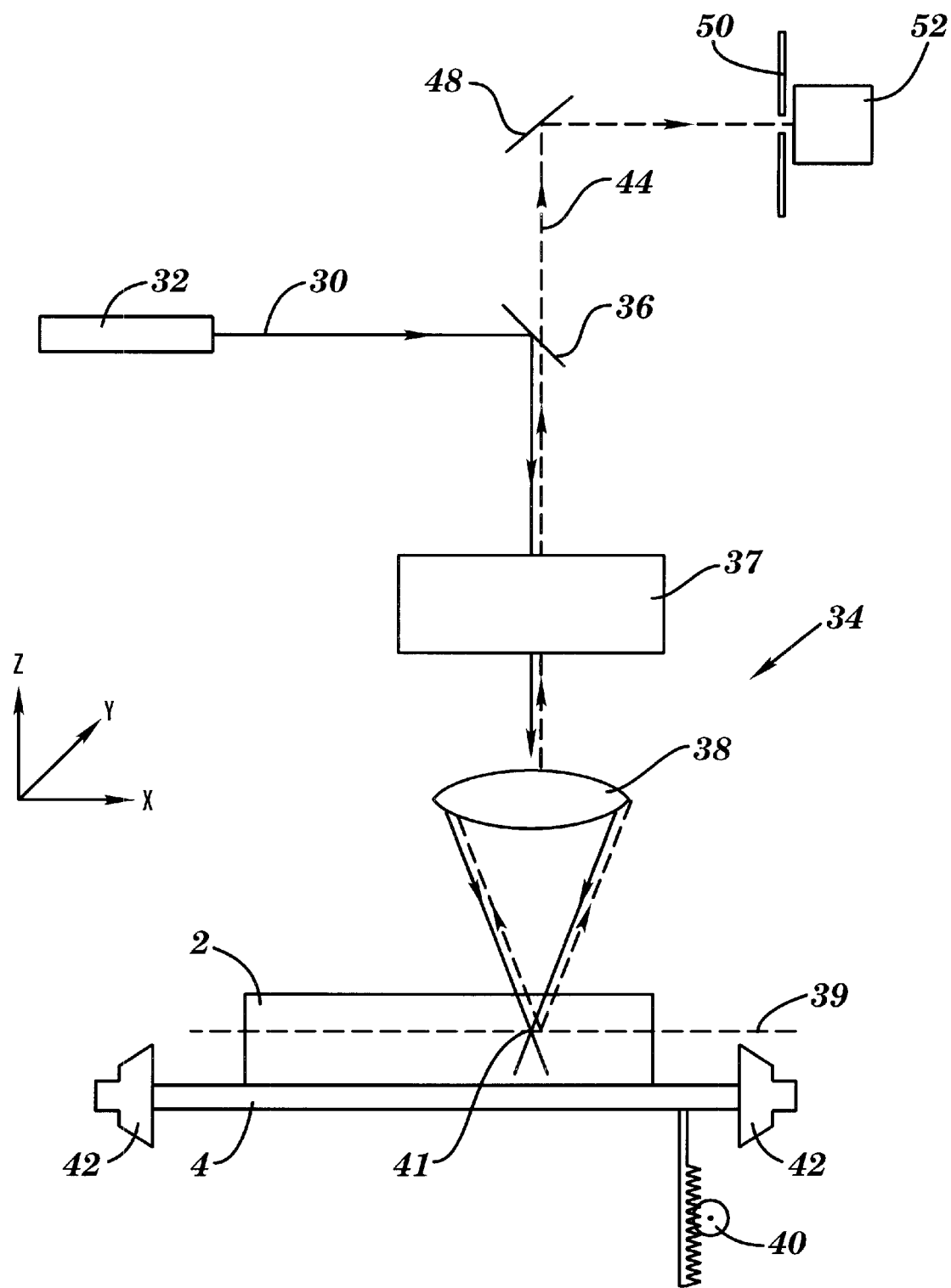
FIG. 32 is a schematic diagram illustrating a method according to the present invention for reading data.

FIG. 32 illustrates a typical configuration for reading data from the data storage medium in accordance with the present invention. The optical memory formed by the foregoing process may be read by successively imaging each of the data-containing planes of matrix 2 by directing laser beam 30 from laser 32 into matrix 2 carried by stage 4, using the optics of confocal microscope 34. Laser beam 30 (indicated by solid arrowed lines) is reflected by dichroic mirror 36 and is focused by objective mirror 38 onto focal plane 39 in matrix 2. The position of stage 4 in the X-Y plane is controlled by four electromagnets, two electromagnets 42 controlling the position in the X direction, and two electromagnets (not shown) controlling the position in the Y direction. (Alternatively, laser beam 30 is translated in the X-Y plane by optional beam scanning optics 37.) By adjusting focal knob 40, the vertical location (along the Z axis) of focal point 41 in matrix 2 can be selected. Thus, by adjusting focal knob 40 and the position of stage 4 (or the optional beam scanning optics 37), laser beam can be made to focus at a selected volume element within matrix 2. At focal point 41, unaltered dye molecules in the selected volume element are excited and fluoresce. Fluorescence produced by the dye molecules in the selected volume element of matrix 2, indicated by dotted arrows 44 in FIG. 32, travels back through microscope 34, retracing the optical path of laser beam 30. Fluorescence 44 passes through objective lens 38, through optional beam scanning optics 37, and to dicroic mirror 36. Because the fluorescence 44 emitted by the dye molecules in matrix 2 is of different wavelength than laser beam 30, fluorescence 44 passes through dichroic mirror 36 and is directed by stationary mirror 48, preferably through confocal aperature 50, to a suitable detector, such as photomultiplier 52. The output of photomultiplier 52 can be displayed, such as on a monitor, or the data can be stored for later manipulation or display. Laser beam 30 can scan each layer of matrix 2 in the X-Y plane to produce a corresponding image, and, by successively focusing microscope 34 on the various planes by way of focus control 40, each layer of the matrix 2 can be read.

The present invention is further illustrated by the following examples.

EXAMPLES

Example 1

Materials and Methods.

2,2'-azobisisobutyronitrile ("AIBN") was purchased from Polyscience, Inc. It was recrystallized twice from methanol. All other chemicals were brought from the Aldrich Chemical Co. and were used as received unless stated otherwise.

Figure 3:
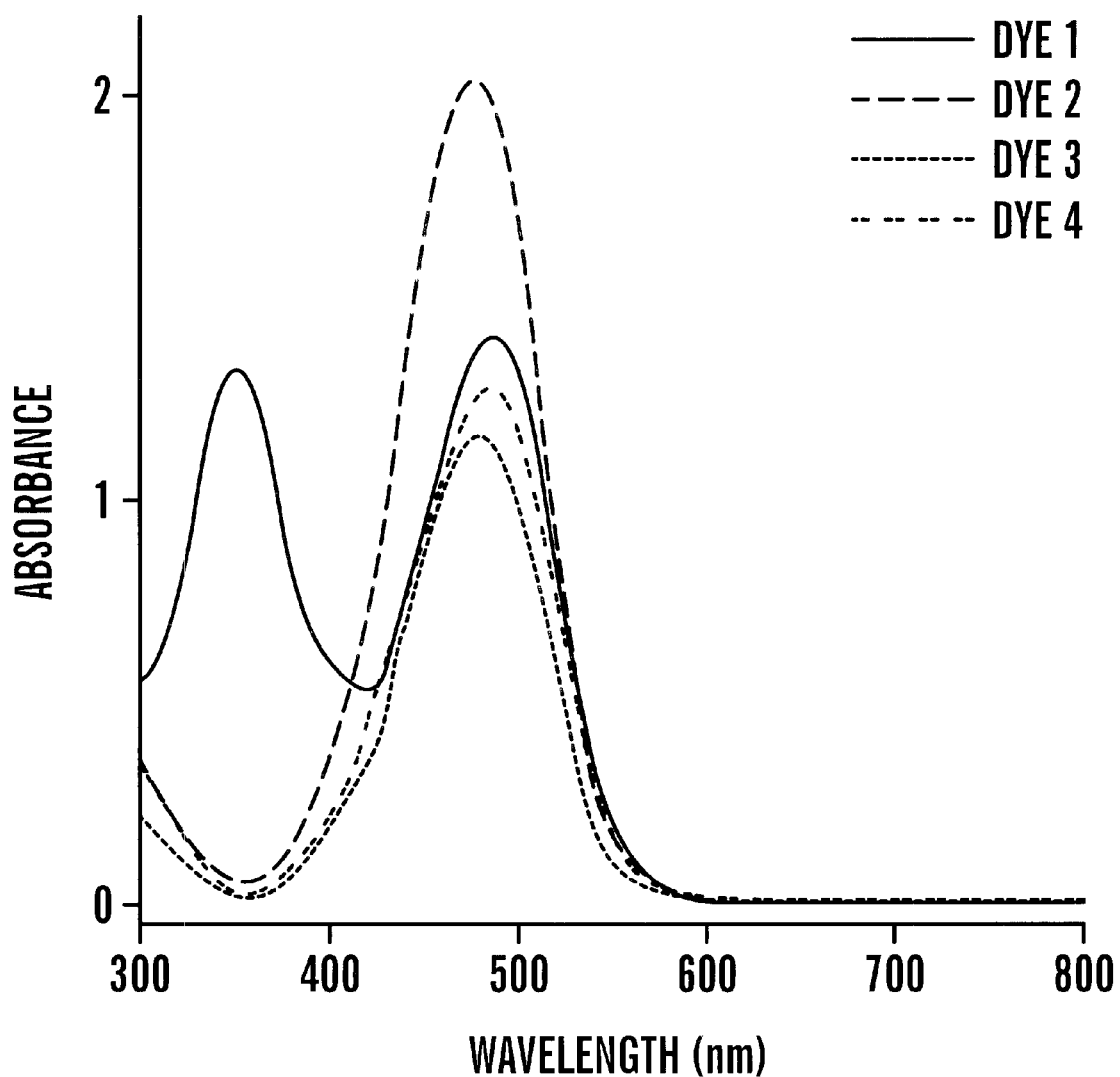
FIG. 3 is an absorbance spectrogram of dilute DMF solutions of dye1 (—), dye2 ( - - - ), dye3 ( ----- ), and dye4 ( ······ ).

Decomposition temperature ("$T_d$") of each dye was measured by differential scanning calorimetry ("DSC") thermogram using a Shimadzu DSC-50GPC under nitrogen. Elemental: analysis were performed by Atlantic Microlab, Inc., P.O. Box 2288, Norcross, Ga. 30019. Proton NMR spectra, TV/visible absorption spectra, and UV/visible emission spectra were recorded using a Varian Gemini-300 300 MHz spectrometer, a Shimazdu UV-3101 PC spectrophotometer, and a Shimazdu RF5000U spectrofluorophotometer, respectively: TV/visible absorption spectra of dyes prepared in these Examples in DMF, are provided in FIG. 3.

Deuterium Oxide (Aldrich, Inc.), 9,10-anthracenedipropionic acid ("ADPA") (Molecular Probes, Inc.), and meso tetra(p-sulfonaphenyl)porphyrin ("TPPS") (Porphyrin Products, Inc.) were obtained commercially and used as supplied. [p-(N-ethyl-N-hydroxyethylamino)styryl]-N-butansulfonpyridinum ("ASPS") was prepared in accordance with the methods described herein and in Zhao et al., *Chemistry of Materials*, 7:1979–1983 (1995) ("Zhao"), which is hereby incorporated by reference. Solutions of ASPS and TPPS in $D_2O$ were prepared by normal volumetric techniques in a darkened laboratory. Photoirradiation of these solutions was carried out at ambient temperature (25° C.), and the solutions were saturated with air except where stated.

Example 2

Preparation of 4-(1-Ethyl-N-hydroxyethylamino) benzaldehyde.

A one liter three-neck flask, fitted with mechanical stirrer, thermometer, and condenser, was charged with 25 g (0.2 mol) of 4-fluorobenzaldehyde), 54g (0.6 mol) of 2-(ethylamino)ethanol, 41.5 g (0.3 mol) of anhydrous potassium carbonate, and 0.5 ml ALIQUAT-336™ (tricaprylyl methylammonium chloride) (Henkel Corp.) in 250 ml dimethylsulfoxide ("DMSO"). The reaction mixture was heated at 95° C. for 72 hours, cooled to room temperature, and then poured into an ice water mixture. The water layer was extracted with dichloromethane, and the combined organics were washed twice with cold water. After solvent evaporation, the red-colored oil was dissolved in 200 ml of ether and poured into 800 ml of 1 N aqueous HCl. After stirring for 10 minutes, the water layer was separated and neutralized using aqueous sodium carbonate. 200 ml dichloromethane were added, and the organic layer was separated and dried with anhydrous sodium sulfate. Removal of the solvent afforded 4-N-ethyl-N-hydroxyethylamino) benzaldehyde as a pale yellow oil. Yield 25 g (65%);

$^1$H-NMR (CDCl$_3$) δ 1.18 (t, 3H), 2.30 (s, 1H), 3.62 (m, 2H), 3.66 (t, 2H), 3.90 (t, 2H), 6.70 (d, 2H), 7.68 (d, 2H), 9.62 (s, 1H) ppm.

Example 3
Preparation of 4-methyl-N-methylpyridinium iodide.

A 500 ml three-neck flask, fitted with a stirrer, thermometer, and condenser, was charged with 9.3 g (0.1 mol) of 4-picoline and 21.6 g (0.11 mol) of methyl iodide in toluene. The solution was stirred at room temperature for 4 hours, and then refluxed for 30 minutes. After cooling, the solution was filtered, and the pale yellow solid, 4-methyl-N-methylpyridinium iodide, was washed with ethyl ether and dried under vacuum. Yield 21.2 g (90%); $^1$H-NMR (DMSO-d$_6$): δ 2.56 (s, 3H), 4.20 (s, 3H), 7.0 (d, 2H), 8.90 (d, 2H) ppm.

Example 4
Preparation 4-methyl-N-(2-hydroxyethyl)pyridinium iodide.

9.3 g (0.1 mol) of 4-picoline was reacted with 19.0 g (0.11 mol) of 2-hydroxyethyliodide under the conditions described in Example 3. The usual workup yielded 23.9 g (90%) of a yellow solid, 4-methyl-N-(2-hydroxyethyl)pyridinium iodide. $^1$H-NMR (DMSO-d$_6$): δ 2.56 (s, 3H), 3.70 (q, 2H), 4.40 (t, 2H), 5.2 (t, 1H), 7.95 (d, 2H), 8.90 (d, 2H) ppm.

Example 5
Preparation of 4-methylpyridinium-N-butansulfon.

A 500 ml three-neck flask, fitted with a stirrer, a thermometer, and a condensor, was charged with 9.3 g (0.1 mol) of 4-picoline, 13.6 g (0.1 mol) of butansultone, and 150 ml of toluene. The solution was mixed, heated to 100° C. for 2 hours, cooled, and filtered. The yellow solid, 4-methylpyridinium-N-butansulfon, was washed with ethyl ether and dried under vacuum. Yield 13.7 (60%). $^1$H-NMR (D$_2$O): δ 1.60 (m, 2H), 1.90 (m,2H), 2.56 (s, 3H), 2.75 (t, 2H) 4.1 (t, 2H), 7.60 (d, 2H), 8.2 (d, 2H) ppm.

Example 6
Preparation of trans-4-[p-(N-ethyl-N-hydroxyethylamino) styryl]-N-methylpyridinium tetraphenyborate ("dye1").

2.5 g (0.013mol) of 4-(N-ethyl-N-hydroxyethylamino) benzaldehyde, prepared according to Example 2, 3.1 g (0.013 mol) of 4-methyl-N-methylpyridinium iodide, prepared according to Example 3, and 30 ml of absolute ethanol were mixed in a 500-ml one neck fitted with a stirrer and condenser. 5 drops of piperidine were added to the mixture, and the solution was refluxed overnight After cooling, 4.5 g (0.013 mol) of sodium tetraphenyborate was added into the solution. The resulting solution was heated to reflux for 10 minutes and then cooled, forming a red solid. The solid was separated by filtration, twice washed with ethanol, twice washed with water, and dried, to yield 4.7 g (60%) of dye1. $^1$H-NMR (DMSO-d$_6$): δ 1.0 (2,3H), 3.30 (q, 2H), 3.4 (t, 2H), 3.80 (q, 2H), 4.10 (s, 3H), 4.80 (t, 1H), 6.70 (t, 4H), 6.8 (t, 8H), 7.02 (d, 1H), 7.10 (d, 8H), 7.5 (d, 2H), 7.8 (d, 2H), 7.9 (d, 1H), 8.0 (d, 2H), 8.62 (d, 2H) ppm. Element analy. calcd. for C$_{42}$H$_{43}$BN$_2$O: C, 83.7; H, 7.1; N, 4.7; Found: C, 83.9; H, 6.7; N, 3.7. T$_d$ 264° C.

Example 7
Preparation of trans-4-[p-(N,N-dimethylamino)styryl]-N-methylpyridinium tetraphenyborate ("dye2"). 14.9 g (0.1 mol) of 4-(N,N-dimethylamino)benzaldehyde were reacted with 23.6 g (0.1 mol) of 4-methyl-N-methylpyridinium iodide, prepared according to Example 3, and the resulting solution was treated with 34.6 g (0.1 mol) of sodium tetraphenyborate, under the conditions described in Example 6, to form dye2 as a red solid in a yield of 70%. $^1$H-NMR (DMSO-d$_6$) δ 3.00 (s, 6H), 4.1 (s, 3H), 6.70 (t, 4H), 6.8 (t, d, 2H), 6.9 (t, 8H), 7.02 (d, 1H), 7.10 (d, 8H) 7.50 d, 2H), 7.9 (d, 2H), 8.62 (d, 2H) ppm. T$_d$ 266° C.

Example 8
Preparation of trans-4-[p-(N-ethyl-N-hydroxyethylamino) styryl]-N-hydroxyethylpyridinium iodide ("dye3").

Following the procedure of Example 6, equimolar amounts of 4-N-ethyl-N-hydroxyethylamino)benzaldehyde, prepared according to Example 2, and 4-methyl-N-(2-hydroxyethyl)pyridinium iodide, prepared according to Example 4, were reacted in ethanol at reflux, overnight. Upon cooling, dye3 precipitated as a red solid and was collected by filtration, washed, and dried. Yield: 67%. 1H-NMR (DMSO)-d$_6$): δ 1.0 (t, 3H), 3.3 (q, 2H), 3.40 (q, 2H), 3.50 (t, 2H), 3.80 (q, 2H), 4.40 (t, 2H), 4.70 (t, 1H), 5.2 (t, 1H), 6.7 (d, 2H), 7.1 (d, 1H), 7.80 (d, 2H), 7.90 (d, 1H), 8.10 (d, 2H), 8.70 (d, 2H) ppm. The elements analy. calcd. for C$_{19}$H$_{25}$IN$_2$O$_2$: C, 51.8; H, 5.7; N, 6.4; Found: C, 51.5; H, 5.7; N, 7.1. T$_d$ 270° C.

Example 9
Preparation of trans-4-[p-(-ethyl-N-hydroxyethylamino) styryl]-N-butansulfonpyridinum ("dye4").

Following the procedure of Example 6, equimolar amounts of 4-(N-ethyl-N-hydroxyethylamino) benzaldehyde, prepared according to Example 2, was reacted with 4-methylpyridinium-N-butansulfon, prepared in accordance with Example 5, in ethanol at reflux, overnight. Upon cooling, dye4 precipitated as a red solid and was collected by filtration, washed, and dried. Yield: 50%. $^1$H-NMR (D$_2$O) δ 1.60 (m, 2H), 1.90 (m, 2H), 2.80 (t, 2H), 2.90 (s, 3H), 3.40 (t, 2H), 3.60 (q, 2H), 4.10 (t, 2H), 4.70 (t, 1H), 6.70 (d, 2H), 6.75 (d, 1H), 7.35 (d, 2H), 7.40 (d, 1H), 7.60 (d, 2H), 8.20 (d, 2H) ppm. The element analy. calcd. for C$_{20}$H$_{26}$N$_2$O$_4$S: C, 61.5; H, 6.6; N, 7.2; S, 8.2. Found C, 61.6; H, 6.7; N, 7.1; S, 8.3. T$_d$ 241° C.

Example 10
Infrared detection.

Figure 4:
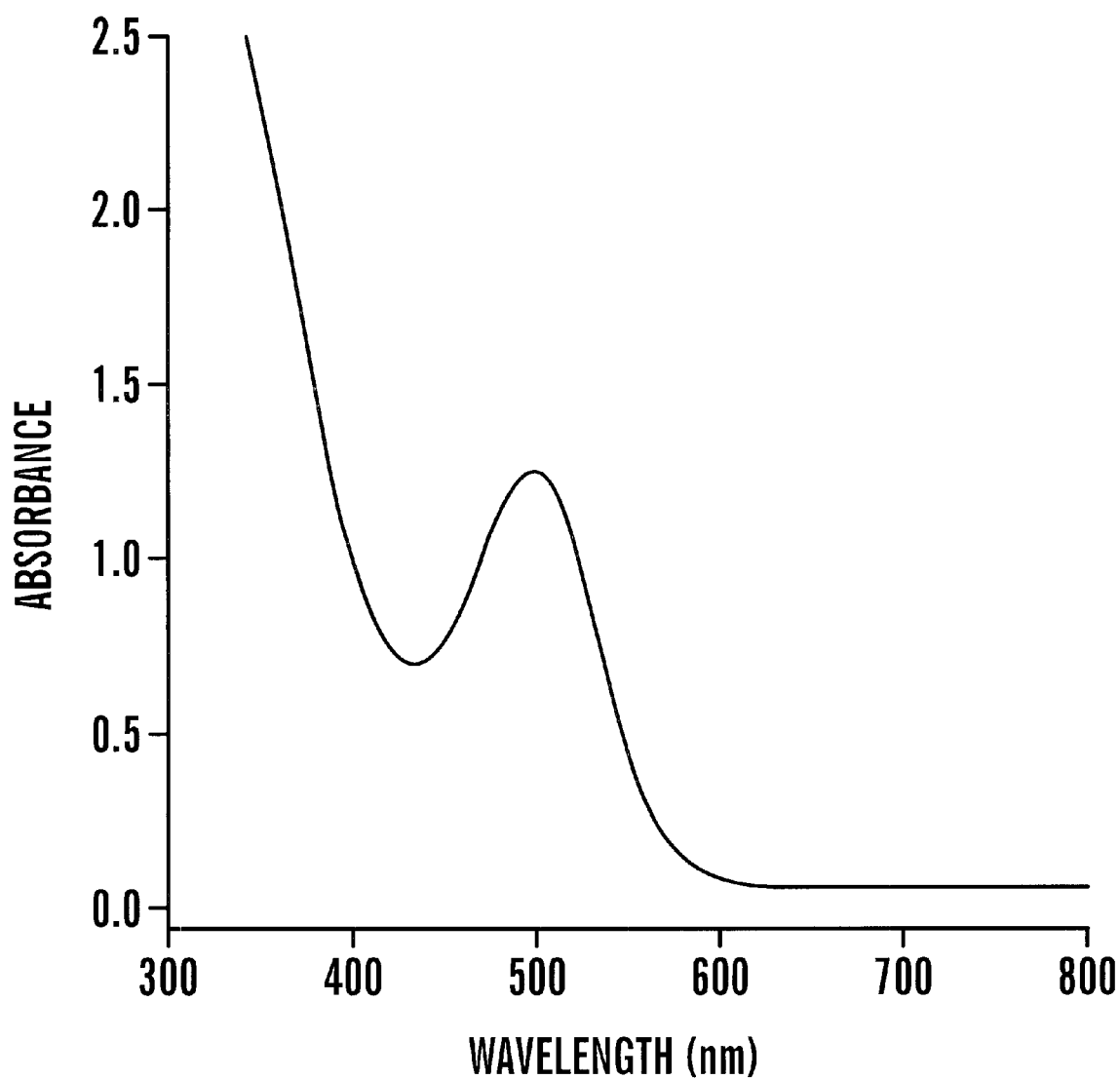
FIG. 4 is an absorbance spectrogram of a 50 μm cross-linked polyurethane polymer sheet containing 1.5 mM of dye1.

Dye 1, prepared in accordance with Example 6, was added to a solution of glycerol and poly(phenylisocyanate)-co-formaldehyde (1:3 glycerol:polymer ratio) in dimethylformamide and cyclopentanone, and the resulting polyurethane coating material was cast to make a film having 50 μm thickness and a dye concentration of 1.5 nm. The coating material was then permitted to cure at 100° C. for 10 minutes. FIG. 4 presents the absorbance spectra of the resulting infrared detection film.

The dye 1-doped film was placed in the path of a 1.06 μm, several MW/cm$^2$ Nd-YAG-generated laser beam, and a localized bright red emission, indicating the presence of invisible infrared radiation, was visually observed on the film. A photograph of the film exposed to the infrared beam, showing the emission, is presented in FIG. 5A. A similar experiment was conducted using a commercially available infrared detector, manufactured by Kodak (available as stock #M11,234 from Edmund Scientific Company, Barrington, N.J.). A photograph of the Kodak card exposed to the Nd-YAG infrared beam is presented in FIG. 5B.

Figure 6:
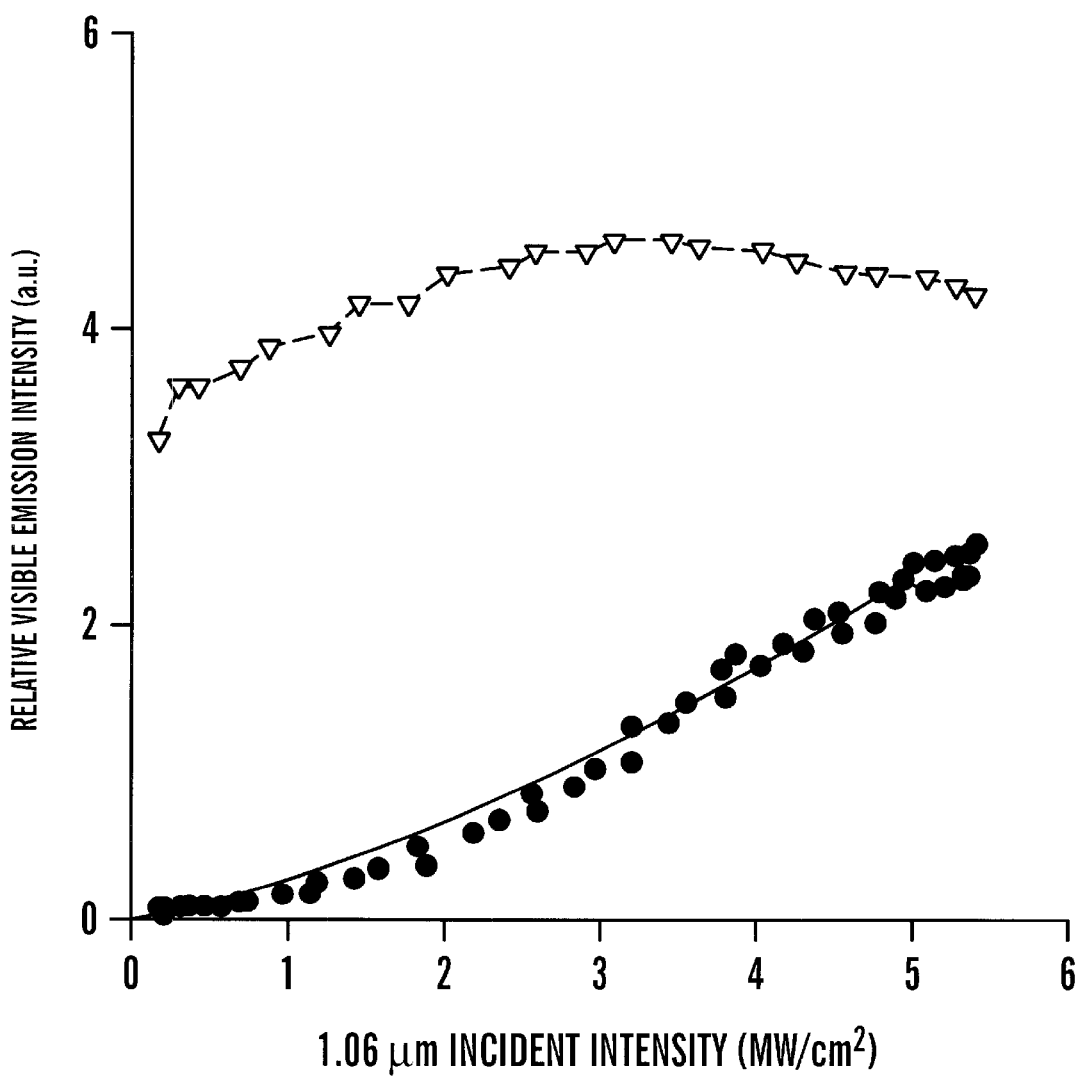
FIG. 6 is a plot of the relative visible emission intensity (in arbitrary units) from a 50 μm cross-linked polyurethane polymer sheet containing 1.5 MM of dye1 (•) and from a Model F-infraredC1 Sensor Card made by KENTEK™ (Newport, N.H.) (▽) as a function of the intensity of an incident 1.06 μm Nd-YAG laser beam.

The emissivity of the dye1-doped polyurethane film prepared above was determined by exposing, the film to various intensities of 1.06 μm Nd-YAG laser radiation and monitoring visible emission using a power meter. The results are presented in FIG. 6, along with the results from a parallel experiment using a Model F-IRC1 IR Sensor Card (available from KENTEK™, Newport N.H.). Referring to FIG. 6, the dye1-doped film (•) exhibits an emission intensity having quadratic dependence on incident infrared laser beam intensity, whereas the Model F-IRC1 detection sheet (▽) shows saturation at intensities as low as 0.5 MW/cm$^2$ and no response to changing intensity at intensities greater than 0.5 MW/cm$^2$.

Example 11

Optical Limiting.

Dye1, prepared in accordance with Example 6, was dispersed in an optical quality epoxy compound, EPO-TEX301 (Epoxy Technology, Inc., Billerica, Mass.) by dissolving the dye powder in the liquid Part A and Part B of the epoxy. Undoped and dye1-doped epoxies were cast by blade casting techniques. Film thickness was the same (0.3 mm) for both films, and the dopant concentration for the doped film was $d_o$=0.003 M.

Figure 7:
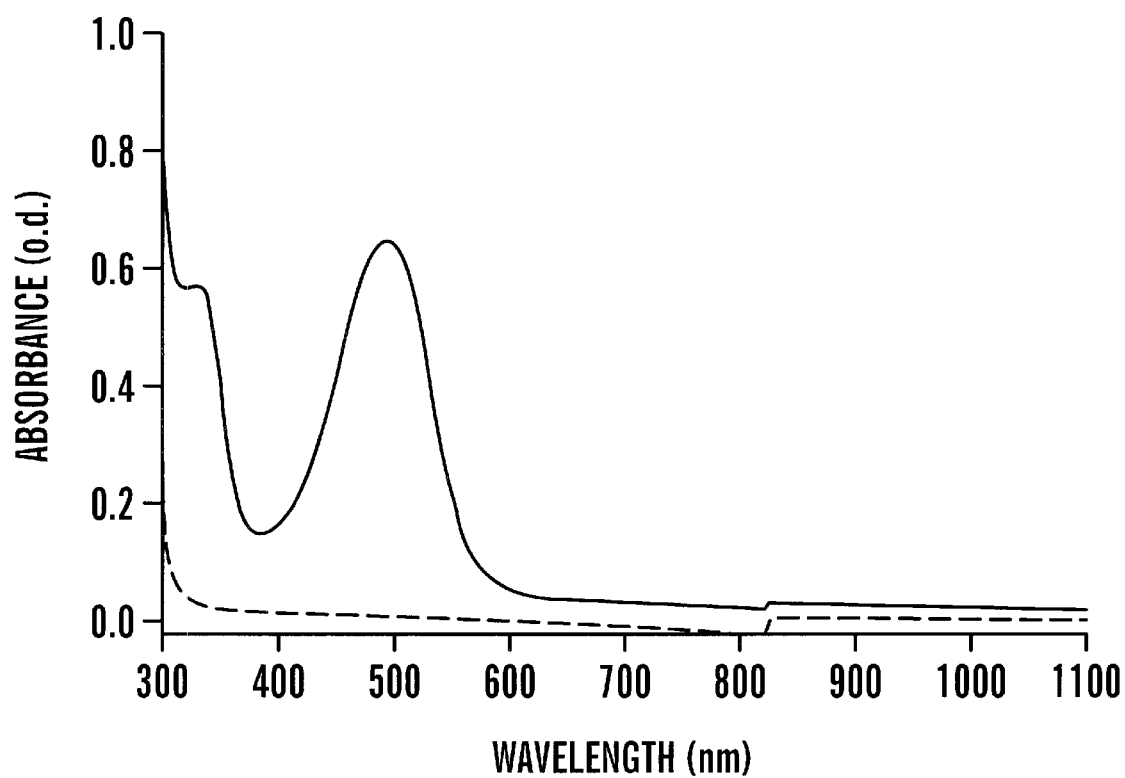
FIG. 7 is a one-photon absorbance spectra of a 0.3 mm-thick, dye1-doped epoxy film (—) and an undoped epoxy film having the same thickness ( - - - ).

FIG. 7 presents the linear absorption spectra of a dye1-doped epoxy film and an undoped pure epoxy film. The film's strong one-photon absorption in the 350~560 nm range and the undoped film's transparency in the whole 310–1100 nm range suggests that the observed linear absorption is due to the dopant. On the other hand, one can also see that the two-photon energy of 700~1100 nm infrared radiation falls in the strong linear absorption band of the doped sample. Therefore, a TPA effect can be expected in this doped material for laser wavelengths within the above spectral range. The observation of very strong frequency upconverted fluorescence emission and the subsequent quantitative measurement of the intensity dependence on the near infrared laser excitation proved a two-photon absorption process.

Figure 8:
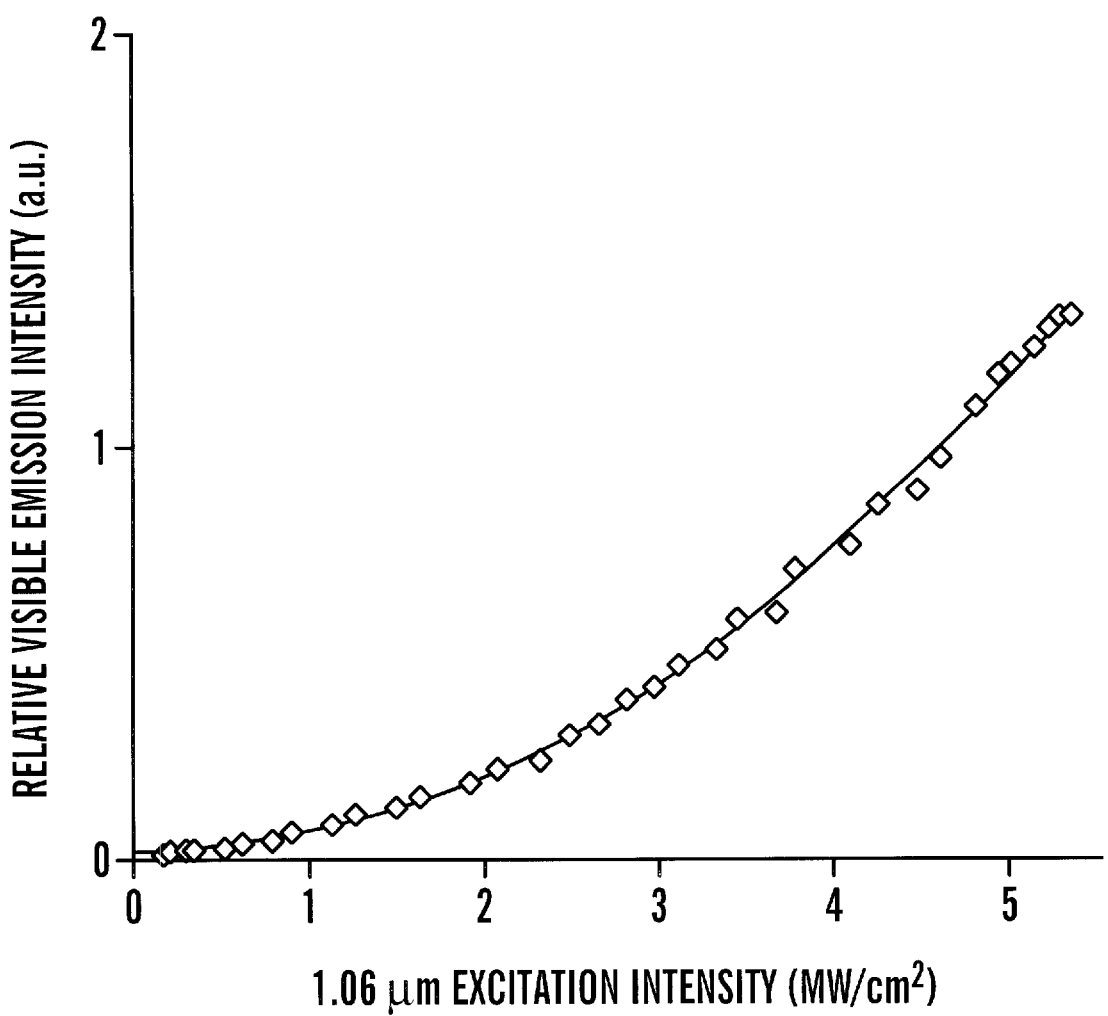
FIG. 8 is a plot of the relative visible emission intensity (in arbitrary units) of a 2-cm long, dye1-doped epoxy (EPO-TEX 301) rod as a function of 1.06-μm excitation intensity.

A 2 cm-long, dye1-doped epoxy (EPO-TEX301) rod with a concentration of $d_o$=0.004M was used for TPA induced fluorescence and optical limiting measurements. An incident near infrared laser beam, having a wavelength of 1.06 μm, a pulsewidth of about 8 ns, a spectral width of about 1 cm$^{-1}$, and a repetition rate of 3 Hz, was provided by a Q-switched Nd-YAG pulsed laser source. The incident 1.06 μm radiation on the sample was a quasi-parallel laser beam of about 1 mm size with a nearly uniform transverse intensity distribution. An orange-red fluorescence emission was readily observed by the human eye in a dark room when the 1.06 μm incident beam intensity reached several MW/cm$^2$. FIG. 8 shows the measured visible fluorescence intensity as a function of the incident 1.06 μm intensity. Each data point was averaged over 10 laser pulses by using a gated integrator and boxcar averager. The solid line is the best fitted curve based on the square law that TPA processes follow.

According to the basic theoretical consideration, the TPA induced decrease of transmissivity can be expressed as $$I(L)=I_o/(1+I_oL\beta), \quad (1)$$

where I(L) is the transmitted beam intensity, $I_o$ is the incident beam intensity, L is the thickness of the sample, and β is the TPA coefficient of the sample medium. In the derivation of Equation (1), it is assumed that the linear attenuation of the medium can be neglected and the beam has a nearly uniform transverse intensity distribution within the medium. Using Equation (1), the value of β can be determined by measuring the transmitted intensity versus the incident intensity for a sample medium with a given L value. Furthermore, the TPA coefficient β (in units of cm/GW) of a given sample is determined by $$\beta=\sigma_2 N_o=\sigma_2 N_A d_o \times 10^{-3}. \quad (2)$$

Here, $N_o$ is the molecular density of the dopant (in units of 1 cm$^3$), $\sigma_2$ is the molecular TPA coefficient (or cross-section) of the same dopant (in units of cm$^4$/GW, $d_o$ is the concentration of the dopant compound in the matrix (in units of M), and finally $N_A$ is Avogadro's number. For known β and $d_o$, the value of $\sigma_2$ can be calculated from Equation (2). Another expression for molecular TPA coefficient (or cross-section), used in some reference papers, is $$\sigma'_2=h\upsilon\sigma_2, \quad (3)$$

where hυ is the energy of an incident photon, and $\sigma'_2$ has units of cm$^4$/photon/sec.

Figure 9:
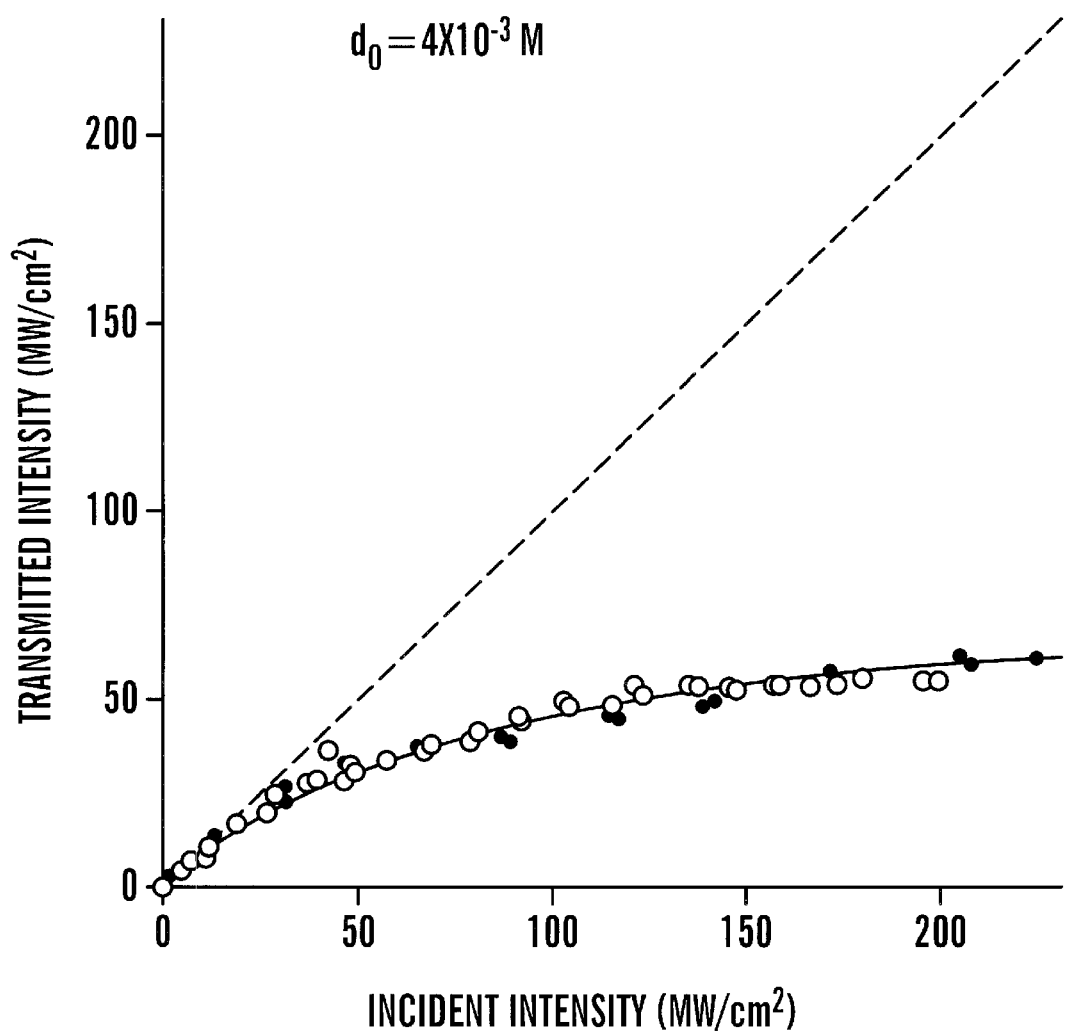
FIG. 9 is a plot of the measured transmitted intensity of a 2-cm long, dye1-doped epoxy rod as a function of 1.06-μm–incident intensity. The solid line is a theoretical curve with a best fit parameter of, β=6 cm/GW. The dashed line represents the theoretical case where β=0.

The measured transmitted intensity as a function of the incident intensity for the 2 cm-long, dye1-doped epoxy rod is shown in FIG. 9. Two groups of experimental data were obtained in two measurement cycles, and each data point was an average result over 10 laser pulses. In FIG. 9, the solid line is the theoretical curve predicted by Equation (1) using a best fit parameter of β=6 cm/GW, and the dashed line is similarly constructed by assuming that there is no TPA (β=0). Consequently, FIG. 9 evidences the TPA induced optical limiting behavior of dye1 at incident intensity levels of 50~250 MW/cm$^2$. Using a value of β=6 cm/GW and Equations (2) and (3), the values of molecular TPA cross-section of dye1 were estimated as $\sigma_2$=2.5×10$^{-18}$ cm$^4$/GW and $\sigma'_2$=4.7×10$^{-46}$ cm$^4$/photon/sec. These measured values of $\sigma_2$ and $\sigma_2$ for dye1 in EPO-TEX301 matrix are 2~3 orders of magnitude greater than the corresponding values of Rhodamine dyes, as reported by Rapp et al., *Chem. Phys. Lett.* 8:529 (1971), Brunner et al., *Kvantovaya Electron.* (Moscow) 2:832 (1975), and Qui et al., *Applied Physics B* 48:115 (1989). The damage threshold of the 2 cm-long, dye1-doped epoxy rod was measured as 250~300 MW/cm$^2$.

Example 12

Preparation of Polymer Matrix Materials for Two-Photon Pumped Cavity Lasing.

Figure 10:
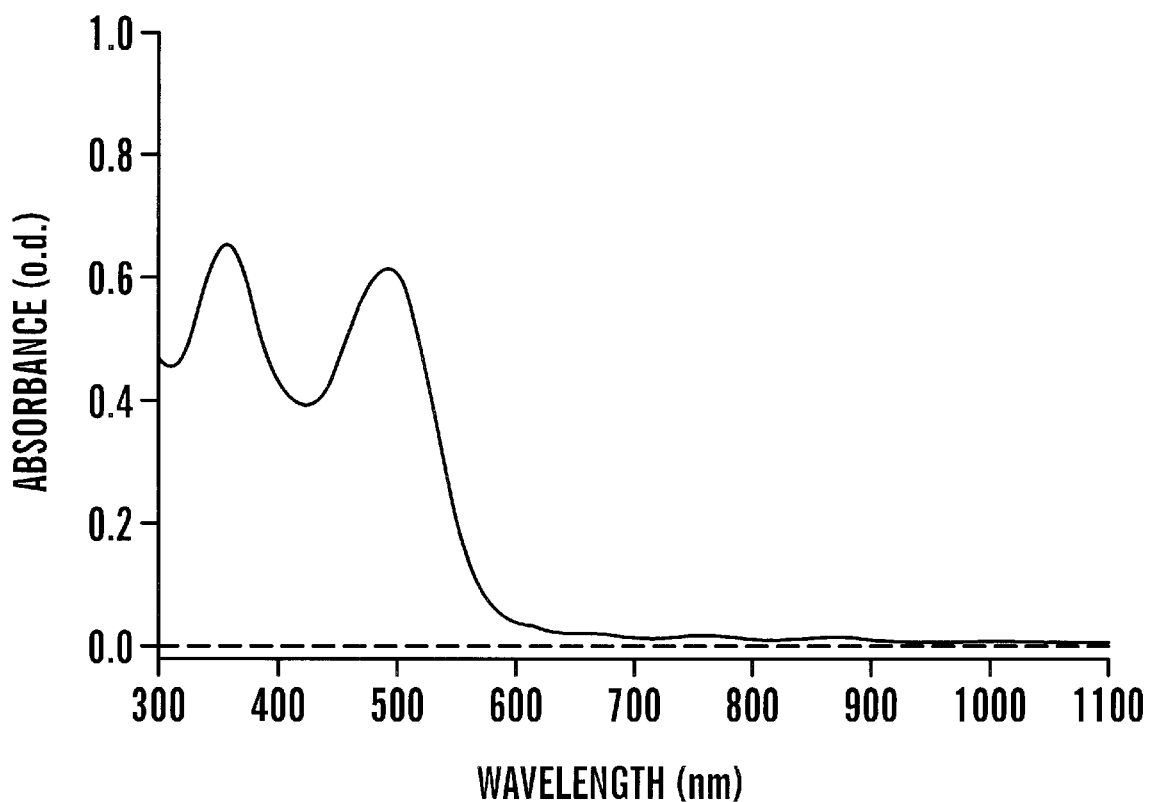
FIG. 10 is a linear absorption spectrogram of a 2 μm-thick dye1 -doped poly(hydroxyethyl methacrylate) ("poly(HEMA)") film (—) and a 2 μm-thick undoped poly (HEMA) film ( - - - ).

A rod was prepared by mixing 5 mg of dye1 in 1.2 g of 2-hydroxyethyl methacrylate ("HEMA") and then adding 1% mole ratio AIBN. The HEMA solution was polymerized in a sealed cylindrical container at 40° C. for a week to produce a poly(hydroxyethyl methacrylate) ("poly(HEMA)") rod, doped with 8×10$^{-3}$M of dye1. The polymer rod, 7 mm in length, was polished on its two end-faces. 2-μm thick, dye1-doped and undoped poly (HEMA) films were also prepared for spectral analyses, which are presented in FIG. 10.

Example 13

Preparation of Dye-doped Sol Gel Glass Materials for Two-photon Pumped Cavity Lasing.

A sol gel glass impregnated with dye1 was prepared in three stages.

First, a low density bulk glass having a density of about 0.7 g/cm$^3$ and a refractive index of about 1.472 was prepared. 9.72 g of tetraethoxysilane, dissolved in 8.9 ml of absolute ethanol, was stirred for 1 hour, followed by addition of 3.2 g of water and then 2 drops of nitric acid. After stirring the solution for 10 minutes, 8 drops of hydrofluoric acid was added, and the solution was again stirred for 10 minutes. The solution was transferred to a cylindrical container, and the container was sealed except for 3 needle holes made in the top of the container. The solution was then aged for two weeks. The resulting bulk glass was then heated in an oven from room temperature to 500° C. at a rate of 0.8° C. per minute and then cooled.

The bulk glass was impregnated with dye and poly (methyl methacrylate) ("PMMA") by the following procedure. The bulk glass was immersed in a cyclopentanone solution of dye1. After removing the glass from the solvent and evaporating residual solvent from the glass, the dye1-doped glass was immersed in methyl methacrylate containing 1% (mole ratio) of AIBN to impregnate the dye1-doped glass with methyl methacrylate. The monomer impregnated glass was then stored in a sealed container at 40° C. for one week to polymerize the monomer. The sample was then cleaned and polished. Polishing consisted of the following steps: manual grinding on 65 μm grade diamond grinding wheels; automatic grading on SiC paper, sequentially with 500, 800 and 1200 grit, lubricating with tap water; and automatic polishing on cloths using 6, 1 and 0.25 μm grade diamond paste as an abrasive, in gradual steps, using a commercial alcoholic-based lubricant. Automated steps were performed on a METASER V™ 2000 (Buehler VK, Ltd., Coventry, England) grinding and polishing machine. The dye-doped sol gel had a dye concentration of about $1.5 \times 10^{-3}$ M and contained 32 vol % silica and 68 vol % PMMA.

The same method was used to prepare dye2-, dye3-, and dye4-doped sol gel glasses.

Example 14
Preparation of Dye-doped Vycor Glass Materials for Two-photon Pumped Cavity Lasing.

Vycor glass, having an average pore size of 40 Å (Corning Glass, Corning, N.Y.), was impregnated with $1.5 \times 10^{-3}$ M of dye1 and PMMA using the same procedure used in Example 13 to impregnate sol gel glass.

Example 15
Two-photon Pumped Cavity Lasing.

Figure 11A:
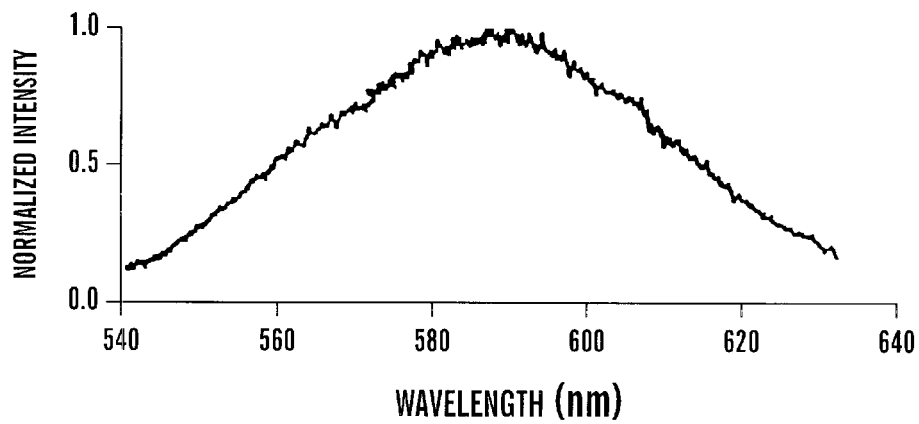
FIG. 11A is a fluorescence spectrogram of a 7 mm-long, dye1-doped poly(HEMA) rod excited with 532 nm radiation.
Figure 11B:
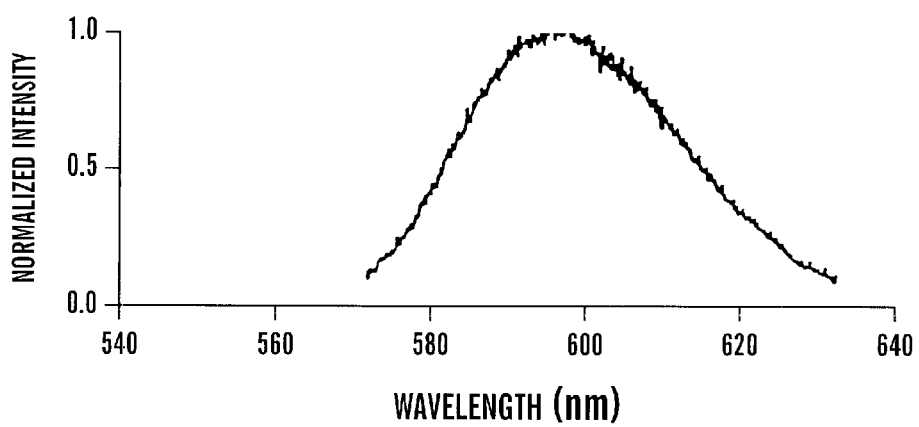
FIG. 11B is a fluorescence spectrogram of the same sample rod excited with 1.06 μm radiation.
Figure 11C:
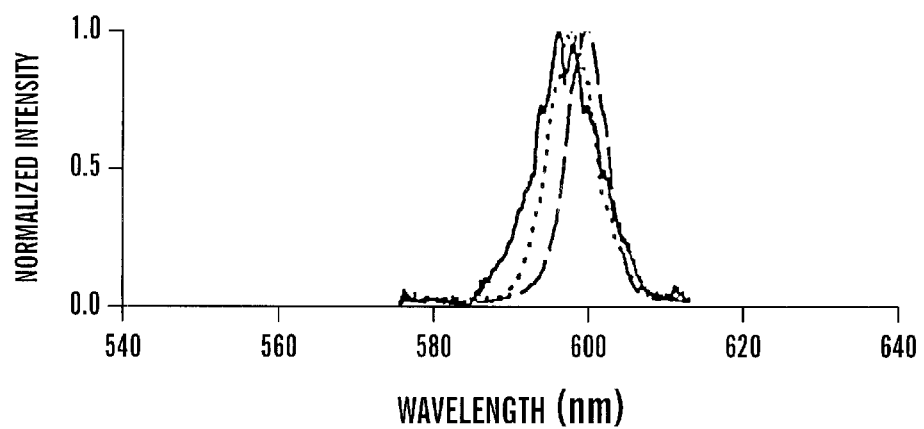
FIG. 11C is a cavity lasing spectrogram of the same sample rod pumped with 1.06 μm laser radiation having energy levels of 0.4 mJ (—), 0.5 mJ ( - - - ), and 0.8 mJ ( - - - ).

Two-photon pumped cavity lasing experiments were conducted using a Q-switched Nd-YAG pulsed laser source having a wavelength of 1.06 μm, a pulsewidth of about 10 ns, a spectral width of about 1 cm$^{-1}$, an angular divergence of about 1.3 mrad, and a variable repetition rate of 1–10 Hz. A 1 cm-long quartz cuvette filled with dye1 solution in cyclopentanone ($d_o \approx 8 \times 10^{-2}$ to $4 \times 10^{-2}$M) and a 7 mm-long, dye1-doped poly(HEMA) rod ($d_o \approx 8 \times 10^{-3}$ M), prepared in accordance with Example 12, were used separately for two-photon pumped ("TPP") lasing observation. The 1.06 μm-pump laser beam was focused on the center of the cuvette or sample rod, and a strong orange-red fluorescence emission was observed when the infrared pump intensity reached several MW/cm$^2$. Once the pump intensity further increased to a certain threshold level, simultaneous forward and backward highly directional superradiation could be observed from the solution or rod samples. To achieve cavity lasing, two parallel plane dielectrc-coating mirrors were employed to form a cavity. The pump beam, focused through a f-10 cm lens, was coupled into the cavity by normal incidence. The reflectivity was r=10% at 1.06 μm and r=99% at 600 nm for the front mirror (input coupler) and r=10% at 1.06 μm and r=50% at 600 nm for the rear mirror (output coupler). The total cavity length was 7~8 cm, and the cuvette or sample rod was located at the center of the cavity. It was found that the pump threshold and the beam divergence of cavity lasing was lower than that of superradiation. FIGS. 11A–11C show the emission spectra of the same 7 mm-long, dye1-doped rod sample under the following different excitation conditions: 532 nm one-photon excited fluorescence emission (FIG. 11A), 1.06 μm two-photon excited fluorescence emission (FIG. 11B), and 1.06 μm pumped cavity lasing (FIG. 11C). Each spectrum was obtained using a grating-spectrograph in conjunction with an optical multichannel analyzer (OMA-III) system. The difference between FIGS. 11A and 11B can be explained by a volume reabsorption effect of the emission. To obtain these two spectra, the excitation beam was incident on the rod end at a +45° angle, and the fluorescence was measured at a −45° angle. In the case of FIG. 11A, the emission was mainly from a shallow surface layer of the sample because of the very short penetration depth of the 532 nm pump radiation, and therefore, the reabsorption effect within the sample can be neglected. However, for the case of FIG. 11B, the incident infrared beam could pass through the whole rod length without obvious depletion, and, consequently, collected fluorescence signals of different spectral components were propagated within the sample for a considerable distance. As a result of the reabsorption, the short wavelength edge of the broad emission band could be attenuated, as can be seen by referring to FIG. 10. FIG. 11C shows the TPP cavity lasing spectra at three different pump levels. Cavity lasing occurred at the central region of the two-photon absorption ("TPA") induced fluorescence band, but the lasing bandwidth (~8 nm) was much narrower than the ordinary one-photon excited fluorescence band width (~60 nm) due to the lasing threshold requirement. In addition, a red-shift of the central lasing wavelength was observed as the pump energy increased. This shift may be caused by the local temperature change of the sample rod.

Figure 12A:
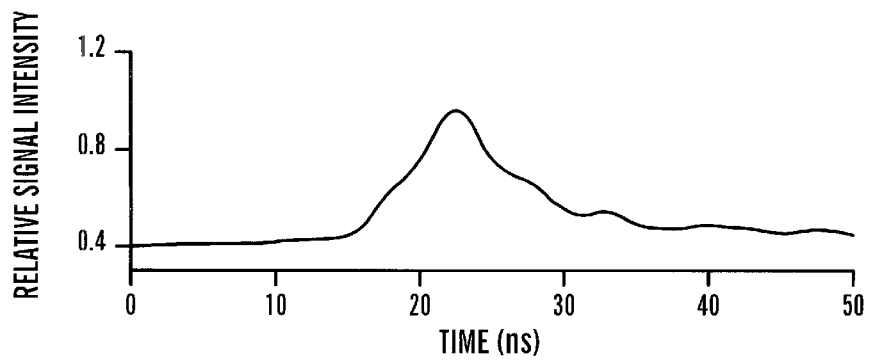
FIGS. 12A–12D are plots of signal intensity versus time which describe pulse waveforms.
Figure 12B:
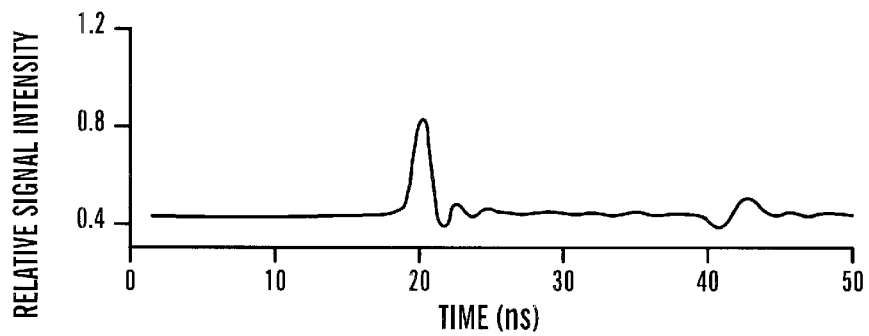
Figure 12C:
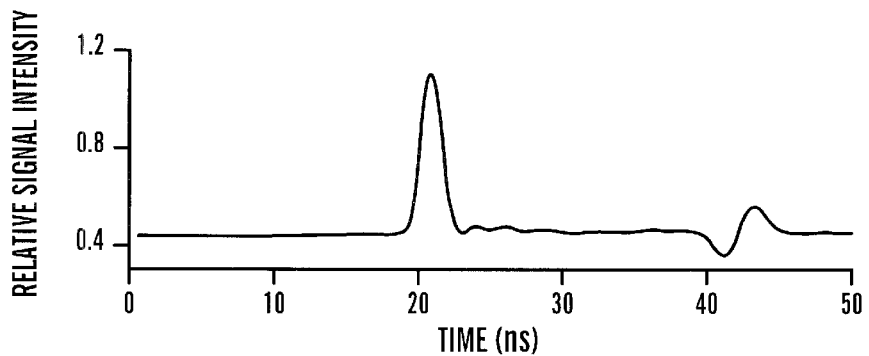
Figure 12D:
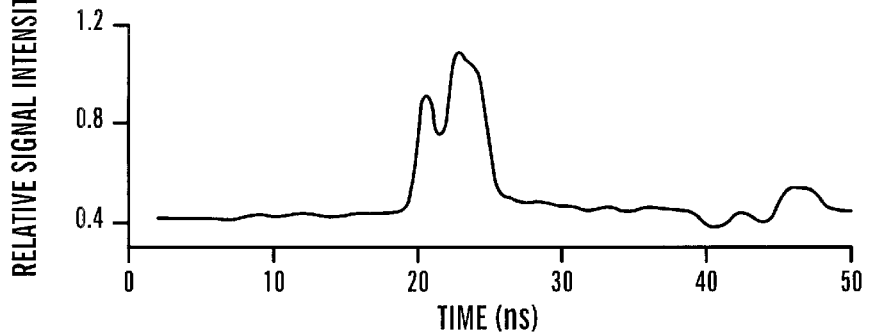

Another feature of the dye-doped polymer matrix is the temporal behavior of the TPP cavity lasing as shown in FIGS. 12A–12D. Each waveform curve represents an average result over 10 pulses by using a fast photodiode detector in conjunction with a 350 MHz oscilloscope (Tektronixs 2467) equipped with a C1001 video camera FIG. 12A shows the pump pulse shape, and FIGS. 12B–12D show the lasing pulses at different pump levels. Compared to the smooth temporal profile of the 10 ns pump pulse, the lasing pulses manifested much shorter rise- and fall-times, i.e. ≦1.5 ns limited by the resolution of the detecting system. In addition, the lasing pulse duration (~1.5 ns at a moderate pump level) was much less than the pump pulse duration.

Figure 13:
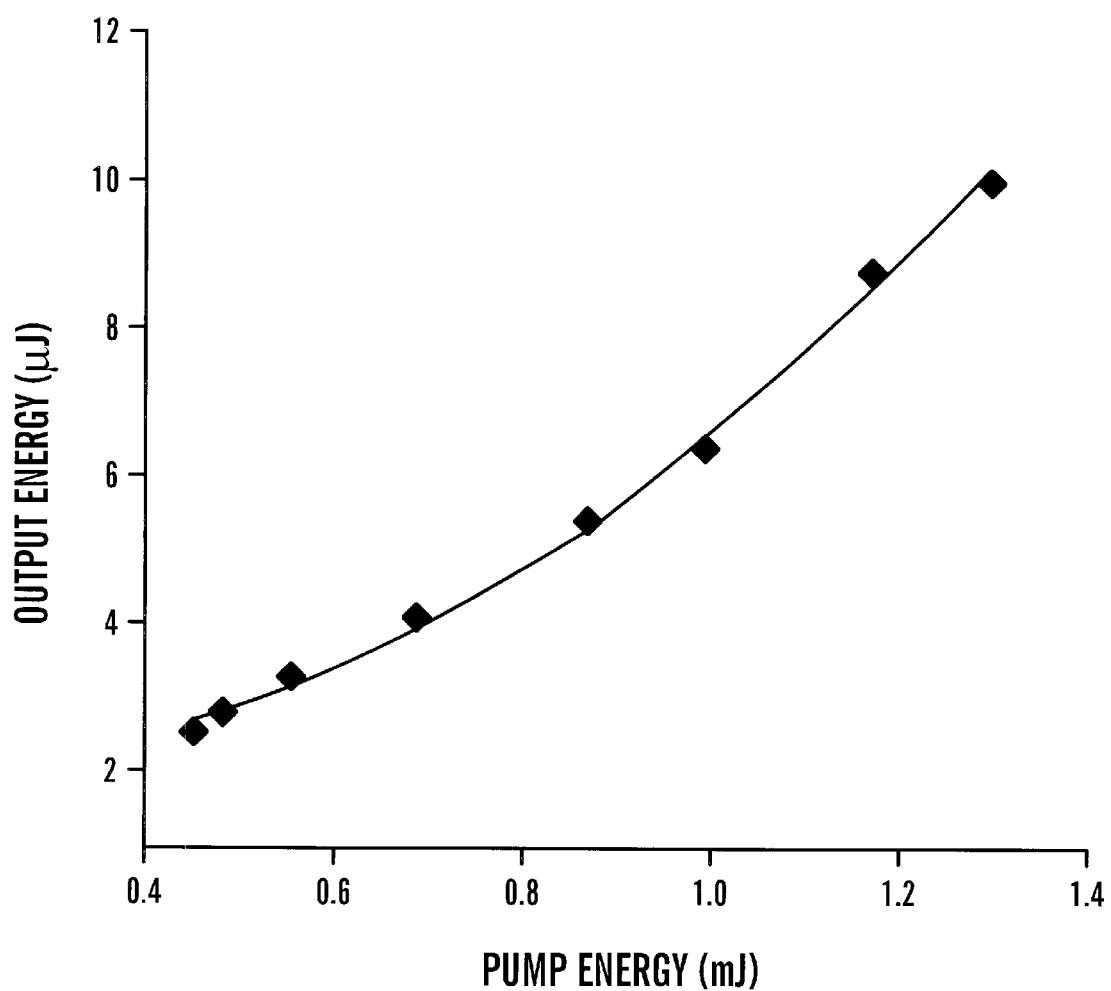
FIG. 13 is a plot of the two-photon pumped, ~600 nm cavity lasing output pulse energy as a function of the input 1.06-μm pulse energy. The solid line depicts a curve based on the square law, fitted by regression analysis.

The lasing output/pump input characteristic curve is given in FIG. 13 for the rod cavity lasing. Each data point was an average result over 10 laser pulses by using a gated integrator and boxcar averager system, and the solid line is the best fitted curve based on the square law that should be followed for a two-photon excitation process. The energy conversion efficiency from pump input to lasing output was estimated as η≈0.8% at input energy level of 1.3 mJ. However, at this pump level the measured one-pass two-photon absorption in the 7 mm-long rod was only about 23%. Therefore, the real conversion efficiency from the absorbed pump energy to the lasing output should be corrected to 3.5%. The dye1 molecular TPA cross-section could be estimated as $\sigma_2 \approx 1.2 \times 10^{-46}$ cm$^4$-sec, based on the measured nonlinear absorption data for a given input intensity level. This is more than two-orders of magnitude larger than the values reported for Rhodamine and other common dyes by Brunner et al., *Kvantovaya Electron. (Moscow)*, 2:832 (1975) and Qui et al., *Applied Physics B*, 48:115 (1989). Finally, the measured lasing life time, in terms of pulse numbers before the pulse energy decreased to 10~15% of its initial value, was longer than $4 \times 10^4$ pulses at a repetition rate of 2 Hz without cooling.

Two-photon pumped cavity lasing was also observed using dye1-doped Vycor glass, prepared according to Example 14, and dye1-doped sol gel glass, prepared according to Example 13. The optical properties of these materials, as well as dye1-doped poly(HEMA) and dye1 dissolved in cyclopentanone are provided in Table 1.

TABLE I

| matrix | Vycor glass 0.0015M | sol-gel glass 0.0015 M | poly(HEMA) 0.008M | cyclopentan solution |
|---|---|---|---|---|
| linear absorption peak (nm) | | | 485 | 480[a] |
| absorption bandwidth (nm) | | | 80 | 100[a] |
| one-photon fluorescence peak (nm) | 575 | 568 | 577 | 590[a] |
| one-photon fluorescence bandwidth (nm) | 60 | 55 | 55 | 58[a] |
| lasing peak(nm) | 600 | 590 | 597 | 623[b] |
| lasing bandwidth (nm) | 8 | 8 | 8 | 14[b] |
| 1.06 µm pump pulsewidth (ns) | 10 | 10 | 10 | 10[b] |
| lasing pulsewidth (ns) | 2 | 1.5 | 2 | 1.5[b] |

[a]0.001 M dye1 concentration
[b]0.003 M dye1 concentration.

Dye-doped Vycor and sol gel matrices exhibited two-photon pumped cavity lasing at dye concentrations of 0.0015M, which was five fold less than the concentration required to achieve two-photon pumped cavity lasing in dye-doped poly(HEMA).

Two-photon pumped cavity lasing was also observed for dye2-, dye3-, and dye4-doped sol gel glass, prepared according to Example 13.

Example 16

Preparation of 4-[N-(2-(hydroxyethyl)-N-methyl)aminophenyl]-4'-(6-(hydroxyhexylsulfonyl)stilbene ("APSS").

APSS was synthesized as described below with reference to the following reaction scheme:

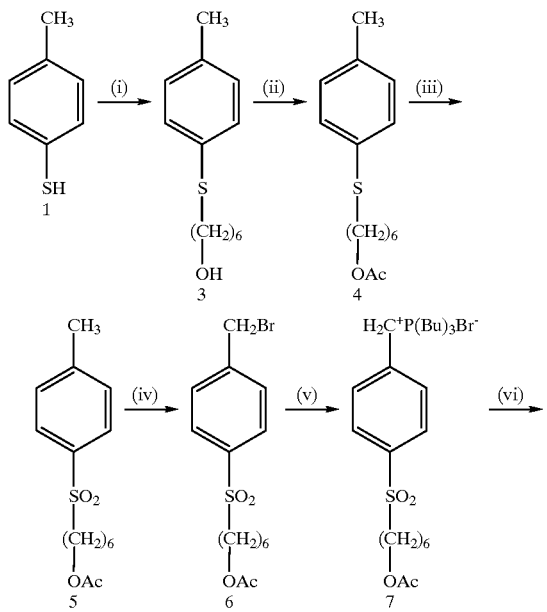

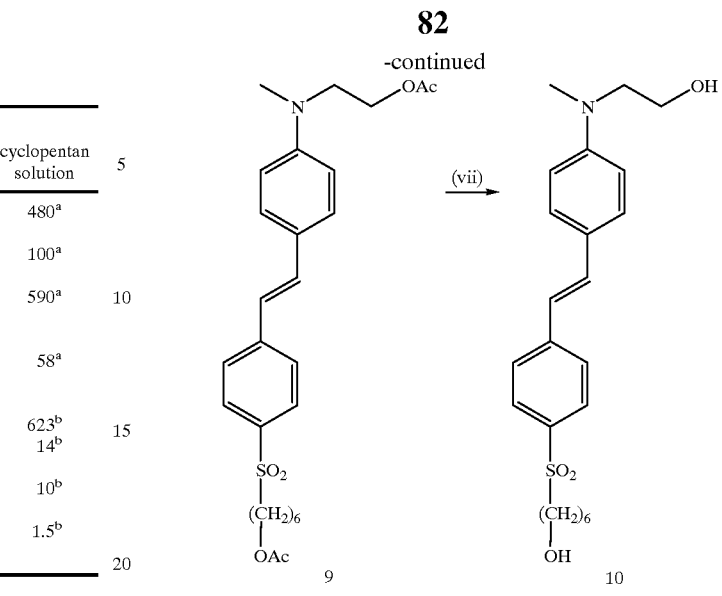

(i) 6-chlorohexanol (2), NaOEt/EtOH; (ii) Ac₂O/AcOH, 90° C.,4h; (iii) H₂O₂, 70° C., 10h; (iv) NBS, peroxide; (v) P(Bu)₃/EtOH, Δ; (vi) 4-(N-methyl-N-acetoxy)amino)benzaldehyde (7), NaOEt/EtOH; (vii) NaOEt/EtOH, Δ, 4h.

24.8 g (0.2 mol) of 4-mercaptotoluene (1) and 13.6 g (0.2 mol) of sodium ethoxide in 150 mL of ethanol were stirred for 1 hr. Then, 25 g (0.18 mol) of 6-chlorohexanol (2) were added to the solution. The solution was heated to reflux for 4 hours, cooled, and poured into 500 mL of water containing NaOH (0.1% by weight). The mixture was stirred overnight and then filtered. The precipitate was collected and washed several times with water to yield 36.4 g (88.7%) of 3 as a white solid having a melting point of 45° C.

22.4 g of 3 was added to 50 g of acetic anhydride in 100 mL of pyridine. The mixture was heated at 90° C. for 4 hours and then washed with water overnight. The product, 4, a yellowish liquid, was separated with CH₂Cl₂ and dried by rotary evaporation. The yield was 93%.

35 g (0.13 mol) of 4 and 200 mL of glacial acetic acid were heated to reflux with stirring. 50 g of hydrogen peroxide (30% solution) were added through a dropping funnel, and the mixture was stirred at reflux for 4 hours. After removing two-thirds of the solvent, the solution was poured into 500 mL of water and stirred for 1 hour. The product was extracted with methylene chloride, washed twice with water, and dried under vacuum to yield 5 as a white liquid (61%).

16 g (53.6 mmol) of 5 in 150 mL of carbon tetrachloride was brought to reflux. Then, 8.5 g (47.8 mmol) of N-bromosuccinimide and 0.7 g (2.9 mmol) of benzoyl peroxide were poured together into the upper solution. The reaction was continued under reflux. When succinimide came to the solvent surface, the reaction was stopped. After cooling, succinimide was removed by filtration. The solution was then mixed with 100 mL of water containing 5% NaOH by weight, and the carbon tetrachloride layer was separated. After removing the carbon tetrachloride, the white solid product was recrystallized in EtOH/H₂O (2:1) to provide 6 in 93% yield.

20 g of 6, 30 mL of tributylphosphine, and 50 mL of ethanol were placed in a 500-mL one-neck flask, and the solution was refluxed overnight. After cooling, 300 mL of n-hexane was poured into the solution, and the mixture was stirred for 30 minutes. The n-hexane layer was removed, and the product, 7, was washed twice with n-hexane and dried.

4-(N-methyl-N-acetoxyethyl)aminobenzaldehyde (8) was prepared by reaction of N-methyl-N-hydroxyethyl)

aminobenzaldehyde with acetic anhydride in acetic acid for 3 hours at 90° C.

To an ethanolic solution of NaOEt (100 mM) at room temperature, 7 (20 mM) and 4-(N-methyl-N-acetoxyethyl) aminobenzaldehyde (8) (20 mM) were added. The the solution was then refluxed for 4 h. After cooling, the solution was poured into 500 mL of water. Crude product was extracted with 200 mL $CH_2Cl_2$. The $CH_2Cl_2$ was removed, and the product was recrystallized twice from $CH_2Cl_2$/ether (1:3) to produce APSS 10 as a yellow solid in 48% yield. Elemental analysis calculated: C, 66.11; H, 7.51; N, 3.33; found: C, 66.14; H, 7.48; N, 3.35.

Figure 14:
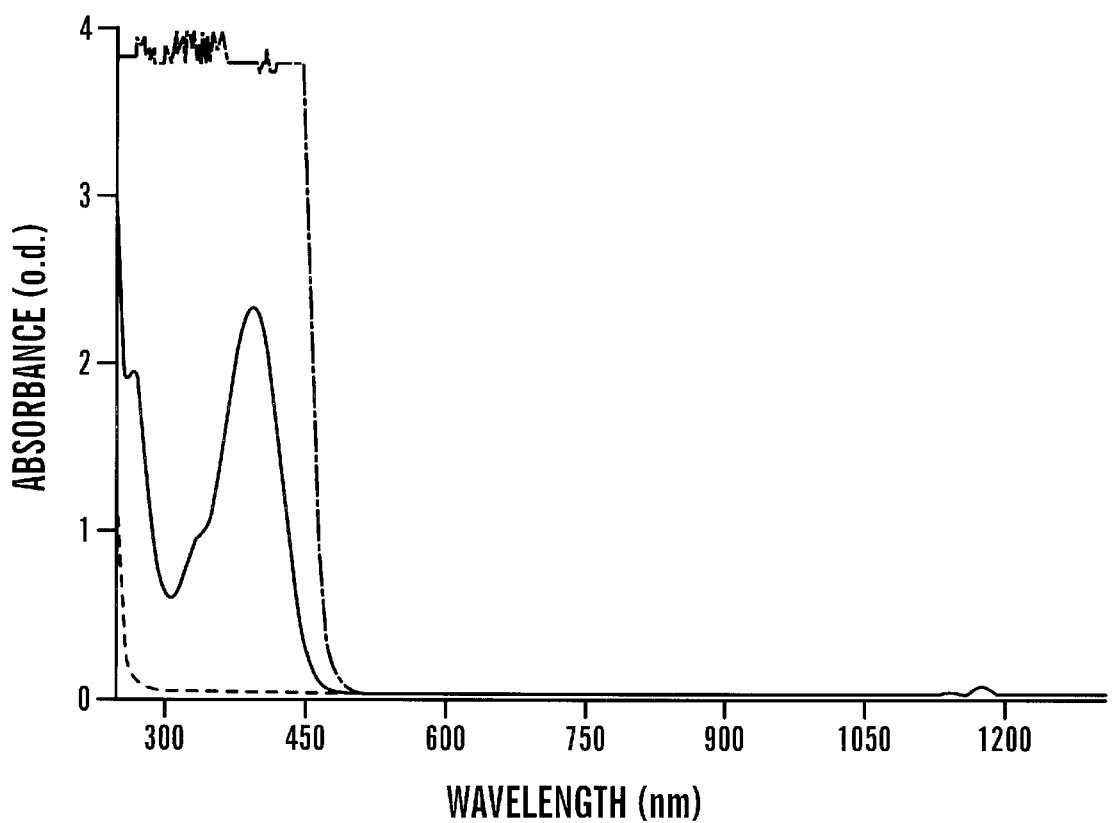
FIG. 14 is a linear absorption spectral distribution of 1-mm path APSS dye solutions in dimethyl sulfoxide of concentration $d_o$=0.0012 M (—) and $d_o$=0.012 M ( -·-·- ). The linear absorption of 1-mm path length pure dimethyl sulfoxide is also provided ( ······ ).

FIG. 14 shows the linear absorption spectra of 1 mm-path length APSS solutions in DMSO at two different concentrations. As a comparison, the absorption spectrum of 1 mm-path length pure solvent (DMSO) is also provided. There is a strong absorption band around 400 nm due to APSS dye, and the solution is transparent in the 570~1100 nm spectral range. However, the two-photon energy of ~800 nm IR radiation falls into the strong absorption band. Therefore, an effective TPA process is expected by ~800 nm excitation. On the other hand, a comparison of the two spectral curves in FIG. 14, shows that, at a higher dye concentration, the tail on the long wavelength side of the absorption band is more obvious. The same effect is expected with increased path length of the solution sample with a given concentration.

Example 17
Experimental Set-up for Two-Photon Pumped Cavity Lasing of APSS.

Figure 15:
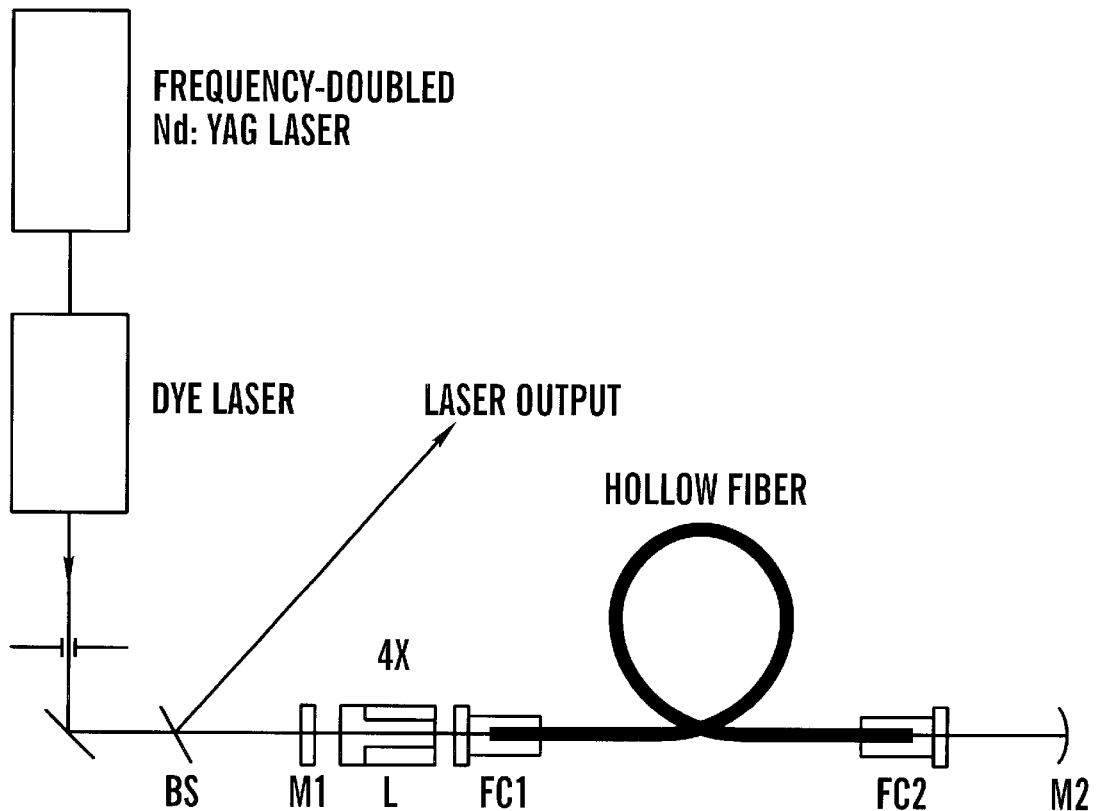
FIG. 15 is a schematic diagram of the experimental setup for two-photon pumped cavity lasing in an APSS solution filled hollow fiber configuration. M1 and M2 denote cavity mirrors; L denotes a microscope objective; FC1 and FC2 denote coupling liquid cells; and BS denotes a beam splitter.

The experimental set-up is schematically shown in FIG. 15. The input 800 nm pump IR laser beam was provided by a pulsed dye laser pumped with a Q-switched and frequency-doubled Nd: YAG laser source. The beam size, pulse duration, angular divergence, and repetition rate of the input pump laser radiation were ~3 mm, ~5 ns, ~1 mrad, and 1–10 Hz, respectively. The pump beam was focused by a 4x-microscope objective into the input end of a 15-cm long hollow quartz fiber filled with APSS, prepared as described in Example 16, in DMSO ($d_o$=0.012 M). The internal diameter of the hollow fiber sample was 100 μm, and the two open ends of the fiber were immersed in two identical liquid coupling cells which were filled with the same dye solution. Each cell was equipped with an optical window. Two mirrors were adapted to form the optical cavity. The front cavity mirror (M1) was a plane dielectric coating mirror with a reflectivity of 40% at ~565 nm and ~1.06 μm. The optical path between the back mirror M2 and the output fiber end was 2 cm. The total optical path length of the cavity was ~30 cm. Under the excitation of the input 800 nm pump beam, a strong TPA induced green fluorescence emission was seen from the hollow fiber. Once the input pump intensity increased to a threshold level, very intense backward cavity lasing was observed through a beam spitter (BS). The stimulated output emission was extremely sensitive to fine alignment of both cavity mirrors, evidencing that the observed effect was cavity lasing as opposed to superradiance. The fiber laser was operated at variable repetition rate from 1 Hz to 10 Hz.

Example 18
Two-Photon Pumped Cavity Lasing Using APSS.

Figure 16:
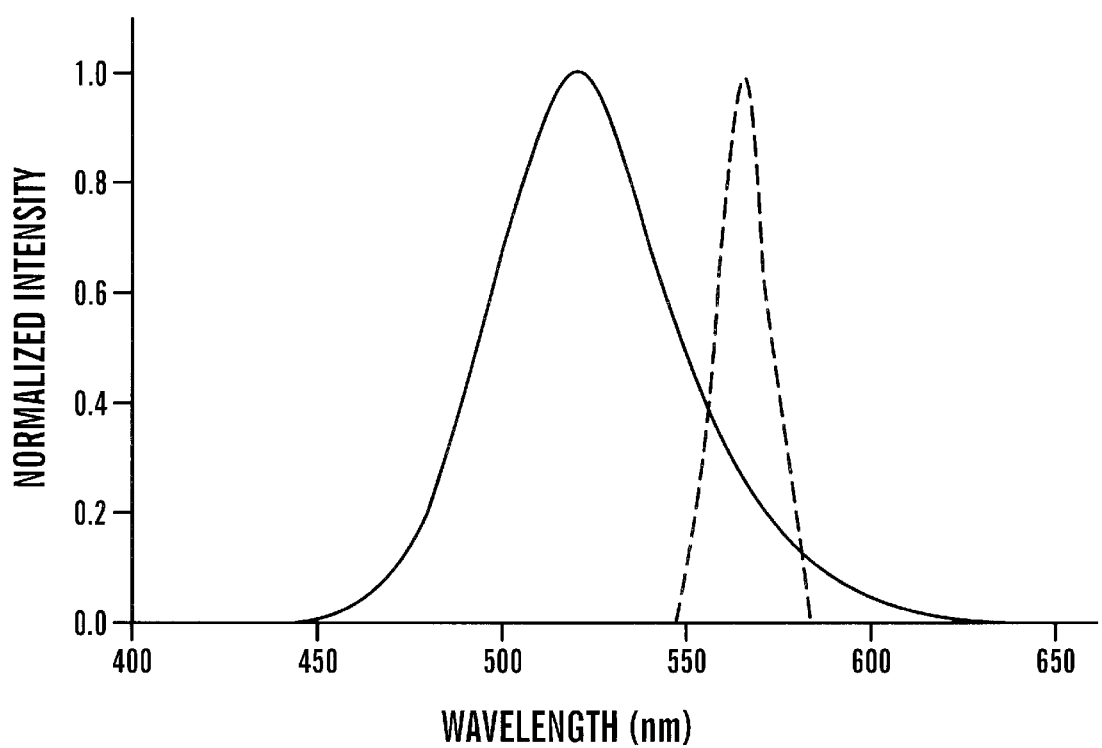
FIG. 16 is a normalized 400 nm one-photon induced fluorescence spectrum (—) and 800-nm pumped lasing spectrum ( - - - ) of an APSS dimethyl sulfoxide solution with $d_o$=0.012 M.

The spectral intensity distribution of two-photon pumped cavity lasing from the above system is shown in FIG. 16 (dashed curve) at a pump energy level of $E_o$=290 μJ. For comparison, the one photon (at 400 nm) induced fluorescence spectrum of the same dye solution with the same concentration is also shown in FIG. 16 (solid curve). The bandwidth of cavity lasing was much narrower than the bandwidth of corresponding one-photon induced fluorescence emission without using any intracavity dispersion element. FIG. 16 also shows that the central lasing wavelength (~565 nm) is obviously red-shifted compared to the central wavelength position (~520 nm) of the fluorescence band. This can be well understood by considering the reabsorption effect of the TPA induced upconverted emission within the hollow fiber. A comparison of FIGS. 14 and 16 shows that the long-wavelength tail of the absorption band and the short-wavelength side of the fluorescence band partially overlap. At high concentration and long transmission length within the medium (such as the 15 cm fiber used in this Example), the absorption at the red-edge of the absorption band became more evident. Therefore, the blue-side and central range of the fluorescence band would be expected to be more difficult to lase. Measurements showed that at different pump levels the relative spectral distributions of cavity lasing output remained basically the same.

Figure 17A:
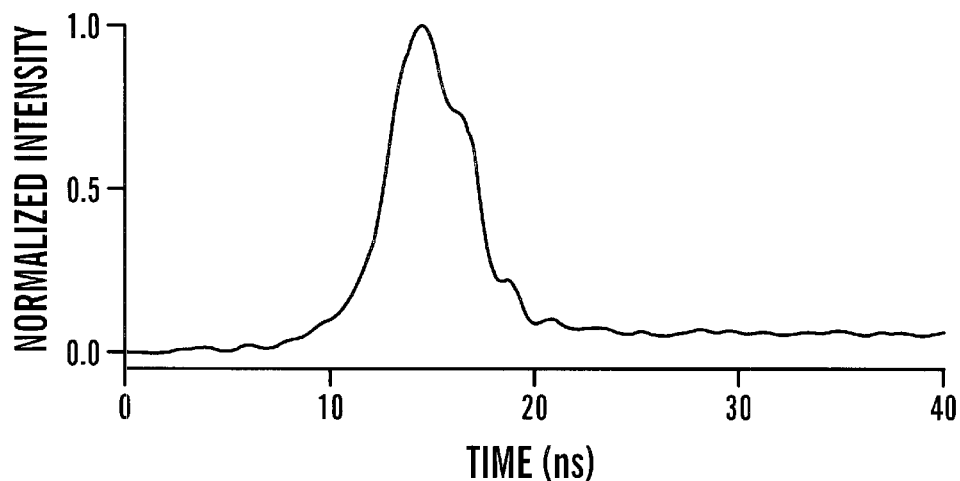
FIG. 17A is a temporal profile of the 800 nm pump pulse.
Figure 17B:
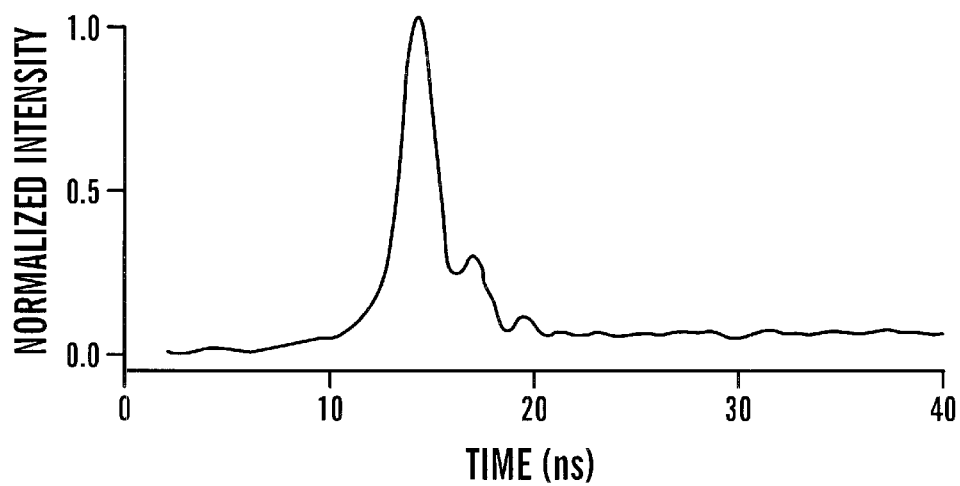
FIGS. 17B and 17C are temporal profiles of ~565 nm cavity lasing pulses at pump energies of 145 μJ and 290 μJ, respectively.
Figure 17C:
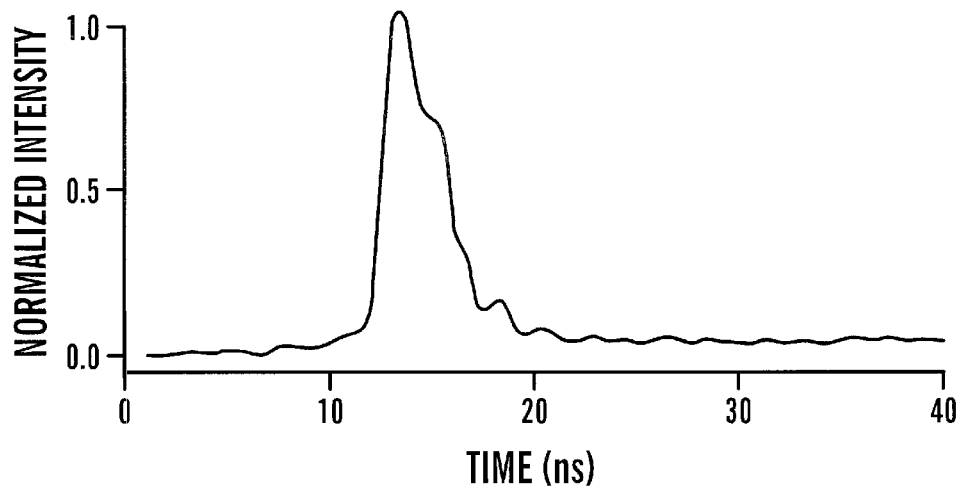
Figure 18:
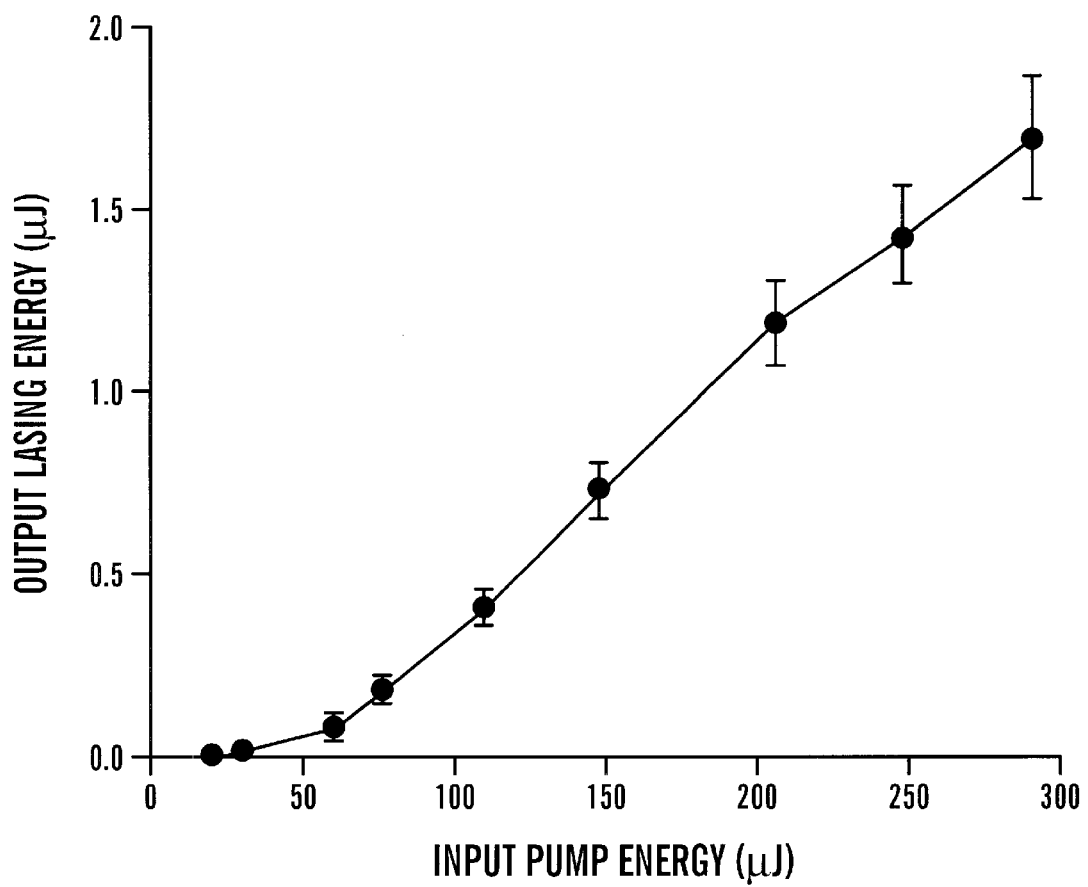
FIG. 18 is a plot of the pulse energy of ~565 nm cavity lasing output as a function of the input 800 nm pulse energy. The repetition rate was 1 Hz.

The temporal behavior of the TPP cavity lasing is shown in FIG. 17. The measured single-pulse waveform was recorded by using a fast photodiode detector in conjunction with a 350 MHz oscilloscope (Tektronix 2467 with C1001 video camera). The temporal resolution of the measurement system was 1–1.5 ns. FIG. 17A shows the pump pulse shape, and FIGS. 17B and 17C show the lasing pulses at two different pump levels. At a pump level of ~150 μJ, the measured one-pass two-photon absorption in the 15 cm-long dye solution filled hollow fiber sample was only about ~25%. Consequently, the net conversion efficiency from the absorbed pump energy to the lasing output was η≈2.3%.

The results demonstrate two advantages of using dye solution filled hollow fiber configuration. First, a much lower pump threshold for lasing, as low as 20–30 μJ, can be achieved due to the longer gain length and extremely low diffraction losses. Second, a good lasing beam quality and more regular transverse-mode structure can be obtained. The output TPP lasing beam possess a very smooth and uniform intensity distribution of the near-field and far-field patterns. The divergence angle of the 5 mm-size output lasing beam was ~1.5 mrad without using any recollimating element.

Example 19
Preparation of 4-[4-[p-N-methyl-N-ethylamino)styryl] styryl]-N-methylpyridinium tetraphenylborate (11).

4-[4-[p-N-methyl-N-ethylamino)styryl]styryl]-N-methylpyridinium tetraphenylborate, having the formula:

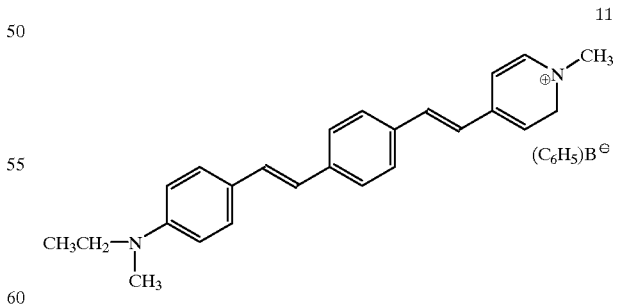

11 was prepared by the following procedure.

In a 500-mL one-neck flask fitted with a stirrer and a condenser, 1.2 g (0.01 mol) of 4-methylbenzaldehyde, 0.01 mol of 4-methyl-N-methylpyridinium tetraphenylborate, and 30 mL of absolute ethanol were mixed. Five drops of piperidine was added to the mixture. The solution was then heated to reflux, refluxed overnight, cooled, and filtered. The collected solid was washed twice with ether and twice with water to obtain 4-[p-N-methyl-N-ethylamino)styryl]-N-methylpyridinium tetraphenylborate in 78% yield as a reddish solid.

0.1 mol of 4-[p-N-methyl-N-ethylamino)styryl]-N-methylpyridinium tetraphenylborate was then mixed with 4-(N-methyl-N-ethylamino)benzaldehyde in 300 mL of ethanol. 1 mL piperidine was added as catalyst, and the solution was heated to 90° C. for 6 hrs. After cooling, the solution was filtered. The solid was washed twice with methanol and twice with ether. The product, 4-[4-[p-N-methyl-N-ethylamino)styryl]styryl]-N-methylpyridinium tetraphenylborate, was obtained in 78% yield as a red solid.

Example 20
Preparation of Sol-Gel Glasses.

Highly porous silica-gel bulk glasses were prepared by a two-step hydrolysis sol-gel process described previously in Gvishi et al., *Appl. Spect.*, 49:834 (1995), Gvishi, *Ph.D. Thesis*, Jerusalem, Israel:The Hebrew University of Jerusalem (1993), and Gvishi et al., *Chemistry of Materials*, 7:1703 (1995), which are hereby incorporated by reference. The sol-gel glass was prepared from a precursor solution containing tetraethoxysilane ("TEOS") (Aldrich 99+% pure) and ethanol in the molar ratio 1:4. After one hour of pre-hydrolysis, water (molar ratio 4) and $HNO_3$ (Aldrich A.C.S. reagent, molar ratio 0.06) were added to complete the hydrolysis. This was followed by the addition of HF (Aldrich 48 wt. % in water 99.99+% pure, molar ratio 0.8) to achieve fast gelation. After mixing, the solution was placed into 4.5-ml methacrylate cuvettes and covered with parafilm containing three pin holes on the top. The cuvettes were then placed in an oven (Precision Scientific Freas Mechanical Convection Oven; Model 605) set at 45° C. for two weeks. The bulk gels were then removed from the cuvettes and placed in a furnace (Fisher Scientific Isotemp Programmable Furnace; Model 495 A) for drying and partial densification to glass by slow heating (500° C./hour) from room temperature to 500° C. The dimensions of the bulk glasses were 10 mm×5 mm×5 mm. Sol-gel glasses prepared by this method have an average pore diameter of 46 Å, a specific surface area of ~850 $m^2/g$, and a pore volume of 68%.

Example 21
Coating Pore Surfaces with $C_{60}$.

Two identically prepared glasses (prepared in accordance with Example 20) were weighed and placed in a saturated $C_{60}$ (Aldrich 99% pure) toluene solution. After the solution was completely adsorbed into the glasses, they were removed and placed on a hot plate at 125° C. for 24 hours to remove the toluene and deposit the $C_{60}$ on the walls of the pores. The glasses were then weighed again to determine the amount of $C_{60}$ adsorbed in the glass (0.5 wt/wt % compared to the silica phase).

Example 22
Introduction of Polymer into the Pores.

The impregnation of the organic polymer phase was done as follows. Two bulk glasses (one of which was already doped with $C_{60}$ in the interfacial phase in accordance with Example 21) were immersed in methyl methacrylate ("MMA") monomer (Aldrich 99% pure) for 10–15 min. The MMA solution diffused into the sol-gel-derived glass pores and was polymerized therein using benzoyl peroxide (2%) as the catalyst which was added before the glass was immersed. The MMA bulks were re-immersed in an MMA solution, which, at this stage, was catalyzed for fill polymerization with benzoyl peroxide (0.5%), kept in a sealed container, and placed in the Freas oven at 45° C. until the polymerization process was completed. Using the other identically prepared two glasses (one of which has already been doped with $C_{60}$ in the interfacial phase in accordance with Example 21) the impregnation of the organic polymer phase was done using a MMA solution containing 5% (wt/wt) BBTDOT. After the polymerization was complete (a three days) the glasses were removed from the surrounding poly(methyl methacrylate) ("PMMA") by a chloroform wash. The glasses were then polished (Buehler Metaserv 200 grinder-polisher) in seven incremental steps, starting with a 180 grit SiC paper and going down to a 0.25 micron diamond paste. The resulting four composite samples ($C_{60}$+BBTDOT-doped, $C_{60}$-doped, BBTDOT-doped, and undoped blank) were of high optical quality.

Example 23
Optical Measurements of the Composite Glasses.

Absorption spectra were obtained using a Shimadzu UV-Vis 260 spectrophotometer and were collected using the blank composite glass as a reference. Fluorescence measurements were performed (90° geometry) with a SLM-Aminco 48000 spectrofluorimeter. An argon-ion laser (Coherent; Innova 90-6) was used as the excitation source with a multiwavelength UV line through a 360±5 nm narrow bandpass filter (Oriel). The fluorescence was collected through a 420 nm longpass filter (Oriel). The emission spectra were background-subtracted and corrected for detector and monochromator transmission nonlinearities.

The passive losses of light from a blank composite glass were determined by measuring the intensity of the beam incident on and the beam transmitted through the bulk. A He-Ne laser (Milles Geriot; class IIIb; 632.8 nm) was used as the light source. The intensity of light before and after transmitting through the bulk was measured using a power meter (Newport; Model 815).

The optical power limiting results were obtained at two wavelengths, 532 and 800 nm. The source of 532 nm was a frequency doubled, Q-switched Nd:YAG laser (Quanta Ray DCR-1A) which delivered 8 ns pulses at a repetition rate of 10 Hz. A dye laser (Quanta Ray PDL-1) with an IR dye, 1-ethyl-2-(4-(p-dimethylaminophenyl)-1,3-butadienyl)-pyridinium perchlorate ("Pyridine 1") from Lambda Physik, was transverse pumped at 532 nm to generate ~5 ns pulses at 800 n. The beam was focused on the center of the sample by a 30 cm focal length lens. Beyond the sample, the transmitted beam was collected by a short focal length aspheric lens and focused onto the surface of a large area photodiode. This ensured that all the transmitted light was collected and artifacts due to self-focusing or defocusing were eliminated. A beamsplitter placed before the sample, directed a part of the beam to a second photodiode which was used to monitor the intensity of the incident beam. The incident laser intensity was controlled by a half-wave plate and polarizer combination. Outputs from both the detectors were processed by a gated integrator and a boxcar averager. An analog to digital converter in conjunction with a personal computer was used to acquire and store the data, and each data point was averaged over 30 laser pulses.

The system was calibrated (for power limiting experiment) using the blank composite glass which showed a linear response. Data were collected for the three doped composite glasses by starting at the lowest intensity and gradually increasing the intensity until damage occurred in the glass. The transmissivity through the samples at low incident beam intensity was also measured. To compare the nonlinearity of the transmitted intensity in the different samples, all data were normalized to transmissivity of 1 at a low incident beam intensity.

Example 24
Optical Characterization of the Composite Glasses.

FIG. 20 presents the absorption spectra of the three composite glasses: the dashed line is for BBTDOT-doped, the dotted line is for $C_{60}$-doped, and the dashed-dotted line is for BBTDOT +$C_{60}$-doped composite glasses. FIG. 20A presents the absorption spectra at the region between 350 and 700 nm. The two glasses doped with BBTDOT exhibit a strong (saturated) absorption band at ~400 nm which has been shown to be due to a single photon absorption of BBTDOT. The $C_{60}$-doped composite glass has minimal absorbance in this region. The two glasses doped with $C_{60}$ show a specific weak absorption band in the region between 550 and 650 as shown more clearly in FIG. 20B The spectrum exhibits two peaks at ~575 and ~622 nm. The weak peak observed at 626 nm, corresponds to the 0→0 transition, was reported previously by Catalan, et al., *Am. Chem. Soc.* 115:9249 (1993), which is hereby incorporated by reference. The glass doped only with BBTDOT does not exhibit this feature.

Figure 21:
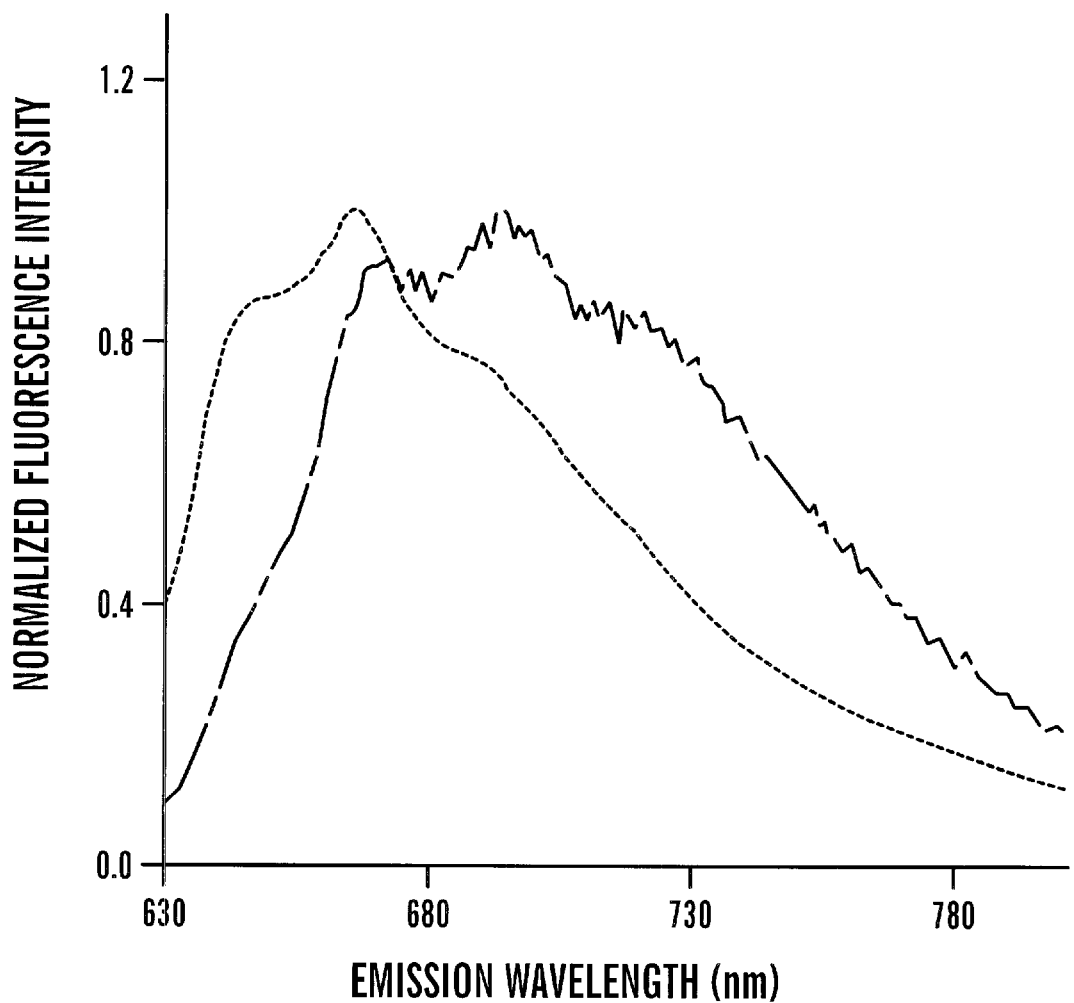
FIG. 21 is the fluorescence emission spectra of $C_{60}$ in toluene solution (dashed curve) and in composite glass (dotted curve). Both were acquired under ambient conditions and with an excitation wavelength of 360 nm.

FIG. 21 presents the fluorescence emission spectra of fullerene in toluene solution (dashed curve) and in the $C_{60}$-doped composite grass (dotted curve) at room temperature. The shape of the spectrum in toluene shows three vibronic peaks (671, 694 and 718 nm) and is similar to the spectrum reported by Kim et al., *J. Am. Chem. Soc.* 114:4429 (1992), which is hereby incorporated by reference, for $C_{60}$ in toluene. In the composite glass, a similar emission contour with a 30 nm blue shift of the spectrum was observed. The blue shift is attributed to different dielectric constants of the media as suggested by Reber et al., *Phys. Chem.* 95:2127 (1991), which is hereby incorporated by reference.

The attenuation of light, "A" was calculated using the following equation: $A = (10/L)\log(I_{output}/I_{input})$ where L is the path length through the composite glass, $I_{output}$ is the intensity of the light transmitted through the composite glass, and $I_{input}$ is the incident light intensity. For the blank composite glass, the recovered attenuation loss was approximately 1 dB/m at 632.8 nm. As seen in FIG. 20, the doped glasses have a linear absorption at 632.8 nm.

Example 25
Optical Power Limiting in Composite Glasses.

Figure 22A:
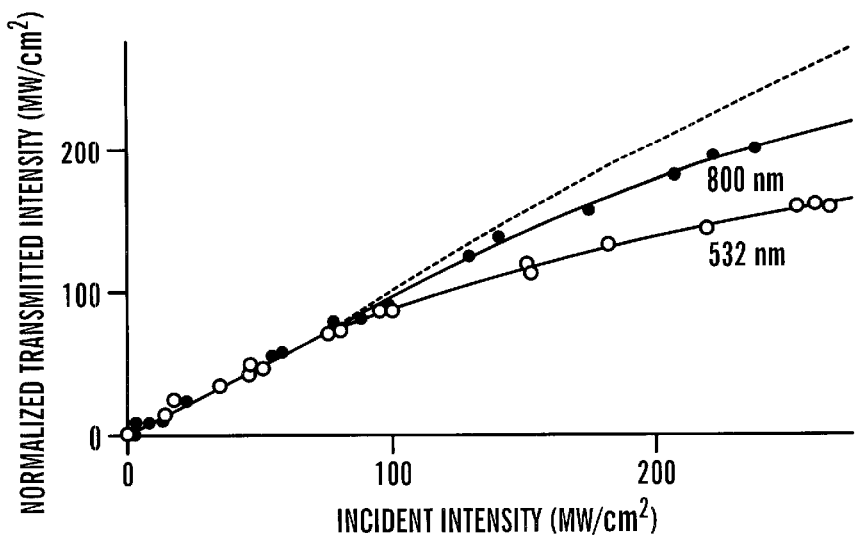
FIG. 22A is for $C_{60}$-doped.
Figure 22B:
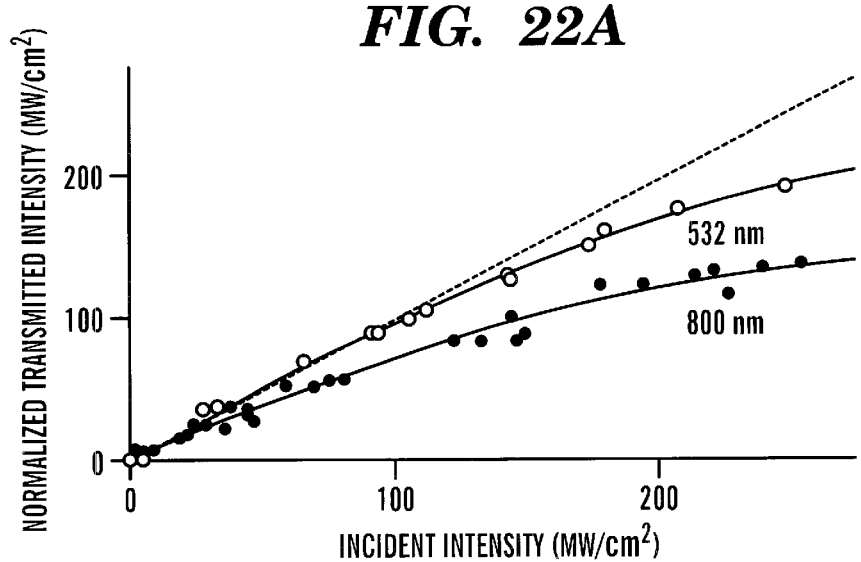
FIG. 22B is for BBTDOT-doped.
Figure 22C:
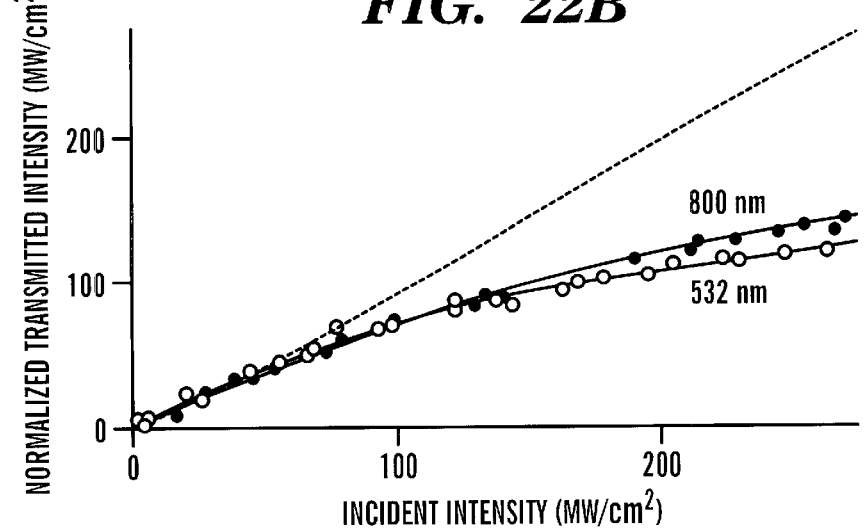
FIG. 22C is for $C_{60}$+BBTDOT-doped composite glasses.

FIG. 22 presents the normalized transmitted intensity as a function of the incident intensity for the three composite glasses at 532 and 800 nm, where FIG. 22A is for $C_{60}$-doped, FIG. 22B is for BBTDOT-doped, and FIG. 22C is for $C_{60}$+BBTDOT-doped composite glasses. It can be seen clearly from FIG. 22A, that $C_{60}$ is more active as an optical limiter at 532 nm than at 800 nm. Due to a significant linear absorption at 532 nm, this sample, which appeared pale brown, shows transmissivity (at a low intensity incidence beam) of 0.40, while at 800 =nm, it is 0.88. The optical limiting behavior of $C_{60}$ has been suggested to be due to a multitude of mechanisms, such as reverse saturable absorption ("RSA"), nonlinear refraction, and thermal effects, which have been discussed in Tutt et al., *Prog. Quant. Electr.* 17:299 (1993), which is hereby incorporated by reference. At 532 nm, the RSA mechanism is dominant due to a one photon absorption process.

BBTDOT has linear absorption maximum at approximately 400 nm and, therefore, has almost no absorption at either 532 or 800 nm light at low intensity. This was supported by the measured transmissivity (at a low intensity incidence beam) of the pale yellow BBTDOT doped sample, which was 0.98 at 800 nm and 0.70 at 532 nm. At higher intensities (50 MW/cm$^2$) of the 800 nm beam, a strong TPA induced blue fluorescence was clearly visible in the sample. As shown FIG. 22B, this glass exhibits a significantly higher nonlinearity at 800 nm than at 532 nm.

On the other hand, the glass doped with $C_{60}$+BBTDOT had a light brown color and showed transmissivity (at a low intensity incidence beam) of 0.92 at 800 nm and 0.30 at 532 nm. The lower transmissivity at 532 nm is due to linear absorption of the $C_{60}$ molecules. It can be clearly seen from FIG. 22C, that this sample shows excellent optical power limiting behavior at both 532 nm and 800 nm. The nonlinear behavior at 532 nm appears to be slightly enhanced compared to the sample doped with only $C_{60}$. This suggests that there is also a favorable contribution from BBTDOT. On the other hand, at 800 nm, the nonlinearity is slightly less than that due to BBTDOT alone. This is probably due to the fact that the local intensity in the sample decreases due to the presence of $C_{60}$ (some linear absorption), and, therefore, the nonlinear absorption in BBTDOT, which varies as the square of the incident intensity, is reduced.

The damage threshold in these glasses was measured to be in the range of 250–300 MW/cm$^2$ corresponding to a fluence of 2.5–3 J/cm$^2$. It is believed that this value is not the intrinsic damage threshold for the composite glasses but, rather, due to particulate contaminants. To ensure that the optical power limiting observed in the dye-doped composite glasses are not biased due to particulate contaminants, the experimental system was calibrated using the blank composite glass. It is believed that processing in a clean room environment could result in glasses that can withstand much higher fluences without damage.

Example 26
Preparation of trans-4-[p-(N-ethyl-N-hydroxyethylamino) styryl]-N-hydroxyethylpyridinium iodide ("ASPI")-doped Glass Rhodamine 6G-doped Glass, and (ASPI+Rhodamine 6G)-doped Glass.

The ASPI glass was prepared by placing a porous sol-gel glass (prepared in accordance with Example 20) in a solution of ASPI in ethanol (4.4×10$^{-3}$ M). After the solution completely impregnated the glass, the glass was removed from the solution and placed on a hot place at ~45° C. for several hours until the ethanol evaporated out of the glass leaving behind ASPI on the surface of the pores in a concentration of ~3.1×10$^{-3}$ M. (This concentration represents the volume of the pores of the glass, ~70%, and assumes that all of the chromophores deposited on the walls of the pores.) The glass was then immersed in a methyl methacrylate ("MMA") monomer (Aldrich 99% pure) containing 2 wt. % of 2,2'-azobisisobutyronitrile ("AIBN") (Polysciences, Inc.), a thermal polymerization initiator, for in situ polymerization. After the glass was completely impregnated with MMA (~30 minutes), it was removed and placed in a vial containing MMA and AIBN (0.5 wt %). The vial was closed and placed in the Freas oven at 45° C. for full polymerization (several days).

The Rhodamine-6G composite glass was prepared by dissolving Rhodamine-6G in MMA. A surfactant (Triton X-100 Aldrich) was added to minimize any aggregation. The concentration of the Rhodamine-6G/MMA solution was ~1×10$^{-4}$ M. The solution was then split. Into one portion 2 wt. % AIBN was added, and into the other portion 0.5 wt % AIBN was added. A porous glass was immersed in the 2% AIBN/MMA solution until completely impregnated and then transferred to the 0.5 wt. % AIBN/MMA solution in a vial. The vial was capped and allowed to fully polymerize in the same fashion as the ASPI-doped glass. The final concentration of Rhodamine-6G in the composite glass was approximately $6.5 \times 10^{-5}$ M (corresponding to the porosity of the glass).

The glass containing both dyes (dual composite) was prepared exactly (same concentrations and processes) as described above by doping the ASPI first, followed by the Rhodamine-6G/MMA and followed by in situ polymerization as described. The ASPI composite glass had ASPI which was absorbed onto the walls of the pores (interfacial phase); the Rhodamine-6G composite glass had Rhodamine-6G in the polymer (PMMA) phase. The dual composite glass had ASPI in the interfacial phase and Rhodamine-6G in the polymer phase. Because, the Rhodamine-6G and ASPI reside in different phases, the dual composite glass is referred to as a multiphasic nanostructured composite glass.

After the polymerization was complete, the glasses were removed from the surrounding PMMA by a chloroform wash. The glasses were then polished (Buehler Metaserv 200 grinder-polisher) in seven incremental steps, starting with a 180 grit up to 4000 grit SiC paper and going down from 1 micron to a 0.25 micron diamond paste.

Example 27

Optical Measurements.

Absorption spectra were obtained using a Shimadzu UV-Vis 260 spectrophotometer with a resolution of ±1 nm. The spectra of solution state were obtained using quartz cuvettes (1 cm path length) throughout.

Emission spectra were collected on a Shimadzu RF-5000U Spectrofluorophotometer (90° geometry) having a resolution of ±2 nm. For solution state measurements, a fluorometric quartz cuvette was used. For the composite glass, the emission was obtained from the surface of the glass (90° geometry) due to significant primary absorption.

Lasing performance studies (both the solution and the composite glass) were performed using a frequency-doubled Quanta-Ray DCR Nd:YAG Q-switched laser having a repetition rate up to 30 Hz and producing 8 ns pulses at 532 nm. During all of the lasing experiments the outcoming beam was reflected using a second harmonic selector and passed through an IR filter. The beam was then passed through an aperture and then through a cylindrical lens which focused the beam into a linear shape on the sample. The sample was in a transverse pump cavity configuration. The cavity consisted of a ~100% reflecting flat mirror (at 0°) and a ~70% reflecting flat outcoupler (at 0°) through the range of 550 to 630 nm.

For the lasing slope efficiency measurements in solution, all measurements were carried out at a repetition rate of 30 Hz. The pump beam and the lasing output were measured with a Scientech 362 power-energy meter. The lasing efficiency measurements in composite glasses were carried out at a repetition rate of 1 Hz. The pump beam and lasing output were measured with a United Detector Technology 350 linear/log optometer and each collected data point was an average of 10 pulses. The lasing efficiencies were calculated from the slope without any additional corrections.

The lasing output vs. wavelength of the composite glasses was measured by passing the lasing output through a monochrometer (SPEX Triplemate Model 1460) and collected on an optical multichannel analyzer (OMA-III, EG&G Princeton Applied Research). The spectrum is a collection of 11 pulses at a 1 Hz repetition rate.

Tunability measurements were carried out at a repetition rate of 1 Hz on the composite glass and 2 Hz in the solution rate. The ~100% reflecting mirror was replaced with a 1200 groove/mm grating, and the lasing output was collected through a monochrometer (Jobin-Yvon UV monochrometer) having a resolution of ±1.6 nm and focused onto a fast photodiode (Si PIN). The output lasing intensity was attenuated by neutral density filters (ESCO Products Inc.) to avoid saturation of the photodiode. The output signal was measured with an oscilloscope (Tektronix 350 MHz, Model 2467). The wavelength was scanned manually, each data point represents an average of 10 pulses, and several measurements were made to ensure repeatability.

Example 28

Optical Characterization of the Solution State.

Figure 23:
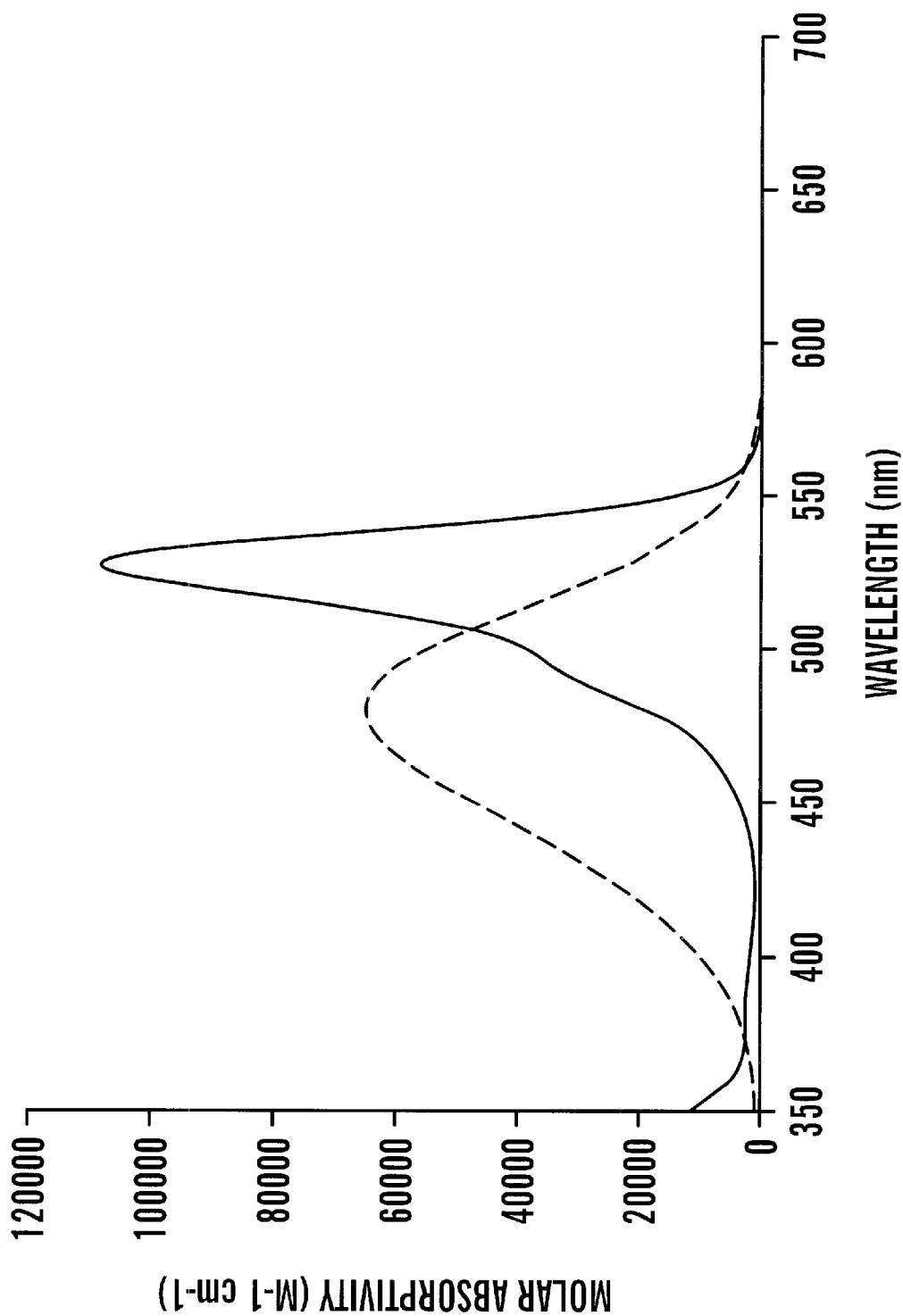
FIG. 23 shows the molar absorptivity, as a function of wavelength, of ethanolic ASPI (dashed curve) and Rhodamine-6G (solid curve).

The molar absorptivity of ASPI in ethanol was determined by measuring five solutions ranging from $2.6 \times 10^{-6}$ to $2.5 \times 10^{-5}$ M. A plot of absorption at the maxima (483 nm) vs. concentration yielded a straight line and by Beer's law the slope yielded a molar absorptivity of $6.8 \times 10^4$ M$^{-1}$ cm$^{-1}$. The molar absorptivity of Rhodamine-6G is well known and is $1.05 \times 10^5$ M$^{-1}$ cm$^{-1}$ (at 530 nm) in ethanol *Lambdachrome Laser Dyes Data Sheet*, Ulrich Brackmann, ed., Gottingen, Germany:Lambda Physik, p. 151 (1994) ("Brackmann"), which is hereby incorporated by reference). From these values a plot of the absorptivity as a function of wavelength was generated and is shown in FIG. 23. The absorption maxima of ASPI and Rhodamine-6G are 483 nm and 530 nm respectively. Both ASPI and Rhodamine-6G have the same extinction coefficient at 509 nm. The observed data are summarized in Table 2.

TABLE 2

| | Solution State | | | Composite Glass | | |
|---|---|---|---|---|---|---|
| | ASPI | Rhodamine-6G | ASPI/Rhodamine-6G | ASPI | Rhodamine-6G | ASPI/Rhodamine-6G |
| Absorbance Max. | 483 nm | 530 nm | — | — | — | — |
| Molar Absorptivity | $6.8 \times 10^{-4}$ | $1.05 \times 10^{-5}$ | — | — | — | — |
| Fluorescence Max. | 600 nm | 562 nm | 595 nm | 586 nm | 546 nm | 594 nm/552 nm |
| Florescence FWHM | 38 nm | 25 nm | 40 nm | 45 nm | 53 nm | 41 nm/43 nm |
| Stokes Shift | 118 nm | 32 nm | — | — | — | — |
| Quantum Yield | $6.5 \times 10^{-3}$ | 0.9 | — | — | — | — |
| Lasing Efficiency | 13.5% | 25.2% | — | 9.4% | 3.8% | 7.3% |
| Lasing Tunability | 599–635 nm | 562–584 nm | 598–643 nm | 585–606 nm | 561–573 nm | 564–601 nm |

Figure 24:
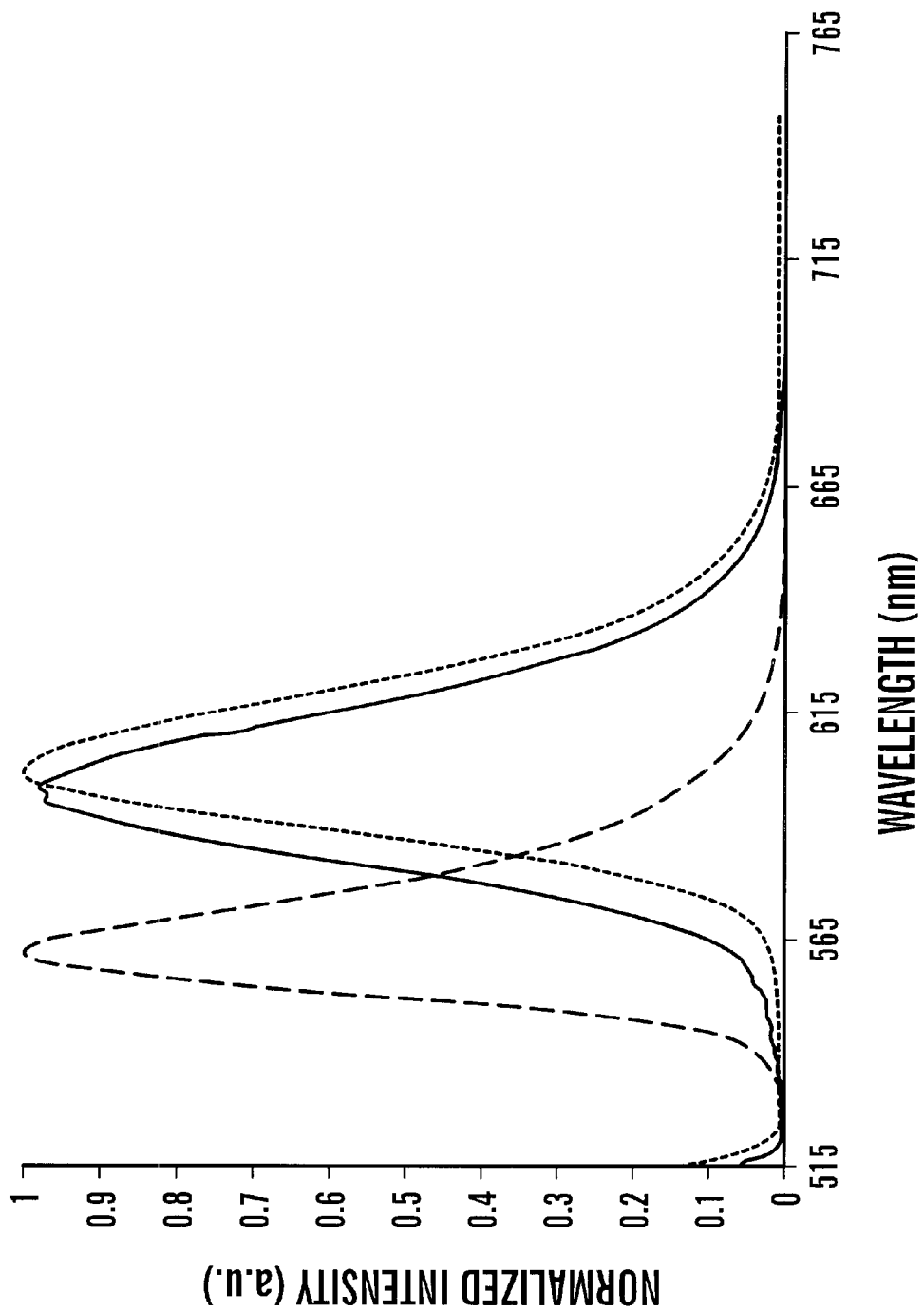
FIG. 24 is a fluorescence emission spectra of ethanolic Rhodamine-6G (6.5×10⁻⁵ M) (dashed curve), ASPI (3.1×10⁻³ M) (dotted curve), and a mixture solution containing Rhodamine-6G (6.5×10–5 M) and ASPI (3.1×10⁻³ M) (solid curve).

Fluorescence emission spectra of ASPI ($3.1 \times 10^{-3}$ M), Rhodamine-6G ($6.5 \times 10^{-5}$ M), and of a mixture solution of ASPI ($3.1 \times 10^{-3}$ M) and Rhodamine-6G ($6.5 \times 10^{-5}$ M in ethanol are shown in FIG. 24. These concentrations were chosen to be comparable with the concentration in the final composite glass. The concentrations used were 70% of the concentration of the solutions used to dope the glasses, which corresponded approximately to the porosity of the glass. Exitation at 509 nm was employed, because both dyes have the same molar absorptivity at this wavelength. The emission maxima for Rhodamine-6G, ASPI, and the mixture solution were 562 nm, 600 nm, and 595 nm, respectively. Approximate emission width (full width at half maximum ("FWHM") was 25 nm for Rhodamine-6G, 38 nm for ASPI, and 40 nm for the mixture solution. Rhodamine-6G had a Stokes shift of 32 nm and exhibited an asymmetric peak that can be attributed to self absorption at this concentration. ASPI had a very large Stokes shift of 118 nm which cannot be attributed to self-absorption because the self-absorption process is insignificant for this dye. Large Stokes shifts were previously attributed to a different charge distribution in the excited state compared to the ground state as it was reported for Coumarin dyes (Drexhage, "Structure and Properties of Laser Dyes," in Schafer, ed., *Dye Lasers*, Berlin:Springer-Verlag, Chapter 5 (1990) ("Drexhage"), which is hereby incorporated by reference). It is also evident from the emission spectra that Rhodamine-6G was completely quenched in the mixture solution when combined with ASPI in such concentrations.

In addition, the quantum yield was measured from the fluorescence data. This was accomplished by measuring the emission of Rhodamine-6G and ASPI in separate solutions. A comparative method was used according to the following equation (Reisfeld, *Nat. Bur. Std.* 76 A:613 (1972), which is hereby incorporated by reference):

$$\phi_s = \phi_r[(n_s A_r f F_s)/(n_r A_s f F_r)] \quad (4)$$

Where $\phi_s$ is the quantum yield of the sample, $\phi_r$ is the quantum yield of the reference, $n_s$ is the refractive index of the sample, $n_r$ is the refractive index of the reference, $A_s$ is the absorbance of the sample at the pump wavelength, $A_r$ is the absorbance of the reference at the pump wavelength, $F_s$ is the integral of the fluorescence emission of the sample (in $cm^{-1}$ units), and $F_r$ is the integral of the fluorescence emission of reference (in $cm^{-1}$ units). The fluorescence quantum yield of Rhodamine-6G used was taken as 0.95 (Drexhage, which is hereby incorporated by reference). The emission of both dyes was measured when excited at 509 nm where the concentrations of the dyes were the same ($2.6 \times 10^{-6}$ M). This produced a fluorescence quantum yield for ASPI of $7 \times 10^{-3}$. A second measurement was carried out where ASPI was at a concentration of $1.8 \times 10^{-6}$ M and Rhodamine-6G was at a concentration of $2.6 \times 10^{-6}$ M. ASPI was excited at 482 nm and Rhodamine-6G was excited at 509 nm. At these two wavelengths both dyes have the same molar absorptivity at their respective concentrations. This measurement produced a fluorescence quantum yield for ASPI of $6 \times 10^{-3}$. Although the measurement is not as accurate as other potential methods, it is apparent that ASPI has a fluorescence quantum yield that is two orders of magnitude lower than that of Rhodamine-6G. The observed fluorescence quantum yield is presented in Table 2.

Figure 25:
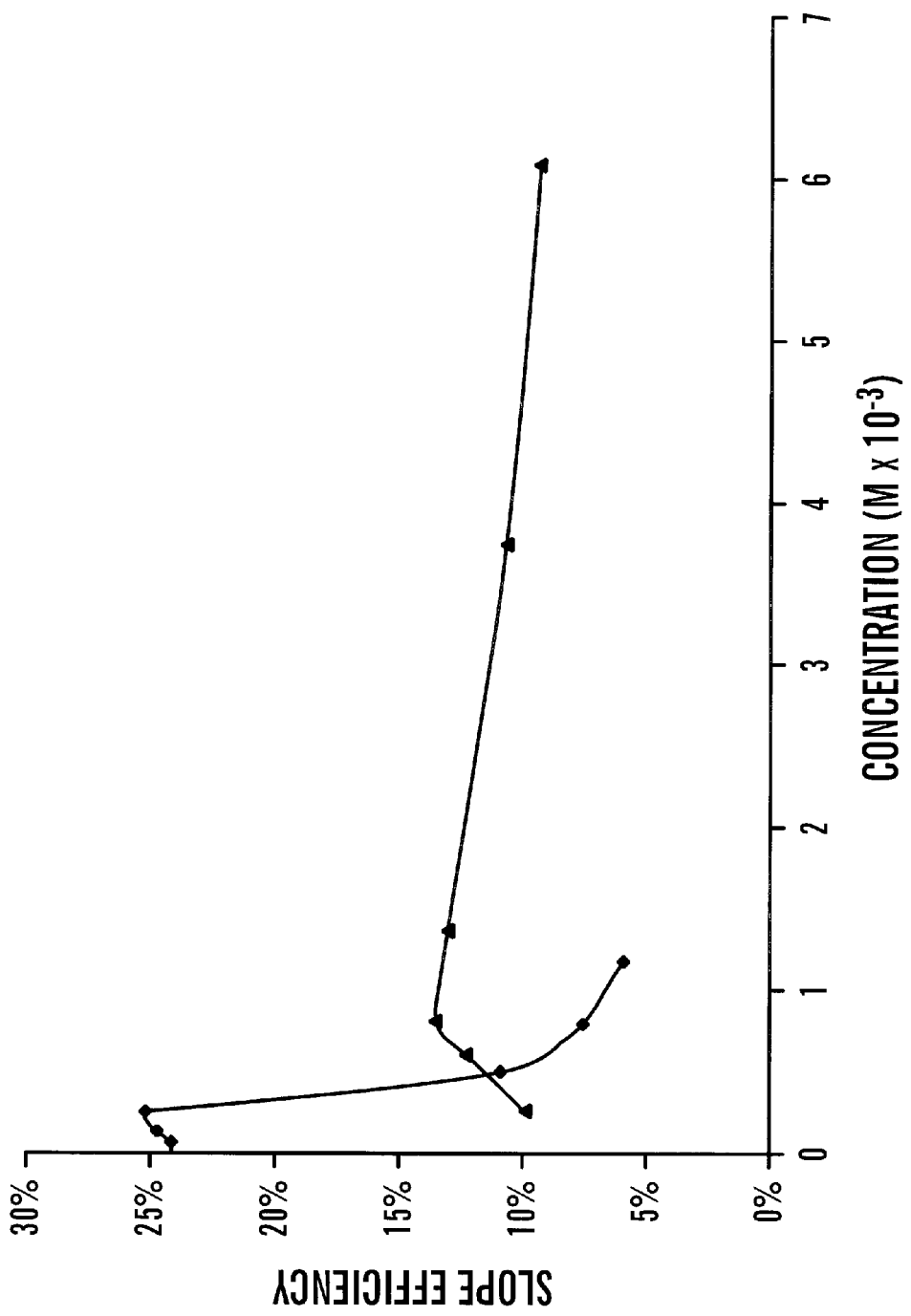
FIG. 25 depicts the lasing slope efficiency of ASPI (triangles) and Rhodamine-6G (diamonds) in ethanol as a function of concentration in ethanolsolution. The dyes were transverse pumped at 532 nm with a 8 nm pulsed frequency-doubled Nd:YAG laser operating at a 30 Hz repetition rate.

FIG. 25 shows the lasing slope efficiency of both Rhodamine-6G and ASPI in ethanol as a function of concentration. Rhodamine-6G was observed to be most efficient at a concentration of $2.5 \times 10^{-4}$ M with a lasing slope efficiency of 25.2% under the condition of our experiment. The optimized Rhodamine-6G concentration observed was the same as that recommended by Brackmann. However, Brackmann reported a higher efficiency than was observed, and this is attributed to the Brackmann's use of a simple cavity. ASPI was found to be most efficient at a concentration of $8.2 \times 10^{-4}$ M with a lasing slope efficiency of 13.5%. The difference between the lasing slope efficiency behavior of Rhodamine-6G and that of ASPI is significant. In particular, a sharp decline in efficiency observed in Rhodamine-6G due to self-absorption was not observed in ASPI. The measurement of the lasing efficiency of ASPI was terminated at a concentration of $6.1 \times 10^{-3}$ M, which is the limit of solubility of ASPI in ethanol. The observed data are summarized in Table 2.

The relatively high lasing slope efficiency of ASPI is surprising considering the low fluorescence quantum yield of ASPI relative to Rhodamine-6G. This result may indicate that the low quantum yield of ASPI is caused by a radiationless energy loss that occurs on the time scale of the excited state under continuous pumping conditions. It is believed that in the cavity, with the short pulsed pumping, the dye was stimulated to emit a photon at a much faster rate than the nonradiative processes. This phenomenon is well known (Schafer, "Principles of Dye Laser Operation," in Schafer, ed., *Dye Lasers*, Berlin:Springer-Verlag, Chapter 1 (1990) ("Schafer"), which is hereby incorporated by reference) and has been demonstrated using dyes that have fluorescence quantum yields as low as $5 \times 10^{-4}$ and lasing conversion efficiencies of 10 to 20%. (Polland et al., *Appl. Phys. B* 32:53 (1983), which is hereby incorporated by reference). In the present case, it is believed that an intersystem crossing occurs from the $S_1$ state to the $T_1$ state (Schafer, which is hereby incorporated by reference). This implies that the dye would not be suitable for cw lasing and that it could possibly act as a saturable absorber (or as a reverse saturable absorber). It also implies that ASPI's quantum yield and lasing properties are related to the pumping rise time (Schafer, which is hereby incorporated by reference). It is also interesting that this chromophore (with a different counter ion, tetraphenylborate), as mentioned above, can operate as a two-photon excitation induced laser when pumped at 1064 nm. Although the iodide is a well known quenching ion (Drexhage, which is hereby incorporated by reference), no difference in the spectroscopic and lasing performance between ASPI and its tetraphenylborate derivative was observed. This indicates that the counter ion only affects the solubility of the chromophore.

Figure 26:
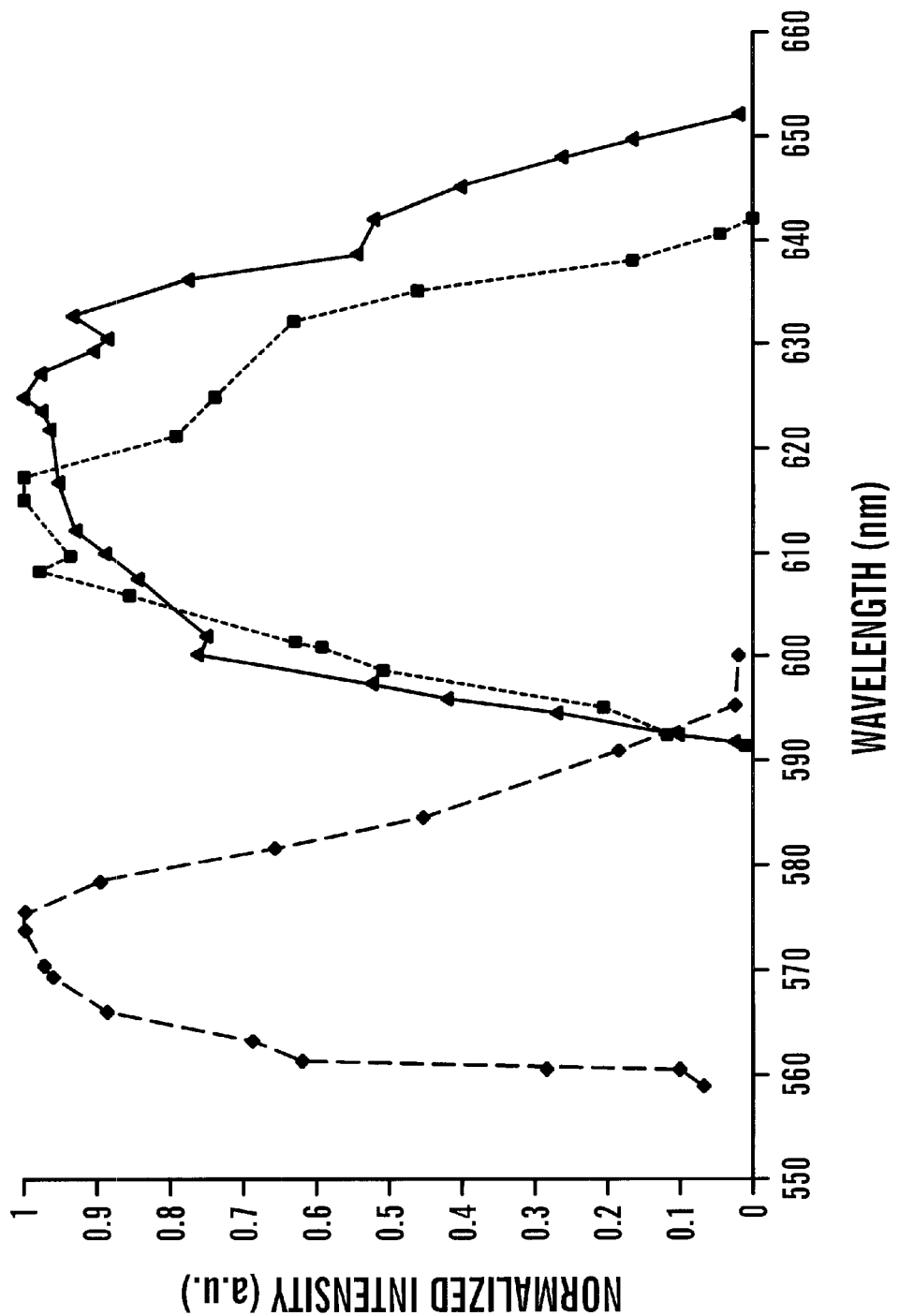
FIG. 26 depicts the lasing tunability of Rhodamine-6G (6.5×10⁻⁵ M) (diamonds), ASPI (3.1×10⁻³) (squares), and a mixture solution containing Rhodamine-6G (6.5×10⁻⁵ M) and ASPI (3.1×10⁻³ M) (diamonds). The dyes were transverse pumped at 532 nm with a 8 ns pulsed frequency-doubled Nd:YAG laser operating at a 2 Hz repetition rate and using a grating as back reflector.

The lasing tunability of ASPI ($3.1 \times 10^{-3}$ M) and Rhodamine-6G ($6.5 \times 10^{-5}$ M) in ethanol is shown in FIG. 26. The tunability FWHM of ASPI, Rhodamine-6G, and the mixture solution are approximately 37 nm, 22 nm, and 45 nm, respectively. The tunability wavelength range is presented in Table 2. It is also apparent that there is no contribution from Rhodamine-6G in the mixture solution; however, there is a significant increase in the range of the tunability of the mixture solution, which is evidence of a higher lasing efficiency. The observed increase in lasing efficiency is possibly due to an effective energy transfer from Rhodamine-6G to ASPI, possibly mediated through a Förster mechanism which results in a fluorescence quenching of Rhodamine-6G in the mixture solution. Another possible quenching mechanism is dynamic quenching which is described by the equation (Eftink "Fluorescence Quenching: Theory and Application," in Lakowicz, ed., *Topics in Fluorescence Spectroscopy. Vol.* 2, New York:Plenum Press, Chapter 2 (1991), which is hereby incorporated by reference):

$$\Phi_f/\Phi_f^o = (1 + K_q[Q])^{-1} \quad (5)$$

where $\Phi_f^o$ is the fluorescence quantum yield in the absence of quencher, $\Phi_f$ is the fluorescence quantum yield in the presence of quencher, [Q] is the concentration of the quencher, and $K_q$ is the Stern-Volmer constant defined as $Kq = k_q \tau_f^o$, where $k_q$ is the dynamic quenching rate and $r_f$ is the fluorescence lifetime in the absence of quencher.

In aqueous solution at room temperature, the bimolecular collision rate is about $10^{10}$ L $mol^{-1}$ $sec^{-1}$ (Ingle et al.,

*Spectrochemical Analysis*, New York:Prentice Hall, p. 343 (1988), which is hereby incorporated by reference), and the quencher concentration was $2.1 \times 10^{-3}$, which yields a maximum quenching of only ~10%. Therefore, dynamic quenching is not considered to be the dominate mechanism for the quenching of Rhodamine-6G. It is believed that the most probable quenching mechanism is Förster energy transfer, which is inversely related to the sixth power of the distance between the donor and the acceptor (Cheung, "Resonance Energy Transfer," in Lakowicz, ed., *Topics in Fluorescence Spectroscopy*, Vol. 2, New York:Plenum Press, Chapter 3 (1991) ("Cheung"), which is hereby incorporated by reference). A simple calculation of the distance between the centers of two molecules was done using the following equation:

$$d = \sqrt[3]{1000/(CN_a)} \tag{6}$$

where d is the distance between the molecules in cm, C is the concentration in moles/liter, and $N_a$ is Avogadro's number. This calculation reveals that the distance between the dye molecules, evenly distributed in the mixture solution, is 80 Å for ASPI to ASPI, and 295 Å for Rhodamine-6G to Rhodamine-6G. When determining the distance between the Rhodamine-6G and the ASPI molecules, Rhodamine-6G was placed at the center of a cube, with ASPI at the corners of the cube, at a distance of 80 Å. The calculation indicates a 70 Å ASPI to Rhodamine-6G distance. The ASPI and Rhodamine-6G distance is well within the range where Förster energy transfer can occur (Cheung, which is hereby incorporated by reference). A comparison of the Förster energy transfer in the composite glasses of the present invention and solution state is presented below.

Example 29
Optical Characterization of the Composite Glasses.

Figure 27:
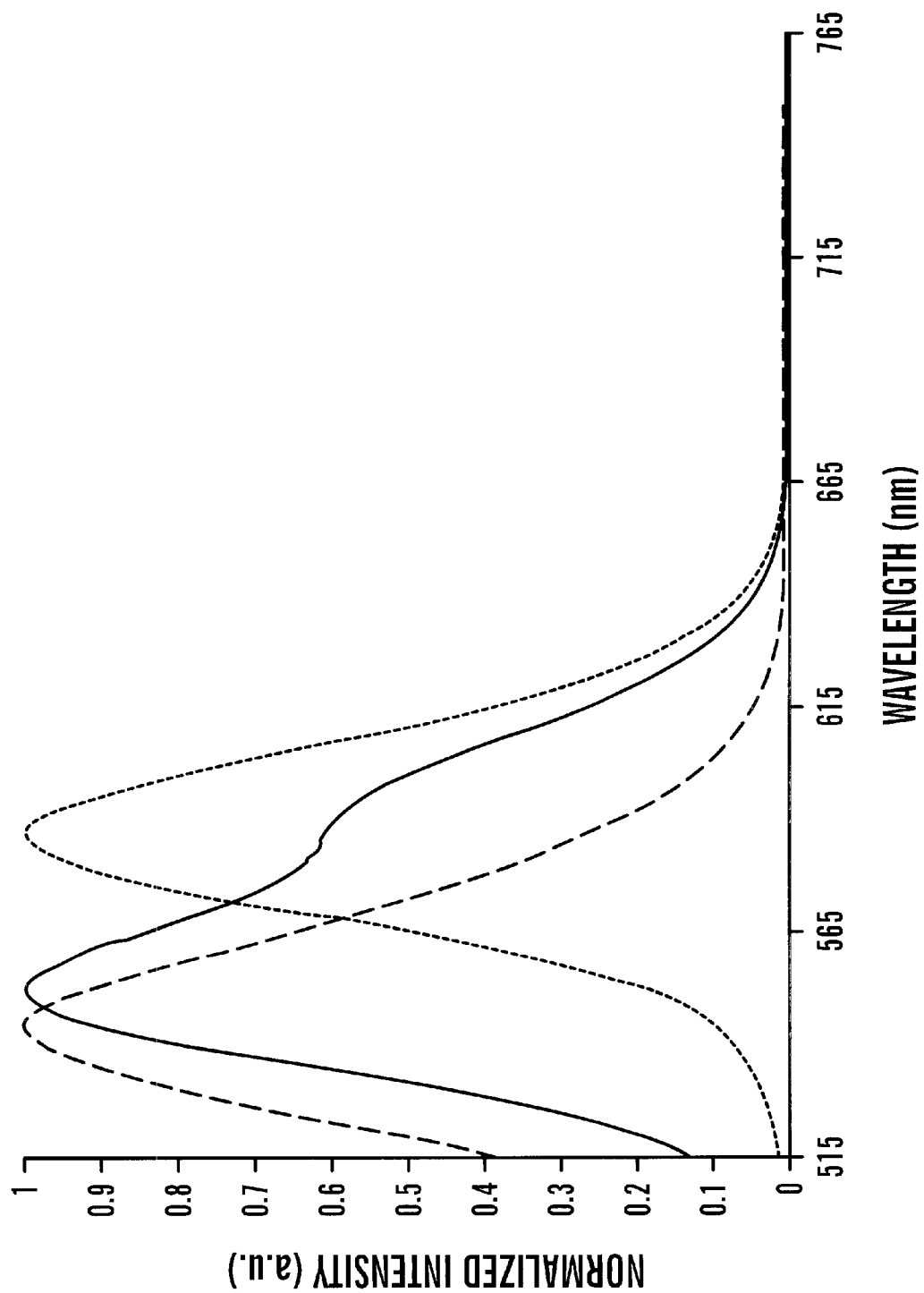
FIG. 27 is fluorescence emission spectra of Rhodamine-6G composite glass (dashed curve), ASPI composite glass (dotted curve), and the composite glass containing both dyes (solid curve).

FIG. 27 presents the fluorescence emission of the dye doped composite glasses. The composite glass containing ASPI has an emission maximum at 586 nm, and the composite glass containing Rhodamine-6G has the emission maximum at 546 nm. The composite glass containing both dyes has emission from both dyes with no significant quenching of emission from either dye. The peaks were reconstructed using a computer software program with an exponential gaussian fit function. The peak of the ASPI emission is at 594 nm and that of Rhodamine-6G is at 552 nm. The FWHM of the emission for ASPI is 45 nm and of Rhodamine-6G is 53 nm. In the glass containing both dyes the FWHMs are 41 nm for ASPI and 43 nm for Rhodamine-6G. The observed fluorescence emission parameters (maxima and widths) in the composite glasses are summarized in Table 2.

Figure 28:
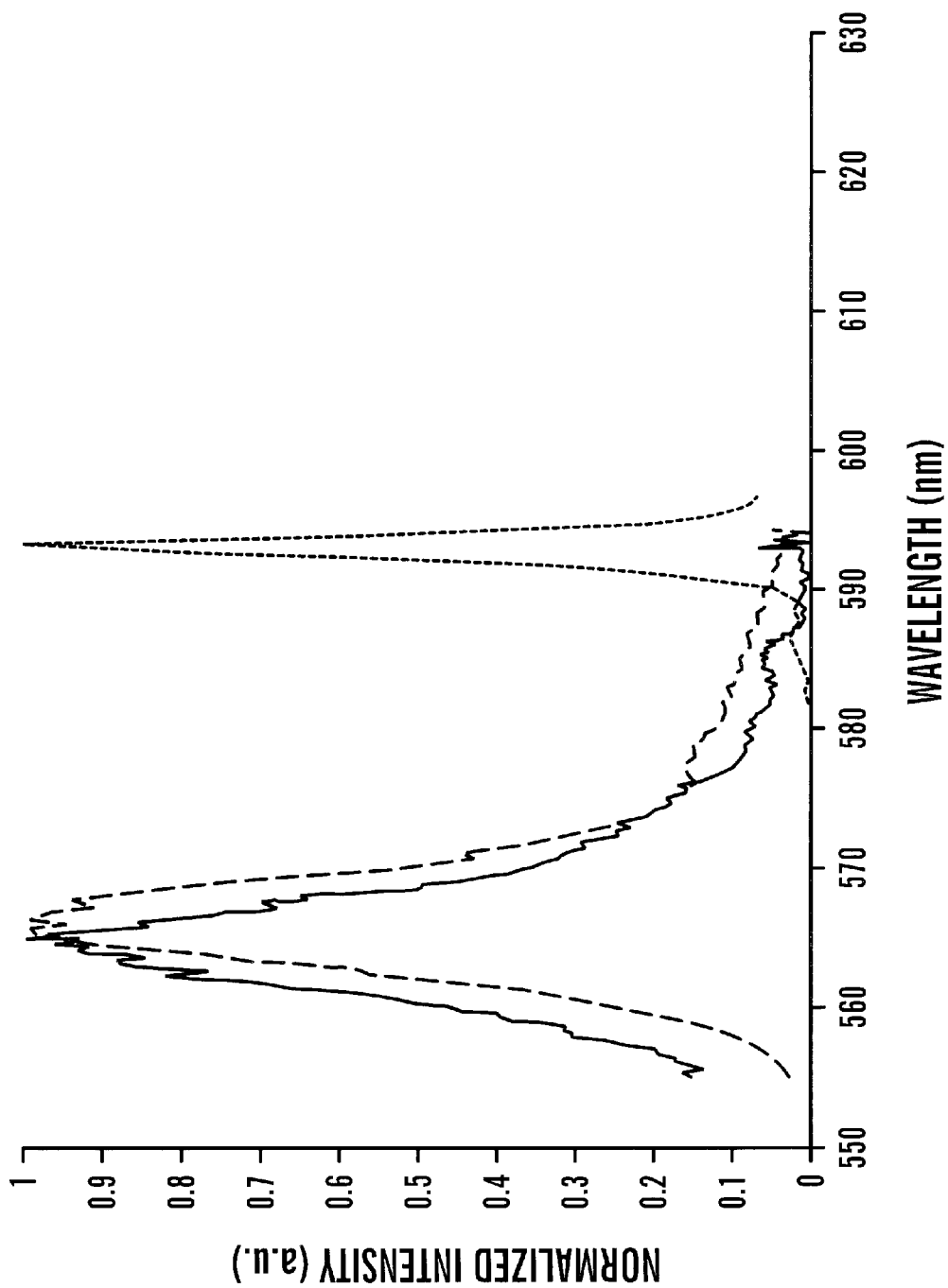
FIG. 28 depicts the lasing output intensity as a function of wavelength of a Rhodamine-6G composite glass (solid curve), a ASPI composite glass (dotted curve), and a composite glass containing both dyes (dashed curve). The composite glasses were transverse pumped at 532 nm with a 8 ns pulsed frequency-doubled Nd:YAG laser operating at a 1 Hz repetition rate and using a ~100% reflecting mirror as back reflector.

Lasing of the dye-doped composite glass was demonstrated in a cavity consisting of a ~100% reflecting mirror and a ~70% reflecting outcoupler. The wavelength dependence of the composite glass dye laser outputs are presented in FIG. 28. The composite glass containing ASPI exhibited a lasing emission maximum at ~593 nm with a FWHM of 2 nm. The composite glass containing Rhodamine-6G had a lasing emission maximum at ~565 nm and a FWHM of 5 nm. The composite glass containing both Rhodamine-6G and ASPI had a lasing emission maximum at ~567 nm and a FWHN of 5 nm. The preferred wavelength lasing mode for the multiphasic composite glass and the above-described cavity arrangement are similar to those for pure Rhodamine-6G. This observation is attributed to the better lasing characteristics of Rhodamine-6G and the cavity configuration itself.

Figure 29:
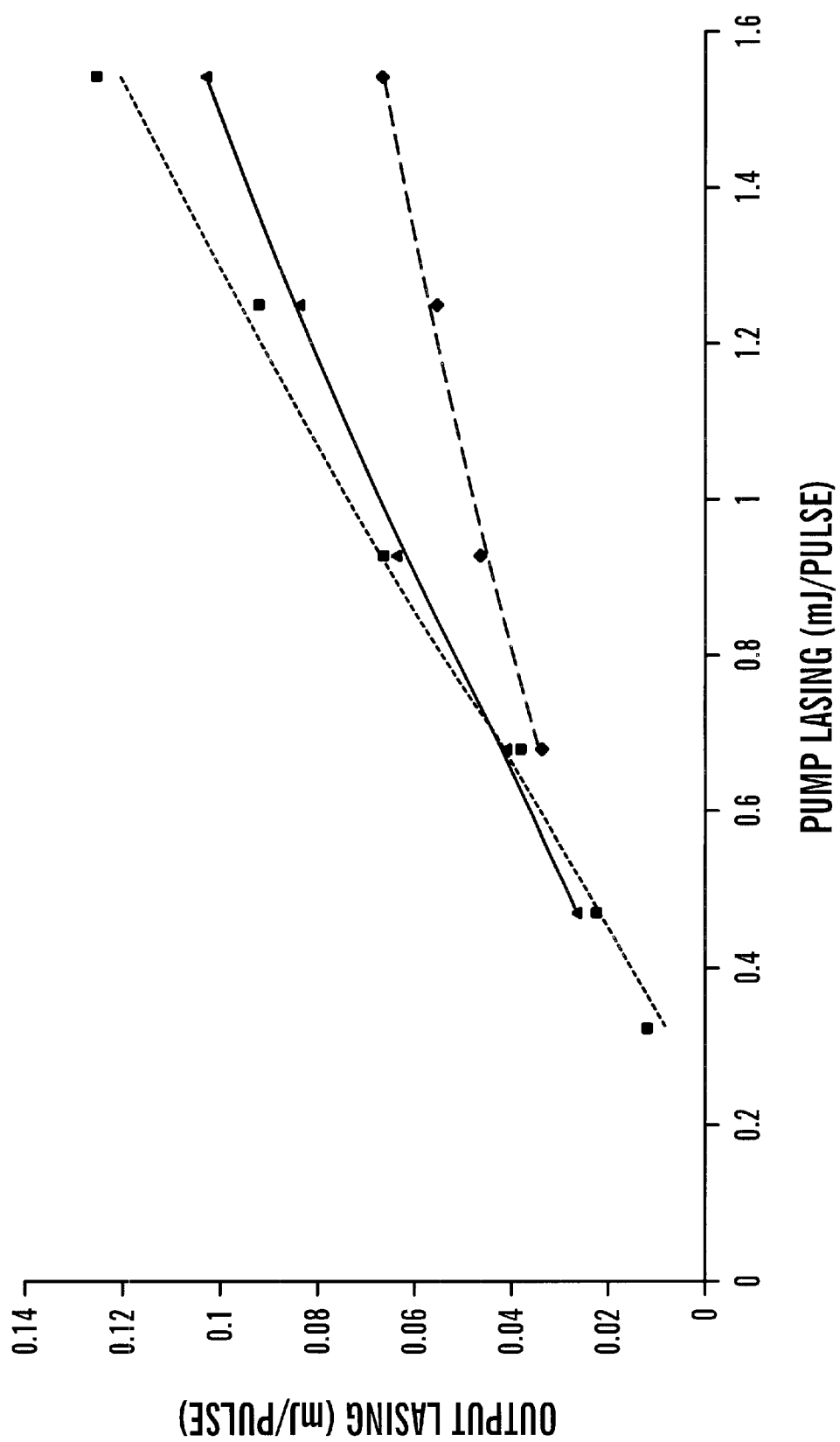
FIG. 29 shows the lasing slope efficiency of ASPI-doped composite glass (squares, dotted line), Rhodamine-6G-doped composite glass (diamonds, dashed line), and composite glass doped with both ASPI and Rhodamine-6G (triangles, solid line). The lines represent a linear least squares best fit to the data.

FIG. 29 presents the lasing slope efficiency of the three composite glasses. The lasing slope efficiencies were as follows: ~9% for the ASPI composite glass, ~3% for the Rhodamine-6G composite glass, and ~7% for the multiphasic composite glass containing both dyes. The observed data for the dye doped composite glasses are summarized in Table 2. The relatively low efficiency of the Rhodamine-6G glass is attributed to dimer or higher order aggregates that have formed in the glass because the doping level used was the highest possible. (Triton X-100 was used to increase the solubility and to minimize aggregation.) In general, lower efficiencies were observed in composite glass, which is believed to be due to slight inhomogeneities in the glass compared to the solution.

Figure 30:
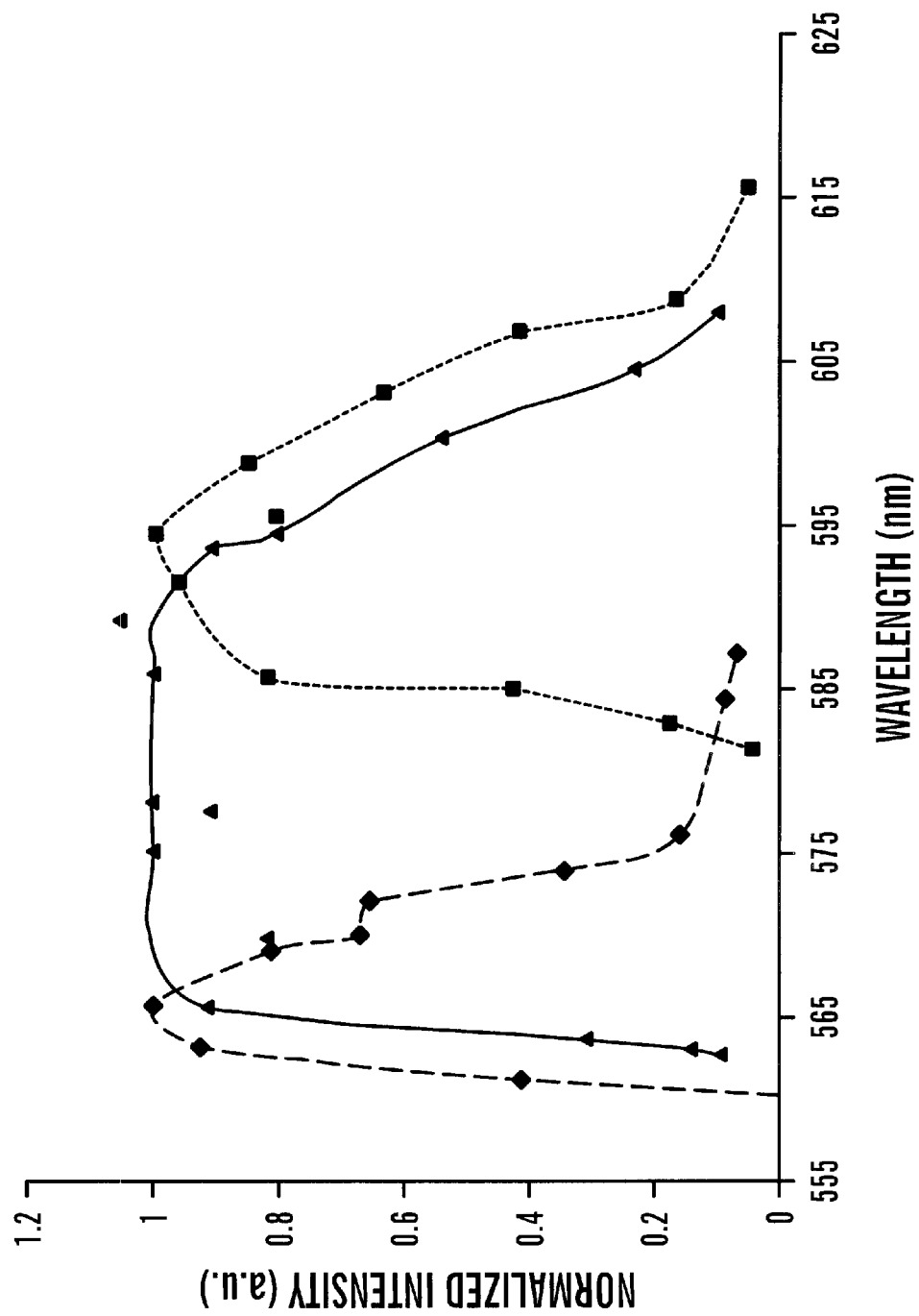
FIG. 30 shows the lasing tunability of Rhodamine-6G composite glass (diamonds, solid line), ASPI composite glass (squares, dotted line), and the multiphasic composite glass containing both Rhodamine-6G and ASPI (triangles, solid line). The composite glasses were transverse pumped at 532 nm with a 8 ns pulsed frequency-doubled Nd:YAG laser operating at a 1 Hz repetition rate and using a grating as back reflector.

FIG. 30 depicts the lasing tunability of the composite glasses. Tunable narrow band laser outputs were observed in a cavity consisting of a grating as the back reflector and a ~70% reflecting outcoupler. The FWHM of the tunability spectra was ~21 nm for the ASPI composite glass, ~12 nm for Rhodamine-6G composite glass, and ~37 nm for the composite glass containing both dyes. From this data it is evident that the glass containing both dyes was tunable across the range of both dyes, (560–610 nm). This in contrast to the solution of ASPI and Rhodamine-6G, where the Rhodamine-6G emission was quenched. The narrowing of the tunability in the composite glasses compared to solution is believed to result from the less homogenous nature of the matrix compared to solution, and, consequently, it is believed that improved tunability can be achieved by more carefully controlling preparation conditions. The tunability ranges are presented in Table 2. The ability to use the composites of the present invention to produce a multi-dye solid state laser tunable over a wide wavelength range implies that multiphasic composite glasses can be used to fabricate a variety of multifunctional devices for photonics.

As discussed above, it is believed that the quenching in the solution state is a result of Förster energy transfer. A detailed discussion of the Förster energy transfer process in the composite glasses follows. The shape of the pores were considered to have been cylindrical, since the porous glass of the present invention obeys the equation for the relation between the diameter and the specific surface area for the cylindrical case as reported in Yamane, "Monolith Formation from the Sol-Gel Process," in Klein, ed., *Sol-Gel Technology for Thin Films, Fibers, Preforms, Electronics and Specialty Shapes*, New Jersey:Noyes Publications, Chapter 10 (1988) ("Yamane"), which is hereby incorporated by reference. When calculating the distance between the absorbed molecules on the pore surface and the molecules contained in the pores of the multiphasic composite glass, the ratio between the specific surface area and the pore volume must be considered. In view of this consideration, and reducing the problem to two dimensions only, the following equation was employed:

$$d = \sqrt{1000 S_a / (CN_a P_v)} \tag{7}$$

where d is the distance (in cm) between molecules deposited on the surface of the pores, C is the concentration (in moles/liter) of the solution used to deposit the molecules, $N_a$ is Avogadro's number, $P_v$ is the pore volume per cc, and $S_a$ is the surface area per cc. The calculation reveals that, when compared to the same concentration in the solution state, the distance between ASPI molecules is increased from 80 Å to 210 Å. This is due to the extremely large surface area to pore ratio (a $\sim 8.5 \times 10^6$). This implies that, for the same concentration in the composite glass and in solution, the distance between the molecules is greater in the composite glass. Assuming that Rhodamine-6G is in the center of the cylindrical pores, the ASPI to Rhodamine-6G distance in the composite glass is 110 Å, compared to a 70 Å ASPI to Rhodamine-6G distance in solution This represents an 1.6-fold increase in the distance between the ASPI and Rhodamine-6G molecules in the composite glass relative to the solution state.

The rate of energy transfer between the donor molecule (Rhodamine-6G) and the acceptor molecule (ASPI) in the Förster energy transfer mechanism can be described by the following equation (Yamane, which is hereby incorporated by reference):

$$k_T = 9(\ln 10)\kappa^2 Q_d J / (128\pi^5 n^4 N_a \tau_d R^6) \quad (8)$$

where $\kappa$ is the orientational factor for the dipole-dipole interaction, $Q_d$ is the fluorescence quantum yield of the donor molecule without the acceptor molecule, n is the refractive index of the medium, $N_a$ is Avogadro's number, $\tau_d$ is the fluorescence lifetime of the donor molecule in the absence of acceptor, R is the distance between the centers of the donor and acceptor molecules, and J is the normalized spectral overlap integral. The equation indicates that the rate of energy transfer is directly proportional to the square of the orientational factor, $\tau$, and inversely proportional to the sixth power of the distance between the center of the molecules. These two factors are significantly changed in the multiphasic composite glass. By increasing the distance between the molecules by a factor of 1.6, the rate of energy transfer is reduced by more than one order of magnitude. Also, in the solution state, the molecules are free to rotate and sample most if not all of the orientational possibilities during the excited state lifetime of Rhodamine-6G. In the solid state, the molecules are effectively frozen in place with little or no rotation allowed. This leads to a further decrease in the energy transfer (Yamane, which is hereby incorporated by reference). By changing the distance between the molecules and decreasing the orientational factor, the composites of the present invention reduce quenching due to Förster energy transfer.

Example 30

Energy Transfer Measurement

An experiment based on the fluorescence emission of porphyrin and ASPS was conducted to show energy transfer from the dye to the porphyrin. $D_2O$ solutions of the ASPS and TPPS were mixed in different concentrations in a quartz cuvette and placed in the sample compartment of a spectrofluorophotometer. 1060 nm laser light at was generated by a Q-switched Nd-YAG laser operating at 10 Hz, and was guided using beam steering optics into the cuvette. The beam energy used in this experiment was approximately 50 mJ in a beam having a 4 mm diameter. IR light-induced fluorescence emission spectrum (due to two-photon absorption from the ASPS alone without porphyrin) showed a fairly broad emission peaking at 610 nm and lacking any fine structure. The porphyrin without the ASPS was also irradiated with the IR laser light to determine any possible contributions from the porphyrin due to two-photon excitation. However, there was no noticeable fluorescence emission from porphyrin under IR pumping. Exciting TPPS at 610 nm using a spectrofluorophotometer produced an emission peak at 650 nm. ASPS and TPPS solutions were mixed together and a series of spectra were collected to determine dependence of fluorescence emission spectrum on the concentration of the different molecular species. The spectra revealed that as the porphyrin concentration increased from zero, ASPS peak emission intensity decreased while the porphyrin peak at 653 nm emerged and intensified. The concentrations of ASPS and TPPS were optimized to have the highest emission of porphyrin at 653 nm.

A mixture of ASPS ($5.4 \times 10^{-3}$ M) and TPPS ($7.7 \times 10^{-4}$ M), excited at 1060 nm, produced an emission having three peaks. The largest, at 610 nm, was due to the two-photon induced emission of ASPS; a peak at 653 nm was attributed to emission from TPPS. The ASPS peak emission intensity at the peak was reduced by about 20% while the porphyrin peak was clearly evident. Reduction in emission intensity at 580 nm matched one of the TPSS absorption peaks. This clearly indicated that some form of energy is transferred from excited ASPS molecules to TPPS molecules.

Example 31

Detection of the Presence of Singlet Oxygen Under IR Light Exposure

ADPA, ASPS and TPPS were dissolved in $D_2O$ separately, at concentrations of $7.4 \times 10^{-4}$ M, $5.4 \times 10^{-3}$ M and $7.7 \times 10^{-4}$ M, respectively. Sodium phosphate buffer solution was added to the porphyrin solution to maintain the pH at 7.4. Singlet oxygen was detected using ADPA, which is a colored compound that bleaches in the presence of singlet oxygen. The laser source used for this experiment was the same as that described in Example 30. The energy in each pulse, however, was increased to 130 mJ while the beam size and repetition frequency were maintained the same. 1.5 ml samples, in a 1 cm pathlength quartz cuvette, were irradiated with laser light continuously for 3 hours, and their absorbance spectra were recorded every hour to monitor the decrease in absorbance at 400 nm characteristic of ADPA in the presence of singlet oxygen.

A mixture of ASPS, TPPS and ADPA was prepared with concentrations the same as above. Sodium phosphate buffer solution was added to maintain the pH.

The mixture containing the ASPS and bleaching compound but not the porphyrin did not show any bleaching when irradiated with 1060 nm light. Similarly, the mixture of the porphyrin and the bleaching compound without the ASPS did not show bleaching. The mixture containing the ASPS, TPPS, and ADPA resulted in bleaching of ADPA when exposed to IR laser light. ADPA absorbance was found to decrease with time. When argon was bubbled into the solution of ASPS, TPPS, and ADPA to remove ambient oxygen, no significant amount of ADPA bleach was evident. From this it was concluded that oxygen is responsible for the ADPA bleaching.

Example 32

Apparatus and Media for Data Storage (4-[N-(2-hydroxyethyl)-N-methyl)aminophenyl]-4'-(6'-hydroxyhexylsulfonyl)stilbene) ("APSS") was prepared in accordance with the methods described herein and in Zhao, which is hereby incorporated by reference.

5 mg of APSS was dissolved in 1.2 g of neat 2-hydroxyethyl methacrylate ("HEMA"). AIBN, in an amount of 1% (by mole relative to HEMA), was added, and the solution was polymerized in a sealed mold at 60° C. for about 48 hours. After polymerization the polymerized product was released from the mold and cut into 3×5×3 mm blocks with a small jeweler saw. To obtain a smooth surface, the APSS-containing polymer blocks were trimmed on an ultramicrotone with a glass knife.

The APSS-containing HEMA polymer block was mounted on the stage of a Biorad MRC 500 (Bio-rad Microscience, Cambridge, Mass.) confocal laser scanning microscope. Computer controlled galvo mirrors in the confocal microscope enabled precise beam scanning of the APSS-containing polymer block.

However, better control and larger usable area was achieved using the low-cost scanning stage described below. The low-cost scanning stage employs four 2" full-range shielded audio speakers, two for X-axis and two for Y-axis. To achieve a strong holding force in each axis, positive voltage was applied to one speaker while relative negative voltage was applied to the other speaker. In this way, one speaker pushed and the other speaker pulled the stage, thus, rendering the stage's motion and position more stable. Between two speakers, within each axis, a thin acrylic rod was used to support the sample. The control circuit permitted the speakers to be addressed up to 16-bit, which provided 65536 steps over arrange of about 1000 µm.

A mode-locked Ti:Sapphire laser oscillator (NJA-4 from Clark-MXR, Inc., Dexter, Mich.) producing a train of 798 nm pulses of duration 90 fs each at a frequency of 92 MHz was used to expose the APSS-containing HEMA block. Although the average beam power was 400 mW, the average power measured at the sample was only about 0.3 mW. The laser beam was directed to the sample through the optics of the confocal microscope. The focal length of the optical microscope was adjusted using a step motor attached to the focusing knob. Exposure was controlled with a shutter placed in the optical path of the laser beam.

An IBM-compatible personal computer was used to control the scanning process, the focusing knob stepper motor and the shutter and to provide position delaying time and retracing cycle time to further stabilize movement of the APSS-containing polymer block.

Example 33
Data Storage

When the focused infrared beam from the Ti:Sapphire laser was incident in the sample, there was a strong two-photon induced green fluorescence at the focal point. The pumping level was increased until photobleaching at the focal point was observed. The dimensions of a single photobleached spot was estimated to be 0.5×0.5×0.8 mm.

A two-dimensional plane of the sample was scanned at a slow rate (678×512 pixels per 10 seconds). This produced a photobleached plane with reduced fluorescence compared to the fluorescence of the surrounding material. The position of the stage was then moved so that the focal point was in a plane below the one previously bleached. The intensity of the beam was reduced, and a second plane was slowly scanned. The process was repeated to produce a series of planes of varying degrees of photobleaching, one behind the other, in the volume of the APSS-containing HEMA block.

Figure 33:
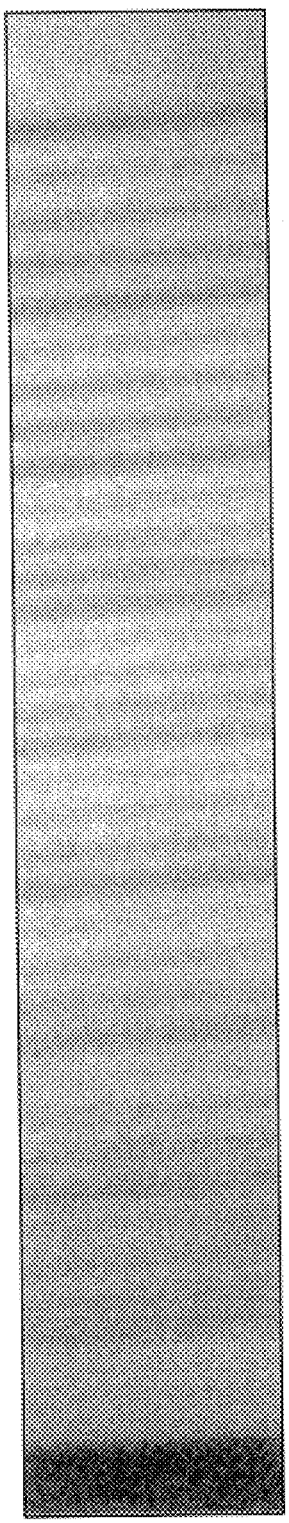
FIG. 33 is a scanned image of a data storage medium according to the present invention showing photobleached planes with varying contrast.

To read these planes, the same laser source was used but the sample was scanned at a faster rate (678×512 pixels per second) and over a larger area so that the illumination dose per unit area was reduced by over two orders of magnitude compared to the writing process. Fluorescence emission from the sample was collected through the objective lens of the confocal microscope, was passed through a spatial filter in the form of a confocal aperture, and was detected by a photomultiplier tube. Under these conditions, emmission from the sample was detected, and no noticeable photobleaching occurred. FIG. 33 is a cross-section of the APSS-containing HEMA block showing a set of photobleached planes with different contrast, separated by 5 µm.

Example 34
Analog Image Archival

Figure 34:
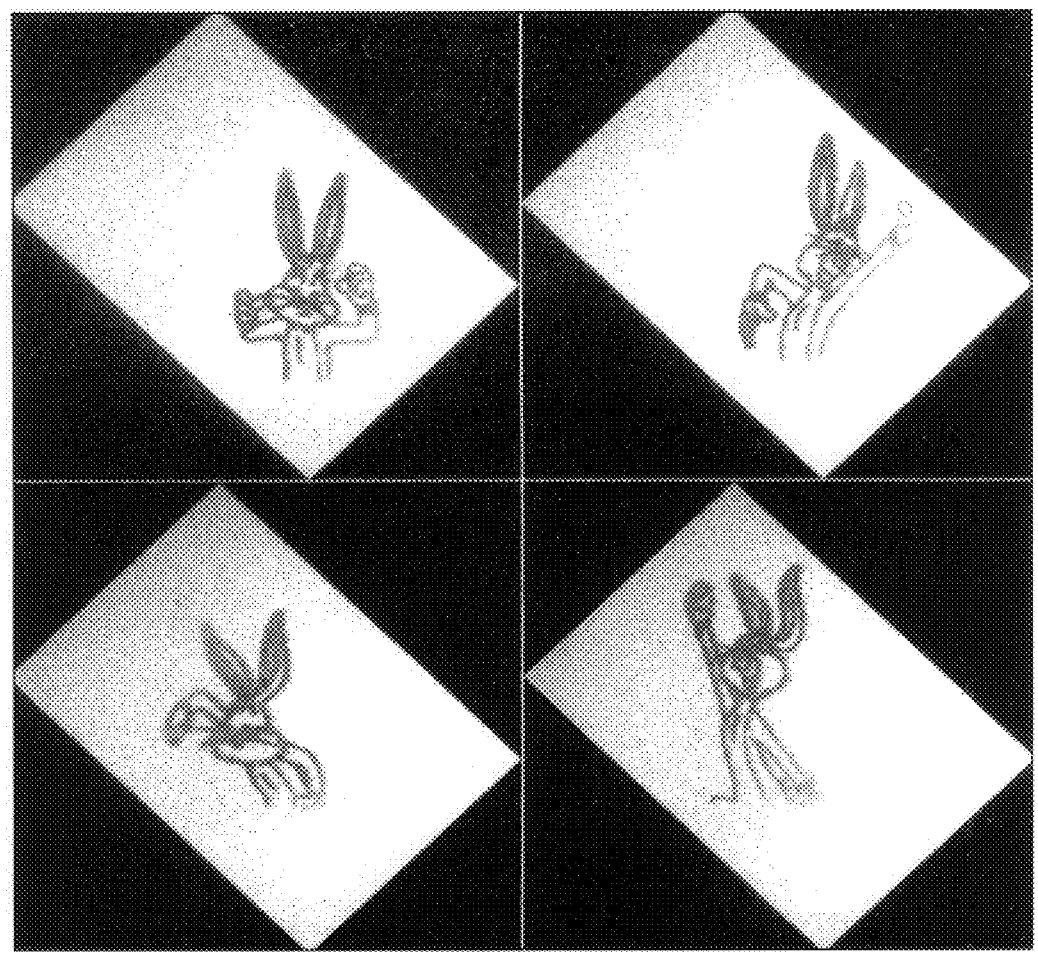
FIG. 34 is a scanned image of four frames of a movie stored in different planes of a data storage medium according to the present invention.

The APSS-containing HEMA block was used to archive black and white images having a continuous grayscale. The level of the greyscale recorded was modulated by varying the intensity of the writing laser. As an example of this method, bitmap images of 22 frames from an animated bugs bunny movie were recorded one behind the other, separated by 5 µm. FIG. 34 shows four selected images in the sequence, read back with a confocal microscope, as described above.

Although the invention has been described in detail for the purpose of illustration, it is understood that such detail is solely for that purpose, and variations can be made therein by those skilled in the art without departing from the spirit and scope of the invention which is defined by the following claims.

What is claimed is:

1. A data storage medium comprising:
   a three-dimensional matrix comprising a first volume element;
   a plurality of dye molecules substantially uniformly dispersed said three-dimensional matrix, wherein a fraction between about 0.3 and about 0.7 of the dye molecules contained in the first volume element are detectably altered and wherein the detectably altered dye molecules are substantially uniformly dispersed through the first volume element.

2. A data storage medium according to claim 1, wherein the matrix comprises a polymer selected from the group consisting of poly(methyl methacrylate), poly(2-hydroxyethyl methacrylate), and combinations thereof.

3. A data storage medium according to claim 1, wherein the first volume element has a volume of from about 0.001 µm$^3$ to about 10 µm$^3$.

4. A data storage medium according to claim 1, wherein the concentration of the dye molecules in the matrix is from about 0.001 M to about 0.4 M.

5. A data storage medium according to claim 1, wherein the dye molecules are detectably alterable by a two-photon upconversion process.

6. A data storage medium according to claim 5, wherein the detectably altered dye molecules are photobleached.

7. A data storage medium according to claim 1, wherein the dye molecules have a two-photon absorption cross section of greater than about $1 \times 10^{-50}$ cm$^4$-sec.

8. A data storage medium according to claim 1, wherein the dye molecules have the formula:

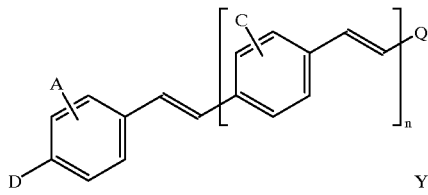

wherein
D is an electron donating group;
Q is an electron acceptor selected from the group consisting of electron acceptors having the formulae:

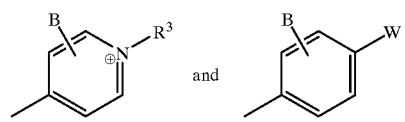

W is an electron accepting group,
R$^3$ is a substituted or unsubstituted alkyl moiety or a substituted or unsubstituted aryl moiety, n is integer from 0 to 4, A, B, and C are substituents of their rings and are each independently selected from the group consisting of alkyl, alkoxy, hydroxyalkyl, sulfoalkyl, carboxyalkyl, and hydrogen, and Y is a counterion.

9. A data storage medium according to claim 8, wherein the dye molecules have the formula:

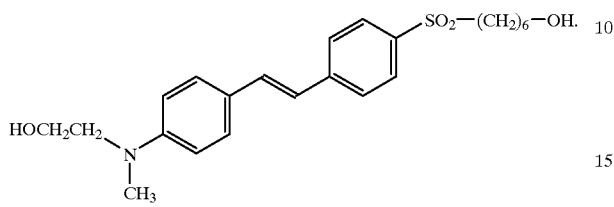

10. A data storage medium according to claim 1, wherein the three-dimensional matrix flirter comprises:
   a second volume element, wherein a fraction of the dye molecules contained in the second volume element are detectably altered and wherein the fraction of the dye molecules detectably altered in the second volume element is detectably different than the fraction of the dye molecules detectably altered in the first volume element; and
   a third volume element, wherein a fraction of the dye molecules contained in the third volume element are detectably altered and wherein the fraction of the dye molecules detectably altered in the third volume element is detectably different than the fractions of the dye molecules detectably altered in the first and second volume elements.

11. A data storage medium according to claim 1, wherein the three-dimensional matrix further comprises:
   254 additional volume elements, wherein a fraction of the dye molecules contained in each of the 254 additional volume elements are detectably altered and wherein the fraction of the dye molecules detectably altered in each of the 254 additional volume elements is detectably different than the fraction of the dye molecules detectably altered in each of the other 254 additional volume elements and in the first volume element.

12. A method of reading data comprising:
   providing an data storage medium according to claim 1 and detecting the fraction of the dye molecules contained in the first volume element that are detectably altered.

13. A method according to claim 12, wherein the dye molecules are two-photon upconversion fluorescers and wherein the detectably altered dye molecules are photobleached, said detecting comprising:
   exposing the first volume element to actinic radiation effective to induce the dye molecules in the first volume element other that the detectably altered dye molecules to two-photon upconversion fluoresce;
   detecting the fluorescence; and
   correlating the fluorescence with the fraction of the dye molecules contained in the first volume element that are detectably altered.

14. A method according to claim 13, wherein the detecting is carried out using a confocal microscope.

15. A method according to claim 13, wherein the exposing the first volume element to actinic radiation is ineffective to photobleach the dye molecules contained in the first volume element.

16. A data storage medium comprising:
   a three-dimensional matrix and a plurality of dye molecules having the formula:

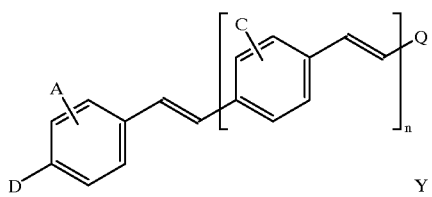

wherein
D is an electron donating group;
Q is an electron acceptor selected from the group consisting of electron acceptors having the formulae:

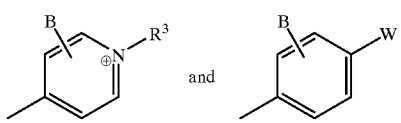

W is an electron accepting group,
$R^3$ is a substituted or unsubstituted alkyl moiety or a substituted or unsubstituted aryl moiety,
n is an integer from 0 to 4,
A, B, and C are substituents of their rings and are each independently selected from the group consisting of alkyl, alkoxy, hydroxyalkyl, sulfoalkyl, carboxyalkyl, and hydrogen, and
Y is a counterion
substantially uniformly dispersed in said three-dimensional matrix.

17. A data storage medium according to claim 16, wherein the three-dimensional matrix comprises a first volume element and wherein all or a fraction of the dye molecules contained in the first volume element are detectably altered.

18. A method for reading data comprising:
   providing a data storage medium according to claim 17 and
   detecting the fraction of the dye molecules contained in the first volume element that are detectably altered.

19. A method according to claim 18, wherein the detectably altered dye molecules are photobleached, said detecting comprising:
   exposing the first volume element to actinic radiation effective to induce the dye molecules in the first volume element other that the detectably altered dye molecules to two-photon upconversion fluoresce;
   detecting the fluorescence; and
   correlating the fluorescence with the fraction of the dye molecules contained in the first volume element that are detectably altered.

20. A method according to claim 19, wherein the detecting is carried out using a confocal microscope.

21. A method according to claim 19, wherein the exposing the first volume element to actinic radiation is ineffective to photobleach the dye molecules contained in the first volume element.

22. A data storage medium according to claim 16, wherein n is 0; A is hydrogen; D is an amine having the formula $NR^1R^2$; $R^1$ and $R^2$ are the same or different and are substituted or unsubstituted alkyl moieties or substituted or unsubstituted aryl moieties; and Q has the formula:

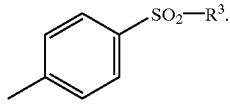

23. A data storage medium according to claim 16, wherein $R^1$ is 2-hydroxyethyl, $R^2$ is methyl, and $R^3$ is 6-hydroxyhexyl.

24. A data storage medium according to claim 16, wherein the dye molecules have the formula:

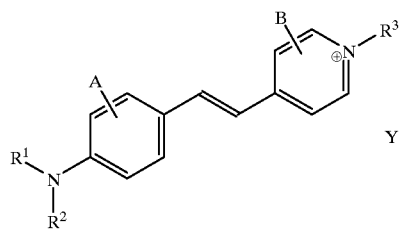

wherein $R^1$ and $R^2$ are the same or different and are substituted or unsubstituted alkyl moieties or substituted or unsubstituted aryl moieties.

25. A data storage medium according to claim 24, wherein Y is tetraphenylborate or iodide.

26. A data storage medium according to claim 24, wherein A and B are hydrogen and $R^1$, $R^2$, and $R^3$ are the same or different and are selected from the group consisting of unsubstituted alkyl, hydroxyalkyl, sulfoalkyl, and carboxyalkyl.

27. A data storage medium according to claim 26, wherein $R^2$ is unsubstituted alkyl and $R^1$ and $R^3$ are selected from the group consisting of hydroxyalkyl, sulfoalkyl, and carboxyalkyl.

28. A data storage medium according to claim 16, wherein the dye molecules have the formula:

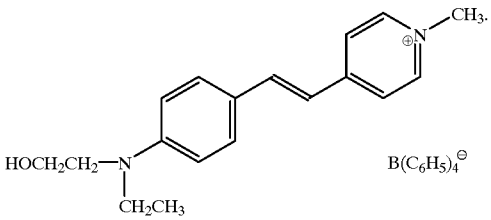

29. A data storage medium according to claim 16, wherein the dye molecules have the formula:

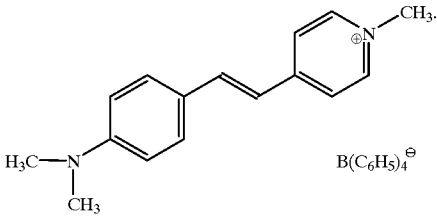

30. A data storage medium according to claim 16, wherein the dye molecules have the formula:

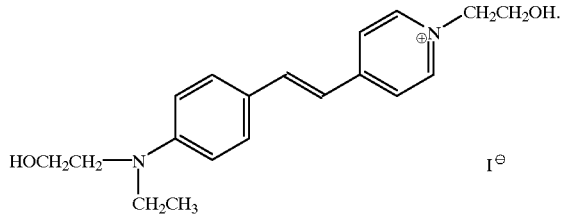

31. A data storage medium according to claim 16, wherein the dye molecules have the formula:

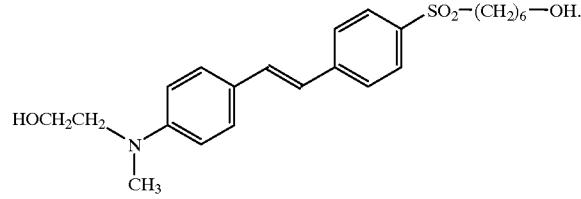

* * * * *